US008093393B2

(12) United States Patent
Bielawska et al.

(10) Patent No.: US 8,093,393 B2
(45) Date of Patent: Jan. 10, 2012

(54) CATIONIC CERAMIDES, AND ANALOGS THEREOF, AND THEIR USE FOR PREVENTING OR TREATING CANCER

(75) Inventors: Alicja Bielawska, Charleston, SC (US); Zdzislaw M. Szulc, Charleston, SC (US); Yusuf A. Hannun, Sullivan's Island, SC (US); Lina M. Obeid, Sullivan's Island, SC (US); Besim Ogretmen, Mt. Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 665 days.

(21) Appl. No.: 11/666,518

(22) PCT Filed: Oct. 31, 2005

(86) PCT No.: PCT/US2005/039271
§ 371 (c)(1),
(2), (4) Date: Oct. 17, 2007

(87) PCT Pub. No.: WO2006/050264
PCT Pub. Date: May 11, 2006

(65) Prior Publication Data
US 2011/0071099 A1    Mar. 24, 2011

Related U.S. Application Data

(60) Provisional application No. 60/623,281, filed on Oct. 29, 2004.

(51) Int. Cl.
C07D 211/00 (2006.01)
C07D 211/92 (2006.01)
(52) U.S. Cl. ........................................ 546/246; 546/347
(58) Field of Classification Search .................. 546/246, 546/347
See application file for complete search history.

(56) References Cited

U.S. PATENT DOCUMENTS

| 2,515,465 | A |   | 7/1950  | Mozingo et al.  |         |
|-----------|---|---|---------|-----------------|---------|
| 3,466,292 | A |   | 9/1969  | Paquette et al. |         |
| 4,016,287 | A |   | 4/1977  | Eberhardt et al.|         |
| 4,151,198 | A |   | 4/1979  | Halmos          |         |
| 4,283,541 | A |   | 8/1981  | Shroff et al.   |         |
| 4,544,670 | A |   | 10/1985 | Studt et al.    |         |
| 4,622,325 | A |   | 11/1986 | Fujii et al.    |         |
| 4,859,761 | A |   | 8/1989  | Flury et al.    |         |
| 4,897,355 | A |   | 1/1990  | Eppstein et al. |         |
| 4,937,232 | A |   | 6/1990  | Bell et al.     |         |
| 5,369,030 | A |   | 11/1994 | Hannun et al.   |         |
| 5,559,154 | A |   | 9/1996  | Weber et al.    |         |
| 5,679,350 | A |   | 10/1997 | Jankun et al.   |         |
| 5,830,916 | A |   | 11/1998 | Hannun et al.   |         |
| 5,851,782 | A |   | 12/1998 | Hannun et al.   |         |
| 5,916,911 | A | * | 6/1999  | Shayman et al.  | 514/428 |
| 6,284,798 | B1|   | 9/2001  | Amtmann et al.  |         |
| 6,610,835 | B1|   | 8/2003  | Liotta et al.   |         |
| 6,696,081 | B2|   | 2/2004  | Grinstaff et al.|         |
| 6,756,504 | B2|   | 6/2004  | Dagan et al.    |         |
| 7,172,879 | B2|   | 2/2007  | Gamble et al.   |         |
| 2003/0133904 | A1 | | 7/2003 | Dagan et al.   |         |
| 2008/0045470 | A1 | | 2/2008 | Bielawska et al.|        |
| 2008/0167352 | A1 | | 7/2008 | Smith et al.   |         |
| 2008/0268073 | A1 | | 10/2008| Sano et al.    |         |

FOREIGN PATENT DOCUMENTS

| GB | 630 712       | 10/1949 |
|----|---------------|---------|
| GB | 1 487 283     | 9/1977  |
| WO | WO00/27883    | 5/2000  |
| WO | WO01/79152    | 10/2001 |
| WO | WO02/22175    | 3/2002  |
| WO | WO03/005965   | 1/2003  |
| WO | WO2004/074247 | 9/2004  |
| WO | WO2006/050264 | 5/2006  |
| WO | WO2006/050265 | 5/2006  |
| WO | WO2006/138660 | 12/2006 |
| WO | WO2010/054223 | 5/2010  |
| WO | WO2010/078247 | 7/2010  |

OTHER PUBLICATIONS

Norgorodov et al. The Journal of Biological Chemistry, 2005, 280, 16096-16105.*
Notification of Transmittal of the International Search Report and the Written Opinion of the International Searching Authority, or the Declaration corresponding to PCT Application No. PCT/US05/39271 dated Mar. 23, 2007.
Notification concerning Transmittal of International Preliminary Report on Patentability (Chapter 1 of the Patent Cooperation Treaty) corresponding to PCT Application No. PCT/US05/39271 dated May 10, 2007.
Lutz et al. Antimalarials. α-phenyl-β-dialkylamino alcohols. *Journal of Organic Chemistry*, vol. 12, (1947), pp. 617-703.
Agrawal et al., "Cell-cycle kinetics and VSV-G pseudotyped retrovirus-mediated gene transfer in blood-derived CD34[+] cells," Experimental Hematology. vol. 24 pp. 738-747 (1996).
Ardail et al., "Subcellular distribution and metabolic fate of exogenous ceramides taken up by HL-60 cells," Biochimica et Biophysica Acta. vol. 1583 pp. 305-310 (2002).
Ashkenazi, A., and Dixit, V.M., "Apoptosis control by death and decoy receptors," Current Opinion in Cell Biology. vol. 11 pp. 255-260 (1999).
Ashkenazi, A., and Dixit, V.M., "Death Receptors: Signaling and Modulation," Science. vol. 281 pp. 1305-1308 (1998).
Bai et al., poster (SERLC, Sep. 11, 2008) titled "Synthesis and Bioevaluation of ω-Amino Analogs of B13 as Potential Anticancer Agents Targeting Acid Ceramidase."

(Continued)

*Primary Examiner* — Nizal Chandrakumar
(74) *Attorney, Agent, or Firm* — Jenkins, Wilson, Taylor & Hunt, P.A.

(57) ABSTRACT

The present invention relates to cationic ceramides, their dihydro-analogs and aromatic analogs and their derivatives, comprising a pyridinium group. Also provided are methods for making cationic ceramides comprising a pyridinium group, and their use for treating or preventing diseases associated with cell overproliferation and sphingolipid signal transduction, such as cancer, inflammation, and stenosis. The compounds are also useful as mitochondritropic agents that are localized to mitochondria carrying with them chemical cargoes, such as drugs, or signaling molecules, such as fluorophores for probing organelle structure and functions.

48 Claims, 52 Drawing Sheets

OTHER PUBLICATIONS

Bai et al., "Synthesis and bioevaluation of ω-N-amino analogs of B13," Bioorganic & Medicinal Chemistry. vol. 17 pp. 1840-1848 (2009).
Bernatowicz et al., "Urethane Protected Derivatives of 1-Guanylpyrazole for the Mild and Efficient Preparation of Guanidines," Tetrahedron Letters. vol. 34, No. 21 pp. 3389-3392 (1993).
Bieberich et al., "Synthesis and characterization of novel ceramide analogs for induction of apoptosis in human cancer cells," Cancer Letters. vol. 181 pp. 55-64 (2002).
Bielawska et al., "(1S,2R)-D-erythro-2-(N-Myristoylamino)-1-phenyl-1-propanol as an Inhibitor of Ceramidase," The Journal of Biological Chemistry. vol. 271, No. 21 pp. 12646-12654 (1996).
Bielawska et al., "Ceramide-mediated Biology," The Journal of Biological Chemistry. vol. 267, No. 26 pp. 18493-18497 (1992).
Bielawska et al., "Novel analogs of D-e-Mapp and B13. Part 2: Signature effects on bioactive sphingolipids," Biooragnic & Medicinal Chemistry. vol. 16 pp. 1032-1045 (2008).
Bielawska et al., "Synthesis of Key Precursors of Radiolabeled Sphingolipids," Methods in Enzymology. vol. 311 pp. 518-535 (1999).
Bielawski et al., "Simultaneous quantitative analysis of bioactive sphingolipids by high-performance liquid chromatography-tandem mass spectrometry," Methods. vol. 39 pp. 82-91 (2006).
Birbes et al., "Selective hydrolysis of a mitochondrial pool of sphingomyelin induces apoptosis," FASEB Journal. vol. 14 pp. 2669-2679 (2001).
Black, W.C., and Percival, M.D., "The Consequences of Lysosomotropism on the Design of Selective Cathepsin K Inhibitors," ChemBioChem. vol. 7 pp. 1525-1535 (2006).
Bose et al., "Ceramide Synthase Mediates Daunorubicin-Induced Apoptosis: An Alternative Mechanism for Generating Death Signals," Cell. vol. 82 pp. 405-414 (1995).
Boya et al., "Mitochondrial membrane permeabilization is a critical step of lysosome-initiated apoptosis induced by hydroxychloroquine," Oncogene. vol. 22 pp. 3927-3936 (2003).
Brown et al., "Mechanism of action of a dominant-negative mutant of c-Jun," Oncogene. vol. 9 pp. 791-799 (1994).
Buchwald et al., "Long-term, continuous intravenous heparin administration by an implantable infusion pump in ambulatory patients with recurrent venous thrombosis," Surgery. vol. 88, No. 4 pp. 507-516 (1980).
Buttle et al., "CA074 Methyl Ester: A Proinhibitor for Intracellular Cathespin B," Archives of Biochemistry & Biophysics. vol. 299, No. 2 pp. 377-380 (1992).
Chad et al., "Site-Directed Mutagenesis of UDP-Galactopyranose Mutase Reveals a Critical Role for the Active-Site, Conserved Arginine Residues," Biochemistry. vol. 46 pp. 6723-6732 (2007).
Chalfant et al., "The structural requirements for ceramide activation of serine-threonine protein phosphatases," J. Lipid Res. vol. 45 pp. 496-506 (2004).
Charles et al., "Ceramide-Coated Balloon Catheters Limit Neointimal Hyperplasia After Stretch Injury in Carotid Arteries," Circ Res. vol. 87 pp. 282-288 (2000).
Cherioux, F., and Audebert, P., "New Star-Shaped Molecules with Extended Electronic Delocalization," Chem. Mater. vol. 10 pp. 1984-1989 (1998).
Cremesti et al., "Ceramide Enables Fas to Cap and Kill," The Journal of Biological Chemistry. vol. 276, No. 26 pp. 23954-23961 (2001).
Dagan et al., "Synthetic, non-natural sphingolipid analogs inhibit the biosynthesis of cellular sphingolipids, elevate ceramide and induce apoptotic cell death," Biochimica et Biophysica Acta. vol. 1633 pp. 161-169 (2003).
Database Beilstein Beilstein Institute for Organic Chemistry, Frankfurt-Main, DE; 1932, Database Accession No. BRN: 3854595 & Slotta, Justus Liebigs Annalen der Chemie. vol. 497 pp. 171-178 (1932).
Database Beilstein Beilstein Institute for Organic Chemistry, Frankfurt-Main, DE; 1933, Database Accession No. BRN: 3684371 & Abderhalden, Schweitzer: Fermentforschung. vol. 13 pp. 128-133 (1933) [Abstract].
Database Beilstein Beilstein Institute for Organic Chemistry, Frankfurt-Main, DE; 1949, Database Accession No. BRN: 3814715 & Cornforth, Chem. Penicillin. pp. 688 and 798 (1949) [Abstract].
Database Bielstein Beilstein Institute for Organic Chemistry, Frankfurt-Main, DE; 1958, Database Accession No. BRN: 3805955 & Kratzl, Berger: Monatshefte fuer Chemie. vol. 89 pp. 160-164 (1958) [Abstract].
Database Beilstein Beilstein Institute for Organic Chemistry, Frankfurt-Main, DE; 1966, Database Accession No. BRN: 4138625 & Ciusa, Barbiroli: Annali di Chimica. vol. 56 pp. 3-6 (1966) [Abstract].
Database Beilstein Beilstein Institute for Organic Chemistry, Frankfurt-Main, DE; 1982, Database Accession No. BRN: 4628299 & Katritzky et al., Journal of Heterocyclic Chemistry. vol. 19 pp. 741-745 (1982) [Abstract].
Davis et al., "Mitochondrial and Plasma Membrane Potentials Cause Unusual Accumulation and Retention of Rhodamine 123 by Human Breast Adenocarcinoma-derived MCF-7 Cells," The Journal of Biological Chemistry. vol. 260, No. 25 pp. 13844-13850 (1985).
Di Paola et al., "Ceramide Interaction with the Respiratory Chain of Heart Mitochondria," Biochemistry. vol. 39 pp. 6660-6668 (2000).
El Bawab et al., "Biochemical Characterization of the Reverse Activity of Rat Brain Ceramidase," The Journal of Biological Chemistry. vol. 276, No. 20 pp. 16758-16766 (2001).
El Bawab et al., "Purification and Characterization of a Membrane-bound Nonlysosomal Ceramidase from Rat Brain," The Journal of Biological Chemistry. vol. 274, No. 39 pp. 27946-27955 (1999).
El Bawab et al., "Substrate specificity of rat brain ceramidase," J. Lipid Res. vol. 43 pp. 141-148 (2002).
Elojeimy et al., "Role of Acid Ceramidase in Resistance to FasL: Therapeutic Approaches Based on Acid Ceramidase Inhibitors and FasL Gene Therapy," Molecular Therapy. vol. 15, No. 7 pp. 1259-1263 (2007).
English et al., "Sphingosine 1-phosphate released from platelets during clotting accounts for the potent endothelial cell chemotactic activity of blood serum and provides a novel link between hemostasis and angiogenesis," FASEB Journal. vol. 14 pp. 2255-2265 (2000).
Extended European Search Report corresponding to European Patent Application No. 05820909.9-2101 dated Jul. 3, 2009.
Fantin et al., "A novel mitochondriotoxic small molecule that selectively inhibits tumor cell growth," Cancer Cell. vol. 2 pp. 29-42 (2002).
Felgner et al., "Lipofection: A highly efficient, lipid-mediated DNA-transfection procedure," PNAS. vol. 84 pp. 7413-7417 (1987).
French et al., "Antitumor Activity of Sphingosine Kinase Inhibitors," The Journal of Pharmacology and Experimental Therapeutics. vol. 318, No. 2 pp. 596-603 (2006).
French et al., "Discovery and Evaluation of Inhibitors of Human Sphingosine Kinase," Cancer Research. vol. 63 pp. 5962-5969 (2003).
Garcia-Ruiz et al., "Direct Effect of Ceramide on the Mitochondrial Electron Transport Chain Leads to Generation of Reactive Oxygen Species," The Journal of Biological Chemistry. vol. 272, No. 17 pp. 11369-11377 (1997).
Garner et al., "A Stereodivergent Synthesis of D-erthyro-Sphingosine and D-threo-Sphingosine from L-Serine," J. Org. Chem. vol. 53, No. 18 pp. 4395-4398 (1988).
Ghafourifar et al., "Ceramide Induces Cytochrome c Release from Isolated Mitochondria," The Journal of Biological Chemistry. vol. 274, No. 10 pp. 6080-6084 (1999).
Ghosh et al., "Probing the function(s) of active-site arginine residue in *Leishmania donovani* adenosine kinase," Biochem. J. vol. 298 pp. 295-301 (1994).
Goodman et al., "Recombinant Adeno-Associated Virus-Mediated Gene Transfer Into Hematopoietic Progenitor Cells," Blood. vol. 84, No. 5 pp. 1492-1500 (1994).
Grether-Beck et al., "Mitochondrial Cytochrome c Release Mediates Ceramide-induced Activator Protein 2 Activation and Gene Expression," The Journal of Biological Chemistry. vol. 278, No. 48 pp. 47498-47507 (2003).
Gu et al., "Induction of p53-regulated genes in lung cancer cells: implications of the mechanism for adenoviral p53-mediated apoptosis," Oncogene. vol. 23 pp. 1300-1307 (2004).

Hakogi et al., "Synthesis of Fluorescence-Labeled Sphingosine and Sphingosine 1-Phosphate; Effective Tools for Sphingosin and Sphingosine 1-Phosphate Behavior," Bioorganic & Medicinal Chemistry Letters. vol. 13 pp. 661-664 (2003).

Hann, B., and Balmain, V., "Building 'validated' mouse models of human cancer," Current Opinion in Cell Biology. vol. 13 pp. 778-784 (2001).

Hannun, Y.A., and Luberto, C., "Ceramide in the eukaryotic stress response," Trends in Cell Biology. vol. 10 pp. 73-80 (2000).

Hannun, "Functions of ceramide in coordinating cellular responses to stress," Science. vol. 274, No. 5294 pp. 1855-1859 (1996).

Hansen et al., "Re-examination and further development of a precise and rapid dye method for measuring cell growth/cell kill," Journal of Immunological Methods. vol. 119 pp. 203-210 (1989).

Hayter et al., "TNFα-induced glutathione depletion lies downstream of cPLA$_2$ in L929 cells," FEBS Letters. vol. 507 pp. 151-156 (2000).

He et al., "Purification and Characterization of Recombinant, Human Acid Ceramidase," The Journal of Biological Chemistry. vol. 278, No. 35 pp. 32978-32986 (2003).

Hla, "Signaling and biological actions of sphingosine 1-phosphate," Pharmacological Research. vol. 47 pp. 401-407 (2003).

Holman et al., "Lysosomotropic acid ceramidase inhibitor induces apoptosis in prostate cancer cells," Cancer Chemother. Pharmacol. vol. 61 pp. 231-242 (2008).

Howard et al., "Intracerebral drug delivery in rats with lesion induced memory deficits," J. Neurosurg. vol. 71 pp. 105-112 (1989).

Huwiler, A., and Zangemeister-Wittke, U., "Targeting the conversion of ceramide to sphingosine 1-phosphate as a novel strategy for cancer therapy," Oncology Hematol. vol. 63 pp. 150-159 (2007).

Hyer et al., "Downregulation of c-FLIP Sensitizes DU145 Prostate Cancer Cells to Fas-Mediated Apoptosis," Cancer Biology & Therapy. vol. 1, No. 4 pp. 401-406 (2002).

Hyer et al., "Quantification and characterization of the bystander effect in prostate cancer cells following adenovirus-mediated FasL expression," Cancer Gene Therapy. vol. 10 pp. 330-339 (2003).

Inaba et al., "Evaluation of Antitumor Activity in a Human Breast Tumor/Nude Mouse Model With a Special Emphasis on Treatment Dose," Cancer. vol. 64 pp. 1577-1582 (1989).

Interview Summary corresponding to U.S. Appl. No. 11/666,519 dated Jun. 15, 2010.

Johnson et al., "Role of Human Sphingosine-1-phosphate Phosphatase 1 in the Regulation of Infra- and Extracellular Sphingosine-1-phosphate Levels and Cell Viability," The Journal of Biological Chemistry. vol. 278, No. 36 pp. 34541-34547 (2003).

Jones et al., "Ceramide Induces Caspase-Independent Apoptosis in Rat Hepatocytes Sensitized by Inhibition of RNA Synthesis," Hepatology. vol. 30 pp. 215-222 (1999).

Jones-Bolin et al., "The effects of the oral, pan-VEGF-R kinase inhibitor CEP-7055 and chemotherapy in orthotopic models of glioblastoma and colon carcinoma in mice," Molecular Cancer Therapeutics. vol. 4, No. 7 pp. 1744-1753 (2006).

Jursic, "An Enantiomeric Discrimination in Aqueous Mixed Chiral Micelles Through Hydrogen Bonding," Tetrahedron Letters. vol. 34, No. 6 pp. 963-966 (1993).

Kamo et al., "Membrane Potential of Mitochondria Measured with an Electrode Sensitive to Tetraphenyl Phosphonium and Relationship between Proton Electrochemical Potential and Phosphorylation Potential in Steady State," J. Membrane Biology. vol. 49 pp. 105-121 (1979).

Karahatay et al., "Clinical relevance of ceramide metabolism in the pathogenesis of human head and neck squamous cell carcinoma (HNSCC): Attenuation of C$_{18}$-ceramide in HNSCC tumors correlates with lymphovascular invasion and nodal metastasis," Cancer Letters. vol. 256 pp. 101-111 (2007).

Kaufmann, A.M., and Krise, J.P., "Lysosomal Sequestration of Amine-Containing Drugs: Analysis and Therapeutic Implications," Journal of Pharmaceutical Sciences. vol. 96, No. 4 pp. 729-746 (2007).

Kim et al., "Synthesis and evaluation of sphingoid analogs as inhibitors of sphingosine kinases," Bioorganic & Medicinal Chemistry. vol. 13 pp. 3475-3485 (2005).

Klymchenko et al., "Ultrasensitive two-color fluorescence probes for dipole potential in phospholipid membranes," PNAS. vol. 100, No. 20 pp. 11219-11224 (2003).

Koch et al., "Molecular Cloning and Characterization of a Full-length Complementary DNA Encoding Human Acid Ceramidase," The Journal of Biological Chemistry. vol. 271, No. 51 pp. 33110-33115 (1996).

Kornfeld, "The Biogenesis of Lysosomes," Annu. Rev. Cell Biol. vol. 5 pp. 483-525 (1989).

Koybasi et al., "Defects in Cell Growth Regulation by $C_{18:0}$-Ceramide and Longevity Assurance Gene 1 in Human Head and Neck Squamous Cell Carcinomas," The Journal of Biological Chemistry. vol. 279, No. 43 pp. 44311-44319 (2004).

Langer, "New methods of drug delivery," Science. vol. 249, No. 4976 pp. 1527-1533 (1990).

Lee et al., "Sphingosine-1-Phosphate as a Ligand for the G Protein-Coupled Receptor EDG-1," Science. vol. 279 pp. 1552-1555 (1998).

Levy et al., "Inhibition of calcification of bioprosthetic heart valves by local controlled-release diphosphonate," Science. vol. 228 p. 190 (1985).

Liu et al., "Acid ceramidase inhibition: a novel target for cancer therapy," Frontiers in Bioscience. vol. 13 pp. 2293-2298 (2008).

Liu et al., "Glutathione Regulation of Neutral Sphingomyelinase in Tumor Necrosis Factor-α-induced Cell Death," The Journal of Biological Chemistry. vol. 273, No. 18 pp. 11313-11320 (1998).

Lowe et al., "Prostate-specific expression of Bax delivered by an adenoviral vector induces apoptosis in LNCaP prostate cancer cells," Gene Therapy. vol. 8 pp. 1363-1371 (2001).

Macchia et al., "Design, Synthesis, and Characterization of the Antitumor Activity of Novel Ceramide Analogues," J. Med. Chem. vol. 44 pp. 3994-4000 (2001).

Maceyka et al., "Sphingosine kinase, sphingosine-1-phosphate, and apoptosis," Biochimica et Biohysica Acta. vol. 1585 pp. 193-201 (2002).

Makino et al., "Comparative study between daily and 5-days-a-week administration of oral 5-fluorouracil chemotherapy in mice: determining the superior regimen," Cancer Chemother. Pharmacol. vol. 48 pp. 370-374 (2001).

Mao et al., "Cloning and Characterization of a Novel Human Alkaline Ceramidase," The Journal of Biological Chemistry. vol. 276, No. 28 pp. 36577-35688 (2001).

Medema et al., "FLICE is activated by association with the CD95 death-inducing signaling complex (DISC)," The EMBO Journal. vol. 16, No. 10 pp. 2794-2804 (1997).

Miller, A.D., and Buttimore, C. "Redesign of Retrovirus Packaging Cell Lines to Avoid Recombination Leading to Helper Virus Production," Molecular and Cellular Biology. vol. 6, No. 8 pp. 2895-2902 (1986).

Mimeault, "New advances on structural and biological functions of ceramide in apoptotic/necrotic cell death and cancer," FEBS Letters. vol. 530 pp. 9-16 (2002).

Miyashita, T., and Reed, J.C., "Tumor Suppressor p53 Is a Direct Transcriptional Activator of the Human *bax* Gene," Cell. vol. 80 pp. 293-299 (1995).

Modica-Napolitano, J.S., and Aprille, J.R., "Delocalized lipophilic cations selectively target the mitochondria of carcinoma cells," Advanced Drug Delivery Reviews. vol. 49 pp. 63-70 (2001).

Muzio et al., "Flice Induced Apoptosis in a Cell-free System," The Journal of Biological Chemistry. vol. 272, No. 5 pp. 2952-2956 (1997).

Nakano, K., and Vousden, K.H., "*PUMA*, a Novel Proapoptotic Gene, Is Induced by p53," Molecular Cell. vol. 7 pp. 683-694 (2001).

Naldini et al., "In Vivo Gene Delivery and Stable Transduction of Nondividing Cells by a Lentiviral Vector," Science. vol. 272 pp. 263-267 (1996).

Nechushtan et al., "Bax and Bak Coalesce into Novel Mitochondria-associated Clusters during Apoptosis," The Journal of Cell Biology. vol. 153, No. 6 pp. 1265-1276 (2001).

Nimkar et al., "A Stereoselective Synthesis of Sphingosine, A Protein Kinase C Inhibitor," Tetrahedron Letters. vol. 29, No. 25 pp. 3037-3040 (1988).

Notification of Transmittal of the International Search Report and the Written Opinion of the International Searching Authority, or the Declaration corresponding to International Application No. PCT/US2009/063586 dated Mar. 5, 2010.
Notification of Transmittal of the International Search Report and the Written Opinion of the International Searching Authority, or the Declaration corresponding to International Application No. PCT/US2009/069583 dated Mar. 22, 2010.
Novgorodov et al., "Activation of sphingosine-1-phosphate receptor S1P5 inhibits oligodendrocyte progenitor migration," The FASEB Journal. vol. 21 pp. 1503-1514 (2007).
Novgorodov et al., "Positively Charged Ceramide Is a Potent Inducer of Mitochondrial Permabilization," Journal of Biological Chemistry. vol. 280, No. 16 pp. 16096-16105 (2005).
Obeid et al. "Programmed cell death induced by ceramide," Science. vol. 259, No. 5102 pp. 1769-1771 (1993).
Official Action corresponding to European Patent Application No. 05820909.9 —2101 dated Oct. 2, 2009.
Official Action corresponding to U.S. Appl. No. 11/666,519 dated Feb. 3, 2010.
Official Action corresponding to U.S. Appl. No. 11/666,519 dated Jul. 14, 2010.
Ogretmen, B., and Hannun, Y.A., "Biologically Active Sphingolipids in Cancer Pathogenesis and Treatment," Nature. vol. 4 pp. 604-616 (2004).
Ogretmen et al., "Role of Ceramide in Mediating the Inhibition of Telomerase Activity in A549 Human Lung Adenocarcinoma Cells," The Journal of Biological Chemistry. vol. 276, No. 27 pp. 24901-24910 (2001).
Onda et al., "Molecular Recognition of Nucleotides by the Guanidinium Unit at the Surface of Aqueous Micelles and Bilayers. A Comparision of Microscopic and Macroscopic Interfaces," J. Am. Chem. Soc. vol. 118 pp. 8524-8530 (1996).
Orlinick, J.R., and Chao, M.V., "TNF-Related Ligands and Their Receptors," Cell. Signal. vol. 10, No. 8 pp. 543-551 (1998).
Pastan et al., "A retrovirus carrying an *MDR1* cDNA confers multidrug resistance and polarized expression of P-glycoprotein in MDCK cells," PNAS. vol. 85 pp. 4486-4490 (1988).
Paugh et al., "A selective sphingosine kinase 1 inhibitor integrates multiple molecular therapeutic targets in human leukemia," Blood. vol. 112, No. 4 pp. 1382-1391 (2008).
Perry, D.K., and Hannun, Y.A., "The role of ceramide in cell signaling," Biochimica et Biophysica Acta. vol. 1436 pp. 233-243 (1998).
Pettus et al., "The sphingosine kinase 1/sphingosine-1-phospate pathway mediates COX-2 induction and $PGE_2$ production in response to TNF-α," FASEB Journal. vol. 17 pp. 1411-1421 (2003).
Radin, "Designing Anticancer Drugs Via the Achilles Heel: Ceramide, Allylic Ketones, and Mitochondria," Bioorganic & Medicinal Chemistry. vol. 11 pp. 2123-2142 (2003).
Raisova et al., "Bcl-2 overexpression prevents apoptosis induced by ceramidase inhibitors in malignant melanoma and HaCaT keratinocytes," FEBS Letters. vol. 516 pp. 47-52 (2002).
Raisova et al., "Resistance to CD95/Fas-induced and ceramide-mediated apoptosis of human melanoma cells is caused by a defective mitochondrial cytochrome *c* release," FEBS Letters. vol. 473 pp. 27-32 (2000).
Rao et al., "$^{31}$P NMR Studies of the Arginine Kinase Reaction," The Journal of Biological Chemistry. vol. 251, No. 22 pp. 6981-6986 (1976).
Rautio et al., "Prodrugs: design and clinical applications," Nature Reviews. vol. 7 pp. 255-270 (2008).
Rebbaa et al., "Doxorubicin-induced apoptosis in caspase-8-deficient neuroblastoma cells in mediated through direct action on mitochondria," Cancer Chemother. Pharmacol. vol. 48 pp. 423-428 (2001).
Robbins and Angell, *Basic Pathology*, 2$^{nd}$ Ed., W.B. Saunders Co., Philadelphia (1976), pp. 68-78 and 112-113.
Roberg et al., "Lysosomal Release of Cathepsin D Precedes Relocation of Cytochrome C and Loss of Mitochondrial Transmembrane Potential During Apoptosis Induced by Oxidative Stress," Free Radical Biology & Medicine. vol. 27, Nos. 11-12 pp. 1228-1237 (1999).

Rosania et al., "Combinatorial Approach to Organelle-Targeted Fluorescent Library Based on the Styryl Scaffold," Journal of the American Chemical Society. vol. 125 pp. 1130-1131 (2003).
Rossi et al., "Inhibition of growth and telomerase activity by novel cationic ceramide analogs with high solubility in human head and neck squamous cell carcinoma cells," Otolaryngology—Head and Neck Surgery. vol. 132, No. 1 pp. 55-62 (2005).
Rubinchik et al., "A Complex Adenovirus Vector That Delivers FASL-GFP with Combined Prostate-Specific and Tetracycline-Regulated Expression," Molecular Therapy. vol. 4, No. 5 pp. 416-426 (2001).
Sage et al., "Inhibition of Endothelial Cell Proliferation by SPARC Is Mediated Through a $Ca^{2+}$-Binding EF-Hand Sequence," Journal of Cellular Biochemistry. vol. 57 pp. 127-140 (1995).
Samsel et al., "The Ceramide Analog, B13, Induces Apoptosis in Prostate Cancer Cell Lines and Inhibits Tumor Growth in Prostate Cancer Xenografts," The Prostate. vol. 58 pp. 382-393 (2004).
Scaffidi et al., "Two CD95 (APO-1/Fas) signaling pathways," The EMBO Journal. vol. 17, No. 6 pp. 1675-1687 (1998).
Schotte et al., "Non-specific effects of methyl ketone peptide inhibitors of caspases," FEBS Letters. vol. 442 pp. 117-121 (1999).
Schulze-Osthoff et al., "Apoptosis signaling by death receptors," Eur. J. Biochem. vol. 254 pp. 439-459 (1998).
Schwandner et al., "TNF Receptor Death Domain-associated Proteins TRADD and FADD Signal Activation of Acid Sphingomyelinase," The Journal of Biological Chemistry. vol. 273, No. 10 pp. 5916-5922 (1998).
Schwarzenberger et al., "Targeted Gene Transfer to Human Hematopoietic Progenitor Cell Lines Through the c-kit Receptor," Blood. vol. 87, No. 2 pp. 472-478 (1996).
Seelan et al., "Human Acid Ceramidase Is Overexpressed But Not Mutated in Prostate Cancer," Genes, Chromosomes & Cancer. vol. 29 pp. 137-146 (2000).
Selzner et al., "Induction of Apoptopic Cell Death and Prevention of Tumor Growth by Ceramide Analogues in Metastatic Human Colon Cancer," Cancer Research. vol. 61 pp. 1233-1240 (2001).
Senchenkov et al., "Targeting Ceramide Metabolism—a Strategy for Overcoming Drug Resistance," J. Natl. Cancer Inst. vol. 93 pp. 347-357 (2001).
Shi et al., "Complex Functions of Mutant *p53* Alleles from Human Prostate Cancer," The Prostate. vol. 51 pp. 59-72 (2002).
Siskind et al., "Ceramide Channels Increase the Permeability of the Mitochondrial Outer Membrane to Small Proteins," The Journal of Biological Chemistry. vol. 277, No. 30 pp. 26796-26803 (2002).
Sobel, R.E., and Sadar, M.D., "Cell Lines Used in Prostate Cancer Research: A Compendium of Old and New Lines—Part 1," The Journal of Urology. vol. 173 pp. 342-359 (2005).
Song et al., "Kinetics and Mechanisms of Activation of α-Amino Acid Ester Prodrugs of Camptothecins," J. Med. Chem. vol. 49 pp. 4344-4355 (2006).
Sullards, M.C., and Merrill, Jr., A.H., "Analysis of Sphingosine 1-Phosphate, Ceramides, and Other Bioactive Sphingolipids by High-Performance Liquid Chromatography-Tandem Mass Spectrometry," Sci. STKE. vol. 67 pp. 1-11 (2001).
Sundararaj et al., "Rapid Shortening of Telomere Length in Response to Ceramide Involves the Inhibition of Telomere Binding Activity of Nuclear Glyceraldehyde-3-phosphate Dehydrogenase," The Journal of Biological Chemistry. vol. 279, No. 7 pp. 6152-6162 (2004).
Szalai et al., "Apoptosis driven by $IP_3$-linked mitochondrial calcium signals," The EMBO Journal. vol. 18, No. 22 pp. 6349-6361 (1999).
Szulc et al., "Novel analogs of D-*ef*-MAPP and B13. Part 1: Synthesis and evaluation as potential anticancer agents," Bioorganic & Medicinal Chemistry. vol. 16 pp. 1015-1031 (2008).
Szulc et al., "Tailoring structure-function and targeting properties of ceramides by site-specific cationization," Bioorganic & Medicinal Chemistry. vol. 14 pp. 7083-7104 (2006).
Takahashi et al., "Human Fas ligand: gene structure, chromosomal location and species specificity," International Immunology. vol. 6, No. 10 pp. 1567-1574 (1994).
Takeya et al., "Synergistic effect of sphingosine 1-phophate on thrombin-induced tissue factor expression in endothelial cells," Blood. vol. 102 pp. 1693-1700 (2003).

Tepper et al., "CD95/Fas-induced Ceramide Formation Proceeds with Slow Kinetics and is Not Blocked by Caspase-3/CPP32 Inhbition," The Journal of Biological Chemistry. vol. 272, No. 39 pp. 24308-24312 (1997).
Tepper et al., "Role for ceramide as an endogenous mediator of Fas-induced cytotoxicity," PNAS. vol. 92 pp. 8443-8447 (1995).
Thornberry, N.A., and Lazebnik, Y., "Caspases: Enemies Within," Science. vol. 281 pp. 1312-1316 (1998).
Tolsma et al., "Peptides Derived from Two Separate Domains of the Matrix Protein Thrombospondin-1 Have Anti-Angiogenic Activity," The Journal of Cell Biology. vol. 122, No. 2 pp. 497-511 (1993).
Trnka, T.M., and Grubbs, R.H., "The Development of $L_2X_2Ru=CHR$ Olefin Metathesis Catalysts: An Organometallic Success Story," Acc. Chem. Res. vol. 34 pp. 18-29 (2001).
Usta et al., "Structural Requirements of Ceramide and Sphingosine Based Inhibitors of Mitochondrial Ceramidase," Biochemistry. vol. 40 pp. 9657-9668 (2001).
van Moorsel et al., "Scheduling of Gemcitabine and Cisplatin in Lewis Lung Tumour Bearing Mice," European Journal of Cancer. vol. 35, No. 5 pp. 808-814 (1999).
Veerman et al., "Antitumor activity of prolonged as compared with bolus administration of 2',2'-difluorodeoxycytidine in vivo against murine colon tumors," Cancer Chemother. Pharmacol. pp. 335-342 (1996).
Vig et al., "Amino Acid Ester Prodrugs of Floxuridine: Synthesis and Effects of Structure, Stereochemistry, and Site of Esterification on the Rate of Hydrolysis," Pharmaceutical , Research. vol. 20, No. 9 pp. 1381-1388 (2003).
Volk, C.A., and Köck, M., "Viscosamine: The First Naturally Occurring Trimeric 3-Alkyl Pyridinium Alkaloid," Organic Letters. vol. 5, No. 20 pp. 3567-3569 (2003).
von Haefen et al., "Ceramide induces mitochondrial activation and apoptosis via a Bax-dependent pathway in human carcinoma cells," Oncogene. vol. 21 pp. 4009-4019 (2002).
Wagenknecht et al., "C2-ceramide signaling in glioma cells: synergistic enhancement of CD95-mediated, caspase-dependent apoptosis," Cell Death and Differentiation. vol. 8 pp. 595-602 (2001).
Watterson et al., "Pleiotropic actions of sphingosine-1-phosphate," Progress in Lipid Research. vol. 42 pp. 344-357 (2003).
Weissman, "Themes and Variations on Ubiquitylation," Nature Reviews Molecular Cell Biology. vol. 2 pp. 169-178 (2001).
Wyllie et al., "Cell Death: The Significance of Apoptosis," International Review of Cytology. vol. 68 pp. 251-306 (1980).
Yamanaka et al., "Engraftment of Tonsillar Mononuclear Cells in Human Skin/SCID Mouse Chimera—Validation of a Nove Xenogeneic Transplantation Model for Autoimmune Diseases—," Microbiol. Immunol. vol. 45, No. 7 pp. 507-514 (2001).
Yatomi et al., "Sphingosine-1-Phosphate: A Platelet-Activating Sphingolipid Released From Agonist-Stimulated Human Platelets," Blood. vol. 86, No. 1 pp. 193-202 (1995).
Zeidan et al., "Acid Ceramidase but Not Acid Sphingomyelinase is Required for Tumor Necrosis Factor-α-induced PGE2 Production," The Journal of Biological Chemistry. vol. 281, No. 34 pp. 24695-24703 (2006).
Bieberich et al., "N-Acylated Serinol Is a Novel Ceramide Mimic Inducing Apoptosis in Neuroblastoma Cells," The Journal of Biological Chemistry. vol. 275, No. 1 pp. 177-181 (2000).
Bielawska et al., "Selectivity of Ceramide-mediated Biology," The Journal of Biological Chemistry. vol. 268, No. 35 pp. 26226-26232 (1993).
Chalfant et al., "FAS Activation Induced Dephosphorylation of SR Proteins," The Journal of Biological Chemistry. vol. 276, No. 48 pp. 44848-44855 (2001).
Chen et al., "Relationship between the pharmacological action and the chemical constitution and configuration of the optical isomers of ephedrine and related compounds," J. Pharmacol. vol. 36 pp. 363-400 (1929) [Abstract].

Emerson, "Syntheses with Styrene Oxide," J. Am. Chem. Soc. vol. 67 pp. 516-518 (1945).
Feng, C., and Wilson, S.D., "Some derivatives of ephedrine," Zhongguo Shenglixue Zazhi. vol. 4 pp. 231-246 (1930) [Abstract].
Papucci et al., Coenzyme Q10 Prevents Apoptosis by Inhibiting Mitochrondrial Depolarization Independently of Its Free Radical Scavenging Property, The Journal of Biological Chemistry. vol. 278, No. 30 pp. 28220-28228 (2003).
Speer, J.H., and Hill, A.J., "Some Nucleus Alkyl Derivatives of Phenethylamine," The Journal of Organic Chemistry. vol. 2, No. 2 pp. 139-147 (1937).
Extended European Search Report corresponding to European Patent Application No. 05821150.9-1211 dated Feb. 10, 2011.
Fujii, A., and Cook, E.S., "Probiotics. Antistaphylococcal and Antifibrinolytic Activities of ω-Guanidino Acids and ω-Guanidinoacyl-L-histidines," Journal of Medicinal Chemistry. vol. 16, No. 12 pp. 1409-1411 (1973).
Lazewska et al., "Piperidine-containing histamine $H_3$-receptor antagonists of the carbamate series: variation of the spacer length," Pharmazie. vol. 56, No. 12 pp. 927-932 (2001).
Libby et al., "A Cascade Model for Restenosis: a Special Case of Atherosclerosis Progression," Circulation. vol. 86, No. 6, Suppl. III pp. III-47-III-52 (1992).
Lim et al., "Synthesis and Cytotoxicity of New 3-Alkyl-1-(1-methyl-2-phenylethyl)ureas Related to Ceramide," Archives of Pharmacal Research. vol. 26, No. 4 pp. 270-274 (2003).
Mahboob, S., and Dhar, M.L., "Studies in Potential Amoebicides: Part II-Synthesis of Some Polymethylene Diamines," Journal of Scientific & Industrial Research. vol. 14B pp. 1-6 (1955).
Mathias et al., "Signal transduction of stress via ceramide," Biochem. J. vol. 335 pp. 465-480 (1998).
Mitani et al., "Transduction of Human Bone Marrow by Adenoviral Vector," Human Gene Therapy. vol. 5 pp. 941-948 (1994).
Nussbaumer et al., "One-step labelling of sphingolipids via a scrambling cross-metathesis reaction," Chem. Commun. vol. 40 pp. 5086-5087 (2005).
Official Action corresponding to U.S. Appl. No. 11/666,519 dated Feb. 25, 2011.
Seebach et al., "Lithiation and electrophilic substitution at alpha-methylene groups of nitrosamines. Reactivity umpolung of secondary amines," Chemische Berichte. vol. 110, No. 5 pp. 1852-1865 (1977) [Abstract].
Taha et al., "A house divided: ceramide, sphingosine, and sphingsine-1-phosphate in programmed cell death," Biochim. Biophys. Acta. vol. 1758, No. 12 pp. 2027-2036 (2006).
Ueoka et al., "Isokinetic Discriminiation of Artificial Membrane Systems in the Enantioselective Hydrolysis," Tetrahedron Letters. vol. 25, No. 13 pp. 1363-1366 (1984).
Yamaguchi et al., "Copper(II) Reagent-Promoted Degradation of N,N'-dialkyldiazenedicarboxamides," Bulletin of the Chemical Society of Japan. vol. 75, No. 2 pp. 329-333 (2002).
Dahm et al., "Mitochondrially targeted ceramide LCL-30 inhibits colorectal cancer in mice," British Journal of Cancer. vol. 98 pp. 98-105 (2008).
Dindo et al., "Cationic long-chain ceramide LCL-30 induces cell death by mitochondrial targeting in SW403 cells," Molecular Cancer Therapeutics. vol. 5, No. 6 pp. 1520-1529 (2006).
Senkal et al., "Potent Antitumor Activity of a Novel Cationic Pyridinium-Ceramide Alone or in Combination with Gemcitabine against Human Head and Neck Squamous Cell Carcinomas in Vitro and in Vivo," The Journal of Pharmacology and Experimental Therapeutics. vol. 317, No. 3 pp. 1188-1199 (2006).

* cited by examiner

UM-SCC-22A Cell Survival Assay

| DRUGS | IC50 ($\mu$M) |
|---|---|
| DNR | 0.08 |
| DOX | 0.12 |
| MTX | 0.10 |
| GMZ | 0.23 |
| CSP | 6.6 |
| PAX | 13 |
| 5-FU | 16 |
| CRBP | >100 |

| Treatment | RBC | Hemoglobin | BUN | Creatinine | Na | Mg | ALT | Amylase |
|---|---|---|---|---|---|---|---|---|
| Control | 8.0 | 13.9 | 19 | 0.4 | 145 | 3.1 | 24 | 763 |
| Pyr-Cer | 8.4 | 14.1 | 23 | 0.6 | 142 | 2.7 | 52 | 1589 |
| GMZ/Cer | n.d. | n.d. | 36 | 0.5 | 147 | 3.1 | 23 | 1526 |

Abbreviations: RBC, red blood cells; BUN, blood urea nitrogen; ALT, Alanine aminotransferase.

The units: RBC (MILL/UL), Hemoglobin (GM/DL), BUN and Creatinine (MG/DL), GGT and amylase (U/L), electrolytes (MEQ/L).

FIG. 22C

L-threo-C$_6$-pyridinium ceramide bromide
(n=5)

| Group | Dose (mg/kg) | Total animals | Percent Mortality | Toxicity |
|---|---|---|---|---|
| 1 | 10 | 4 | 0 | none |
| 2 | 20 | 4 | 0 | none |
| 3 | 40 | 4 | 0 | none |
| 4 | 60 | 4 | 0 | none |
| 5 | 80 | 10 | 0 | n.d. |
| 6 | 100 | 10 | 10 | abdominal bloating |
| 7 | 120 | 10 | 20 | abdominal bloating, |
| 8 | 150 | 4 | 50 | intestinal malfunction |

FIG. 27A

CATIONIC CERAMIDES, AND ANALOGS THEREOF, AND THEIR USE FOR PREVENTING OR TREATING CANCER

This application claims priority to U.S. provisional application No. 60/623,281, filed Oct. 29, 2004, which is incorporated by reference in its entirety.

This invention was made with government support under grant numbers DOD: GC3532-03-42153CM, NIH/NCI: RO188932, NIH:PO1/CA971432-01, and RO1 AG16583. The government has certain rights in the invention.

1. FIELD OF THE INVENTION

The invention relates to cationic ceramides, dihydro ceramides, their analogs and their derivatives. The invention also relates to methods of making the compounds and various uses of the compounds, such as the prevention and treatment of diseases associated with cell overproliferation and sphingolipid signal transduction.

2. BACKGROUND OF THE INVENTION

Ceramide is a potent signal transducer that affects cell growth, differentiation and death (Hannun, Y. A. (1996) *Science* 274, 1855-1859; Obeid, L. M., Linardic, C. M., Karolak, L. A., and Hannun, Y. A. (1993) *Science* 259, 1769-1771; Perry, D. K. and Hannun, Y. A., (1998) *Biochim Biophys Acta* 436, 233-243). It occupies a central position in sphingolipid metabolism. As an acceptor of carbohydrates, phosphorylcholine and phosphate, it serves as precursor of the various complex sphingolipids. Alternatively, the enzymatic breakdown of these sphingolipids releases ceramide which may consequently be hydrolyzed into fatty acid and sphingosine; the latter exerting effector functions on its own as well as acting as a precursor of sphingosine phosphate, another signal mediator and regulator of various cell functions. Ceramides are generated by hydrolysis of sphingomyelin in response to different stimuli, such as tumor necrosis factor, Fas/CD95 ligand, interleukin-1, and vitamin D3. A controlled level of ceramide, therefore, reflects an intricate balance between the catabolic and anabolic pathways of ceramide.

One of the most studied effects of ceramides is the ability to induce cell death. Endogenous ceramide levels are elevated in tumors after irradiation or therapy with anticancer drugs (Bose et al., *Cell,* 82:405-414, 1995; Selzner et al., *Cancer Res.* 61:1233-1240, 2001). Exogenous ceramides emerged as a promising new approach for cancer therapy. It has been shown that exogenous ceramide can induce cell death in a variety of cancer cell types with normal cells being less susceptible (von Haefen et al., *Oncogene* 21:4009-4019, 2002; Jones et al., *Hepatology,* 30:215-222, 1999).

Most studies of the effects of ceramides on cancer cells are restricted to the use of short-chain ceramides ($C_2$-$C_8$) because naturally occurring long-chain ceramides ($C_{16}$-$C_{24}$) are unable to penetrate cell membranes. Mitochondria have been identified as a target of ceramides. However, studies on the direct effect of ceramides on mitochondria are hampered by the fact that the ceramides are readily distributed to various organelles such as Golgi apparatus and endoplasmic reticulum (Radin, *Bioorg Med Chem,* 11:2123-2142, 2003; Ardail et al., *Biochim Biophys Acta,* 1583:305-310, 2002). Therefore, there is great interest in ceramides that can enter a cancer cell and target itself to the mitochondria where it induces cell death. The present invention provides a class of ceramide conjugates which have these desirable pharmacological properties making these conjugates suitable for development as therapeutic agents or drug delivery vehicles.

Citation of references hereinabove shall not be construed as an admission that such references are prior art to the present invention.

3. SUMMARY OF THE INVENTION

The present invention provides ceramide conjugates with pyridinium salts and their analogs, collectively herein referred to as CCPS analogs. The compounds of the invention are designed according to the concept of incorporating pyridinium salt moieties into the structure of ceramides to form a structurally distinct class of cationic lipids. The invention also provides methods for making CCPS analogs, and methods for using these compounds for the prevention and treatment of diseases associated with cell overproliferation and sphingolipid signal transduction.

In one embodiment, the invention relates to compounds of formula I:

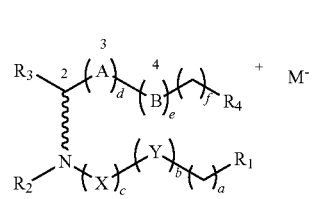

wherein:

$R_1$ is

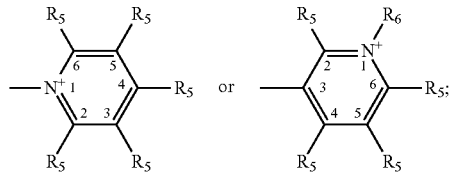

$R_2$ is —H or —($C_1$-$C_6$)alkyl;

$R_3$ is —$CH_3$, $CH_2R_7$, —$COOR_{12}$, —CHO—$CH_2OR_{12}$, —$CH_2SH$, —$CH_2NH_2$, —$CH_2N_3$, —$CH_2NH(OH)$, —CH=N(OH), —CH=N($NH_2$), —$CH_2F$, —$CH_2Cl$, —$CH_2Br$, or —$CH_2OP(O)_2OR_4$, $R_4$ is —H; —$CH_3$; —$(CH_2)_2N((CH_3)_3$— or -phenyl, optionally substituted with one or more $R_8$;

each $R_5$ is independently —H; —($C_1$-$C_{10}$)alkyl, —($C_2$-$C_{10}$)alkenyl, or —($C_2$-$C_{10}$) alkynyl, each of which is unsubstituted or substituted with one or more $R_9$; -halo; —OH; —$NO_2$; —C(O)OH; —C(O)$NH_2$; —C(O)$NHR_7$; —C(O)N—$CH_2R_7$; —$OR_{10}$; —C(O)$R_{10}$; —C(O)$CF_3$; —C(O)$NR_{10}$; —C(OH)$R_{10}$; —OC(O)$R_{10}$; —C(O)$OR_{10}$; or —N($R_{10}$)$_2$;

$R_6$ is —H, —($C_1$-$C_{16}$)alkyl, —($C_2$-$C_{16}$)alkenyl, —($C_2$-$C_{16}$)alkynyl, each of which, other than —H, is unsubstituted or substituted with one or more $R_9$;

$R_7$ is -five-membered monocyclic N-, O- or S-based heterocycle; or a -six-membered monocyclic N-, O- or S-based heterocycle; each of which can be unsubstituted or substituted with one or more $R_9$;

$R_8$ is —($C_1$-$C_6$)alkyl; —C(O)$R_{10}$; -halo, —$NO_2$, —OH; —$NH_2$; —NH($R_{10}$), or —N($R_{10}$)$_2$;

$R_9$ is -halo; —OH; —C(O)($R_{10}$); —$CF_3$; —$NH_2$; —NH($R_{10}$); or —N($R_{10}$)$_2$; or -phenyl, unsubstituted or substituted with one or more —$R_8$;

$R_{10}$ is —($C_1$-$C_6$)alkyl;

$R_{11}$ is H, $R_{12}$, $COR_{12}$ $R_{12}$ is H, —($C_1$-$C_{20}$)alkyl, —($C_2$-$C_{20}$)alkenyl, glucose or galactose a is an integer from 0 to 26;
b is 0 or 1;
c is 0 or 1;
d is 0 or 1;
e is 0 or 1;
f is an integer from 0 to 20;
X is —C(O)—, —C(S)—, —CH($R_{10}$)—, —C(=NH)—, or —N(H)—;
Y is —N(H)—, —O—, —C(O)—, —CH($R_{10}$)—, —$CH_2$C(O)—, or —$CH_2$CH($R_{10}$)—;
A is —$CH_2$—, —CH(OH)—, —CH($R_7$)—, —C(O)—, —C(=NOH)—, or —C(=N—$NH_2$)—;
B is —$CH_2CH_2$—, —CH(OH)$CH_2$—, -trans-CH=CH—, phenyl, optionally substituted with one or more $R_8$ and M⁻ is a counter anion.

In another embodiment, the invention relates to compounds of formula II:

II wherein:

$R_1$ is $R_2$ is —H or —($C_1$-$C_6$)alkyl;

$R_3$ is —$CH_3$, —$CH_2R_7$, —$COOR_{12}$, CHO, $CH_2OR_{12}$, —$CH_2SH$, —$CH_2NH_2$, —$CH_2N_3$, —$CH_2$NH(OH), —CH=N(OH), —CH=N($NH_2$), —$CH_2OCH_3$, —$CH_2F$, —$CH_2Cl$, —$CH_2Br$, —$CH_2OC(O)R_7$, or —$CH_2OP(O)_2OR_4$;

$R_4$ is —H; —$CH_3$, —($CH_2$)$_2$N(($CH_3$)$_3$—; or -phenyl, optionally substituted with one or more $R_8$;

each $R_5$ is independently —H; —($C_1$-$C_{10}$)alkyl, —($C_2$-$C_{10}$)alkenyl, or —($C_2$-$C_{10}$)alkynyl, each of which is unsubstituted or substituted with one or more $R_9$; -halo; —OH; —$NO_2$; —C(O)OH; —C(O)$NH_2$; —C(O)$NHR_7$; —C(O)NH—OH; —$CH_2R_7$; —$OR_{10}$; —C(O)$R_{10}$; —C(O)$CF_3$; —C(O)$NR_{10}$; —C(OH)$R_{10}$; —OC(O)$R_{10}$; —C(O)$OR_{10}$; or —N($R_{10}$)$_2$;

$R_6$ is —H, —($C_1$-$C_{16}$)alkyl, —($C_2$-$C_{16}$)alkenyl, —($C_2$-$C_{16}$)alkynyl, each of which, other than —H, is unsubstituted or substituted with one or more $R_9$;

$R_7$ is -five-membered monocyclic N-, O- or S-based heterocycle; or a -six-membered monocyclic N-, O- or S-based heterocycle; each of which can be unsubstituted or substituted with one or more $R_9$;

$R_8$ is —($C_1$-$C_6$)alkyl; —C(O)$R_{10}$; -halo, —$NO_2$, —OH; —$NH_2$; —NH($R_{10}$), or —N($R_{10}$)$_2$;

$R_9$ is -halo; —OH; —C(O)($R_{10}$); —CF3; —$NH_2$; —NH($R_{10}$); or —N($R_{10}$)$_2$;

or -phenyl, unsubstituted or substituted with one or more —R8;

$R_{10}$ is —($C_1$-$C_6$)alkyl;

$R_{11}$ is H, $R_{12}$, $COR_{12}$;

$R_{12}$ is H, —($C_1$-$C_{20}$)alkyl, —($C_2$-$C_{20}$)alkenyl, glucose or galactose;

a is an integer from 0 to 26;
b is 0 or 1;
c is 0 or 1;
d is 0 or 1;
e is 0 or 1;
f is an integer from 0 to 20;
X is —C(O)—, —C(S)—, —CH($R_{10}$)—, —C(=NH)—, or —N(H)—;
Y is —N(H)—, —O—, —C(O)—, —CH($R_{10}$)—, —$CH_2$C(O)—, or —$CH_2$CH($R_{10}$)—;

and

M⁻ is a counter anion.

The preferred compounds of the invention display desirable pharmacological properties, such as but not limited to improved solubility, cellular uptake, membrane permeability, and intracellular targeting. The invention further relates to methods for making compounds of formula I and formula II.

In yet another embodiment, the invention provides the use of compounds of formula I or formula II to treat diseases associated with cell overproliferation or sphingolipid signal transduction. In a specific embodiment, the compounds of the invention are used to induce cell death, preferably cancer cell death. The present invention encompasses methods, pharmaceutical compositions, and dosage forms for the treatment or prevention of various cancers and hyperproliferative diseases in animals, including humans. The methods of the invention comprise administering to a patient in need of such treatment or prevention a therapeutically or prophylactically effective amount of a compound of the invention, or a pharmaceutically acceptable salt, or solvate thereof. The use of CCPS analogs to treat breast cancer, colon cancer, and head and neck squamous cell carcinoma are particularly preferred as demonstrated in the Examples sections.

Pharmaceutical compositions of the invention comprise a therapeutically or prophylactically effective amount of a compound of formula I or formula II. Preferred compounds are those that are active in inducing cell death, decreasing cell proliferation and/or viability. Pharmaceutical compositions of the invention can further comprise other anticancer drugs or therapeutic substances.

In yet another embodiment, the invention provides the use of compounds of formula I or formula II to deliver a cargo moiety to a preferred intracellular location, such as but not limited to the mitochondria.

The present invention can be understood more fully by reference to the following detailed description and illustrative examples, which exemplify non-limiting embodiments of the invention.

4. BRIEF DESCRIPTION OF THE DRAWINGS

Figure 4A:
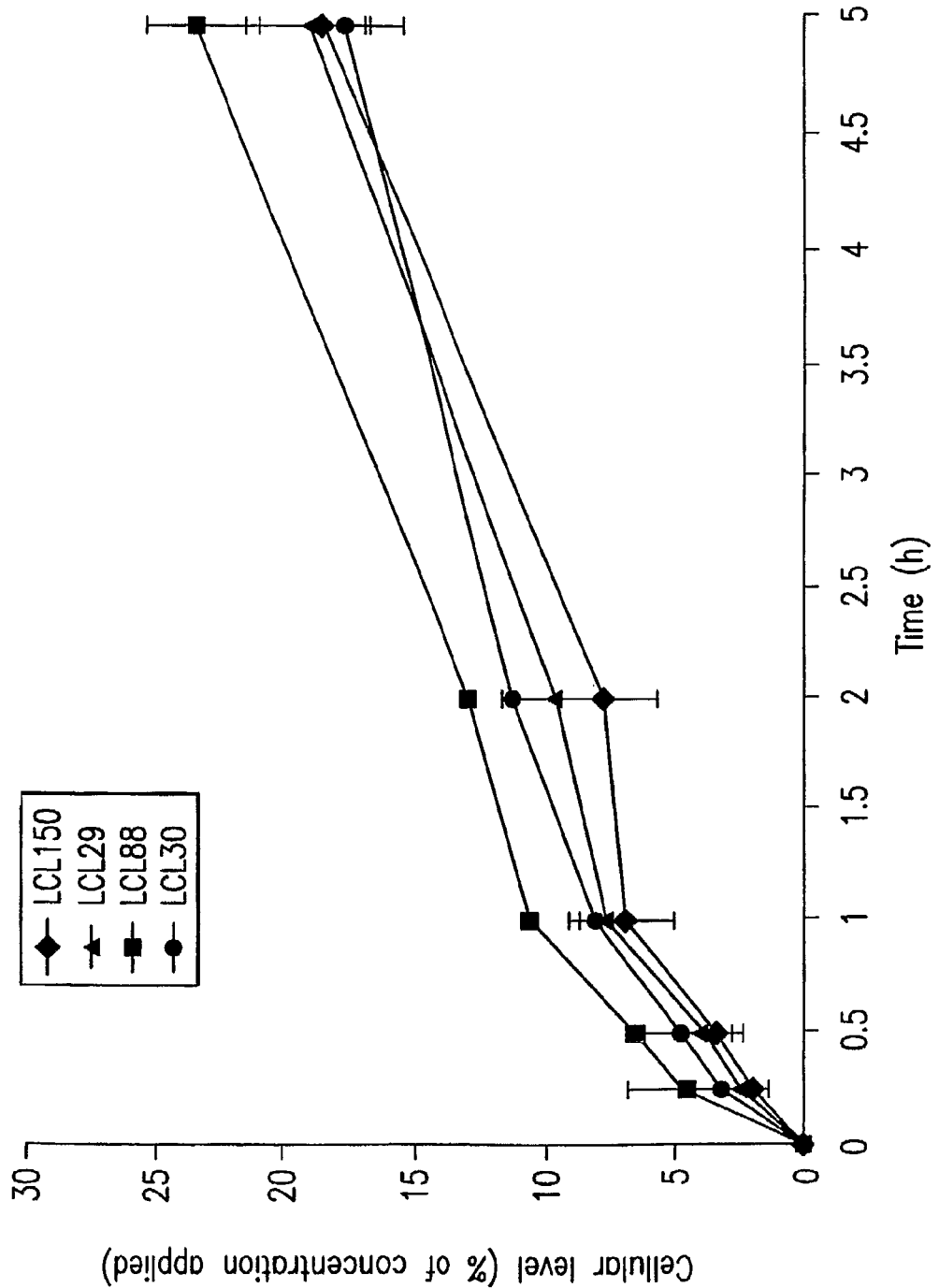
Figure 4B:
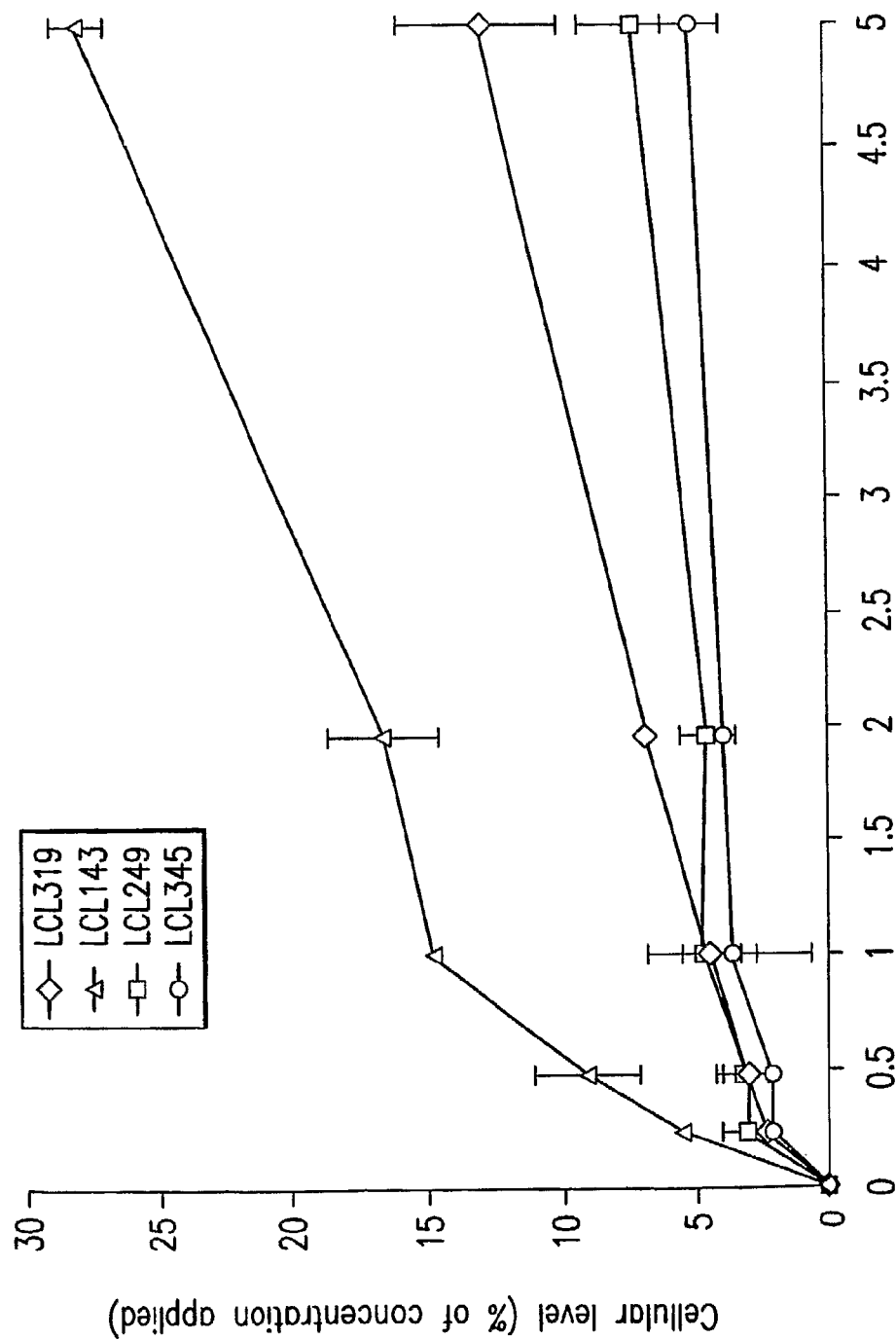
Figure 4C:
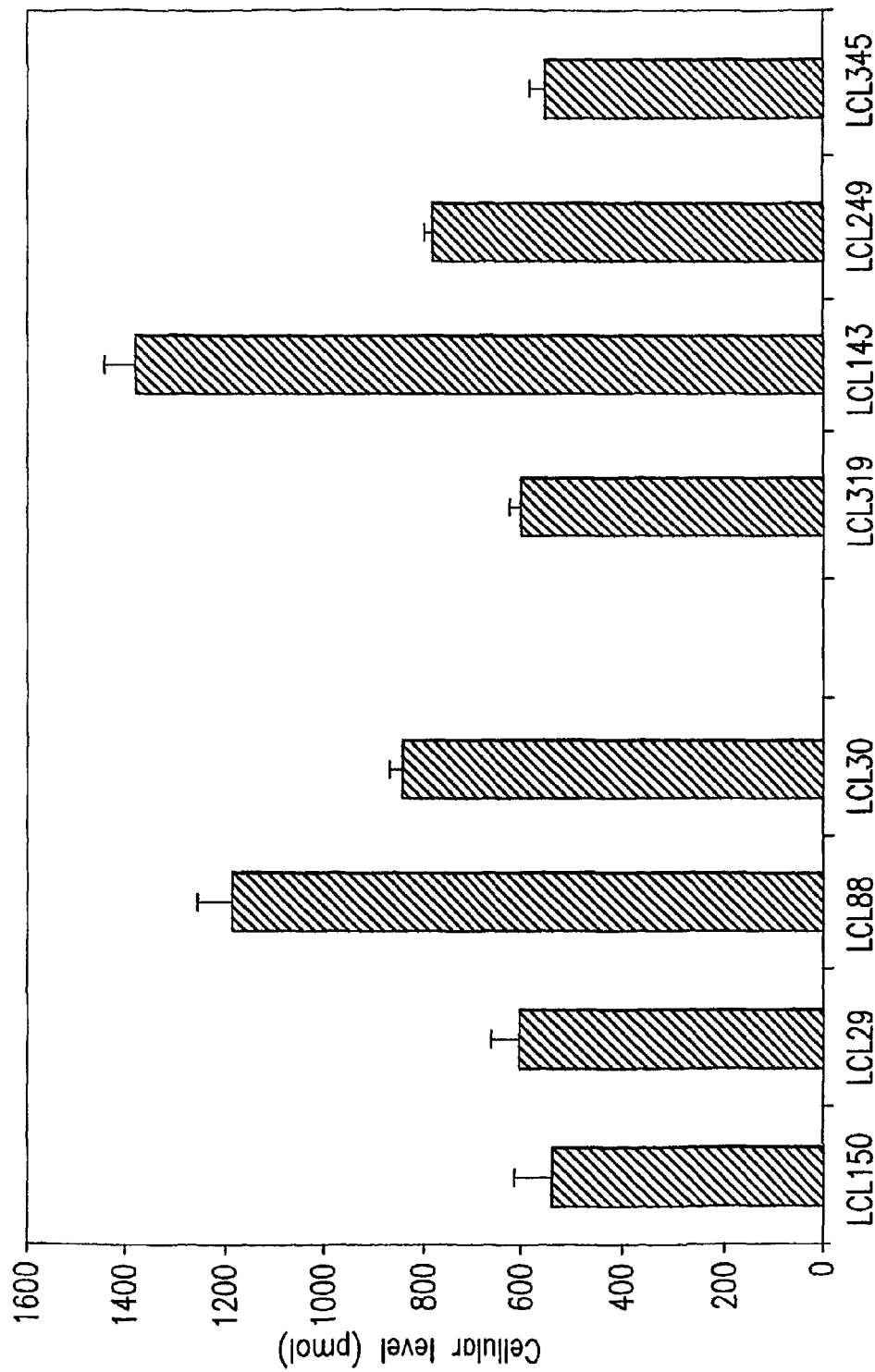

FIGS. 4A-4C show the cellular levels of CCPS analogs. MCF 7 cells were treated with 5 µM concentration of CCPS analogs over the time and cellular level of the nonmetabolized CCPSs was measured by MS methodology as shown under Experimental. Results are expressed as % of concentration applied. These assays were performed using duplicate samples in two independent experiments; FIG. 4A shows cellular levels of CCPS analogs: LCL150, 29, 88 and 30; FIG. 4B shows cellular levels of dihydroCCPS analogs: LCL319, 134, 249 and 345. FIG. 4C shows cellular levels of LCL150, LCL 29, LCL 88, LCL 30, LCL 319, LCL 143, LCL 249, LCL 345.

Figure 5A:
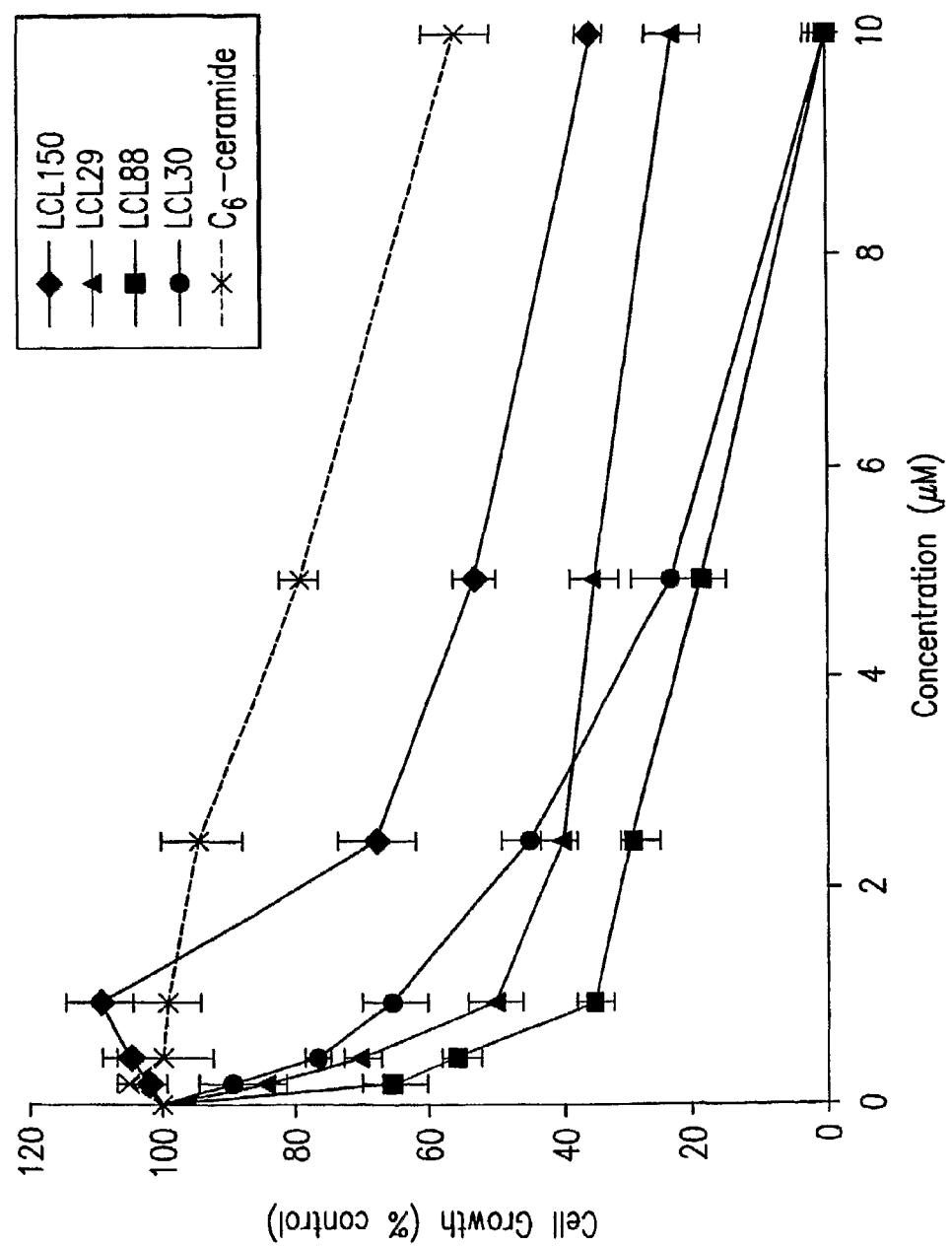
Figure 5B:
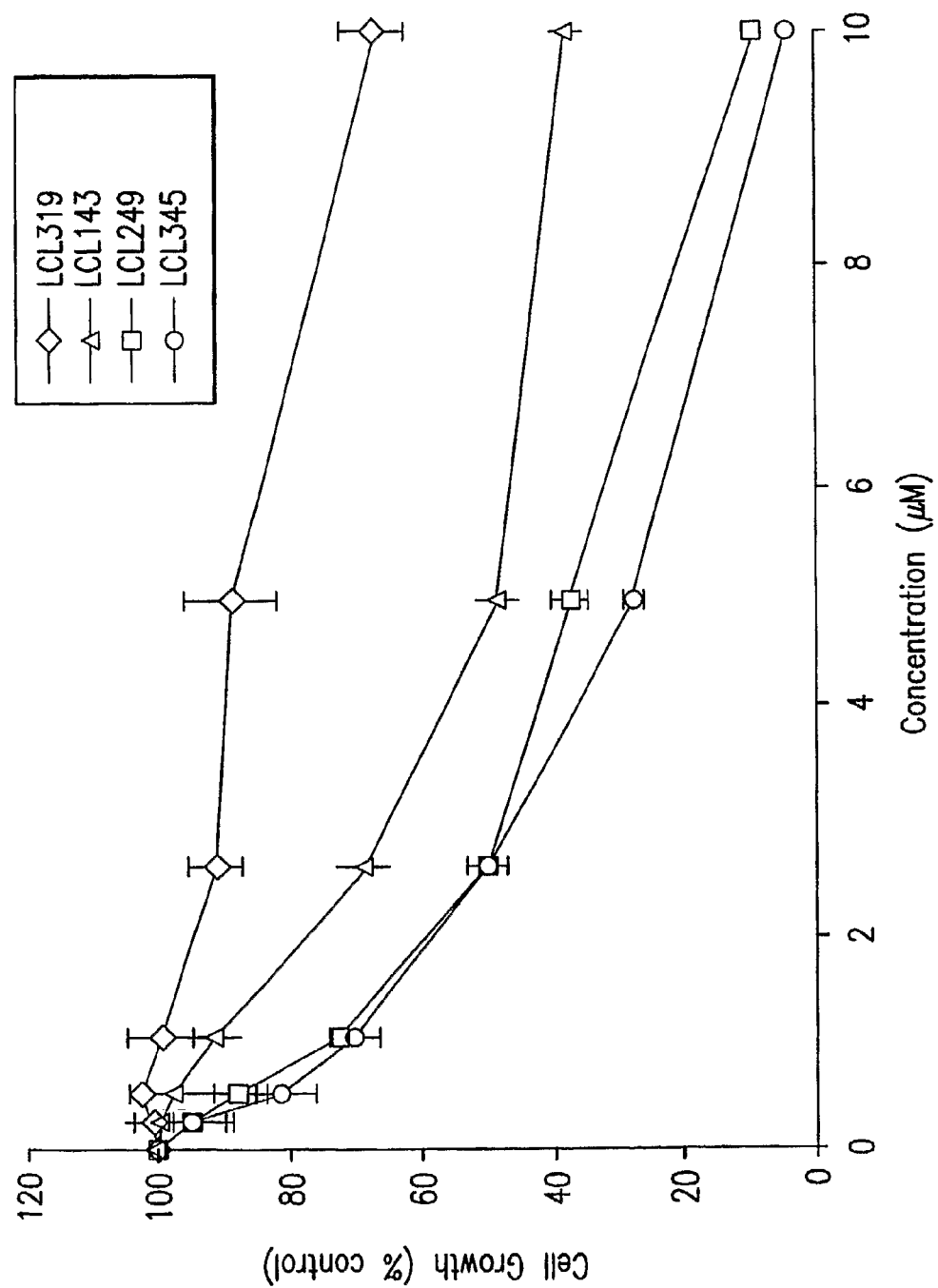
Figure 5C:
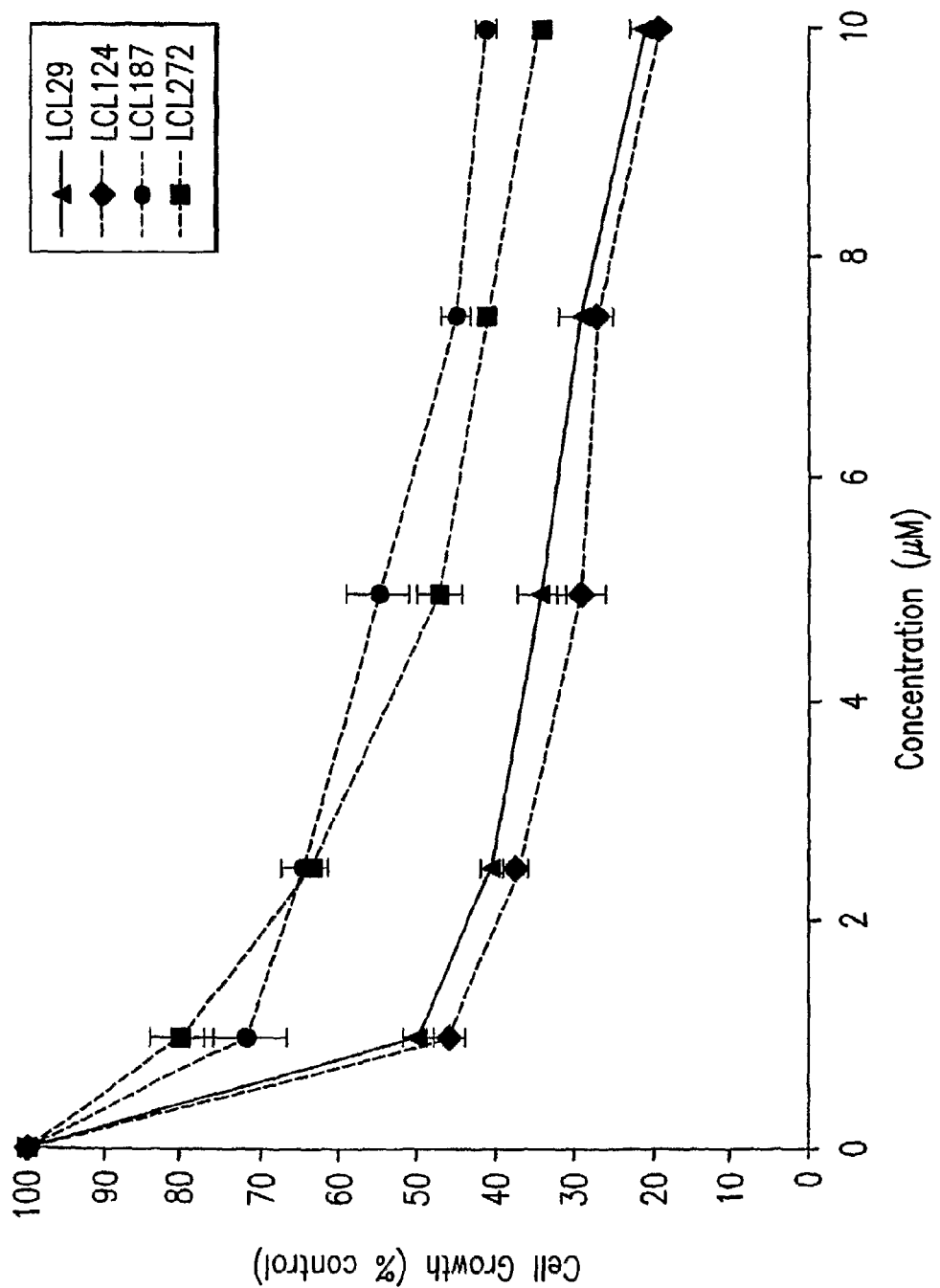
Figure 5D:
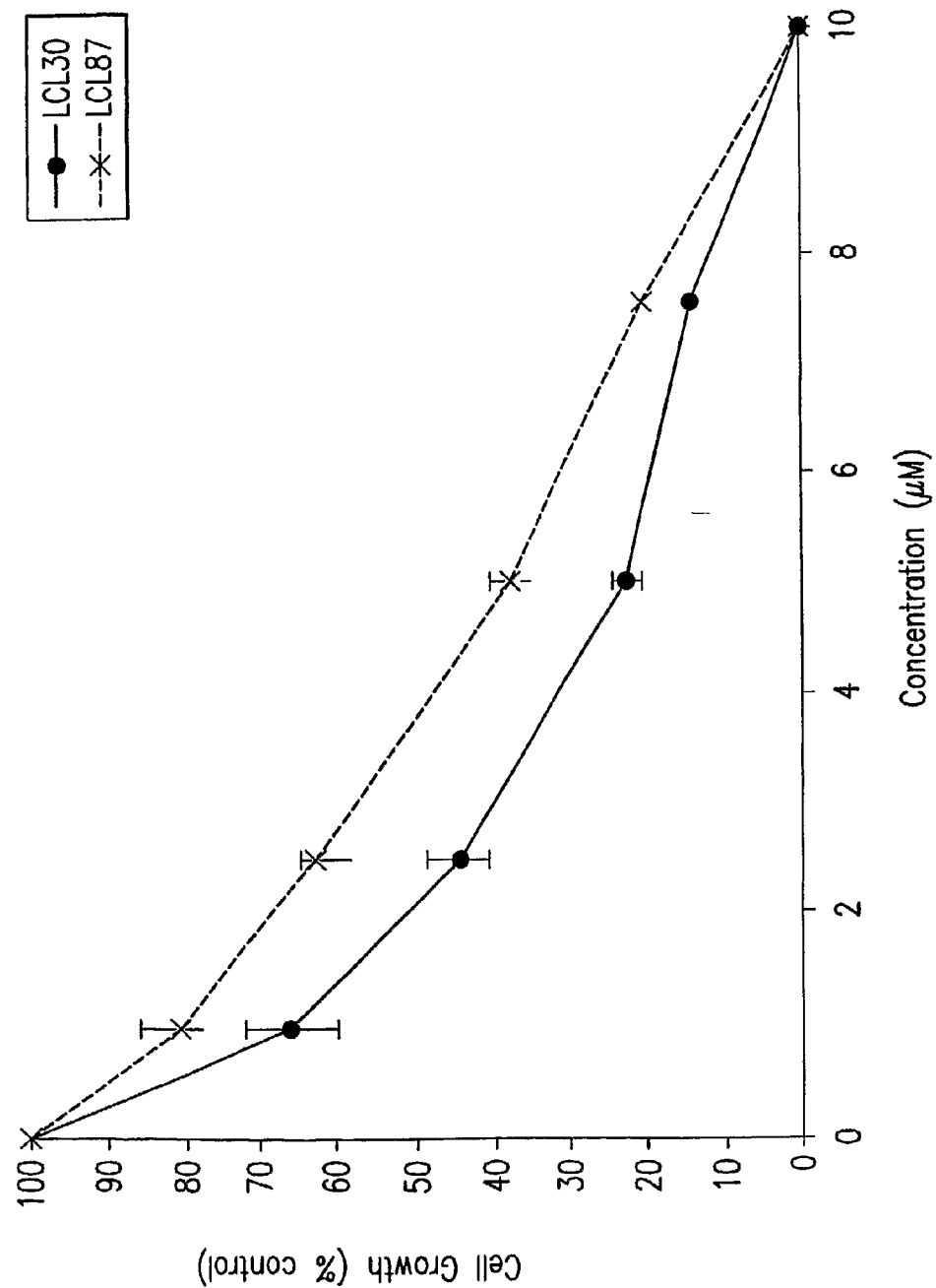
Figure 5E:
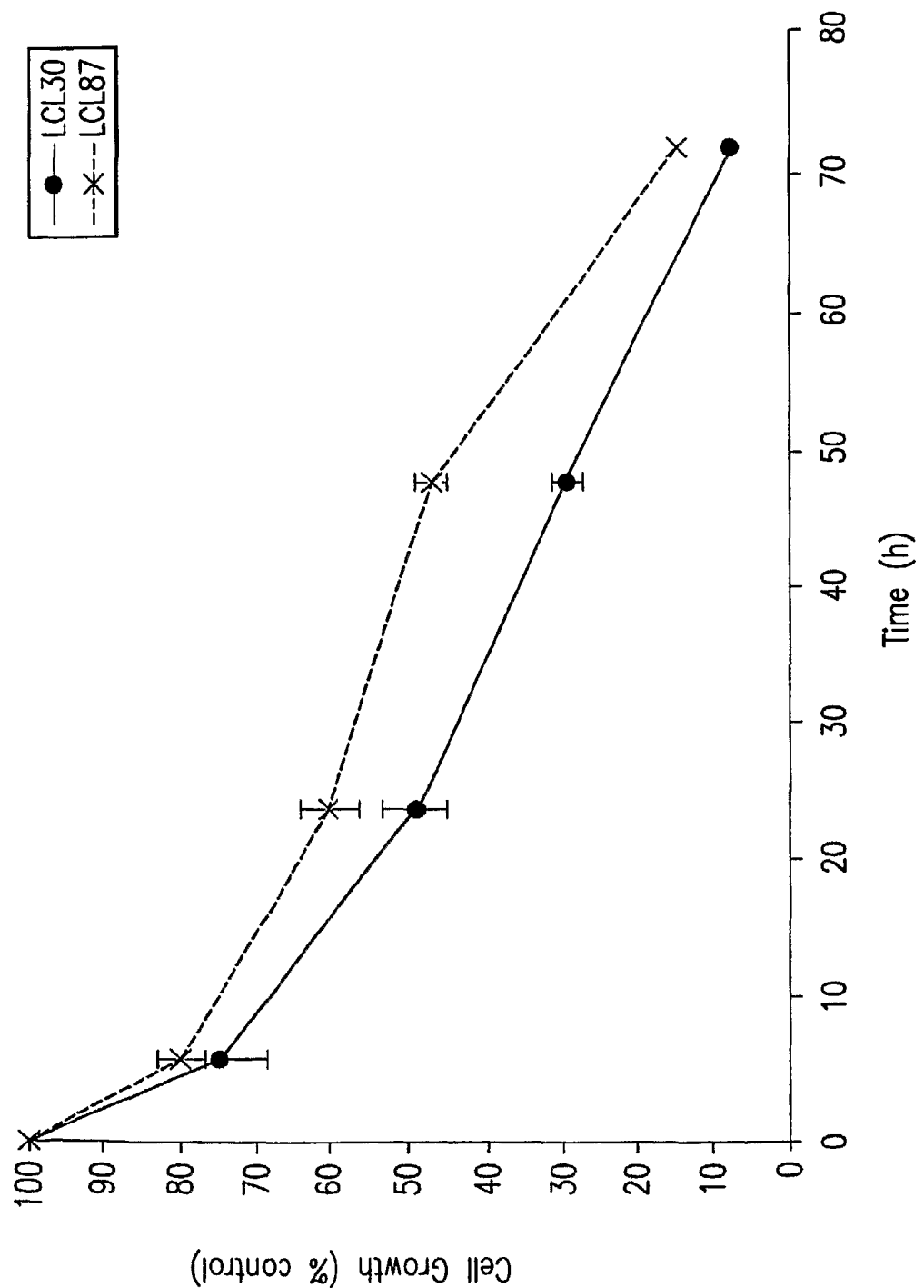
Figure 5F:
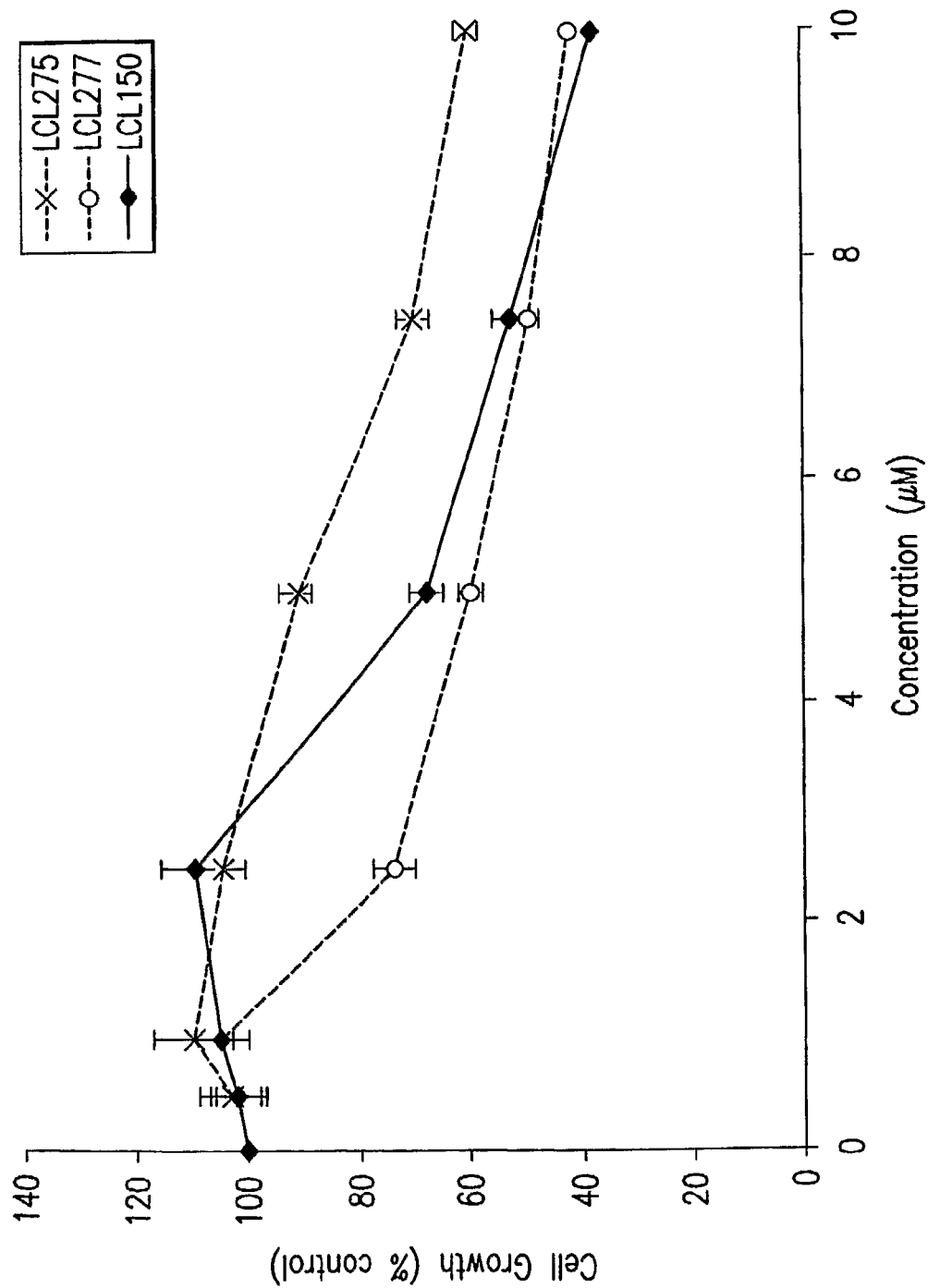

FIGS. 5A-5F show the dose dependent effects of CCPS analogs on survival of MCF7 breast carcinoma cells in comparison to the activity of D-e-$C_6$-ceramide, which is commonly used as a model of ceramide action. Cell proliferation and cell viability were determined by Trypan blue exclusion assay. These assays were performed using duplicate samples in two or three independent experiments. FIG. 5A shows the concentration dependent inhibitory effect of D-e-Cn-CCPS homologs and D-e-$C_6$-ceramide at 48 h treatment (Class A). FIG. 5B shows the concentration dependent inhibitory effect of D-e-Cn-dhCCPS homologs at 48 h treatment (Class A). FIG. 5C shows the concentration dependent inhibitory effect of $C_6$-CCPS stereoisomers at 48 h. FIG. 5D shows the concentration dependent inhibitory effect of LCL 30 and LCL87 vs. change in concentration. FIG. 5E shows the concentration dependent inhibitory effect of LCL 30 and LCL 87 over time. FIG. 5F shows the concentration dependent inhibitory effect of LCL275 and 277 (Class B) in comparison to LCL150.

Figure 6A:
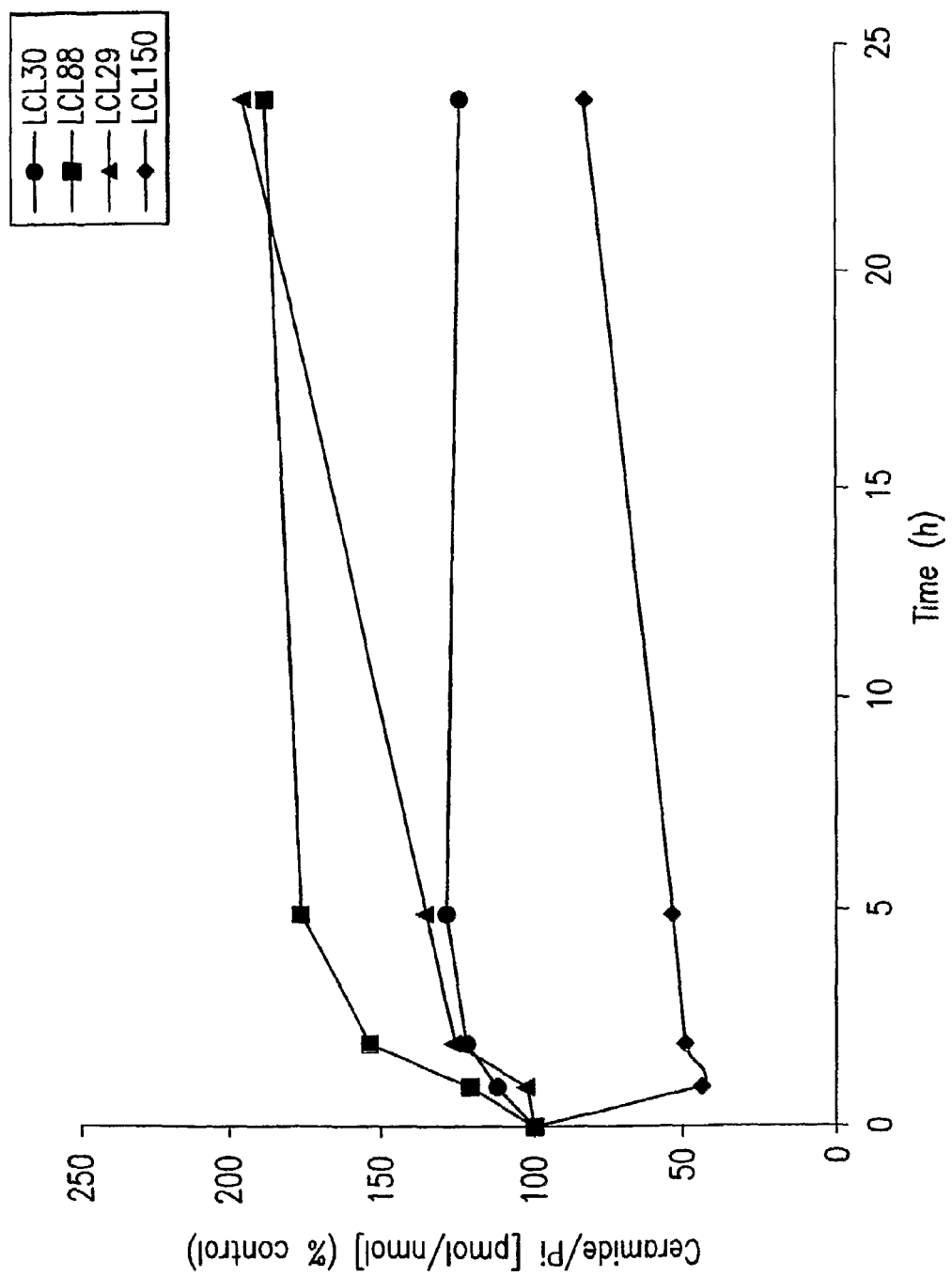
Figure 6B:
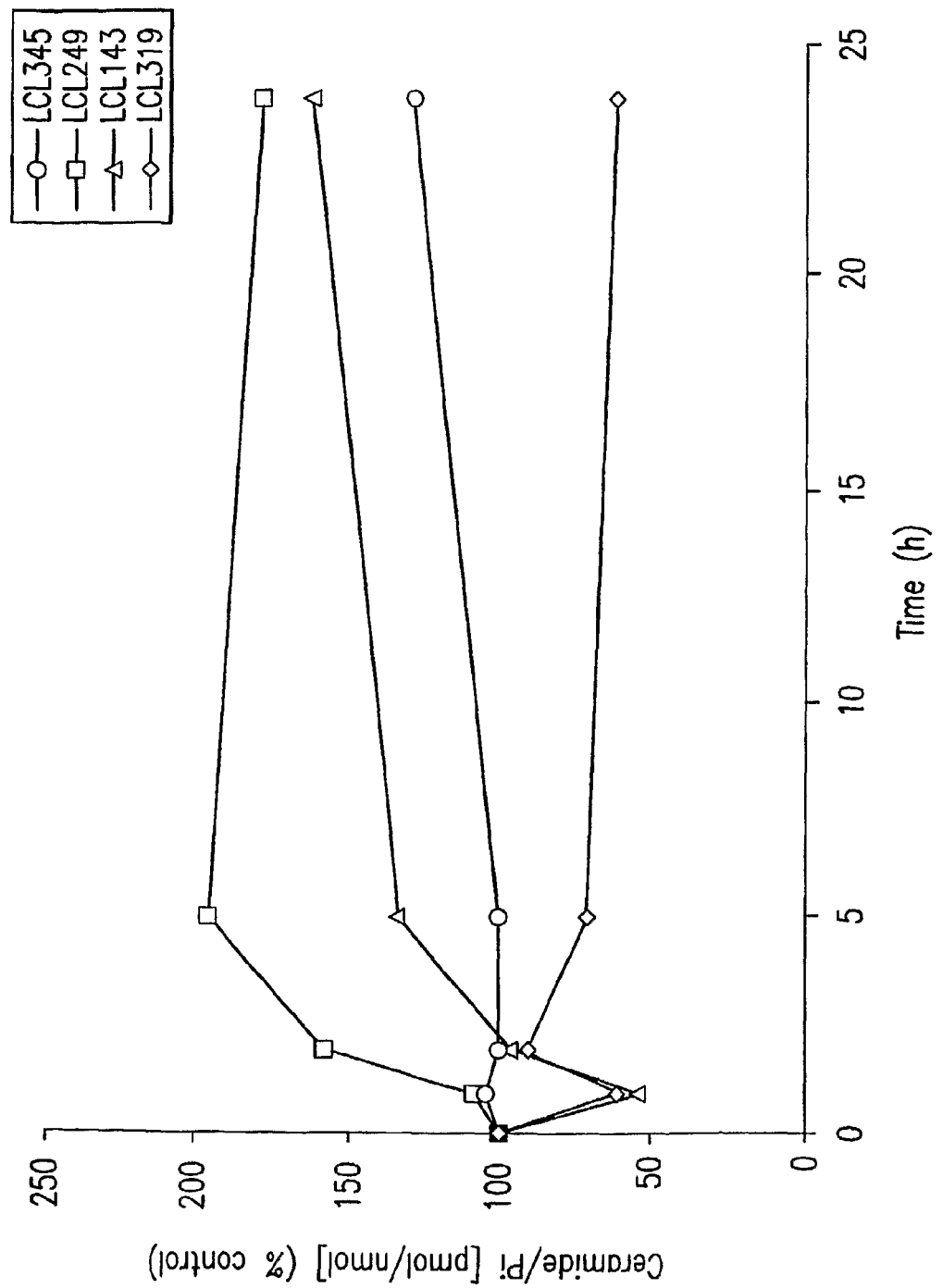
Figure 6C:
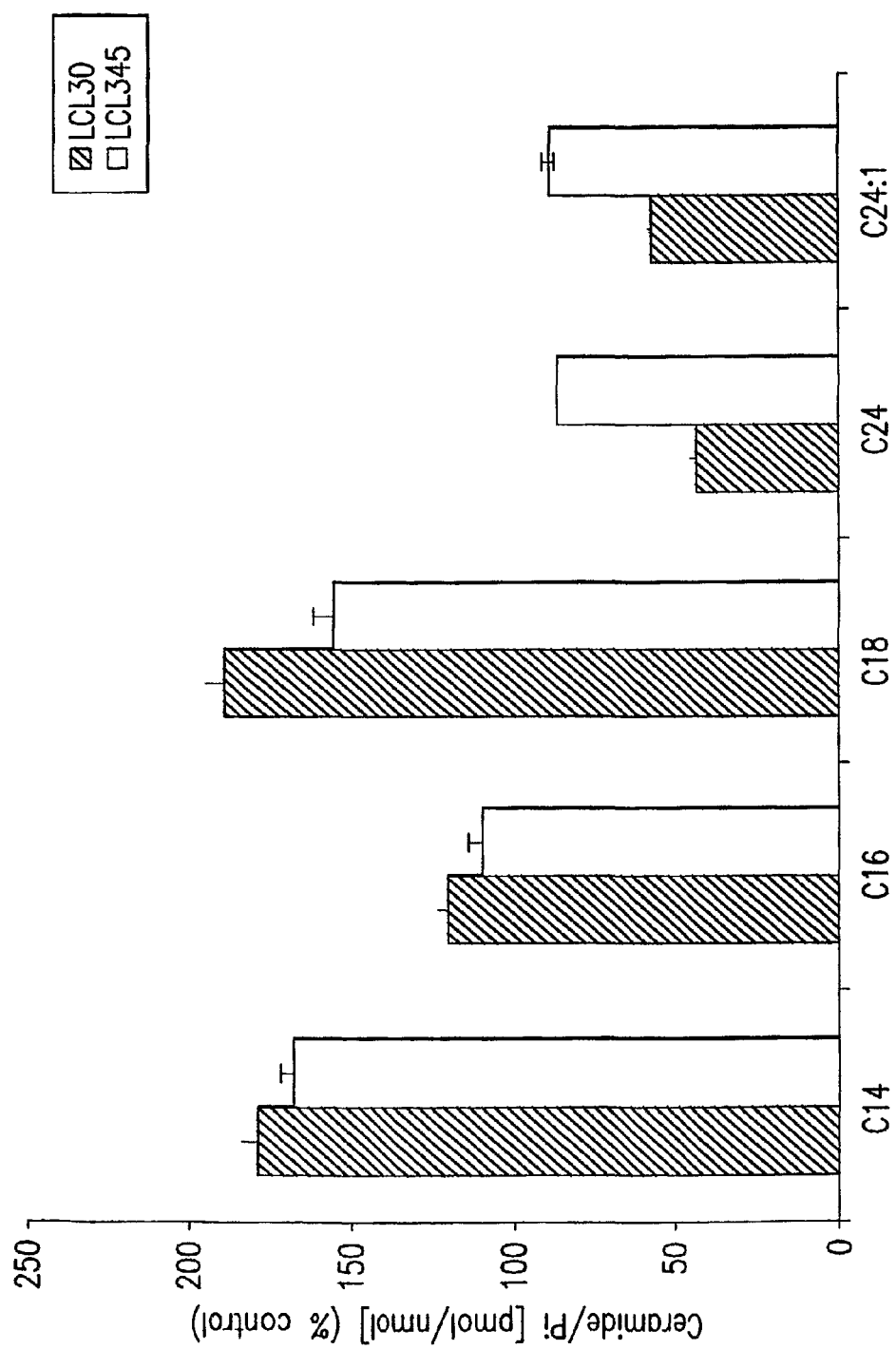

FIGS. 6A-C show the regulatory effect of D-e-Cn-CCPS homologs on endogenous ceramide. To examine the effects of newly synthesized CCPS analogs on the level and composition of the endogenous ceramide (ECer) we have used the LC/MS approach as described in the Experimental section. Data are expressed as changes in the total ceramide level (pmol) or individual ceramide components (pmol) normalized to the phospholipid level, Pi (nmol) present in the Bligh & Dyer lipid extract and shown as changes to the control cells: Ceramide/Pi[pmol/nmol] (% Control). FIG. 6A shows the time dependent effect of 5 µM $C_2$-$C_{16}$ CCPS homologs on the total endogenous ceramide Cer. FIG. 6B shows the time dependent effect of 5 µM C2-C16 dhCCPS homologs on the total endogenous ceramide. FIG. 6C shows the regulatory effect of 5 µMLCL30 and 5 µM LCL345 (dihydro analog of LCL30) on endogenous ceramide species. Results shown for 1 h treatment.

Figure 7A:
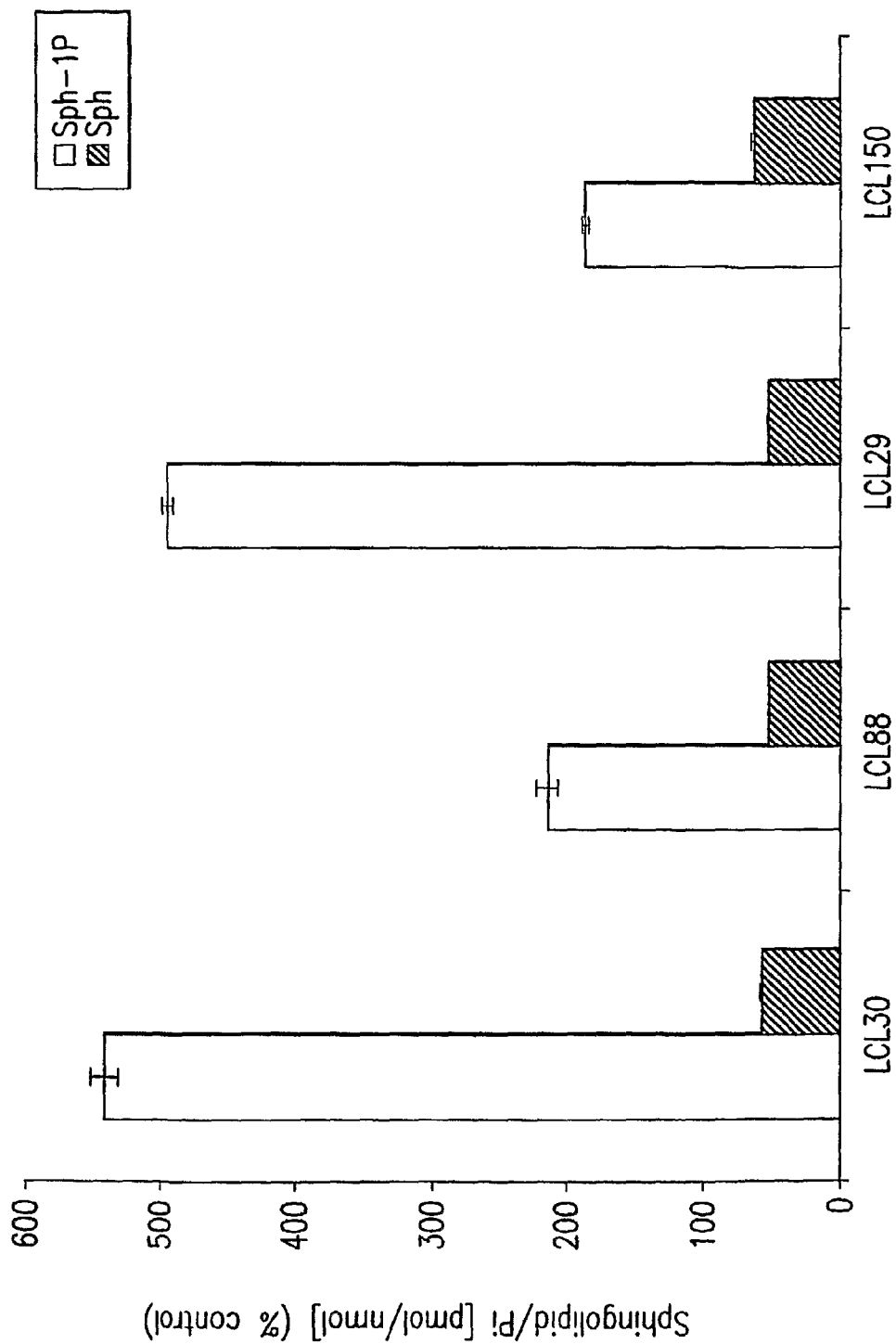
Figure 7B:
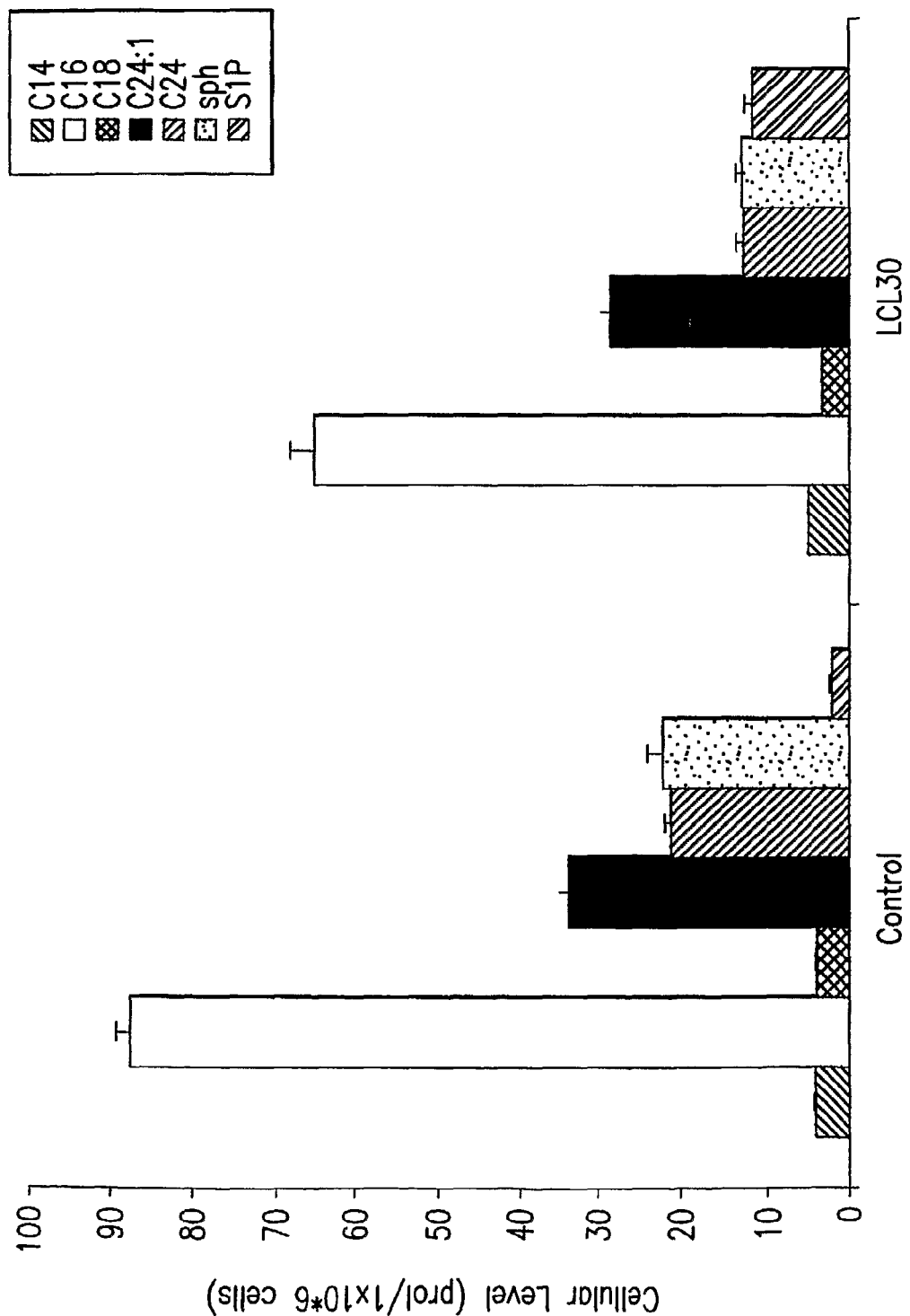

FIGS. 7A-B show the early effect (15 min) of CCPS analogs on endogenous S1P and Sph. Simultaneous analysis of sphingolipids was performed by LC-MS analysis as shown under Experimental. FIG. 7A. Effect of $C_2$-$C_{16}$-CCPS on end S1P and Sph. Results are shown as changes to the control cells and expressed as Sphingolipids/Pi[pmol/nmol] (% Control). FIG. 7B. Level of endogenous Sph, Sph-1P and ceramides after treatment with 5 µMLCL30 for 15 min in comparison to the Control. Data are shown as the absolute level of sphingolipids (pmol) per $1 \times 10^6$ MCF7 cells.

Figure 8A:
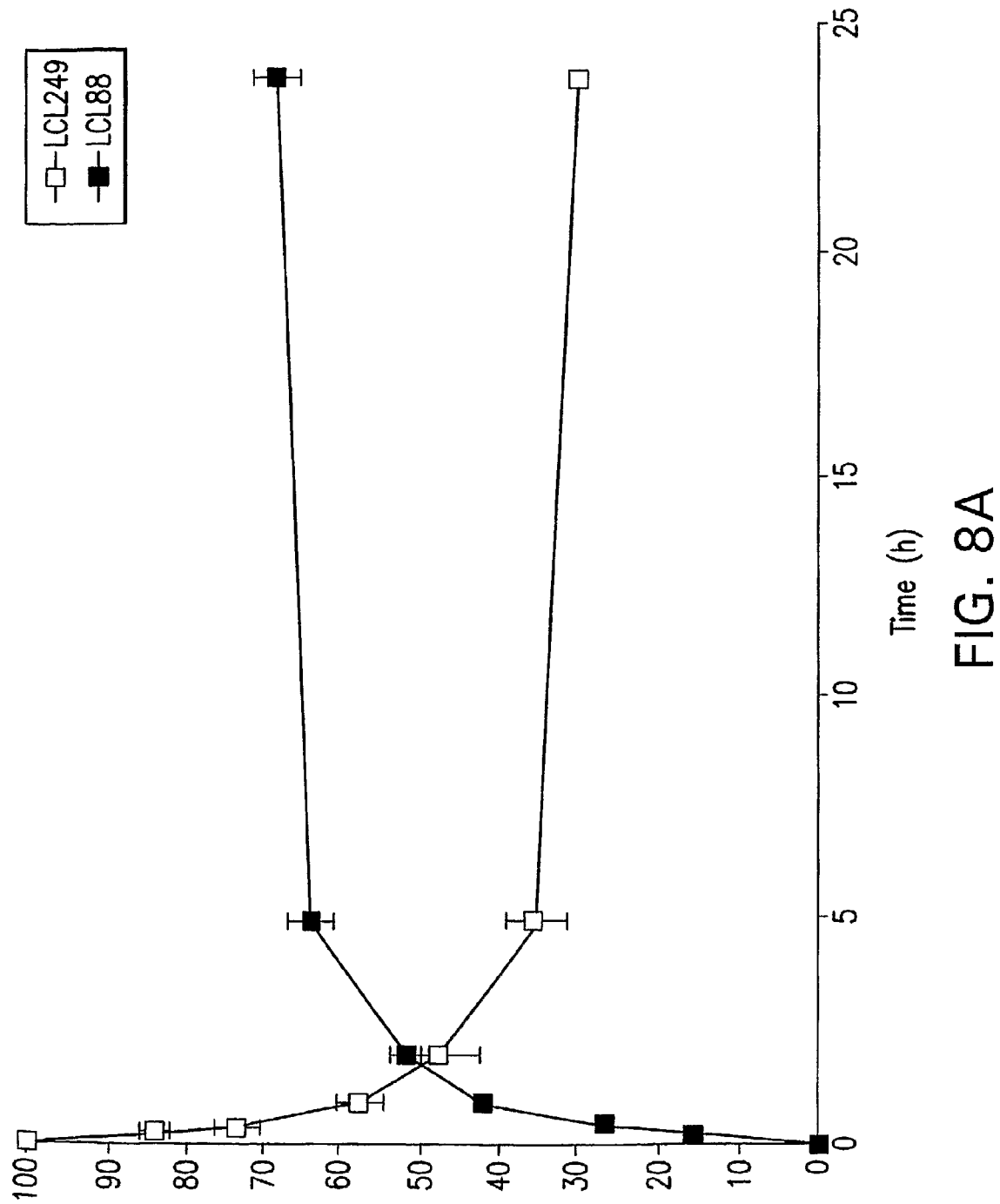
Figure 8B:
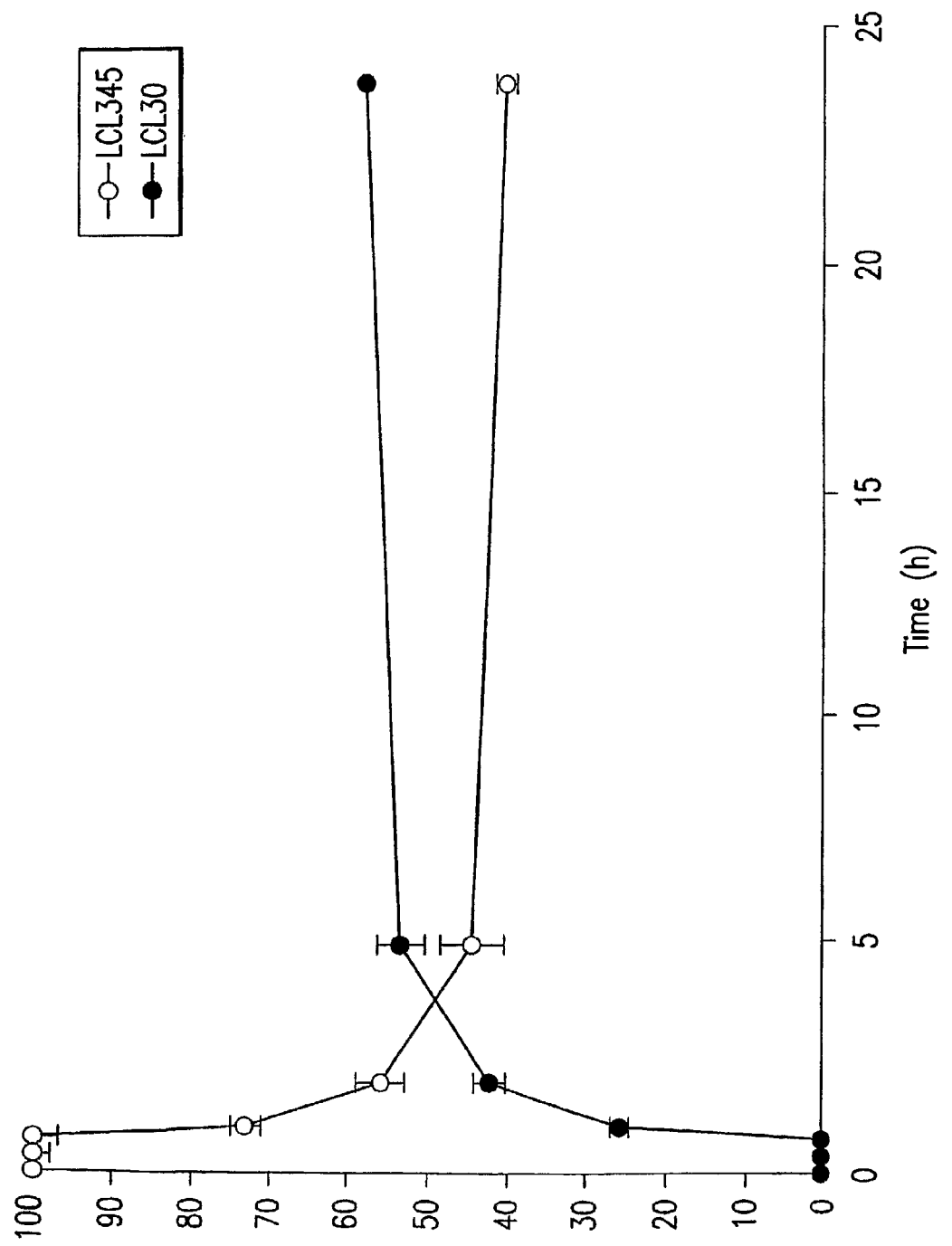

FIGS. 8A and 8B show that dh-CCPS analogs serve as substrates for dihydroceramide 4,5-desaturase in MCF7 cells to generate the corresponding CCPS analogs. Absolute levels (pmol) of dhCCPS and CCPS analogs was established by MS approach as shown in the Examples (see Section 6). Data are expressed as changes of particular dhCCPS and CCPS to the total level of dhCCPS+CCPS (100%). FIG. 8A shows the time dependent formation of $C_{12}$-CCPS (LCL88) from C12-dhCCPS (LCL249). FIG. 8B shows that time dependent formation of C16-CCPS (LCL30) from $C_{16}$-dhCCPS (LCL345).

Figure 9:
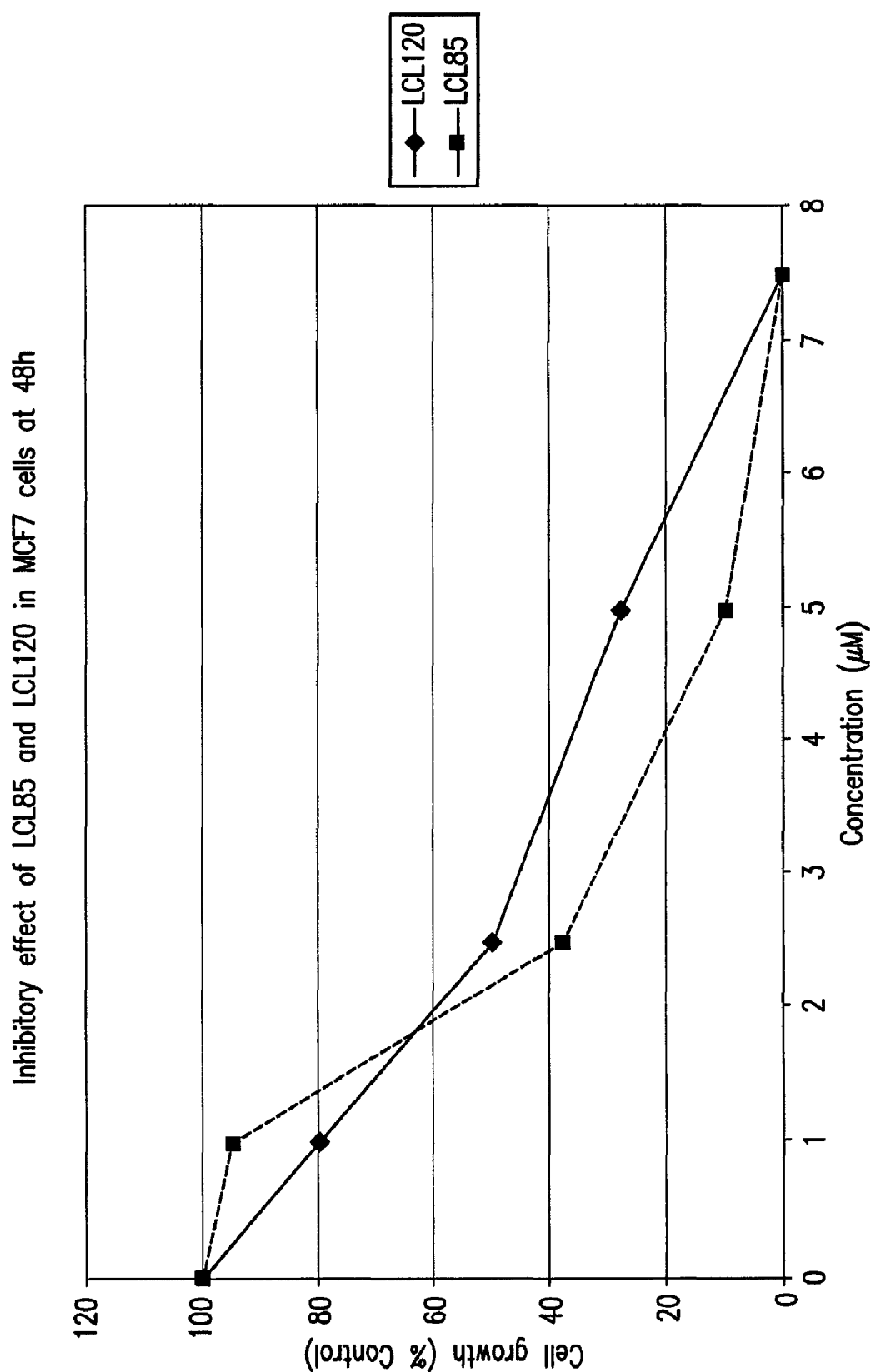

FIG. 9 shows inhibitory effect of LCL85 and LCL120 in MCF 7 cells at 48 h.

Figure 10:
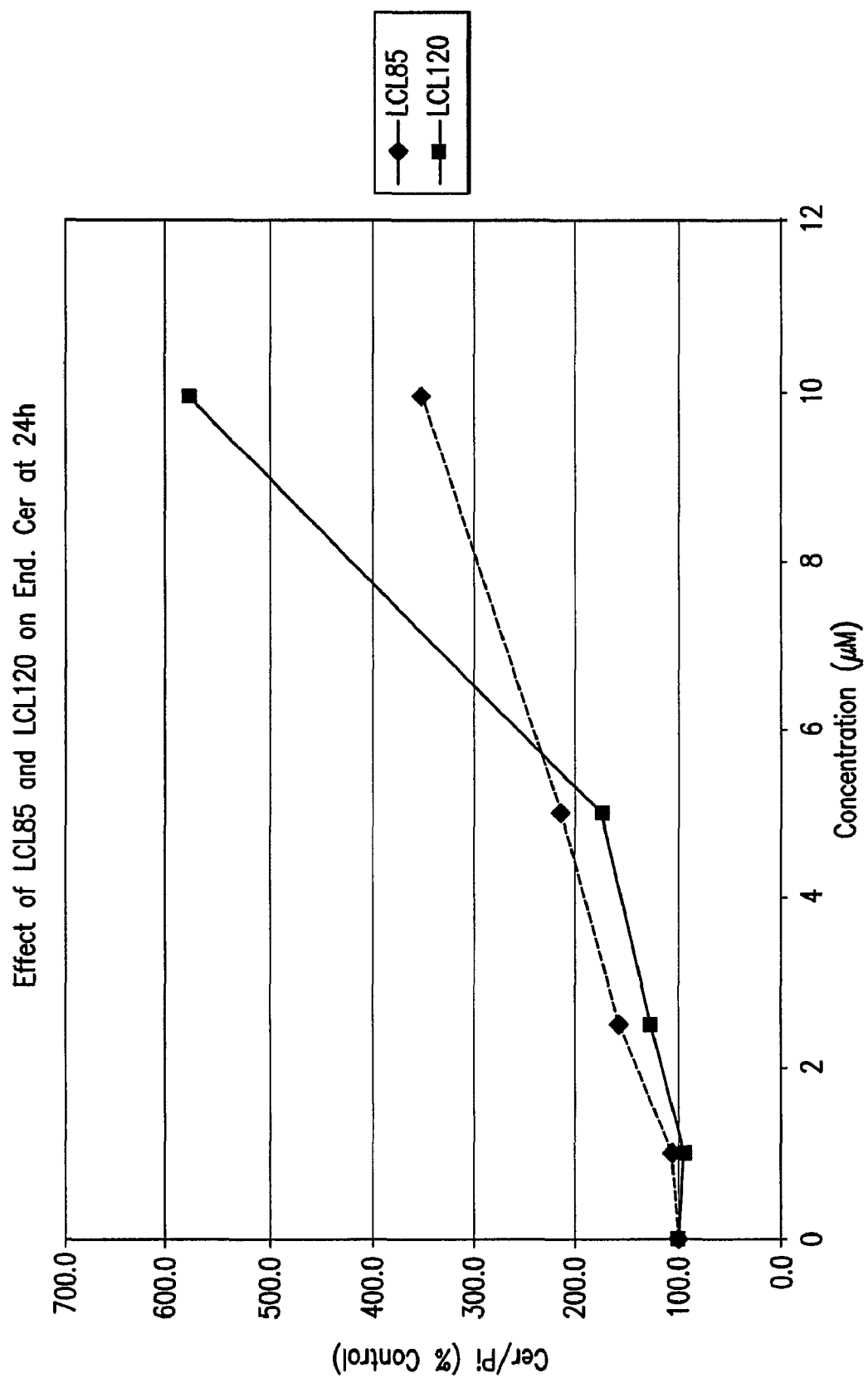

FIG. 10 shows the effect of LCL 85 and LCL120 on endogenous ceramide at 24 h.

Figure 11:
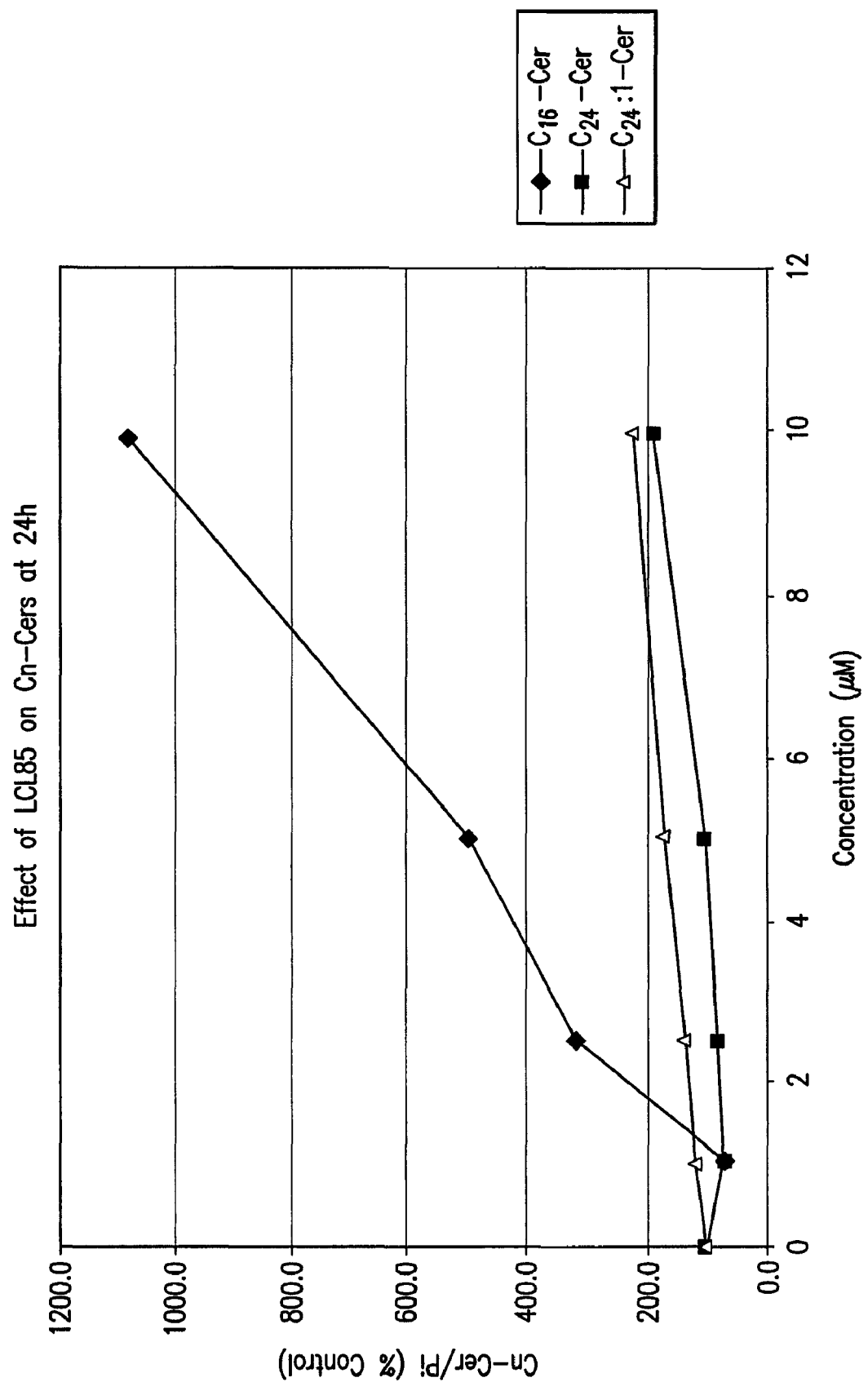

FIG. 11 shows the effect of LCL85 on endogenous $C_n$-Cers compositions at 24 h.

Figure 12A:
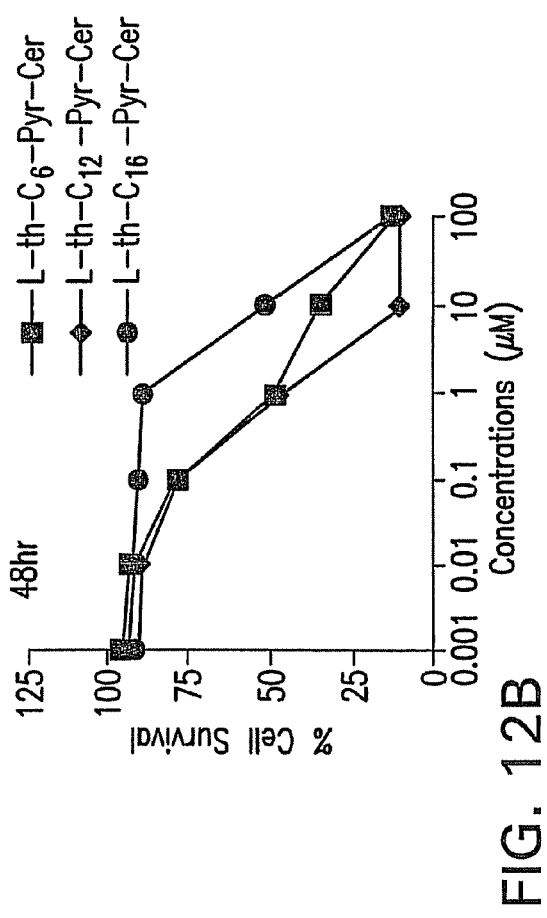
Figure 12B:
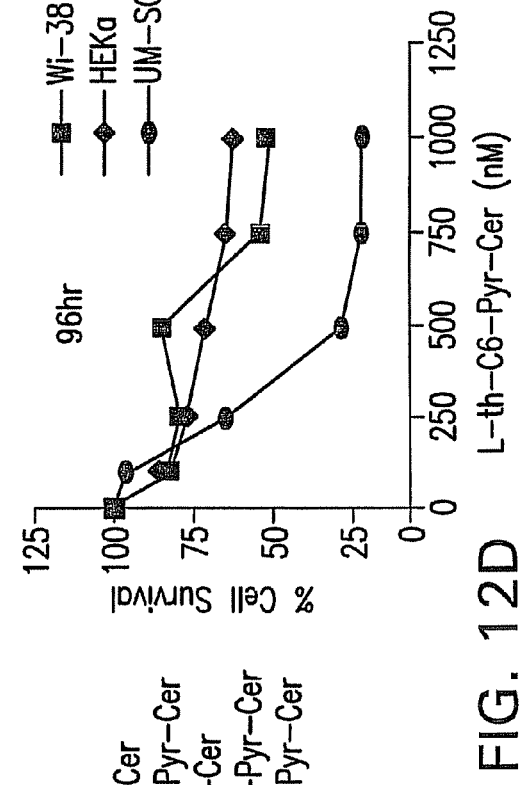
Figure 12C:
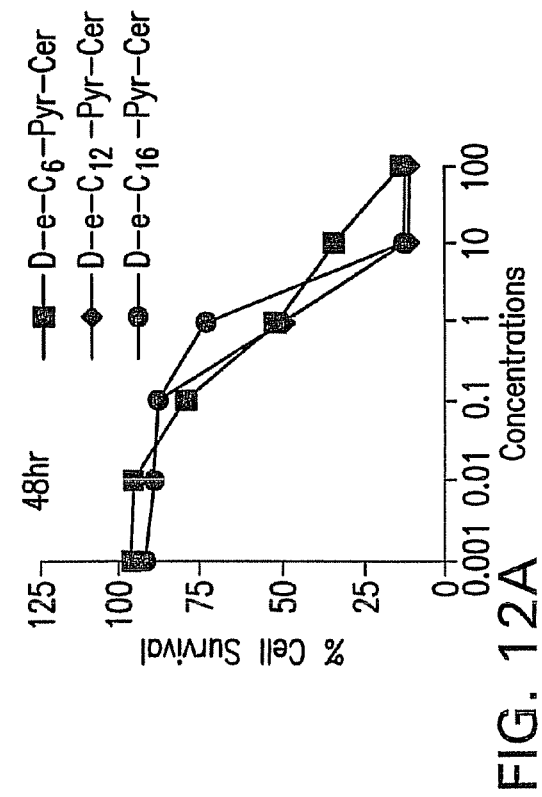
Figure 12D:
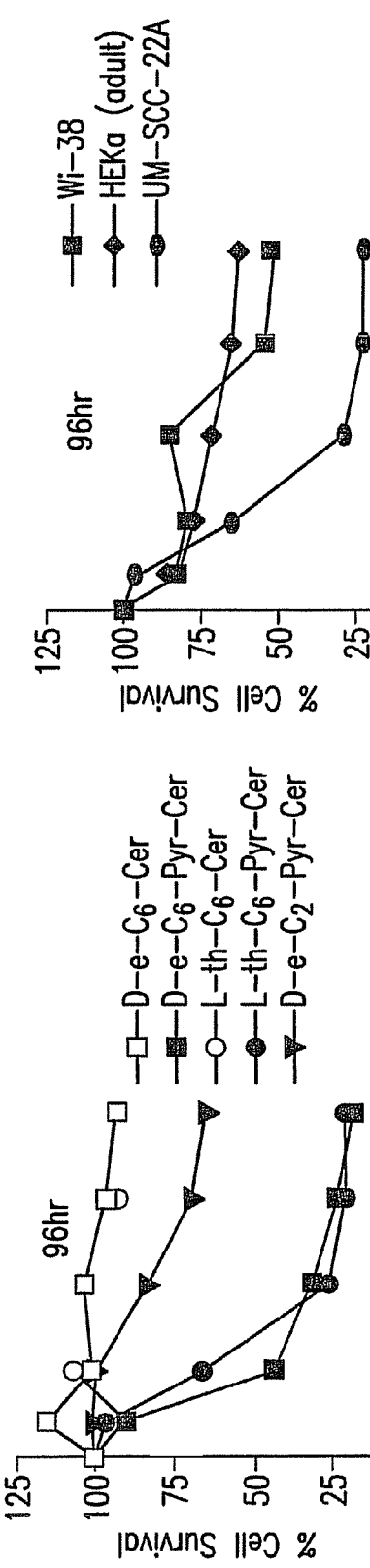

FIGS. 12A to 12D. Effects of pyridinium ceramides on cell survival in vitro. The IC50 concentrations of D-e-$C_6$, D-e-$C_{12}$—, D-e-$C_{16}$—, L-th-$C_6$—, L-th-$C_{12}$, L-th-$C_{16}$-CCPS (LCL-29, 88, 30, 124, 89 and 87, respectively) were determined by MTT assays (FIGS. 12A and 12B, respectively). The effects of short chain pyridinium ceramides on cell growth were determined and compared to that of conventional ceramides using MTT assays (FIG. 12C). The effects of L-th-$C_6$-Pyr-ceramide (LCL-124) on cell growth in UM-SCC-22A, non-cancerous Wi-38 and HEKa cells were also examined using MTT assays (FIG. 12D). The MTT assays were performed using triplicate samples in at least two independent experiments. Standard deviations for each point were between 0.5-5%.

Figure 13A:
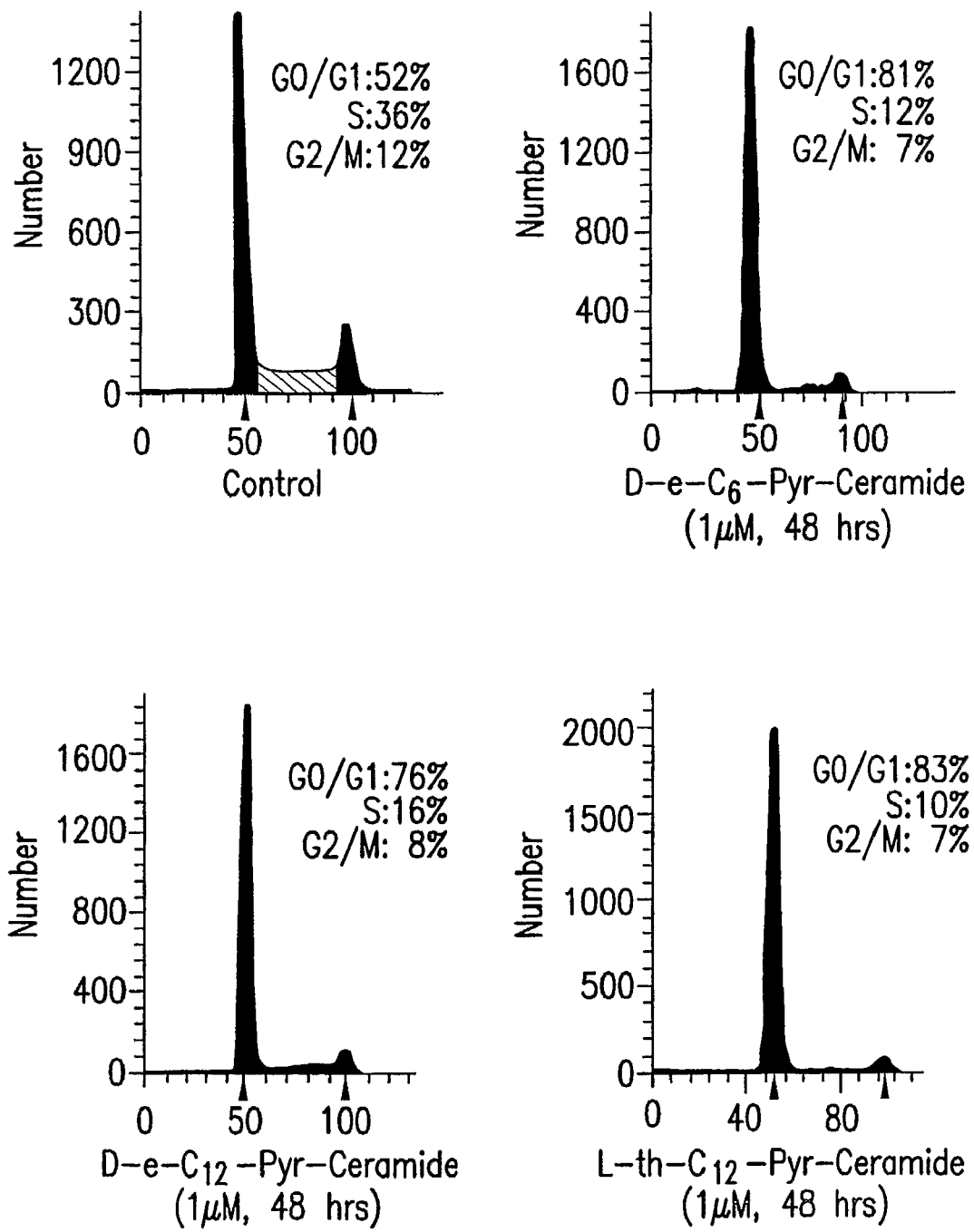
Figure 13B:
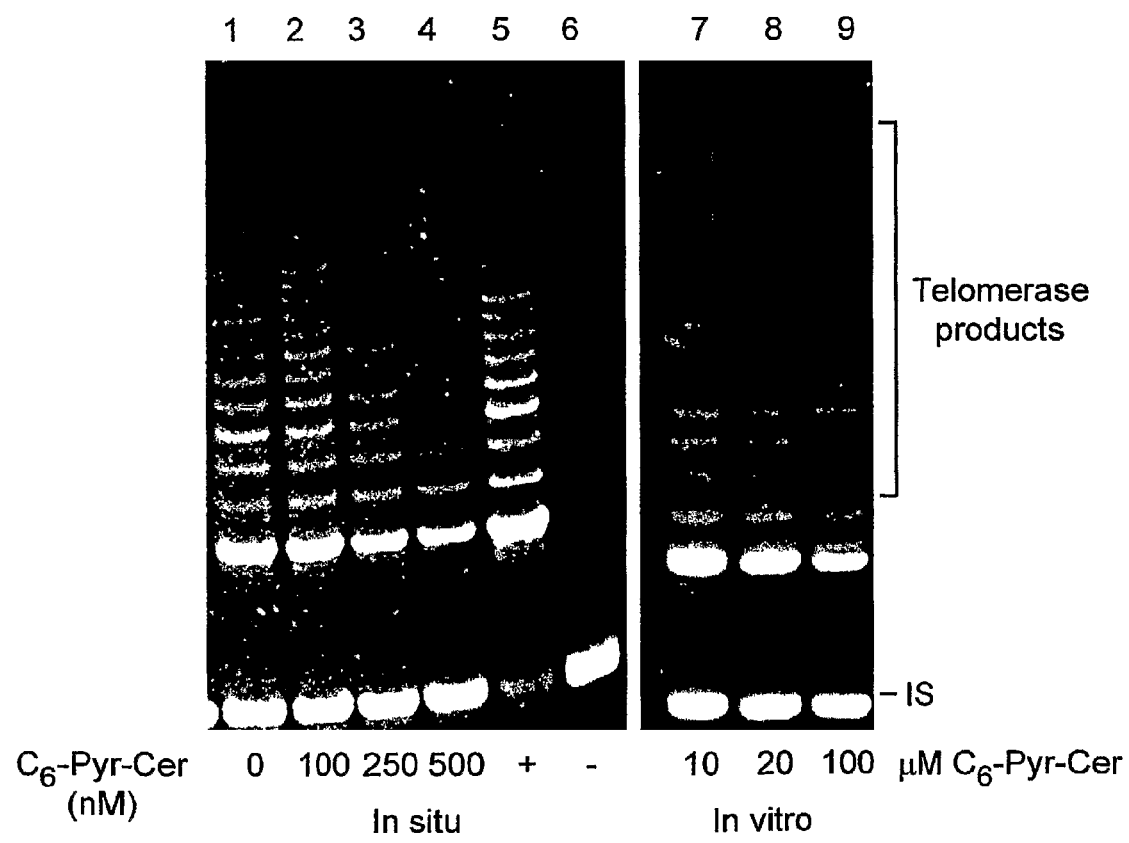

FIGS. 13A to 13B. Roles of CCPS on cell cycle profiles, and telomerase activity of UM-SCC-22A cells. (FIG. 13A) The effects of D-e-$C_6$—, D-e-$C_{12}$- and L-th-$C_{12}$-pyridinium ceramides (at 1 µM for 48 hr) on cell cycle profiles of UM-SCC-22A cells were determined and compared to that of untreated cells using flow cytometry as described in Materials and Methods. (FIG. 13B) The effects of 0, 100, 250 and 500 nM L-t-$C_6$-Pyr-Cer (LCL-124) (lanes 1-4, respectively) at 96 hr treatment in UM-SCC-22A cells on telomerase activity was assessed using TRAP assay. Lanes 5 and 6 contain positive (+) and negative (−) controls. To examine whether $C_6$-Pyr-Cer inhibits telomerase activity directly, cell extracts (as shown in lane 1) were incubated in the presence of various concentrations of L-th-$C_6$-Pyr-ceramide (LCL-124; 10, 20 and 100 µM) and telomerase activity was determined using TRAP assay (lanes 7-9, respectively). The presence of non-telomeric 36 bp internal standard (IS) in the TRAP assay serves as a control for polymerase chain reaction, and used for quantitation/normalization of the activity of telomerase. The results shown are representative of at least two independent experiments.

FIGS. 14A to 14D. Synergistic effects of $C_6$-Pyr-Cer in combination with GMZ or DOX on cell growth and telomerase activity in UM-SCC-22A cells. (FIG. 14A) The effects of various chemotherapeutic agents on cell growth in UM-SCC-22A cells were determined using MTT assays, and the IC50 concentrations of each agent were determined from cell growth plots as described. (FIG. 14B) The synergistic effects of DOX and L-th-$C_6$-Pyr-Cer (LCL-124) on cell growth were assessed using isobologram studies as described in Materials and Methods. (FIG. 14C) The effects of 1 μM L-th-$C_6$-Pyr-Cer (LCL-124) or cetyl-pyridinium-bromide, without ceramide conjugate (used as a control) on the growth inhibition potential of GMZ in UM-SCC-22A cells were determined using MTT assays. (FIG. 14D) The effects of GMZ (100 nM), L-th-$C_6$-Pyr-Cer (LCL-124; 1 μM) or GMZ and L-th-$C_6$-Pyr-Cer (LCL-124) (100 nM and 1 μM, respectively) on telomerase activity in UM-SCC-22A cells at 48 hr were examined using TRAP assay, and compared to that of untreated controls (lanes 2, 3, 4 and 1, respectively). The data shown are representative of at least two independent experiments performed in triplicate samples. Standard deviations in each sample were between 0.1-0.5.

Figure 15A:
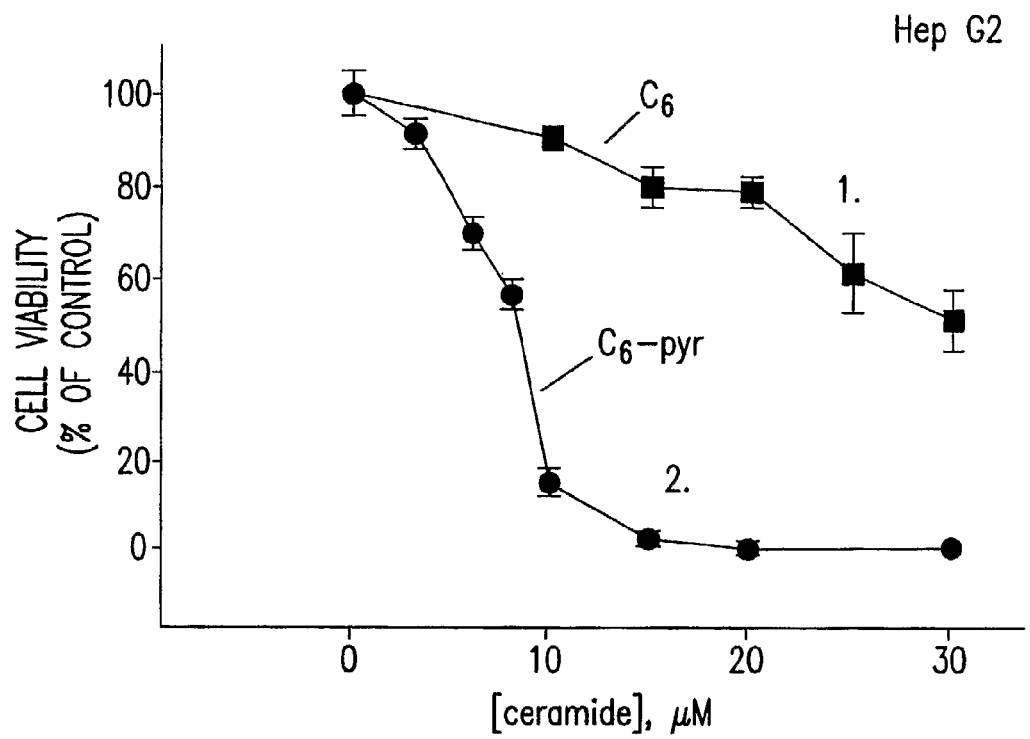
Figure 15B:
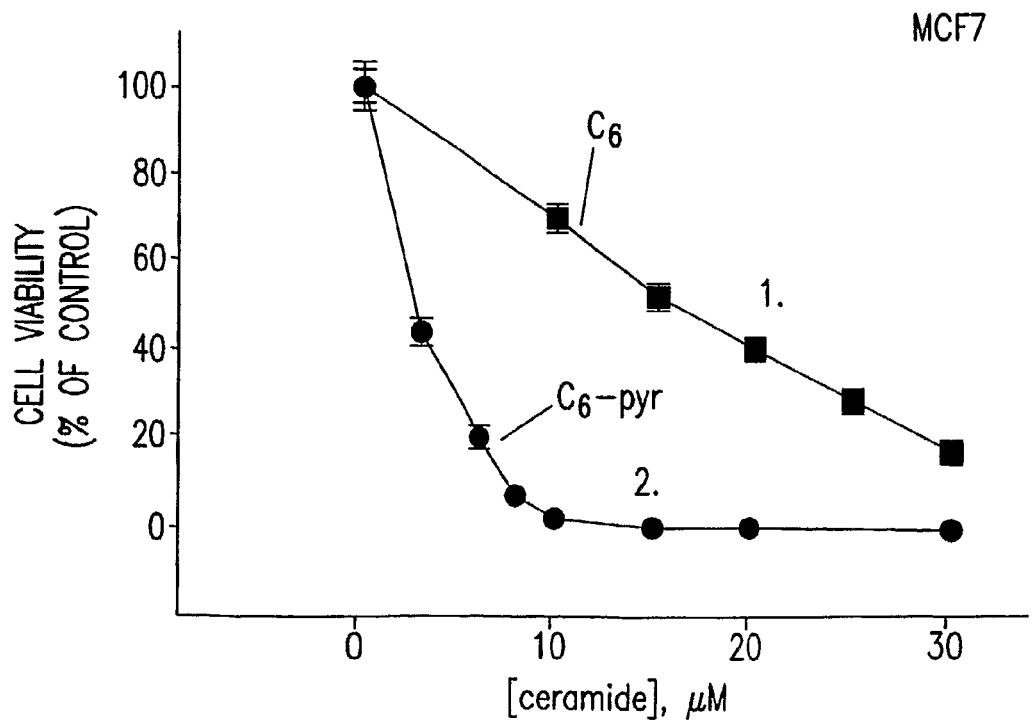

FIGS. 15A to 15B. Dose-response curves of ceramides effect on viability of Hep G2 and MCF7 cells. Hep G2 and MCF7 cells were incubated at the condition described in Section 9.1. D-erythro-$C_6$ ceramide (curves 1) or D-erythro-$C_6$ pyridinium ceramide bromide (LCL-29) (curves 2) at concentrations indicated were present from the beginning of the experiment. Cell viability was assessed 46 hours after addition of ceramides. Data are expressed as a mean+SEM of n=3.

Figure 16:
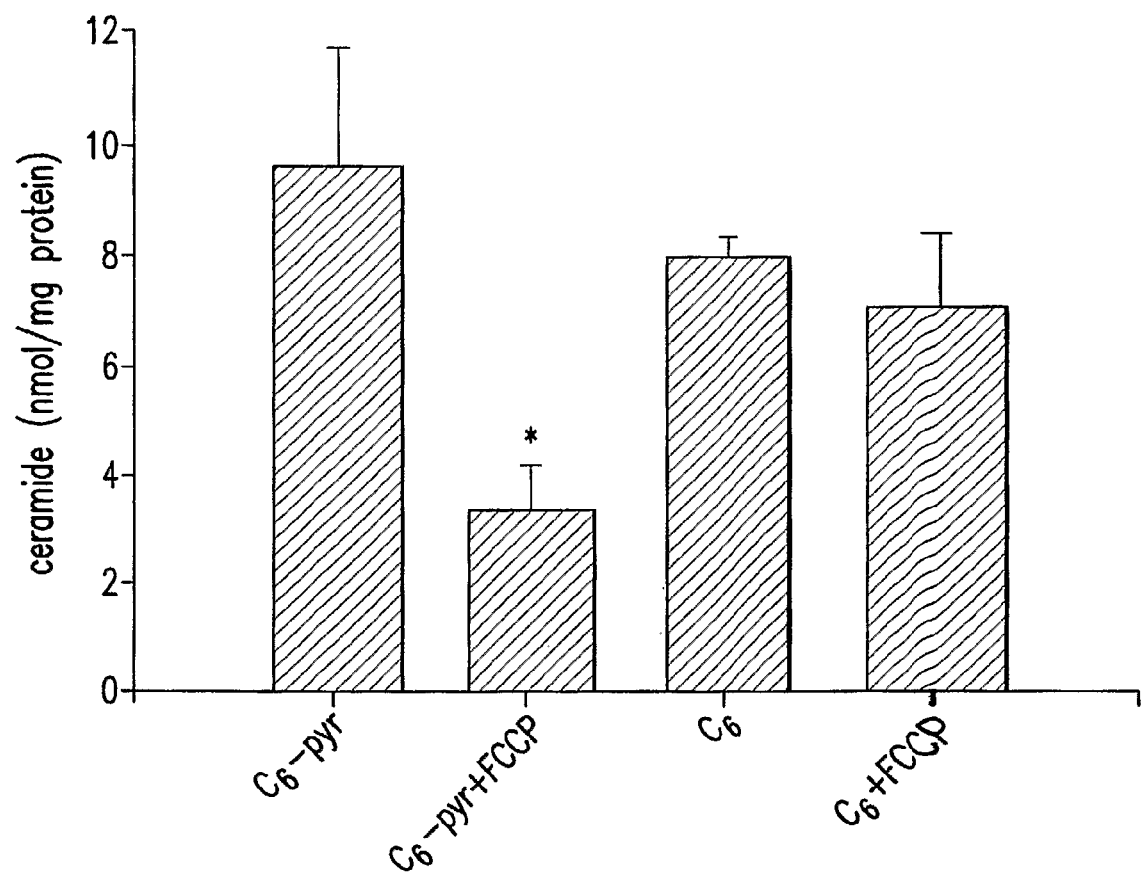

FIG. 16. Accumulation of D-erythro-$C_6$-ceramide and D-erythro-$C_6$ pyridinium ceramide bromide (LCL-29) in isolated rat liver mitochondria. Mitochondria were incubated at the condition described in Section 9.1 except that 1 μM of CSA and 1 mM EGTA were present from the beginning of the experiment and 10 μM of D-erythro-$C_6$-ceramide or D-erythro-$C_6$ pyridinium ceramide bromide (LCL-29) was added two minutes later after the addition of mitochondria. The plot shows amount of accumulated D-erythro-$C_6$-ceramide and D-erythro-$C_6$-pyridinium ceramide bromide (LCL-29) by energized and de-energized mitochondria. Bar 1 and 3 (control), binding of ceramides to mitochondria that develop high ΔΨ as a result of succinate oxidation under standard conditions. Bar 2 and 4 (+FCCP), ΔΨ was dissipated by addition of FCCP at 1 μM plus antimycin A at 0.5 μg/mg protein from the beginning of the experiment. Results are expressed as mean+SEM of n=3, *p=0.01 versus control.

Figure 17A:
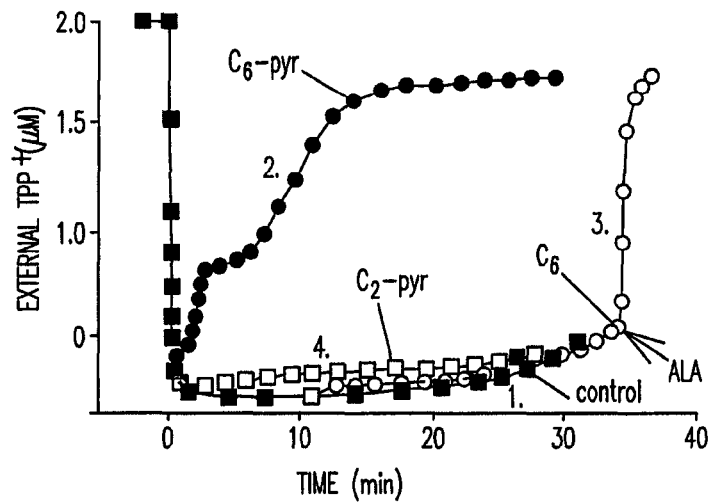
Figure 17B:
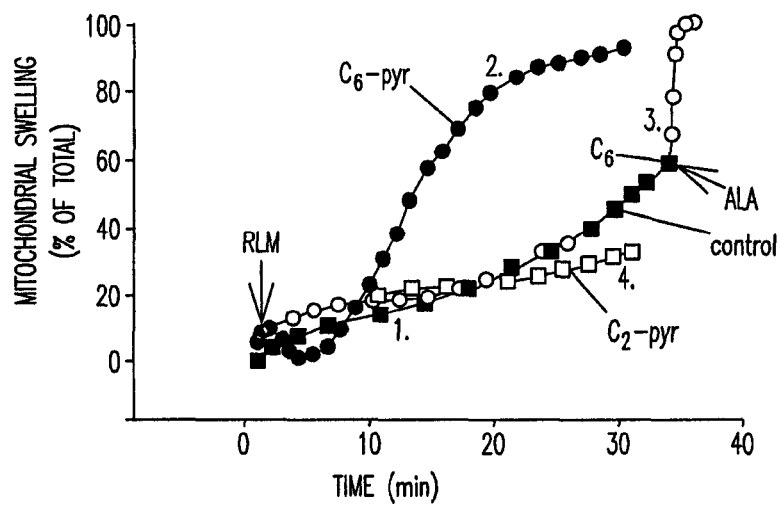
Figure 17C:
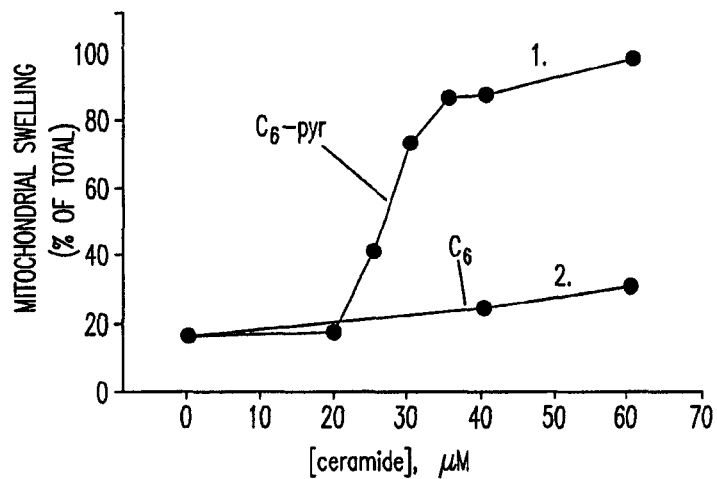

FIG. 17A to 17C. Effects of ceramides on ΔΨ value (17A) and mitochondrial large-amplitude swelling (17B, 17C) Mitochondria were incubated at the condition described under Section 9.1 except that 2 μM of TPP+ was present from the beginning of the experiment. Alamethicin (ALA), a pore-forming peptide (7 μg/mg protein), was added as indicated to induce permeabilization and determine the full extend of potential changes in the parameters of interest. Where indicated ceramides at 40 μM were present from the beginning of the experiment. FIGS. 17A and 17B show time-courses of ceramides effect on ΔΨ and mitochondrial swelling. Traces 1, no additions; traces 2, D-erythro-$C_6$ pyridinium ceramide bromide (LCL-29); traces 3, D-erythro-$C_6$ ceramide; traces 4; D-erythro-$C_2$ pyridinium ceramide bromide (LCL-150). FIG. 17C shows dose-response curves of ceramides effect on mitochondrial swelling. Degree of mitochondrial swelling was determined 30 min after ceramide treatment. Trace 1, D-erythro-$C_6$ pyridinium ceramide bromide (LCL-29); trace2, D-erythro-$C_6$ ceramide.

Figure 18A:
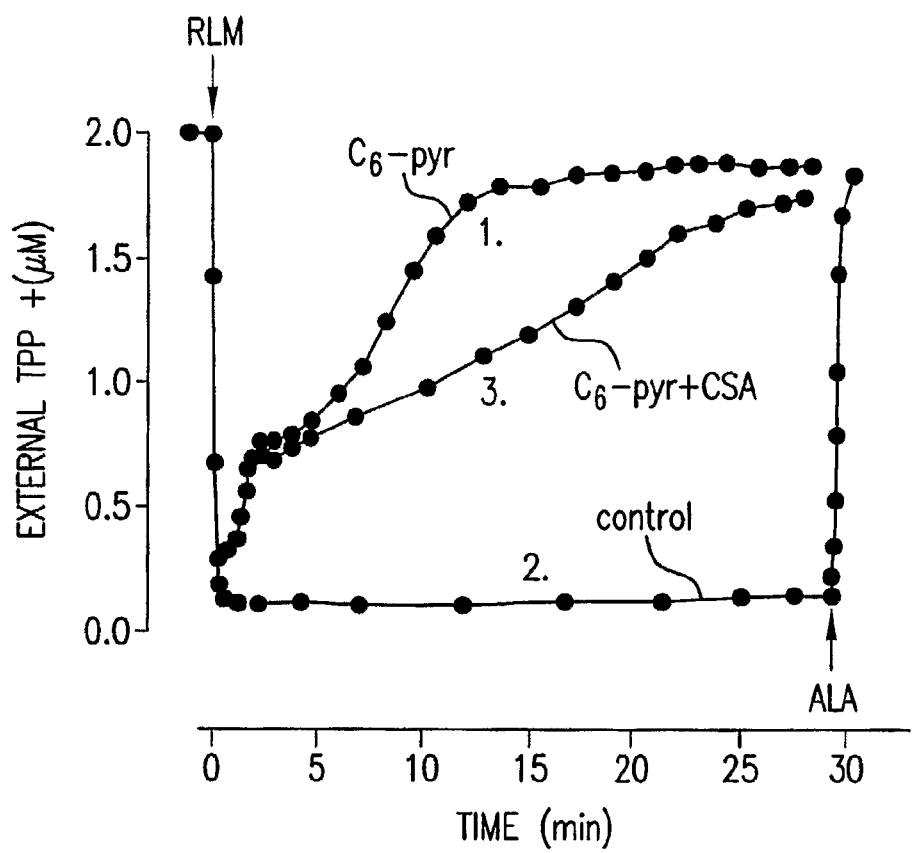
Figure 18B:
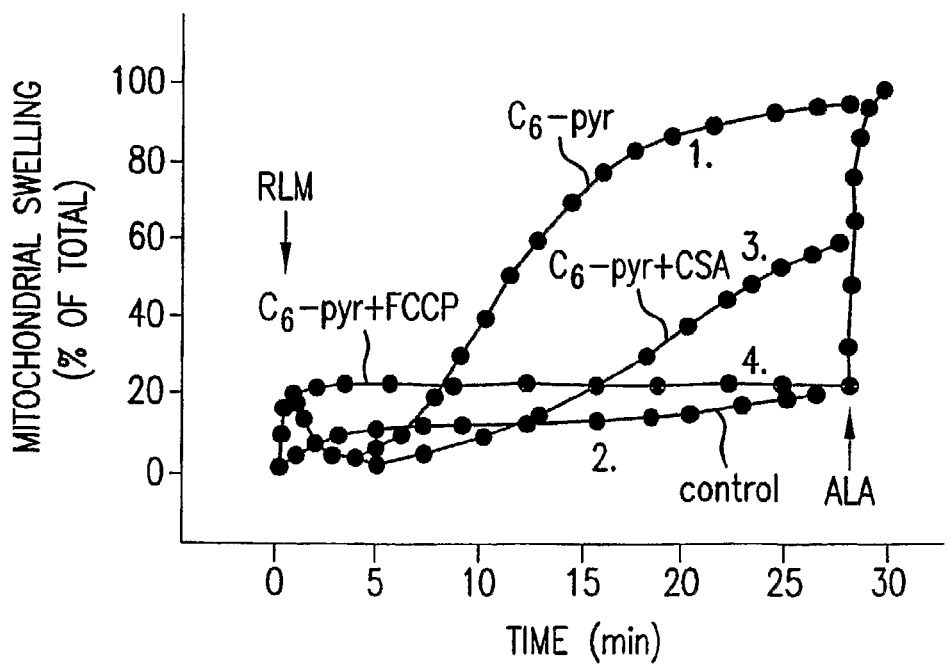

FIG. 18A to 18B. CSA and FCCP suppress D-erythro-$C_6$ pyridinium ceramide bromide (LCL29)-induced decrease in ΔΨ (18A) and large amplitude mitochondrial swelling (18B). Mitochondria were incubated at the condition described under Section 9.1 except that 2 μM of TPP+ was present from the beginning of the experiment. Trace 2, no addition. Trace 3, CSA at 1 μM was present from the beginning of the experiment. Trace 4, FCCP at 1 μM was present from the beginning of the experiment. For traces 1, 3 and 4, D-erythro-$C_6$ pyridinium ceramide bromide (LCL-29) at 40 μM was present from the beginning of the experiment. Alamethicin (ALA), a pore-forming peptide (7 μg/mg protein), was added as indicated to induce permeabilization and determine the full extent of potential changes in the parameters of interest.

Figure 19A:
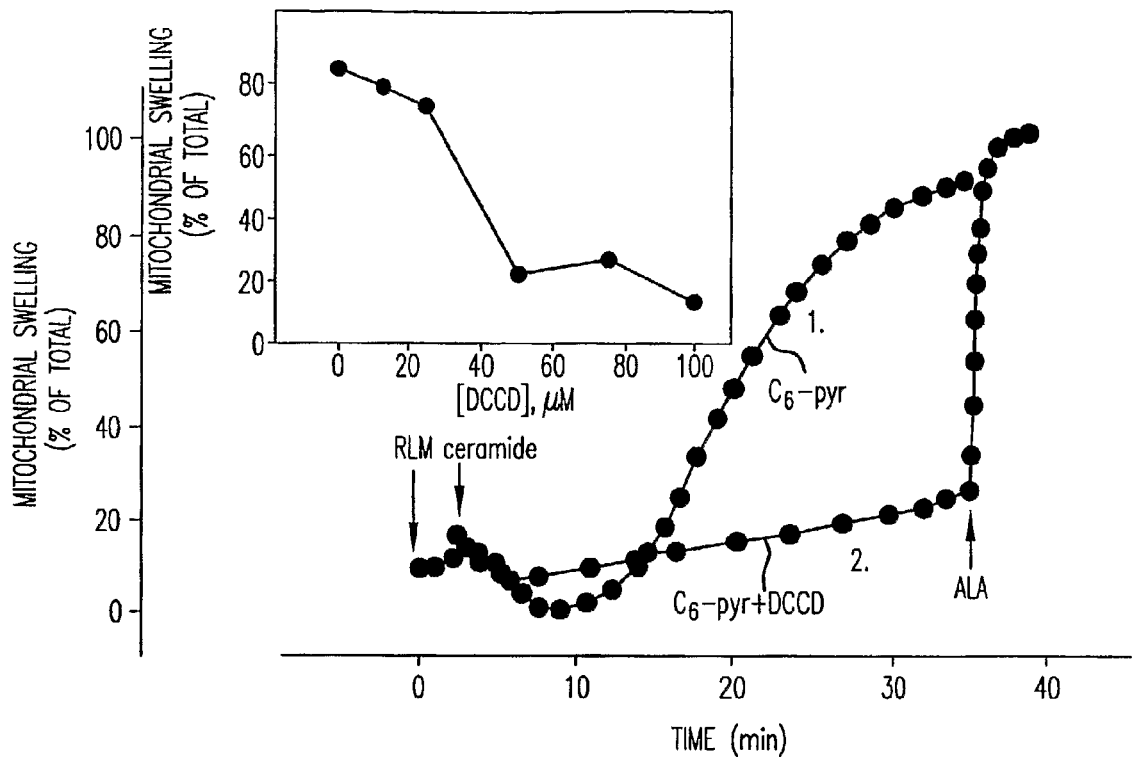
Figure 19B:
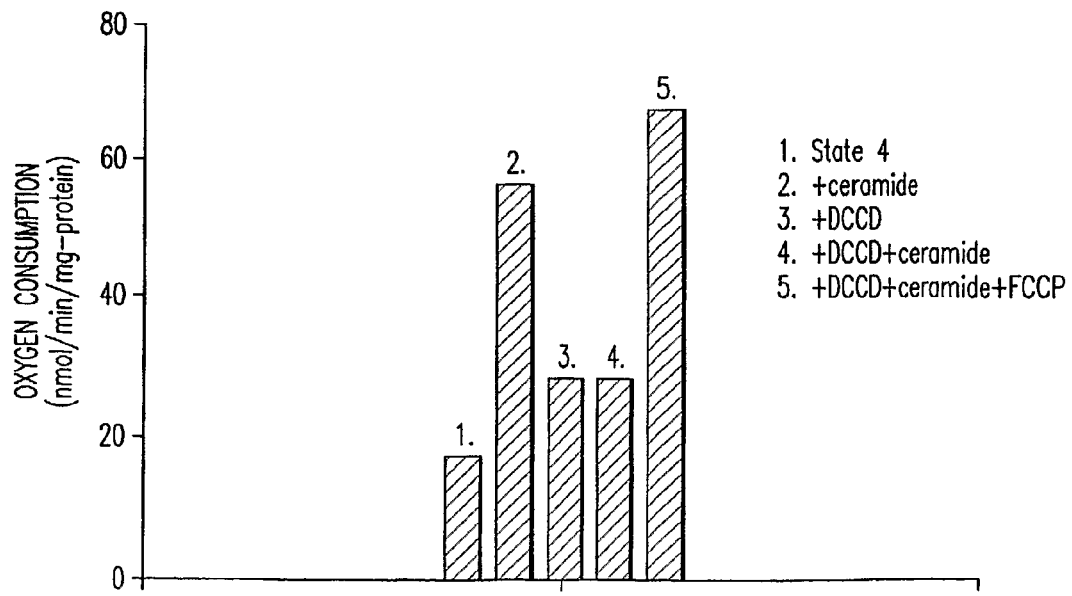

FIGS. 19A and 19B. DCCD suppresses D-erythro-$C_6$ pyridinium ceramide-bromide (LCL-29) induced large amplitude swelling (19A) and electrogenic ion fluxes (19B) in isolated rat liver mitochondria. Mitochondria were incubated at the condition described under "Experimental procedures". FIG. 19A traces 1 and 2, D-erythro-$C_6$ pyridinium ceramide bromide (LCL-29) at 40 μM was added were indicated. Trace 2, DCCD at 100 μM was added from the beginning of the experiment. Alamethicin (ALA) was added as indicated to determine full degree of permeabilization. Insert shoes dose-response curve of DCCD effect on D-erythro-$C_6$ pyridinium ceramide bromide (LCL-29)-induced permeabilization. The curve was generated from experiments similar to that depicted in traces 1 and 2 with indicated concentration of DCCD present from the beginning of the experiment. Degree of mitochondrial swelling was assessed 30 min after of the addition of D-erythro-$C_6$ pyridinium ceramide bromide (LCL-29). FIG. 19B, respiration of rat liver mitochondria at state 4 was measured. DCCD at 100 μM were presented from the beginning of the experiments. $C_6$ pyridinium ceramide at 40 μM was added 2 min after the addition of mitochondria. In experiments 1-4, the data shows respiratory rate 1 min. after addition of D-erythro-$C_6$ pyridinium ceramide bromide (LCL-29). It should be noted that respiratory rate in the presence of DCCD was linear for at least 8 min. In experiment 5, FCCP at 1 μM was added 8 min. after addition of D-erythro-$C_6$ pyridinium ceramide bromide (LCL-29).

Figure 20A:
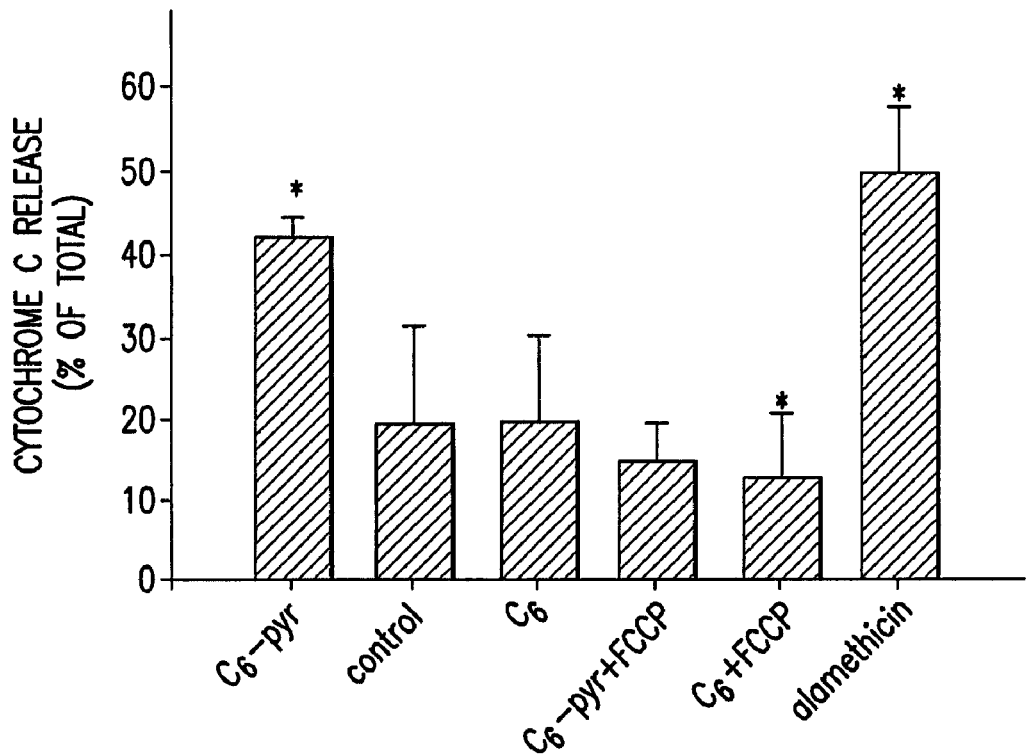
Figure 20B:
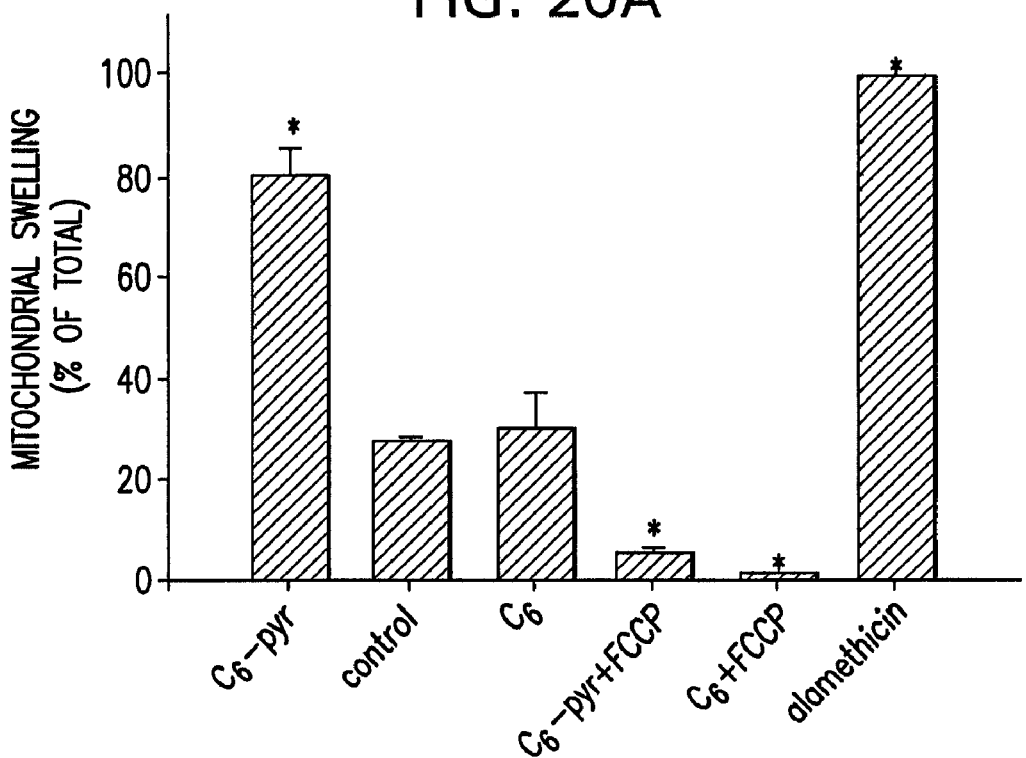

FIGS. 20A and 20B. D-erythro-$C_6$ pyridinium ceramide bromide (LCL-29)-induced large-amplitude swelling (B) is accompanied by cytochrome C release (20A). Mitochondria were incubated at the condition described in Section 9.1. Ceramides (40 μM) were added at 2 minutes and mitochondria were incubated for additional 20 min followed by addition of CSA (1 μM) and EGTA (1 mM) to prevent further permeabilization. Two min after the addition of CSA and EGTA samples were collected and treated for cytochrome C analysis. Alamethicin (ALA, 7 μg/mg protein) was added as indicated to determine the full degree of permeabilization and maximum cytochrome C release. Where indicated FCCP at 1 μM plus antimycin A at 0.5 μg/mg protein were present from the beginning of the experiment. Total amount of cytochrome C is 1.95 μg/mg protein. Data are expressed as mean+SEM of n=3, *p<0.05 versus control.

Figure 21:
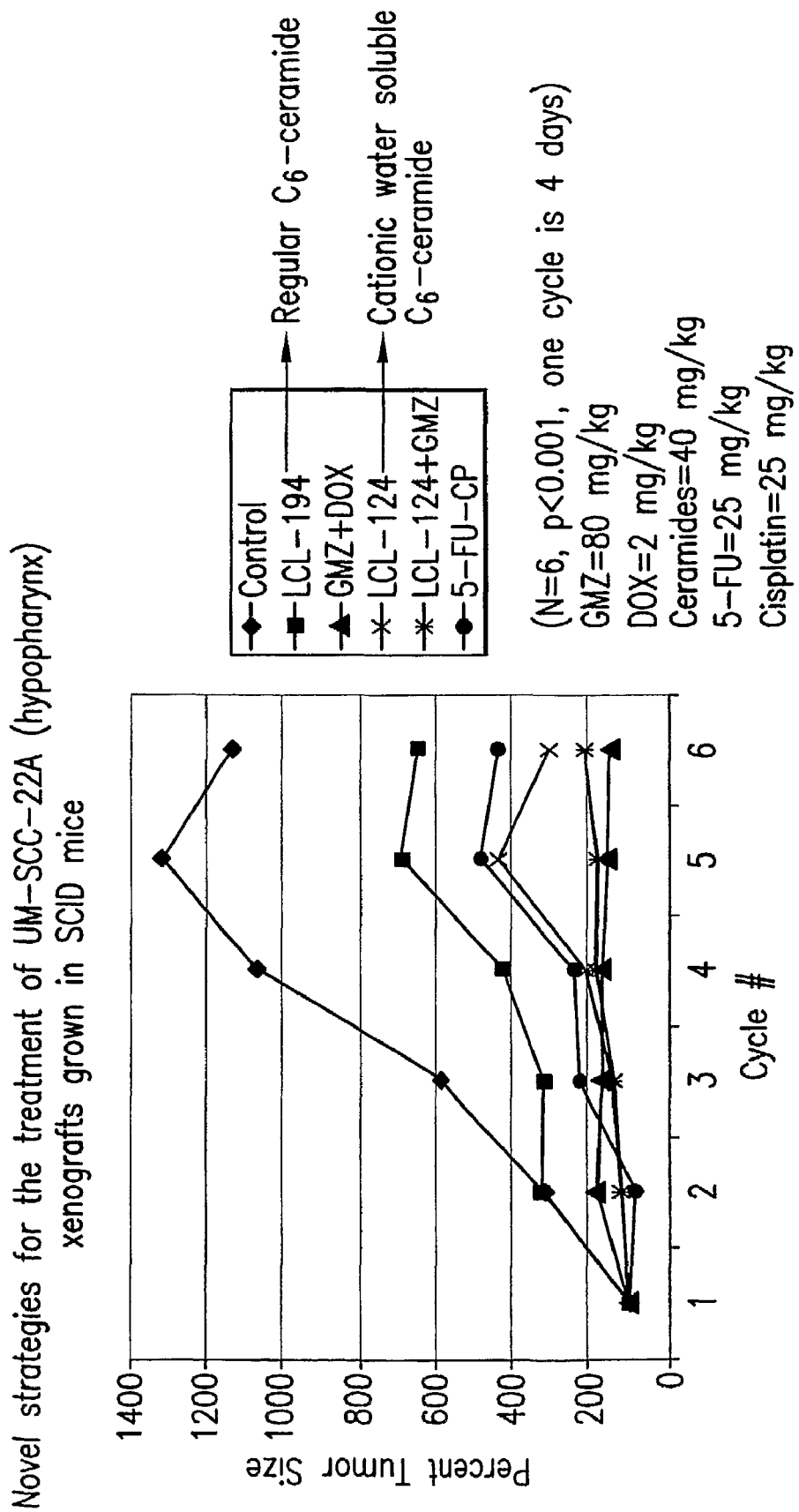

FIG. 21. Treatment of UM-SCC-22A (hypopharynx) xenografts in SCID mice. The therapeutic efficacy of L-t-$C_6$-Pyr-Cer and GMZ combination in the inhibition of HNSCC tumor growth and/or progression in vivo. Once the xenograft achieved a standard volume, the animals were randomized to receive no treatment (control), LCL-194 alone (40 mg/kg), LCL-124 alone (40 mg/kg), LCL-124 (40 mg/kg) plus GMZ (80 mg/kg), GMZ (80 mg/kg)+DOX (2 mg/kg), or 5FU plus cisplatin (25 mg/kg each). Tumors were measured every 4 days for 24 days.

Figure 22A:
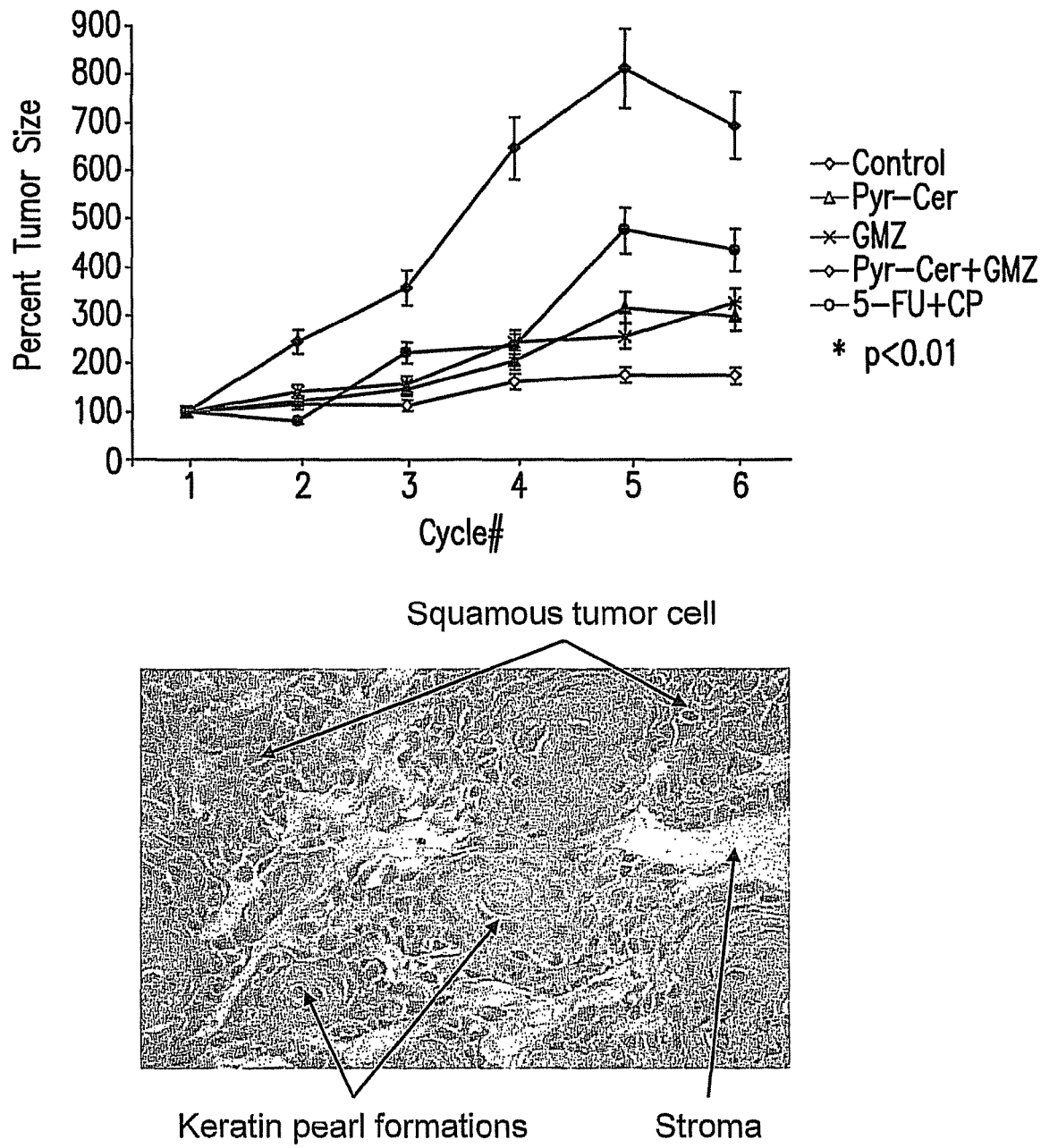
Figure 22B:
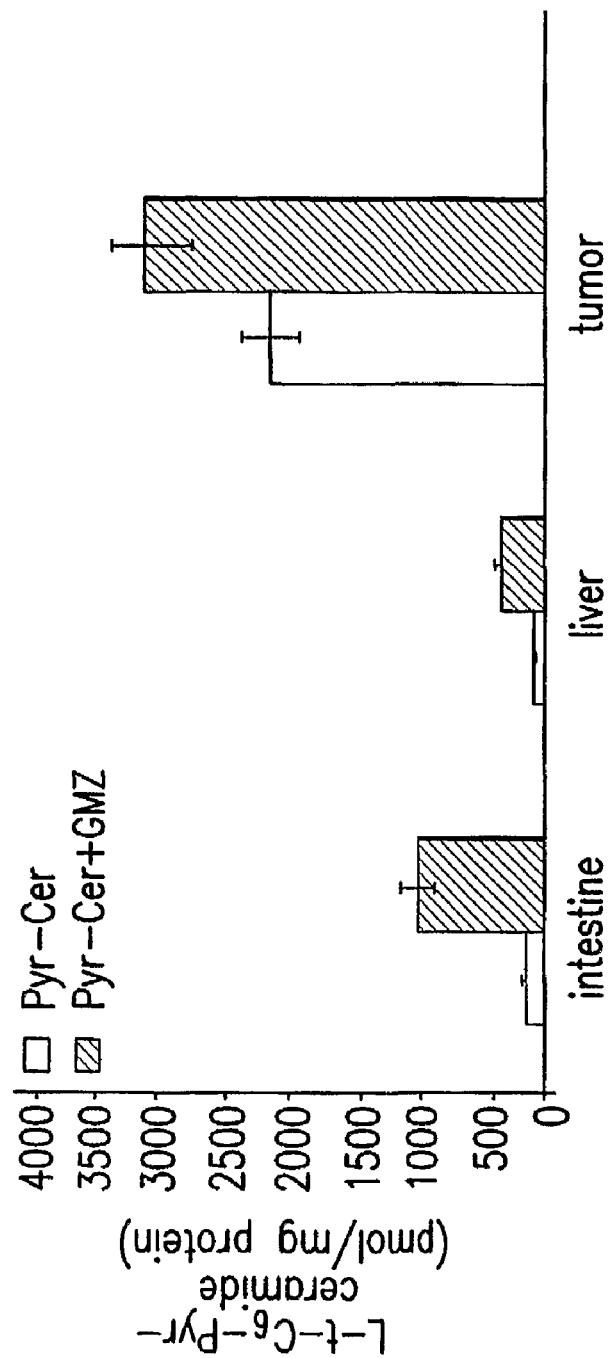

FIGS. 22A-C The therapeutic efficacy of L-t-C6-Pyr-Cer and GMZ combination in the inhibition of HNSCC tumor growth and/or progression in vivo. A) Upper Panel: In vivo therapeutic efficacy of L-t-$C_6$-Pyr-Cer in combination with GMZ was determined in SKID mice harboring the UM-SCC-22A xenografts implanted in both flanks. The animals were treated with L-t-$C_6$-Pyr-Cer and GMZ at 40 mg/kg/each every 4 days for 20 days. The therapeutic effects of the 5-FU/CP combination in this HNSCC model were also examined. In these experiments, each group contained 6 mice, harboring 12 tumors, in this study. Error bars represent standard deviations, and p values were calculated. Lower Panel: The histopathologic analysis of the tumors after treatment confirming that they were SCC. B) The accumulation of L-t-$C_6$-Pyr-Cer in tumor sites, or in the intestines and liver was measured by LC/MS after the completion of the study. The effects of GMZ on the levels of L-t-$C_6$-Pyr-Cer in these tissues were also examined by LC/MS. The experiments were performed in at least two independent trials as duplicates, and error bars represent standard deviations. C) The blood counts, the levels of serum enzymes, and electrolytes were analyzed in response to L-t-$C_6$-Pyr-Cer alone or in combination with GMZ in SKID mice.

Figure 23A:
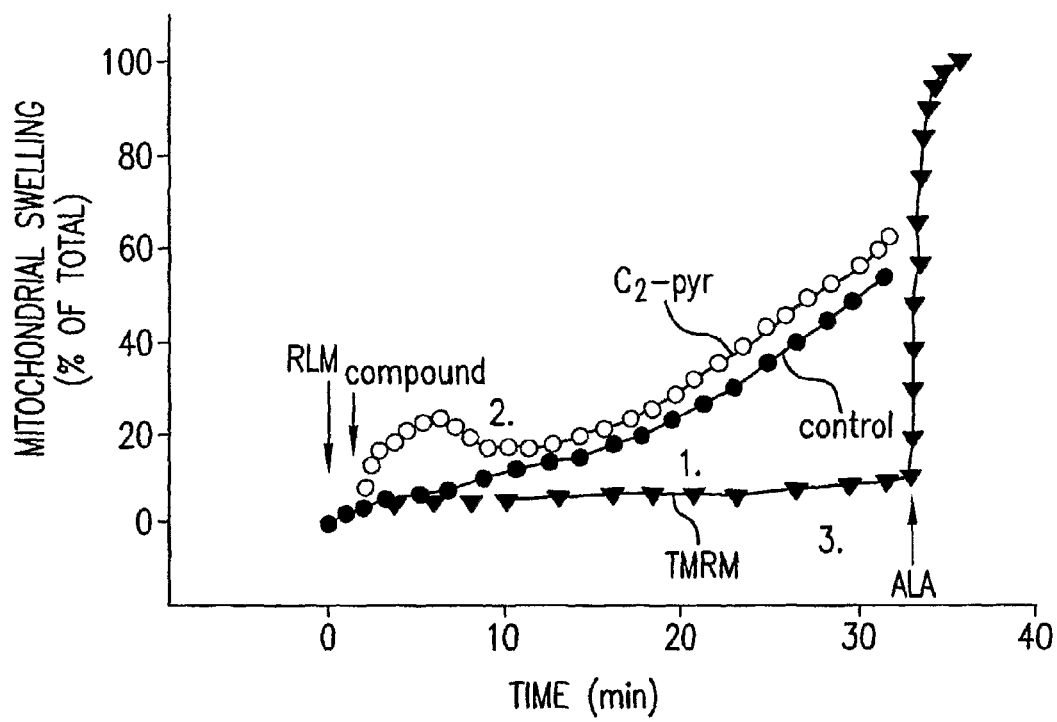

FIG. 23. Effect of hydrophobic cations on the time-course of mitochondrial large-amplitude swelling. Alamethicin (ALA), a pore-forming peptide (7 μg/mg protein), was added as indicated to induce permeabilization and determine the full extent of mitochondrial swelling. Where indicated cations at 60 μM were added to the incubation medium. Trace 1, no additions; trace 2, $C_2$ pyridinium ceramide; trace 3, TMRM; trace 4, cetyl pyridinium; trace 5, $TPP^+$. Trace 3 was corrected for the absorbance of TMRM. Determination of cation binding to mitochondria: Determination of $C_2$ pyridinium ceramide binding to mitochondria-mitochondria were incubated at essentially the same conditions, however 100 μM DCCD was present from the beginning of the experiment. Four minutes after the addition of ceramides mitochondria were sedimented and amount of ceramides in the pellet was determined by MS. $TPP^+$ binding was determined by $TPP^+$-selective electrode as described in "Experimental Procedures". Because TMRM, similar to $TPP^+$, rapidly equilibrates across the inner membrane according to its electrochemical potential, its accumulated amount was assumed to be equal of that of $TPP^+$.

FIG. 24. Time-course (A) and dose-response (B) of the effect of $C_6$ pyridinium dihydroceramide on mitochondrial large-amplitude swelling. Mitochondria were incubated at the condition described under "Experimental procedures". Alamethicin (ALA), a pore-forming peptide (7 μg/mg protein), was added as indicated to induce permeabilization and determine the full extent of mitochondrial swelling. Where indicated ceramides at 30 μM were added to the incubation medium. Panel A shows time-courses of ceramides effect on mitochondrial swelling. Trace 1, no additions; trace 2, $C_6$ pyridinium ceramide; trace 3, $C_6$ pyridinium dihydroceramide. Panel B shows dose-response curves of ceramides' effect on mitochondrial swelling. Degree of mitochondrial swelling was determined 15 min after ceramide treatment. Trace 1, $C_6$ pyridinium dihydroceramide; trace 2, $C_6$ pyridinium ceramide. Determination of pyridinium ceramide binding to mitochondria: $C_6$ pyridinium ceramide and dihydroceramide were determined for $C_2$ pyridinium ceramide.

FIG. 25. The sub-cellular accumulation, and growth inhibitory properties of L-t-$C_6$-Pyr-Cer in HNSCC cells. A) Chemical structure of L-t-$C_6$-Pyr-Cer is shown. B) The subcellular accumulation of L-t-$C_6$-Pyr-Cer at 1-48 hr was detected by LC/MS in UM-SCC-22A cells after differential centrifugation, as described in Materials and Methods. C) The growth inhibitory effects of L-t-$C_6$-Pyr-Cer against UM-SCC-22A, UM-SCC-14A and UM-SCC-1 cells were assessed by MTT assays after treatment of cells with increasing concentrations of the compound for 48 hr. Experiments were done in duplicates at least in three independent trials, and error bars represent standard deviations. When not seen, error bars are smaller than the diameter of the legends on the graphs.

FIG. 26. Synergistic effects of L-t-$C_6$-Pyr-Cer, in combination with GMZ, on the growth and cell cycle profiles of UM-SCC-22A cells. A) The synergistic interactions of L-t-$C_6$-Pyr-Cer and GMZ in the inhibition of growth were examined by quantitative isobologram studies. The IC50 concentrations of GMZ in the presence of increasing concentrations of L-t-$C_6$-Pyr-Cer was determined by MTT assays, and the data were plotted in isobolograms. A straight line joining points on x- and y-axes represent the IC50 concentrations of GMZ and L-t-$C_6$-Pyr-Cer alone. The points on the isobologram representing the IC50 values of GMZ obtained in the presence of 100, 250 and 500 nM L-t-$C_6$-Pyr-Cer fell within the left of the straight line, which indicates synergism. The experiments were performed as triplicates in at least three independent experiments. Error bars represent standard deviations. B) The effects of L-t-$C_6$-Pyr-Cer (500 nM) and GMZ (50 nM), alone or in combination, on cell cycle profiles of UM-SCC-22A cells were determined by flow-cytometry, after 48 hr treatment.

FIG. 27. The determination of MTD, and pharmacokinetic parameters, such as clearance from the serum, and bioaccumulation in various organs, of L-t-$C_6$-Pyr-Cer in vivo. A) MTD of L-t-$C_6$-Pyr-Cer was determined in dose escalation studies, in which BALB/c mice were treated (by IP injections) with increasing concentrations of the compound (10-150 mg/kg), dissolved in sterile saline solution, for 24 hr. The MTD of the compound was assessed as 80 mg/kg, which did not result any detectable toxicity in any of the animals. The toxic concentrations of the compound at or >100 mg/kg caused severe abdominal bloating, and intestinal malfunction. B and C) The levels of L-t-$C_6$-Pyr-Cer in the serum (B) or in the vital organs (C) of the BALB/c mice were measured by LC/MS after IP injection of the compound for various time points. The experiments were performed in two independent trials as duplicates, and error bars represent standard deviations.

FIG. 28. The effects of L-t-$C_6$-Pyr-Cer, alone or in combination with GMZ, on the levels of endogenous ceramides and SM in HNSCC tumors, in vivo. The effects of L-t-$C_6$-Pyr-Cer, alone or in combination with GMZ, on the levels of endogenous ceramides (A and B) or SM (C and D) in HNSCC tumors extracted from SKID mice (summarized in FIGS. 4A and B) were examined by LC/MS. The levels of $C_{14}$-, $C_{16}$-, $C_{18}$-, $C_{24}$-, $C_{24}$:1-, dihydro-$C_{16}$-ceramides, and sphingosine are shown in (A), and $C_{18}$:1-, $C_{20}$-ceramides, and dihydro-sphingosine, and sphingosine-1-phosphate levels are shown in (B). The levels of $C_{16}$-, $C_{22}$-, $C_{24}$ and $C_{24}$:1-SM levels are shown in (C), and $C_{14}$-, $C_{18}$-, $C_{18}$:1-, $C_{20}$, $C_{20}$:1, and $C_{22}$:1 SM levels are shown in (D). The experiments were performed in two independent trials, and error bars represent standard deviations.

FIG. 29. The role of L-t-$C_6$-Pyr-Cer, alone or in combination with GMZ, in the inhibition of telomerase in HNSCC tumors in vivo. The role of L-t-$C_6$-Pyr-Cer, alone or in combination with GMZ, in the regulation of telomerase activity (A), telomere length analysis (B), the levels of hTERT mRNA (C), and protein (D) in HNSCC tumors extracted from SKID mice after studies summarized in FIG. 22, were examined by TRAP, TRF, Q-PCR, and Western blotting, respectively, as described in Materials and Methods. In (B), DNA samples obtained from tumors treated with GMZ (G), L-t-$C_6$-Pyr-Cer (Cer), and the combination of L-t-$C_6$-Pyr-Cer with GMZ (G/C, lanes 2-4, respectively) were compared to that of untreated (U) tumors (lane 1). Lanes 5 and 6 contain DNA samples with low (L) and high (H) molecular weight (3.9 and 10.2 kb, respectively) telomeres. In (D) The levels of hTERT protein in samples obtained from tumors treated with GMZ (G), L-t-$C_6$-Pyr-Cer (Cer), and the combination of L-t-$C_6$-Pyr-Cer with GMZ (G/Cer, lanes 2-4, respectively) were determined by Western blot analysis using rabbit polyclonal anti-hTERT antibody, and compared to that of untreated (U) tumors (lane 1). Lanes 5 and 6 contain samples from telomerase positive (+) and negative (−) extracts. Beta-actin levels of these samples were used as loading controls (lanes 1-6, lower panel). The data shown are representative of two independent trials, and error bars represent standard deviations.

Figure 30:
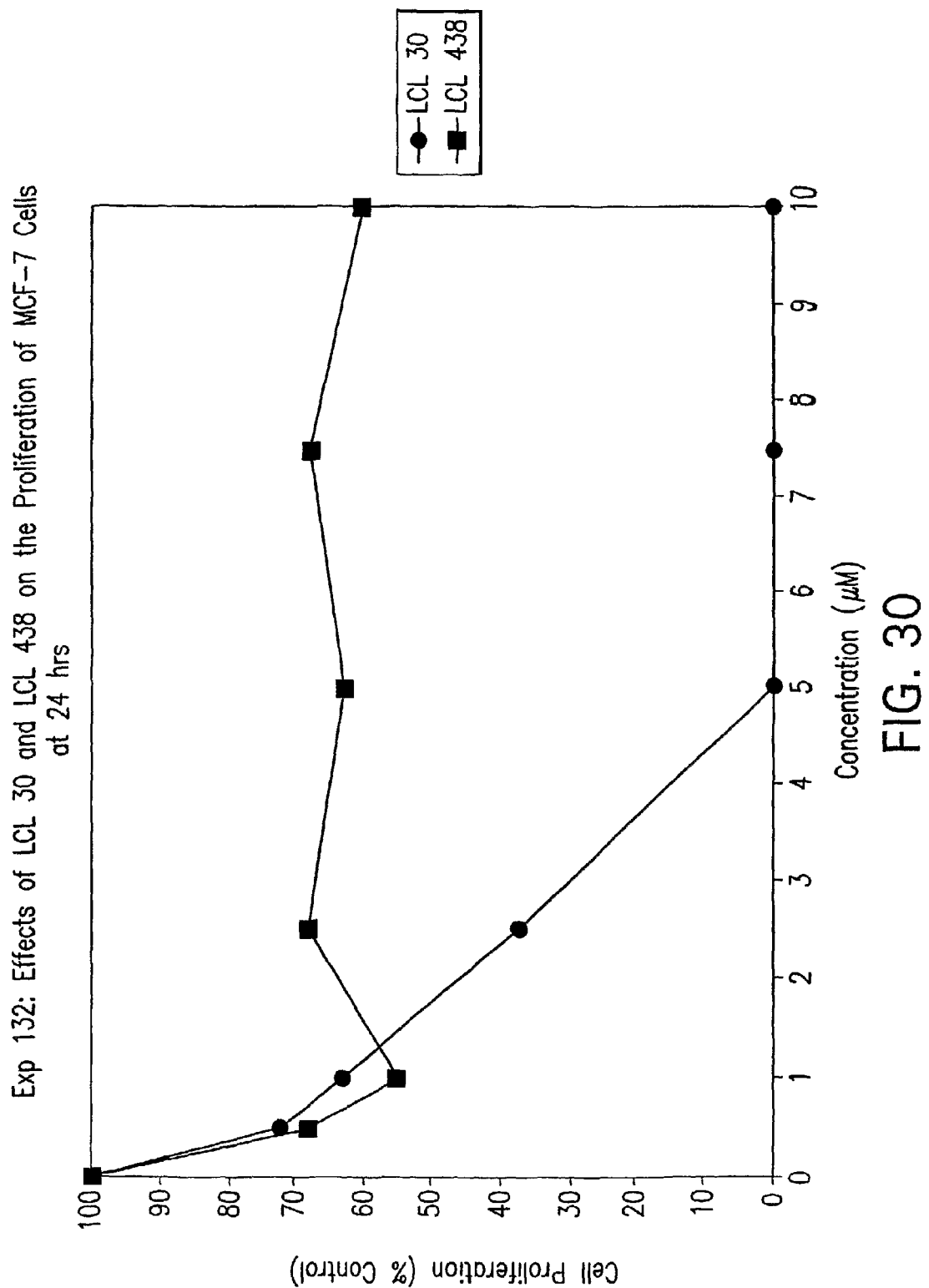

FIG. 30. Effects of LCL3 and LCL438 on the proliferation of MCF-7 cells at 24 hours.

5. DETAILED DESCRIPTION OF THE INVENTION

The invention relates to hybrid sphingolipids and their analogs conjugated with a pyridinium salt, specifically hybrid ceramides and analogs conjugated with pyridinium salt, collectively referred to as CCPS analogs. The present invention also includes methods of designing, methods of making, and methods of using such cationic analogs.

In one embodiment, the present invention provides compounds having Formula I or Formula II. The CCPS analogs have pyridinium cations incorporated into the N-acyl parts as an ω-substituent; inside the N-acyl-chains; or into the sphingosine or in general into the aminoalcohol backbone as an ω-substituent. The CCPS analogs were designed to target ceramides or their analogs into negatively charged organelles such as mitochondria and nuclei, and to decipher the NMR structure of natural ceramides under physiological conditions. As used herein, the phrase "CCPS analogs" also includes the dihydrogenated analogs of CCPS: "dhCCPS analogs". Compounds encompassed by the invention are described in details in Sections 5.2 and 5.3. The terms "CCPS analog" and "pyridinium ceramide" and pyridinium ceramide analogs are used interchangeably to refer to the compounds of the invention. These compounds are generally known as ceramidoids.

In the course of investigation by the present inventors of chemical etiology of sphingolipis (SPLs) structure and their biological functions (see Chalfant C E, (2003). *J Lipid Res.;* 45(3):496-506; El-Bawab, S. (2002) *J. Lipid Res.* 43, 141-148; Usta, J (2001). *Biochemistry* 40 (32), 9657-9668; and El Bavab, (2000), *J. Biol. Chem.* 276, 16758-167) and search for new molecules that show desirable properties (e.g., improved solubility and cellular uptake and directed targeting to the specific cellular compartments), mimic action of natural SPLs and affect their metabolism, novel SPL analogs bearing cations in the molecules are developed. Specifically, the introduction of the pyridinium cation into the ceramide ("Cer") structure can impose a controlled targeting and delivery of parent compounds into negatively charged cellular organelles such as mitochondria and nuclei.

According to the invention, the design for the CCPS analogs is based on the following observations: (i) some lipophilic cations were reported to localize preferentially into mitochondria, (ii) much of the action in the mammalian apoptotic program takes place at the mitochondrial level, (iii) Cer formation is intimately related to mitochondrial function in apoptosis, and (iv) the acute accumulation of Cer both directly and indirectly, profoundly affects mitochondrial function (see Davis, S, (1985) *J. Biol. Chem.,* 260, 13844-13850; Modica-Napolitano, J S. (2001), *Adv. Drug Delivery Rev.,* 49, 63-70; Fantin, V. R. *Cancer Cell,* (2002), 2, 29-42; Rosania, G. R., (2003) *J. Am. Chem. Soc.,* 125, 1130-1131; Grether-Beck, S. (2003), *J. Biol. Chem.,* 48, 47498-47507; Siskind, L. J. *J. Biol. Chem.,* (2002), 277, 26796-26803; Bribes, H.; et al *FASEB J.* 2001, 14, 2669-2679; Mimeault, M. (2002) *FEBS Lett.,* 530, 9-16; Radin, N. C., (2003) *Bioorg. Med. Chem. Lett,* 11, 2123-2142). The CCPS analogs, which include water soluble Cers, can be delivered to the cells and serve as model compounds to study behavior and apoptotic action of natural Cers under physiological conditions in the context of mitochondrial damage (see Di Paola (2000), *Biochemistry,* 39, 6660-6668; Bribes, H.; et al *FASEB J.* 2001, 14, 2669-2679; Szalai, G. (1999), *Embo J.* 18, 6349-6361))

Figure 1:
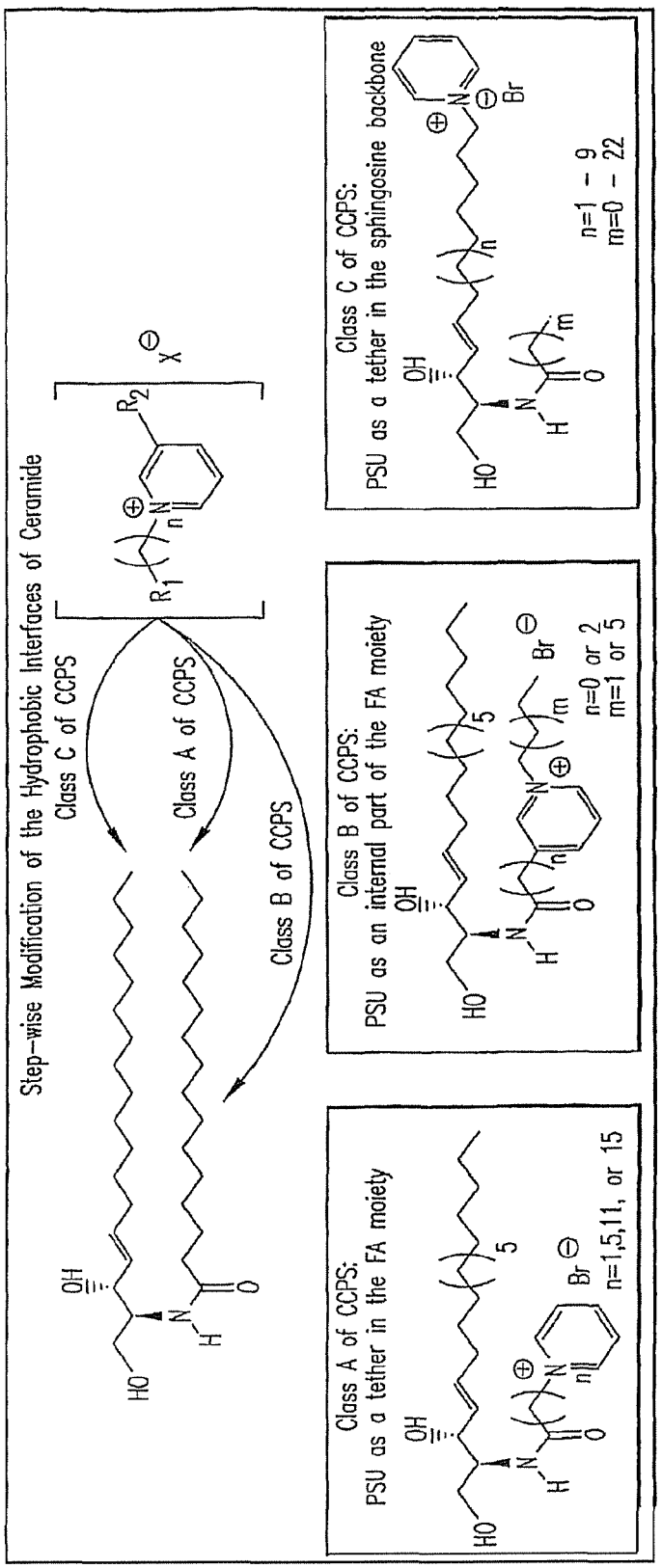
FIG. 1 shows the general method for designing compounds of formula I (Class A and Class B CCPS analogs) and formula II (Class C analogs).

In one embodiment, the present invention encompasses a structurally distinct class of hybrid cationic Cers, the CCPS analogs, that incorporate pyridinium salt moieties (PSM) into the N-acyl part of the Cer structure at three distinct locations (FIG. 1). Compounds of Class A, and D represents analogs possessing the PSM unit as a tether in the N-acyl part of the conjugated molecule; Compounds of Class B represent analogs where the PSM unit is either in the vicinal or the juxta position to the N-carbonyl group of the conjugated molecule; and Compounds of Class C represents analogs possessing the PSM unit as a tether in sphingosine backbone. The location of the PSM unit plays an important role for the physicochemical, biophysical and biological properties of these developed analogs. The arrangements of the PSM unit found in the structure of a naturally occurring trimeric pyridinium alkaloid, viscosamine, was used here as a model template (see Volke, Ch. A. (2003), *Org. Lett.,* 5, 3567-3569)

Figure 2A:
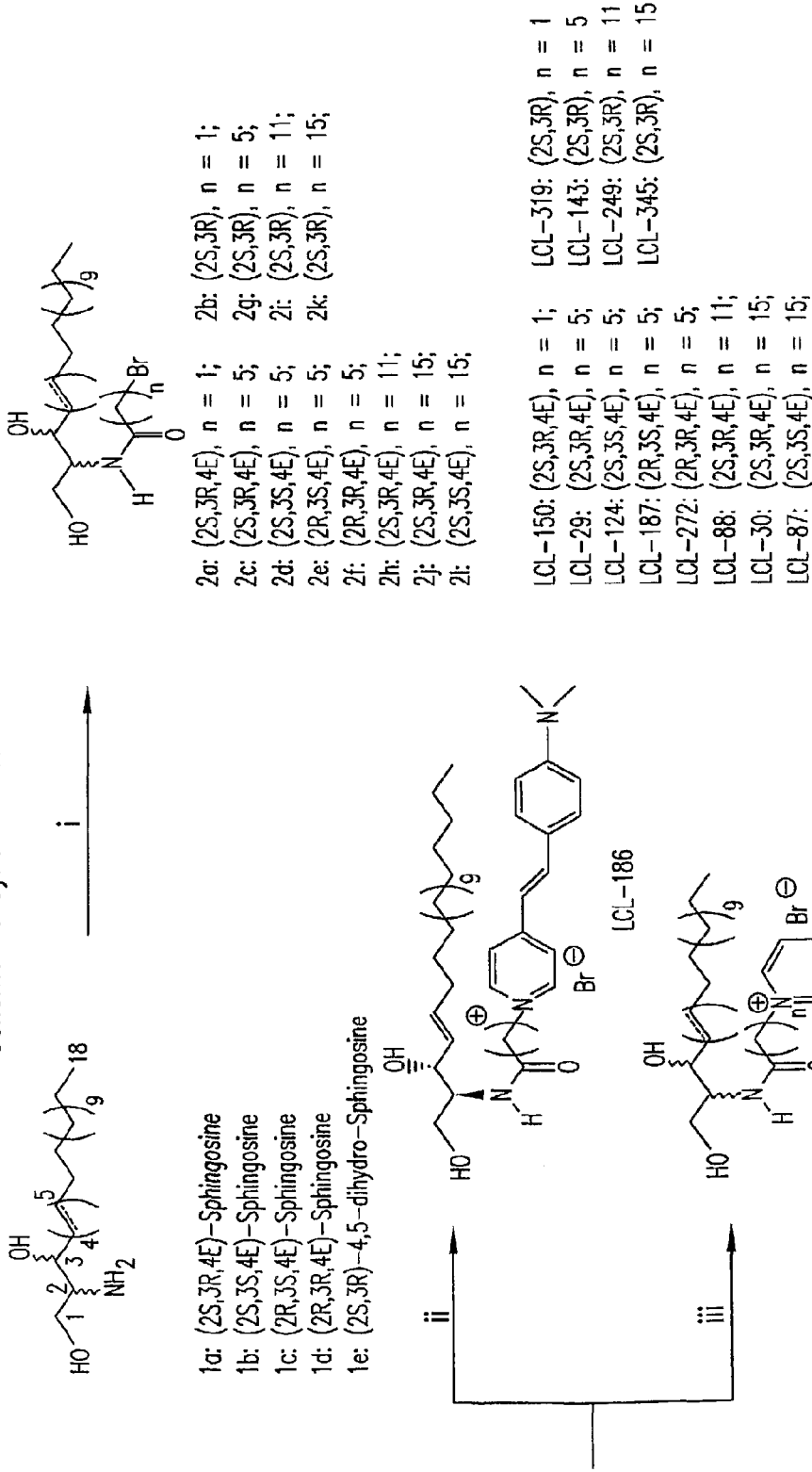
FIG. 2A shows Scheme 1, the synthesis of class A ceramidoids.
Figure 2B:
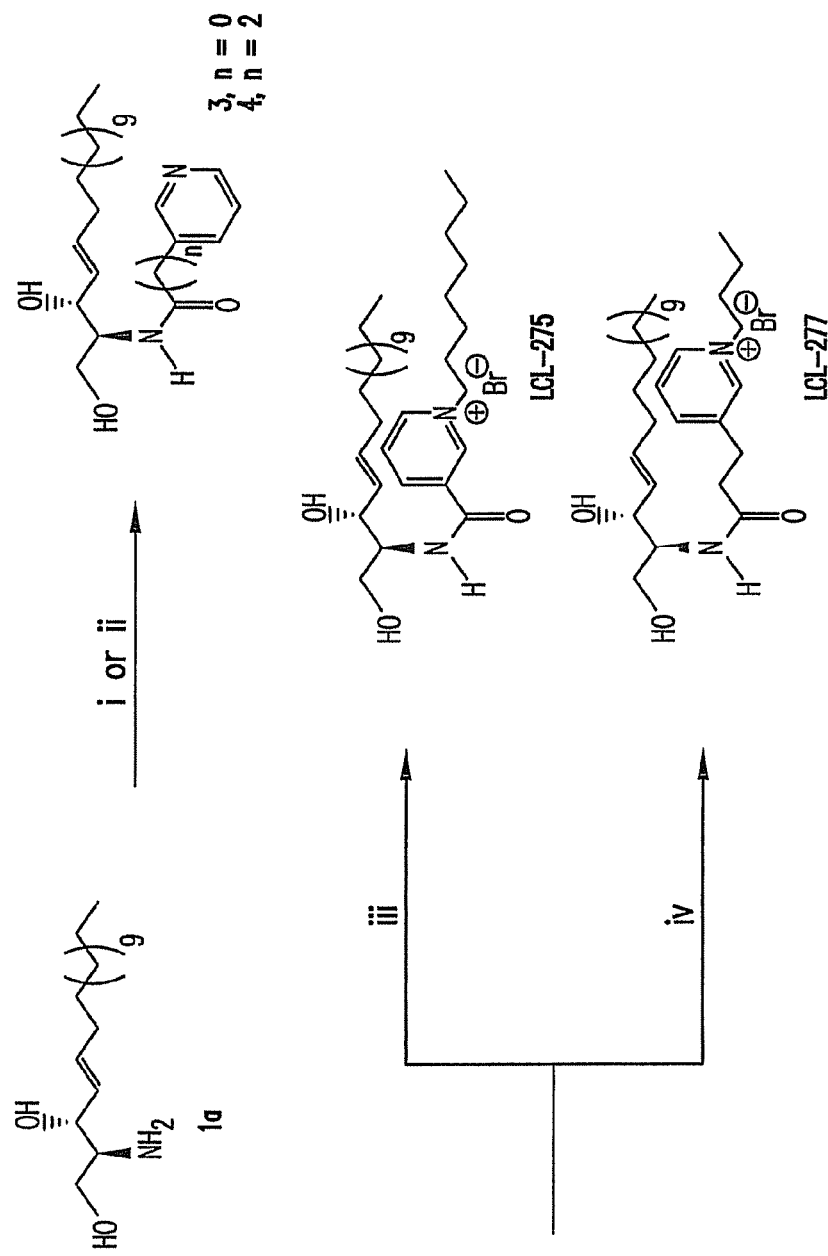
FIG. 2B shows Scheme 2, the synthesis of class B ceramidoids.
Figure 2C:
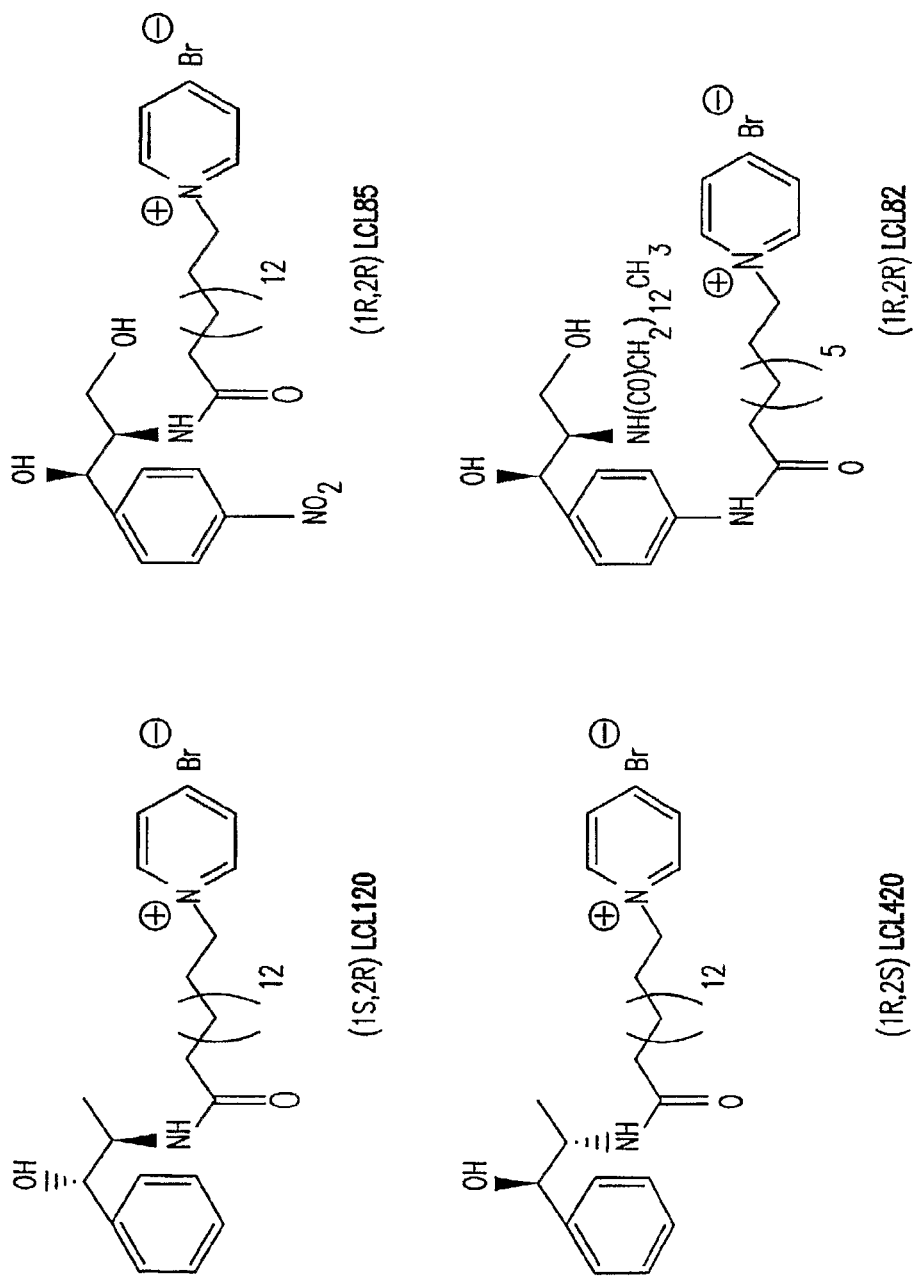
FIG. 2C shows structures of LCL120, LCL 85, LCL 420 and LCL82.
Figure 3A:
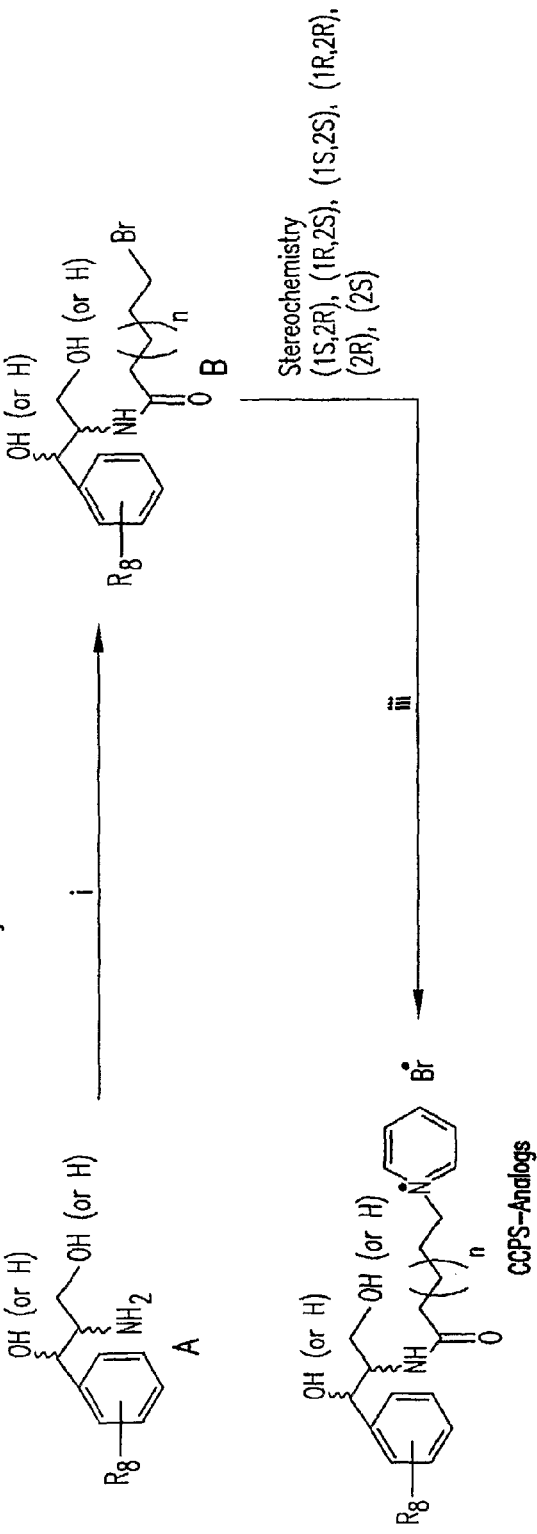
FIG. 3A shows Scheme 3, the synthesis of class D ceramidoids.
Figure 3A:
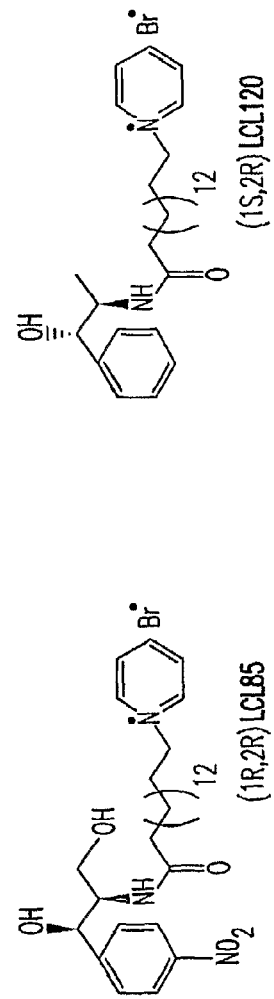

The varied structural and stereochemical examples of exemplary CCPS analogs of the invention are shown in Schemes 1, 2 and 3 (see FIGS. 2A, 2B & 3) see Section 5.4.1). These exemplary compounds serve as model compounds to study structure-function relationship of this group of compounds. These selected CCPS analogs establish effects of specific structural modifications: (i) chain length in N-acyl-part, ($C_2$, $C_6$, $C_{12}$ and $C_{16}$ homologs), (ii) stereochemistry at $C_2$ and $C_3$ positions of sphingoid-backbone (isomers: 2S,3R; 2S,3S; 2R,3S, and 2R,2R, (iii) saturation/desaturation of C4-C5-positions of sphingoid backbone and (iv) location and substitution of pyridine moiety, on physicochemical properties and biological activity of these newly synthesized analogs of Cer.

In another embodiment, fluorescent CCPS analog such as (2S,3R,4E)-2-N-[6'-[1"-[4"'-(N,N-dimethylaminostyryl)]-pyridinium]-hexanoyl]-sphingosine bromide (LCL-186), which contains a pyridinium ring connected to another aromatic ring via a vinyl linker, are encompassed. This combination generates fluorescence due to the presence of 10-π-electron-conjugated systems and suggests that LCL 186 can be used as advanced photonic molecules (see Klymchenko, A. S., (2003), *PNAS USA* 100(20), 11219-11224).

In various embodiments, exemplary short ($C_2$- and $C_6$) and long-chain ($C_{12}$- and $C_{16}$-) D-erythro-ω-pyridinium ceramide bromides relating to Compounds of Class A (LCL 150, LCL 29, LCL 88, and LCL 30), their representative dihydro analogs (LCL 319, LCL 143, LCL 249, and LCL 319), the remaining stereoisomers of $C_6$-homolog (LCL 124, LCL 187, and LCL 272), L-threo-diastereoisomer of $C_{16}$-homolog (LCL 87), fluorescent analog LCL-186, were synthesized. Exemplary D-erythro-analogs relating to Compounds of Class B (LCL 275 and LCL 277) were also synthesized.

The CCPS analogs have enhanced water solubility and cellular uptake, and are resistant to acid and base hydrolysis under extreme physiological conditions. Dynamic NMR studies showed that incorporation of the pyridinium moiety into the hydrophobic interface of class A of CCPSs did not change the conformational preferences in their polar interface.

TABLE 1

Solubility of Selected Ceramides and Ceramidoids in Water at 22° C. and 37° C.

| Ceramides and Ceramidoids | Solubility at 22° C. [mg/mL] ([mM]) | Solubility at 37° C. [mg/mL] ([mM]) |
| --- | --- | --- |
| C16-Cer | ND | 0.0003 (0.0005) |
| C6-Cer | ND | 0.0014 (0.0036) |
| C2-Cer | ND | 0.01 (0.029) |
| LCL-345 | 0.3 (0.42) | 1.4 (2.0) |
| LCL-30 | 0.5 (0.72) | 2.8 (4.0) |
| LCL-87 | 0.8 (1.2) | 3.6 (5.2) |
| LCL-319 | 0.9 (1.8) | 45 (90) |
| LCL-150 | 1.2 (2.4) | 82 (164) |
| LCL-275 | 62 (103) | 120 (200) |
| LCL-88* | 34 (53) | 495 (773) |
| LCL-29* | 715 (1290) | ND |
| LCL-124* | 845 (1521) | ND |

ND: Not determined due to the extremely low or high level of lipid solubility.
*These lipids form viscous solutions (glasses) at the higher concentrations as reported.

In another embodiment, the invention provides the uses of CCPS analogs to prevent or treat in a subject various conditions involving cell overproliferation or sphingolipid signal transduction, in particular, cancer. The use of these compounds as pharmaceutical compounds are described in details in section 5.5. Uses of these compounds in combination with other therapeutic agents are also contemplated. Related pharmaceutical compositions and formulations are described in details in section 5.6.

As one of the non-limiting objectives of the invention is to create a library of compounds that have tunable physico-chemical properties, the present inventors show in Section 9 that CCPS analogs accumulate in the mitochondria after entering cells. Accordingly, in one embodiment, these CCPS analogs can be used to as a targeting agent for delivery of a molecular cargo to cells, and to the mitochondria in particular. In one embodiment, the cargo is conjugated to a CCPS analog of the invention. In other embodiments, the CCPS analogs of the invention can be used as a component of micelles, cationic liposomes, or artificial membranes. The CCPS analogs can be used as a delivery vehicle for a variety of cargo molecules, such as but not limited to hydrophobic drugs, therapeutic nucleic acids, antisense molecules, RNAi molecules, etc. Accordingly, the invention provides a method for targeting a cargo molecule to mitochondria comprising forming a delivery complex of the cargo molecule with a CCPS analog of the invention, and administering the delivery complex to a subject or a cell. In an embodiment, the delivery complex comprises a CCPS analog and a cargo molecule, wherein the cargo molecule is covalently linked to the CCPS analog. In another embodiment, the delivery complex is a micelle or a liposome that comprises one or more different CCPS analogs, and a cargo molecule. Many methods well known in the art can be used to form liposomes comprising CCPS analogs, see, for example, D. D. Lasic, Liposomes in Gene Delivery, CRC Press, 1997.

In another embodiment, these compounds can be used as molecular probes to investigate signal transduction, sphingolipid metabolism, glycerolipid metabolism in organelles, such as but not limited to studies in vitro, in vivo, in cells, in isolated organelles. For example, the fluorescent analog, LCL-186, bearing N,N-dimethylaminostyryl-substituent in the pyridinium moiety was synthesized to monitor intracellular localization of this class of compounds by normal and/or confocal microscopy. Preferably, the organelle is mitochondria.

5.1. Definitions

As used herein, the term "1-pyridinium" means a group of formula:

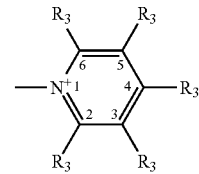

As used herein, the term "3-pyridinium" means a group of formula:

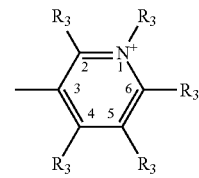

The group "2-ethenyl-(4-N,N-dimethlyamino)phenyl" has the structure:

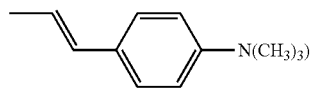

"—$(C_1-C_6)$alkyl" means a saturated straight chain or branched non-cyclic hydrocarbon having from 1 to 6 carbon atoms. Representative saturated straight chain —$(C_1-C_6)$ alkyls include -methyl, -ethyl, -n-propyl, -n-butyl, -n-pentyl, and -n-hexyl. Representative saturated branched —$(C_1-C_6)$ alkyls include -isopropyl, -sec-butyl, -isobutyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl and the like.

"—$(C_2-C_6)$alkenyl" means a straight chain or branched non-cyclic hydrocarbon having from 2 to 6 carbon atoms and including at least one carbon-carbon double bond. Representative straight chain and branched —$(C_2-C_6)$alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl and the like.

"—$(C_2-C_6)$alkynyl" means a straight chain or branched non-cyclic hydrocarbon having from 2 to 6 carbon atoms and including at lease one carbon-carbon triple bond. Representative straight chain and branched $(C_2-C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—$(C_1-C_{10})$alkyl" means a saturated straight chain or branched non-cyclic hydrocarbon having from 1 to 10 carbon atoms. Representative saturated straight chain —$(C_1-C_{10})$ alkyls include -methyl, -ethyl, -n-propyl, -n-butyl, -n-pentyl, -n-hexyl, -n-heptyl, -n-octyl, -n-nonyl, and -n-decyl. Representative saturated branched —($C_1$-$C_{10}$)alkyls include -isopropyl, -sec-butyl, -isobutyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl, -2-methylhexyl, -3-methylhexyl, -4-methylhexyl, -5-methylhexyl, -2,3-dimethylbutyl, -2,3-dimethylpentyl, -2,4-dimethylpentyl, -2,3-dimethylhexyl, -2,4-dimethylhexyl, -2,5-dimethylhexyl, -2,2-dimethylpentyl, -2,2-dimethylhexyl, -3,3-dimethylpentyl, -3,3-dimethylhexyl, -4,4-dimethylhexyl, -2-ethylpentyl, -3-ethylpentyl, -2-ethylhexyl, -3-ethylhexyl, -4-ethylhexyl, -2-methyl-2-ethylpentyl, -2-methyl-3-ethylpentyl, -2-methyl-4-ethylpentyl, -2-methyl-2-ethylhexyl, -2-methyl-3-ethylhexyl, -2-methyl-4-ethylhexyl, -2,2-diethylpentyl, -3,3-diethylhexyl, -2,2-diethylhexyl, -3,3-diethylhexyl and the like.

"—($C_2$-$C_{10}$)alkenyl" means a straight chain or branched non-cyclic hydrocarbon containing from 2 to 10 carbon atoms and including at least one carbon-carbon double bond. Representative straight chain and branched ($C_2$-$C_{10}$)alk1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

"—($C_2$-$C_{10}$)alkynyl" means a straight chain or branched non-cyclic hydrocarbon having from 2 to 10 carbon atoms and including at lease one carbon-carbon triple bond. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

"$M^-$" means a pharmaceutically acceptable counter anion. Non-limiting examples pharmaceutically acceptable counter anion useful in the present invention include -halo (e.g., $F^-$, $Cl^-$, $Br^-$, $I^-$); carboxylates such as acetate or propanoate; phosphates such as $PO_4^{3-}$, $PO_4H^{2-}$ and $PO_4H^{2-}$; $OH^-$, and the like.

5.2. The Compounds of Formula I

In one embodiment, the invention encompasses the compounds of formula I wherein:
$R_1$ is 1'-pyridinium or -3'-pyridinium;
$R_2$ is —H or —($C_1$-$C_6$)alkyl;
$R_3$ is —$CH_3$, —$CH2R_7$, —$COOR_{12}$—, —CHO—, —$CH_2OR_{12}$, —$CH_2SH$, —$CH_2NH_2$, —$CH_2N_3$, —$CH_2NH$(OH), —CH=N(OH), —CH=N($NH_2$), —$CH_2OCH_3$, —$CH_2F$, —$CH_2Cl$, —$CH_2Br$, —$CH_2OC(O)R_7$, or —$CH_2OP(O)_2OR_4$;
$R_4$ is —H; —$CH_3$, —$(CH_2)_2N((CH_3)_3$—; or -phenyl, optionally substituted with one or more $R_8$;
each $R_5$ is independently —H; —($C_1$-$C_{10}$)alkyl, —($C_2$-$C_{10}$)alkenyl, or —($C_2$-$C_{10}$)alkynyl, each of which is unsubstituted or substituted with one or more $R_9$; -halo; —OH; —$NO_2$; —C(O)OH; —C(O)$NH_2$; —C(O)$NHR_7$; —C(O)NH—OH; —$CH_2R_7$; —$OR_{10}$; —C(O)$R_{10}$; —C(O)$CF_3$; —C(O)$NR_{10}$; —C(OH)$R_{10}$; —OC(O)$R_{10}$; —C(O)$OR_{10}$; or —N($R_{10}$)$_2$;
$R_6$ is —H, —($C_1$-$C_{16}$)alkyl, —($C_2$-$C_{16}$)alkenyl, —($C_2$-$C_{16}$)alkynyl, each of which, other than —H, is unsubstituted or substituted with one or more $R_9$;

$R_7$ is -five-membered monocyclic N-, O- or S-based heterocycle; or a -six-membered monocyclic N-, O- or S-based heterocycle; each of which can be unsubstituted or substituted with one or more $R_9$;
$R_8$ is —($C_1$-$C_6$)alkyl; —C(O)$R_{10}$; -halo, —$NO_2$, —OH; —$NH_2$; —NH($R_{10}$), or —N($R_{10}$)$_2$;
$R_9$ is -halo; —OH; —C(O)($R_{10}$); —$CF_3$; —$NH_2$; —NH($R_{10}$); or —N($R_{10}$)$_2$; or -phenyl, unsubstituted or substituted with one or more —$R_8$;
$R_{10}$ is —($C_1$-$C_6$)alkyl;
$R_{11}$ is H, $R_{12}$, $COR_{12}$;
$R_{12}$ is H, —($C_1$-$C_{20}$)alkyl; —($C_2$-$C_{20}$)alkenyl, glucose or galactose;
a is an integer from 0 to 26;
b is 0 or 1;
c is 0 or 1;
d is 0 or 1;
e is 0 or 1;
f is an integer from 0 to 20;
A is —$CH_2$—, —CH(OH)—, —CH($R_7$)—, —C(O)—, —C(=NOH)—, or —C(=N—$NH_2$)—;
B is —$CH_2CH_2$—, —CH(OH)$CH_2$—, -trans-CH=CH—, —C≡C—,

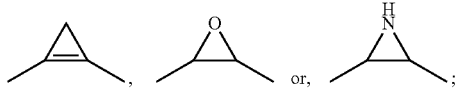

and
X is —C(O)—, —C(S)—, —CH($R_{10}$)—, —C(=NH)—, or —N(H)—;
Y is —N(H)—, —O—, —C(O)—, —CH($R_{10}$)—, —$CH_2$C(O)—, or —$CH_2$CH($R_{10}$)—; and
$M^-$ is a counter anion.
In one embodiment $R_1$ is -1'-pyridinium.
In another embodiment $R_1$ is -3'-pyridinium.
In another embodiment, $R_2$ is H, or —($C_1$-$C_6$)alkyl
In one embodiment $R_3$ is —$CH_2OH$.
In one embodiment each $R_5$ is independently —H, —($C_1$-$C_{10}$)alkyl, —($C_2$-$C_{10}$)alkenyl, or —($C_2$-$C_{10}$)alkynyl, each of which is unsubstituted or substituted with one or more $R_9$.
In another embodiment each $R_5$ is —H.
In another embodiment, one of $R_5$ is -2-ethenyl-(4-N,N-dimethlyamino)phenyl.
In another embodiment $R_1$ is -1'-4'-(2-ethenyl-(4-N,N-dimethlyamino)phenyl)-pyridinium.
In one embodiment d is 1, and A is —CH(OH)—.
In another embodiment d is 1, and A is —(R)—CH(OH)—.
In another embodiment d is 1, and A is (S)—CH(OH)—.
In one embodiment e is 1, and B is —$CH_2CH_2$—, -trans-CH=CH—, or —CH(OH)$CH_2$.
In another embodiment e is 1, and B is —$CH_2CH_2$—.
In another embodiment e is 1, and B is -trans-CH=CH—.
In another embodiment e is 1, and B is

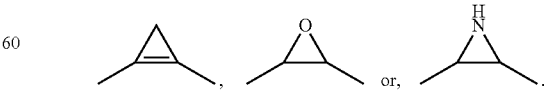

In another embodiment e is 1, and B is —CH(OH)$CH_2$.
In another embodiment e is 1, and B is —(R)—CH(OH)$CH_2$.
In another embodiment e is 1, and B is (S)—CH(OH)$CH_2$.

In another embodiment e is 1, and B is phenyl.

In another embodiment e is 1, and B is phenyl, substituted with one or more $R_8$.

In one embodiment c is 1; and X is —C(O)—, —N(H)—, or —C(=N(H))—.

In another embodiment c is 1; and X is —C(O)—.

In another embodiment c is 1; and X is —N(H)—.

In another embodiment c is 1; and X is —C(=N(H))—

In another embodiment b is 1; and Y is —CH$_2$—, —N(H)—, or a bond.

In one embodiment $R_1$ is 3-pyridinium; and $R_6$ is —H, —(C$_1$-C$_{16}$)alkyl, —(C$_2$-C$_{16}$)alkenyl, or —(C$_2$-C$_{16}$)alkynyl.

In another embodiment $R_1$ is 3-pyridinium; and $R_6$ is —H or —(C$_1$-C$_{16}$)alkyl.

In another embodiment $R_1$ is 3-pyridinium; and $R_6$ is —(C$_1$-C$_{16}$)alkyl.

In another embodiment f is an integer from 10 to 15.

In another embodiment f is 12 or 13.

In another embodiment a is an integer from 0 to 16.

In another embodiment, M- is F$^-$, Cl$^-$, Br$^-$, I$^-$, acetate, propanoate, PO$_4^{3-}$, PO$_4$H$^{2-}$, PO$_4$H$^{2-}$; or OH$^-$.

In another embodiment, M- is Br$^-$.

In one embodiment $R_1$ is -1'-pyridinium; $R_3$ is —CH$_2$OH; c is 1; d is 1; e is 1; A is —CH(OH)—; and B is —CH$_2$CH$_2$—, -trans-CH=CH—, or —CH(OH)CH$_2$.

In another embodiment $R_1$ is -1'-pyridinium; $R_3$ is —CH$_2$OH; b is 0; c is 1; d is 1; e is 1; A is —CH(OH)—; and B is —CH$_2$CH$_2$—, -trans-CH=CH—, or —CH(OH)CH$_2$; X is —C(O)—.

In another embodiment R1 is -1'-pyridinium; $R_3$ is —CH$_2$OH; each $R_5$ is —H; A is —CH(OH)—; B is -trans-CH=CH—; X is —C(O)—; b is 0; c is 1; d is 1; e is 1; f is 12; and a is 1, 5, 11 or 15.

In another embodiment $R_1$ is -1'-pyridinium; $R_2$ is —H; $R_3$ is —CH$_2$OH; $R_4$ is —CH$_3$; each $R_5$ is —H; a is 1, 5, 11 or 15; b is 0; c is 1; d is 1; e is 1; f is 12; A is —(R)—CH(OH)—; B is -trans-CH=CH—; X is —C(O)—; and carbon atom 2 of the compound of formula I is the (S)-conformer.

In another embodiment $R_1$ is -1'-pyridinium; $R_2$ is —H; $R_3$ is —CH$_2$OH; $R_4$ is —CH$_3$; each $R_5$ is —H; a is 1, 5, 11 or 15; b is 0; c is 1; d is 1; e is 1; f is 12; A is —(R)—CH(OH)—; B is -trans-CH=CH—; X is —C(O)—; and carbon atom 2 of the compound of formula I is the (R)-conformer.

In another embodiment $R_1$ is -1'-pyridinium; $R_2$ is —H; $R_3$ is —CH$_2$OH; $R_4$ is —CH$_3$; each $R_5$ is —H; a is 1, 5, 11 or 15; b is 0; c is 1; d is 1; e is 1; f is 12; A is —(S)—CH(OH)—; B is -trans-CH=CH—; X is —C(O)—; and carbon atom 2 of the compound of formula I is the (S)-conformer.

In another embodiment $R_1$ is -1'-pyridinium; $R_2$ is —H; $R_3$ is —CH$_2$OH; $R_4$ is —CH$_3$; each $R_5$ is —H; a is 1, 5, 11 or 15; b is 0; c is 1; d is 1; e is 1; f is 12; A is —(S)—CH(OH)—; B is -trans-CH=CH—; X is —C(O)—; and carbon atom 2 of the compound of formula I is the (R)-conformer.

In another embodiment $R_1$ is -1'-4'-(2-ethenyl-(4-N,N-dimethylamino)phenyl)-pyridinium; $R_2$ is —H; $R_3$ is —CH$_2$OH; $R_4$ is —CH$_3$; each $R_5$ is —H; a is 1, 5, 11 or 15; b is 0; c is 1; d is 1; e is 1; f is 12; A is —(R)—CH(OH)—; B is -trans-CH=CH—; X is —C(O)—; and carbon atom 2 of the compound of formula 1 is the (S)-conformer.

In one embodiment $R_1$ is -1'-pyridinium; $R_3$ is —CH$_2$OH; d is 1; e is 1; A is —CH(OH)—; and B is —CH$_2$CH$_2$—.

In one embodiment $R_1$ is -1'-pyridinium; $R_3$ is —CH$_2$OH; each $R_5$ is —H; b is 0; c is 1; d is 1; e is 1; A is —CH(OH)—; B is —CH$_2$CH$_2$—; and X is —C(O)—.

In another embodiment $R_1$ is -1'-pyridinium; $R_2$ is —H; $R_3$ is —CH$_2$OH; $R_4$ is —CH$_3$; each $R_5$ is —H; a is 1, 5, 11 or 16; b is 0; c is 1; d is 1; e is 1; f is 12; A is —(S)—CH(OH)—; B is —CH$_2$CH$_2$—; X is —C(O)—; and carbon atom 2 of the compound of formula 1 is the (R)-conformer.

In another embodiment $R_1$ is -1'-pyridinium; $R_2$ is —H; $R_3$ is —CH$_2$OH; $R_4$ is —CH$_3$; each $R_5$ is —H; a is 1, 5, 11 or 16; b is 0; c is 1; d is 1; e is 1; f is 12; A is —(S)—CH(OH)—; B is —CH$_2$CH$_2$—; X is —C(O)—; and carbon atom 2 of the compound of formula 1 is the (S)-conformer.

In another embodiment $R_1$ is -1'-pyridinium; $R_2$ is —H; $R_3$ is —CH$_2$OH; $R_4$ is —CH$_3$; each $R_5$ is —H; a is 1, 5, 11 or 16; b is 0; c is 1; d is 1; e is 1; f is 12; A is —(R)—CH(OH)—; B is —CH$_2$CH$_2$—; X is —C(O)—; and carbon atom 2 of the compound of formula 1 is the (S)-conformer.

In another embodiment $R_1$ is -1'-pyridinium; $R_2$ is —H; $R_3$ is —CH$_2$OH; $R_4$ is —CH$_3$; each $R_5$ is —H; a is 1, 5, 11 or 16; b is 0; c is 1; d is 1; e is 1; f is 12; A is —(R)—CH(OH)—; B is —CH$_2$CH$_2$—; X is —C(O)—; and carbon atom 2 of the compound of formula 1 is the (R)-conformer.

In one embodiment R1 is -1'-pyridinium; $R_3$ is —CH$_2$OH; each $R_5$ is —H; d is 1; e is 1; A is —CH(OH)—; and B is —CH(OH)CH$_2$—.

In another embodiment R1 is -1'-pyridinium; $R_3$ is —CH$_2$OH; each $R_5$ is —H; b is 0; c is 1; d is 1; e is 1; A is —CH(OH)—; B is —CH(OH)CH$_2$—; and X is —C(O)—.

In another embodiment R1 is -1'-pyridinium; $R_2$ is —H; $R_3$ is —CH$_2$OH; $R_4$ is —CH$_3$; each $R_5$ is —H; a is 1, 5, 11 or 12; b is 0; c is 1; d is 1; e is 1; f is 12; A is (R)—CH(OH)—; B is —CH(OH)CH$_2$—; X is —C(O)—; and carbon atom 2 of the compound of formula 1 is the (S)-conformer.

In another embodiment R1 is -1'-pyridinium; $R_2$ is —H; $R_3$ is —CH$_2$OH; $R_4$ is —CH$_3$; each $R_5$ is —H; a is 1, 5, 11 or 12; b is 0; c is 1; d is 1; e is 1; f is 12; A is (R)—CH(OH)—; B is —CH(OH)CH$_2$—; X is —C(O)—; and carbon atom 2 of the compound of formula 1 is the (R)-conformer.

In another embodiment R1 is -1'-pyridinium; $R_2$ is —H; $R_3$ is —CH$_2$OH; $R_4$ is —CH$_3$; each $R_5$ is —H; a is 1, 5, 11 or 12; b is 0; c is 1; d is 1; e is 1; f is 12; A is (S)—CH(OH)—; B is —CH(OH)CH$_2$—; X is —C(O)—; and carbon atom 2 of the compound of formula 1 is the (S)-conformer.

In another embodiment R1 is -1'-pyridinium; $R_2$ is —H; $R_3$ is —CH$_2$OH; $R_4$ is —CH$_3$; each $R_5$ is —H; a is 1, 5, 11 or 12; b is 0; c is 1; d is 1; e is 1; f is 12; A is (S)—CH(OH)—; B is —CH(OH)CH$_2$—; X is —C(O)—; and carbon atom 2 of the compound of formula 1 is the (R)-conformer.

In one embodiment $R_1$ is -3'-pyridinium; $R_3$ is —CH$_2$OH; d is 1; e is 1; A is —CH(OH)—; and B is —CH$_2$CH$_2$—, -trans-CH=CH—, or —CH(OH)CH$_2$.

In another embodiment $R_1$ is -3'-pyridinium; $R_3$ is —CH$_2$OH; each $R_5$ is —H; $R_6$ is —H or —(C$_1$-C$_{12}$)alkyl; b is 0; c is 1; d is 1; e is 1; A is —CH(OH)—; and B is —CH$_2$CH$_2$—, -trans-CH=CH—, or —CH(OH)CH$_2$; X is —C(O)—.

In another embodiment $R_1$ is -3'-pyridinium; $R_3$ is —CH$_2$OH; each $R_5$ is —H; $R_6$ is —H or —(C$_2$-C$_{10}$)alkyl; b is 0; c is 1; d is 1; e is 1; f is 12; A is —CH(OH)—; B is -trans-CH=CH—; and X is —C(O)—.

In another embodiment $R_1$ is -3'-pyridinium; $R_2$ is —H; $R_3$ is —CH$_2$OH; $R_4$ is —CH$_3$; each $R_5$ is —H; $R_6$ is —(C$_2$-C$_{10}$)alkyl; a is 0, 2, 4, 6, 12, or 16; b is 0; c is 1; d is 1; e is 1; f is 12; A is —(R)—CH(OH)—; B is -trans-CH=CH—; X is —C(O)—; and carbon atom 2 of the compound of formula I is the (S)-conformer.

In another embodiment $R_1$ is -3'-pyridinium; $R_2$ is —H; $R_3$ is —CH$_2$OH; $R_4$ is —CH$_3$; each $R_5$ is —H; $R_6$ is —(C2-C10) alkyl; a is 0, 2, 4, 6, 12, or 16; b is 0; c is 1; d is 1; e is 1; f is 12; A is —(R)—CH(OH)—; B is -trans-CH=CH—; X is —C(O)—; and carbon atom 2 of the compound of formula I is the (R)-conformer In another embodiment $R_1$ is -3'-pyridinium; $R_2$ is —H; $R_3$ is —$CH_2OH$; $R_4$ is —$CH_3$; each $R_5$ is —H; $R_6$ is —(C2-C10) alkyl; a is 0, 2, 4, 6, 12, or 16; b is 0; c is 1; d is 1; e is 1; f is 12; A is —(S)—CH(OH)—; B is -trans-CH=CH—; X is —C(O)—; and carbon atom 2 of the compound of formula I is the (S)-conformer In another embodiment $R_1$ is -3'-pyridinium; $R_2$ is —H; $R_3$ is —$CH_2OH$; $R_4$ is —$CH_3$; each $R_5$ is —H; $R_6$ is —(C2-C10) alkyl; a is 0, 2, 4, 6, 12, or 16; b is 0; c is 1; d is 1; e is 1; f is 12; A is —(S)—CH(OH)—; B is -trans-CH=CH—; X is —C(O)—; and carbon atom 2 of the compound of formula I is the (R)-conformer In one embodiment, $R_1$ is -1'-pyridinium and $R_4$ is -phenyl.

In another embodiment, $R_1$ is -1'-pyridinium; $R_3$ is —$CH_2OH$; $R_4$ is -phenyl; c is 1; and A is —CH(OH)—.

In another embodiment, $R_1$ is -1'-pyridinium; $R_2$ is —H; $R_3$ is —$CH_2OH$; $R_4$ is -phenyl; b is 0; c is 1; d is 1; e is 0; f is 0; and A is —CH(OH)—.

In another embodiment, $R_1$ is -1'-pyridinium; $R_2$ is —H; $R_3$ is —$CH_2OH$; $R_4$ is -phenyl; b is 0; c is 1; d is 1; e is 0; f is 0; and A is —CH(OH)—.

In another embodiment, $R_1$ is -1'-pyridinium; $R_2$ is —H; $R_3$ is —$CH_2OH$; $R_4$ is -phenyl; each $R_5$ is —H; a is 1, 5, 11 or 16; b is 0; c is 1; d is 1; e is 0; f is 0; A is —(S)—CH(OH)—; and carbon atom 2 of the compound of formula I is the (R)-conformer.

In another embodiment, $R_1$ is -1'-pyridinium; $R_2$ is —H; $R_3$ is —$CH_2OH$; $R_4$ is -phenyl; each $R_5$ is —H; a is 1, 5, 11 or 16; b is 0; c is 1; d is 1; e is 0; f is 0; A is —(S)—CH(OH)—; and carbon atom 2 of the compound of formula I is the (S)-conformer.

In another embodiment, $R_1$ is -1'-pyridinium; $R_2$ is —H; $R_3$ is —$CH_2OH$; $R_4$ is -phenyl; each $R_5$ is —H; a is 1, 5, 11 or 16; b is 0; c is 1; d is 1; e is 0; f is 0; A is —(R)—CH(OH)—; and carbon atom 2 of the compound of formula I is the (R)-conformer.

In another embodiment, $R_1$ is -1'-pyridinium; $R_2$ is —H; $R_3$ is —$CH_2OH$; $R_4$ is -phenyl; each $R_5$ is —H; a is 1, 5, 11 or 16; b is 0; c is 1; d is 1; e is 0; f is 0; A is —(R)—CH(OH)—; and carbon atom 2 of the compound of formula I is the (R)-conformer.

In one embodiment $R_1$ is -1'-pyridinium; $R_2$ is —$CH_2OH$; b is 1; c is 1; d is 1; e is 1; A is —CH(OH)—; B is —$CH_2CH_2$—, -trans-CH=CH—, or —$CH(OH)CH_2$; X is —C(O)—; and Y is —N(H)—.

In another embodiment $R_1$ is -1'-pyridinium; $R_3$ is —$CH_2OH$; each $R_5$ is —H; a is 2, 6, 12 or 16; b is 1; c is 1; d is 1; e is 1; f is 12; A is —CH(OH)—; B is -trans-CH=CH—; X is —C(O)—; and Y is —N(H)—.

In another embodiment $R_1$ is -1'-pyridinium; $R_2$ is —H; $R_3$ is —$CH_2OH$; $R_4$ is —$CH_3$; each $R_5$ is —H; a is 2, 6, 12 or 16; b is 1; c is 1; d is 1; e is 1; f is 12; A is —(S)—CH(OH)—; B is -trans-CH=CH—; X is —C(O)—; Y is —N(H)—; and carbon atom 2 of the compound of formula 1 is the (R)-conformer.

In another embodiment $R_1$ is -1'-pyridinium; $R_2$ is —H; $R_3$ is —$CH_2OH$; $R_4$ is —$CH_3$; each $R_5$ is —H; a is 2, 6, 12 or 16; b is 1; c is 1; d is 1; e is 1; f is 12; A is —(S)—CH(OH)—; B is -trans-CH=CH—; X is —C(O)—; Y is —N(H)—; and carbon atom 2 of the compound of formula 1 is the (S)-conformer.

In another embodiment $R_1$ is -1'-pyridinium; $R_2$ is —H; $R_3$ is —$CH_2OH$; $R_4$ is —$CH_3$; each $R_5$ is —H; a is 2, 6, 12 or 16; b is 1; c is 1; d is 1; e is 1; f is 12; A is —(R)—CH(OH)—; B is -trans-CH=CH—; X is —C(O)—; Y is —N(H)—; and carbon atom 2 of the compound of formula 1 is the (R)-conformer.

In another embodiment $R_1$ is -1'-pyridinium; $R_2$ is —H; $R_3$ is —$CH_2OH$; $R_4$ is —$CH_3$; each $R_5$ is —H; a is 2, 6, 12 or 16; b is 1; c is 1; d is 1; e is 1; f is 12; A is —(R)—CH(OH)—; B is -trans-CH=CH—; X is —C(O)—; Y is —N(H)—; and carbon atom 2 of the compound of formula 1 is the (S)-conformer.

In one embodiment $R_1$ is -1'-pyridinium; $R_3$ is —$CH_2OH$; c is 1; d is 1; e is 1; A is —CH(OH)—; B is —$CH_2CH_2$—, -trans-CH=CH—, or —$CH(OH)CH_2$; X is —C(=N(H))—; Y is —N(H)—.

In another embodiment $R_1$ is -1'-pyridinium; $R_3$ is —$CH_2OH$; each $R_5$ is —H; a is 2, 6, 12 or 16; c is 1; d is 1; e is 1; f is 12; A is —CH(OH)—; B is -trans-CH=CH—; X is —C(=N(H))—; Y is —N(H)—.

In another embodiment $R_1$ is -1'-pyridinium; $R_2$ is —H; $R_3$ is —$CH_2OH$; $R_4$ is —$CH_3$; each $R_5$ is —H; a is 2, 6, 12 or 16; c is 1; d is 1; e is 1; f is 12; A is —(S)—CH(OH)—; B is -trans-CH=CH—; X is —C(=N(H))—; Y is —N(H)—; and carbon atom 2 of the compound of formula 1 is the (S)-conformer.

In another embodiment $R_1$ is -1'-pyridinium; $R_2$ is —H; $R_3$ is —$CH_2OH$; $R_4$ is —$CH_3$; each $R_5$ is —H; a is 2, 6, 12 or 16; c is 1; d is 1; e is 1; f is 12; A is —(S)—CH(OH)—; B is -trans-CH=CH—; X is —C(=N(H))—; Y is —N(H)—; and carbon atom 2 of the compound of formula 1 is the (R)-conformer In another embodiment $R_1$ is -1'-pyridinium; $R_2$ is —H; $R_3$ is —$CH_2OH$; $R_4$ is —$CH_3$; each $R_5$ is —H; a is 2, 6, 12 or 16; c is 1; d is 1; e is 1; f is 12; A is —(R)—CH(OH)—; B is -trans-CH=CH—; X is —C(=N(H))—; Y is —N(H)—; and carbon atom 2 of the compound of formula 1 is the (S)-conformer.

In another embodiment $R_1$ is -1'-pyridinium; $R_2$ is —H; $R_3$ is —$CH_2OH$; $R_4$ is —$CH_3$; each $R_5$ is —H; a is 2, 6, 12 or 16; c is 1; d is 1; e is 1; f is 12; A is —(R)—CH(OH)—; B is -trans-CH=CH—; X is —C(=N(H))—; Y is —N(H)—; and carbon atom 2 of the compound of formula 1 is the (R)-conformer.

In one embodiment $R_1$ is -1'-pyridinium; $R_3$ is —$CH_2OH$; b is 0; c is 0; A is —CH(OH)—; and B is —$CH_2CH_2$—, -trans-CH=CH—, or —$CH(OH)CH_2$.

In another embodiment $R_1$ is -1'-pyridinium; $R_3$ is —$CH_2OH$; each $R_5$ is —H; a is, 2, 6, 12, or 16; b is 0; c is 0; f is 12; A is —CH(OH)—; and B is -trans-CH=CH—.

In another embodiment $R_1$ is -1'-pyridinium; $R_2$ is —H; $R_3$ is —$CH_2OH$; $R_4$ is —CH3; each $R_5$ is —H; a is, 2, 6, 12, or 16; b is 0; c is 0; f is 12; A is —(R)—CH(OH)—; B is -trans-CH=CH—; and carbon atom 2 of the compound of formula 1 is the (S)-conformer.

In another embodiment $R_1$ is -1'-pyridinium; $R_2$ is —H; $R_3$ is —$CH_2OH$; $R_4$ is —CH3; each $R_5$ is —H; a is, 2, 6, 12, or 16; b is 0; c is 0; f is 12; A is —(R)—CH(OH)—; B is -trans-CH=CH—; and carbon atom 2 of the compound of formula 1 is the (R)-conformer.

In another embodiment $R_1$ is -1'-pyridinium; $R_2$ is —H; $R_3$ is —$CH_2OH$; $R_4$ is —CH3; each $R_5$ is —H; a is, 2, 6, 12, or 16; b is 0; c is 0; f is 12; A is —(S)—CH(OH)—; B is -trans-CH=CH—; and carbon atom 2 of the compound of formula 1 is the (S)-conformer.

In another embodiment $R_1$ is -1'-pyridinium; $R_2$ is —H; $R_3$ is —$CH_2OH$; $R_4$ is —CH3; each $R_5$ is —H; a is, 2, 6, 12, or 16; b is 0; c is 0; f is 12; A is —(S)—CH(OH)—; B is -trans-CH=CH—; and carbon atom 2 of the compound of formula 1 is the (R)-conformer.

In one embodiment $R_1$ is -1'-pyridinium; and $R_3$ is —CH(OH)($C_6H_5$).

In another embodiment R$_1$ is -1'-pyridinium; R$_3$ is —CH(OH)(C$_6$H$_5$); d is 0; e is 0; and f is 0.

In another embodiment R$_1$ is -1'-pyridinium; R$_2$ is —H; R$_3$ is —(S)—CH(OH)(C$_6$H$_5$); R$_4$ is —H; each R$_5$ is —H; a is 1, 5, 11, or 15; d is 0; e is 0; f is 0; and carbon atom 2 of the compound of formula 1 is the (S)-conformer.

In another embodiment R$_1$ is -1'-pyridinium; R$_2$ is —H; R$_3$ is —(S)—CH(OH)(C$_6$H$_5$); R$_4$ is —H; each R$_5$ is —H; a is 1, 5, 11, or 15; d is 0; e is 0; f is 0; and carbon atom 2 of the compound of formula 1 is the (R)-conformer.

In another embodiment R$_1$ is -1'-pyridinium; R$_2$ is —H; R$_3$ is —(R)—CH(OH)(C$_6$H$_5$); R$_4$ is —H; each R$_5$ is —H; a is 1, 5, 11, or 15; d is 0; e is 0; f is 0; and carbon atom 2 of the compound of formula 1 is the (S)-conformer.

In another embodiment R$_1$ is -1'-pyridinium; R$_2$ is —H; R$_3$ is —(R)—CH(OH)(C$_6$H$_5$); R$_4$ is —H; each R$_5$ is —H; a is 1, 5, 11, or 15; d is 0; e is 0; f is 0; and carbon atom 2 of the compound of formula 1 is the (R)-conformer.

In another embodiment R$_1$ is -1'-pyridinium; R$_3$ is —CH(OH)(C$_6$H$_4$R$_8$); and R$_4$ is —H; d is 0; e is 0; and f is 0.

In another embodiment R$_1$ is -1'-pyridinium; R$_3$ is —CH(OH)(4-NO$_2$—C$_6$H$_4$); and R$_4$ is —H; d is 0; e is 0; and f is 0.

In another embodiment R$_1$ is -1'-pyridinium; R$_2$ is —H; R$_3$ is —(S)—CH(OH)(4-NO$_2$—C$_6$H$_4$); R$_4$ is —H; each R$_5$ is —H; a is 1, 5, 11, or 15; d is 0; e is 0; f is 0; and carbon atom 2 of the compound of formula 1 is the (R)-conformer.

In another embodiment R$_1$ is -1'-pyridinium; R$_2$ is —H; R$_3$ is —(S)—CH(OH)(4-NO$_2$—C$_6$H$_4$); R$_4$ is —H; each R$_5$ is —H; a is 1, 5, 11, or 15; d is 0; e is 0; f is 0; and carbon atom 2 of the compound of formula 1 is the (S)-conformer.

In another embodiment R$_1$ is -1'-pyridinium; R$_2$ is —H; R$_3$ is —(R)—CH(OH)(4-NO$_2$—C$_6$H$_4$); R$_4$ is —H; each R$_5$ is —H; a is 1, 5, 11, or 15; d is 0; e is 0; f is 0; and carbon atom 2 of the compound of formula 1 is the (R)-conformer.

In another embodiment R$_1$ is -1'-pyridinium; R$_2$ is —H; R$_3$ is —(R)—CH(OH)(4-NO$_2$—C$_6$H$_4$); R$_4$ is —H; each R$_5$ is —H; a is 1, 5, 11, or 15; d is 0; e is 0; f is 0; and carbon atom 2 of the compound of formula 1 is the (S)-conformer.

Illustrative Compounds of Formula I are Listed Below:

(2S,3R,4E)-2-N-[1-(1'-pyridinium)-acetyl]-sphingosine bromide (LCL 150);
(2S,3R,4E)-2-N-[6'-(1"-pyridinium)-hexanoyl]-sphingosine bromide (LCL 29);
(2S,3R,4E)-2-N-[12'-(1"-pyridinium)-dodecanoyl]-sphingosine bromide (LCL 88);
(2S,3R,4E)-2-N-[16'-(1"-pyridinium)-hexadecanoyl]-sphingosine bromide (LCL 30);
(2S,3S,4E)-2-N-[16'-(1"-pyridinium)-tetadecanoyl]-sphingosine bromide;
(2R,3R,4E)-2-N-[16'-(1"-pyridinium)-tetadecanoyl]-sphingosine bromide;
(2R,3R,4E)-2-N-[1-(1'-pyridinium)-acetyl]-sphingosine bromide;
(2R,3R,4E)-2-N-[6'-(1"-pyridinium)-hexanoyl]-sphingosine bromide (LCL 272);
(2R,3R,4E)-2-N-[12'-(1"-pyridinium)-dodecanoyl]-sphingosine bromide;
(2R,3R,4E)-2-N-[16'-(1"-pyridinium)-hexadecanoyl]-sphingosine bromide;
(2S,3S,4E)-2-N-[1'-(6"-pyridinium)-acetyl]-sphingosine bromide;
(2S,3S,4E)-2-N-[6'-(1"-pyridinium)-hexanoyl]-sphingosine bromide (LCL 124);
(2S,3S,4E)-2-N-[12'-(1"-pyridinium)-dodecanoyl]-sphingosine bromide;
(2S,3S,4E)-2-N-[16'-(1"-pyridinium)-hexadecanoyl]-sphingosine bromide (LCL 87).
(2R,3S,4E)-2-N-[1'-(6"-pyridinium)-acetyl]-sphingosine bromide;
(2R,3S,4E)-2-N-[6'-(1"-pyridinium)-hexanoyl]-sphingosine bromide; (LCL187)
(2R,3S,4E)-2-N-[12'-(1"-pyridinium)-dodecanoyl]-sphingosine bromide
(2R,3S,4E)-2-N-[16'-(1"-pyridinium)-hexadecanoyl]-sphingosine bromide;
(2S,3R,4E)-2-N-[1-[1'-(N,N-dimethylaminostyryl)]-pyridinium]-acetyl]-sphingosine bromide;
(2S,3R,4E)-2-N-[6'-[1"-[4'"-(N,N-dimethylaminostyryl)]-pyridinium]-hexanoyl]-sphingosine bromide (LCL 186);
(2S,3R,4E)-2N-[12'-[1"-[4'"-(N,N-dimethylaminostyryl)]-pyridinium]-dodecanoyl]-sphingosine bromide;
(2S,3R,4E)-2-N-[16'-[1"-[4'"-(N,N-dimethylaminostyryl)]-pyridinium]-hexadecanoyl]-sphingosine bromide;
(2S,3R)-2-N-(1'-[1"-pyridinium)-acetyl]-4,5-dihydrosphingosine bromide (LCL 319);
(2S,3R)-2-N-[6'-(1"-pyridinium)-hexanoyl]-4,5-dihydrosphingosine bromide (LCL 143);
(2S,3R)-2-N-[12'-(1"-pyridinium)-dodecanoyl]-4,5-dihydrosphingosine bromide (LCL 249);
(2S,3R)-2-N-[12'-(1"-pyridinium)-tetracanoyl]-4,5-dihydrosphingosine bromide;
(2R,3R)-2-N-[12'-(1"-pyridinium)-tetracanoyl]-4,5-dihydrosphingosine bromide;
(2S,3S)-2-N-[12'-(1"-pyridinium)-tetracanoyl]-4,5-dihydrosphingosine bromide;
(2R,3S)-2-N-[12'-(1"-pyridinium)-tetracanoyl]-4,5-dihydrosphingosine bromide;
(2S,3R)-2-N-[16'-(1"-pyridinium)-hexadecanoyl]-4,5-dihydrosphingosine bromide (LCL 345);
(2S,3S)-2-N-[1'-(1"-pyridinium)-acetyl]-4,5-dihydrosphingosine bromide;
(2S,3S)-2-N-[6'-(1"-pyridinium)-hexanoyl]-4,5-dihydrosphingosine bromide;
(2S,3S)-2-N-[12'-(1"-pyridinium)-dodecanoyl]-4,5-dihydrosphingosine bromide;
(2S,3S)-2-N-[16'-(1"-pyridinium)-hexadecanoyl]-4,5-dihydrosphingosine bromide;
(2S,3S,4R)-2-N-[1'-(1"-pyridinium)-acetyl]-4-hydroxy-4,5-dihydrosphingosine bromide;
(2S,3S,4R)-2-N-[6'-(1"-pyridinium)-hexanoyl]-4-hydroxy-4,5-dihydrosphingosine bromide;
(2S,3S,4R)-2-N-[12'-(1"-pyridinium)-dodecanoyl]-4-hydroxy-4,5-dihydrosphingosine bromide;
(2S,3S,4R)-2-N-[16'-(1"-pyridinium)-hexadecanoyl]-4-hydroxy-4,5-dihydrosphingosine bromide;
(2S,3R,4R)-2-N-[1'-(1"-pyridinium)-acetyl]-4-hydroxy-4,5-dihydrosphingosine bromide;
(2S,3R,4R)-2-N-[6'-(1"-pyridinium)-hexanoyl]-4-hydroxy-4,5-dihydrosphingosine bromide;
(2S,3R,4R)-2-N-[12'-(1"-pyridinium)-dodecanoyl]-4-hydroxy-4,5-dihydrosphingosine bromide;
(2S,3R,4R)-2-N-[16'-(1"-pyridinium)-hexadecanoyl]-4-hydroxy-4,5-dihydrosphingosine bromide;
(1R,2R) 2-N-(16-(1'-Pyridinium)-hexadecanoyl)-1-(4-NO$_2$-phenyl-1,3-dihydroxy-propane bromide;
(1S,2S)-2-N-[1'-(1"-pyridinium)-acetyl]-1-phenyl-1,3-propanediol bromide;
(1S,2S)-2-N-[6'-(1"-pyridinium)-hexanoyl]-1-phenyl-1,3-propanediol bromide;
(1S,2S)-2-N-[12'-(1"-pyridinium)-dodecanoyl]-1-phenyl-1,3-propanediol bromide;

(1S,2S)-2-N-[16'-(1"-pyridinium)-tetradecanoyl]-1-phenyl-1,3-propanediol bromide;
(1S,2R)-2-N-[1'-(1"-pyridinium)-acetyl]-1-phenyl-1,3-propanediol bromide;
(1S,2R)-2-N-[6'-(1"-pyridinium)-hexanoyl]-1-phenyl-1,3-propanediol bromide;
(1S,2R)-2-N-[12'-(1"-pyridinium)-dodecanoyl]-1-phenyl-1,3-propanediol bromide;
(1S,2R)-2-N-[16'-(1"-pyridinium)-hexadecanoyl]-1-phenyl-1,3-propanediol bromide;
(1S,2R)-2-N-[1'-(1"-pyridinium)-acetyl]-1-phenyl-1-propanol bromide;
(1S,2R)-2-N-[6'-(1"-pyridinium)-hexanoyl]-1-phenyl-1-propanol bromide;
(1S,2R)-2-N-[12'-(1"-pyridinium)-dodecanoyl]-1-phenyl-1-propanol bromide;
(1S,2R)-2-N-[14'-(1"-pyridinium)-tetradecanoyl]-1-phenyl-1-propanol bromide;
(1S,2R)-2-N-[16'-(1"-pyridinium)-hexadecanoyl]-1-phenyl-1-propanol bromide (LCL 120);
(1S,2S)-2-N-[1'-(1"-pyridinium)-acetyl]-1-phenyl-1-propanol bromide;
(1S,2S)-2-N-[6'-(1"-pyridinium)-hexanoyl]-1-phenyl-1-propanol bromide;
(1S,2S)-2-N-[12'-(1"-pyridinium)-dodecanoyl]-1-phenyl-1-propanol bromide;
(1S,2S)-2-N-[16'-(1"-pyridinium)-hexadecanoyl]-1-phenyl-1-propanol bromide;
(1R,2S)-2-N-[1'-(1"-pyridinium)-acetyl]-1-phenyl-1-propanol bromide;
(1R,2S)-2-N-[6'-(1"-pyridinium)-hexanoyl]-1-phenyl-1-propanol bromide;
(1R,2S)-2-N-[12'-(1"-pyridinium)-dodecanoyl]-1-phenyl-1-propanol bromide;
(1R,2S)-2-N-[16'-(1"-pyridinium)-hexadecanoyl]-1-phenyl-1-propanol bromide;
(1R,2R)-2-N-[1'-(1"-pyridinium)-acetyl]-1-phenyl-1-propanol bromide;
(1R,2R)-2-N-[6'-(1"-pyridinium)-hexanoyl]-1-phenyl-1-propanol bromide;
(1R,2R)-2-N-[12'-(1"-pyridinium)-dodecanoyl]-1-phenyl-1-propanol bromide;
(1R,2R)-2-N-[16'-(1"-pyridinium)-hexadecanoyl]-1-phenyl-1-propanol bromide;
(1S,2S)-2-N-[1'-(1"-pyridinium)-acetylamino]-1-(4'''-nitrophenyl)-1,3-propanediol bromide;
(1S,2S)-2-N-[6'-(1"-pyridinium)-hexanoylamino]-1-(4'''-nitrophenyl)-1,3-propanediol bromide;
(1S,2S)-2-N-[12'-(1"-pyridinium)-dodecanoylamine]-1-(4'''-nitrophenyl)-1,3-propanediol bromide;
(1S,2S)-2-N-[16'-(1"-pyridinium)-hexadecanoyl]-1-(4'''-nitrophenyl)-1,3-propanediol bromide;
(1S,2R)-2-N-[1'-(1"-pyridinium)-acetylamino]-1-(4'''-nitrophenyl)-1,3-propanediol bromide;
(1S,2R)-2-N-[6'-(1"-pyridinium)-hexanoylamino]-1-(4'''-nitrophenyl)-1,3-propanediol bromide;
(1S,2R)-2-N-[12'-(1"-pyridinium)-dodecanoylamine]-1-(4'''-nitrophenyl)-1,3-propanediol bromide;
(1S,2R)-2-N-[16'-(1"-pyridinium)-hexadecanoyl]-1-(4'''-nitrophenyl)-1,3-propanediol bromide;
(1R,2S)-2-N-[1'-(1"-pyridinium)-acetylamino]-1-(4'''-nitrophenyl)-1,3-propanediol bromide;
(1R,2S)-2-N-[6'-(1"-pyridinium)-hexanoylamino]-1-(4'''-nitrophenyl)-1,3-propanediol bromide;
(1R,2S)-2-N-[12'-(1"-pyridinium)-dodecanoylamine]-1-(4'''-nitrophenyl)-1,3-propanediol bromide;
(1R,2S)-2-N-[16'-(1"-pyridinium)-hexadecanoyl]-1-(4'''-nitrophenyl)-1,3-propanediol bromide.
(1R,2R)-2-N-[1'-(1"-pyridinium)-acetylamino]-1-(4'''-nitrophenyl)-1,3-propanediol bromide;
(1R,2R)-2-N-[6'-(1"-pyridinium)-hexanoylamino]-1-(4'''-nitrophenyl)-1,3-propanediol bromide;
(1R,2R)-2-N-[12'-(1"-pyridinium)-dodecanoylamine]-1-(4'''-nitrophenyl)-1,3-propanediol bromide;
(1R,2R)-2-N-[16'-(1"-pyridinium)-hexadecanoyl]-1-(4'''-nitrophenyl)-1,3-propanediol bromide (LCL 85);
(1S,2S)-2-N-[1'-(1"-pyridinium)-acetylamino]-1-(4'''-phenyl)-1,3-propanediol bromide;
(1S,2S)-2-N-[6'-(1"-pyridinium)-hexanoylamino]-1-(4'''-phenyl)-1,3-propanediol bromide;
(1S,2S)-2-N-[12'-(1"-pyridinium)-dodecanoylamine]-1-(4'''-phenyl)-1,3-propanediol bromide;
(1S,2S)-2-N-[16'-(1"-pyridinium)-hexadecanoyl]-1-(4'''-phenyl)-1,3-propanediol bromide;
(1S,2R)-2-N-[1'-(1"-pyridinium)-acetylamino]-1-(4'''-phenyl)-1,3-propanediol bromide;
(1S,2R)-2-N-[6'-(1"-pyridinium)-hexanoylamino]-1-(4'''-phenyl)-1,3-propanediol bromide;
(1S,2R)-2-N-[12'-(1"-pyridinium)-dodecanoylamine]-1-(4'''-phenyl)-1,3-propanediol bromide;
(1S,2R)-2-N-[16'-(1"-pyridinium)-hexadecanoyl]-1-(4'''-phenyl)-1,3-propanediol bromide;
(1R,2S)-2-N-[1'-(1"-pyridinium)-acetylamino]-1-(4'''-phenyl)-1,3-propanediol bromide;
(1R,2S)-2-N-[6'-(1"-pyridinium)-hexanoylamino]-1-(4'''-phenyl)-1,3-propanediol bromide;
(1R,2S)-2-N-[12'-(1"-pyridinium)-dodecanoylamine]-1-(4'''-phenyl)-1,3-propanediol bromide;
(1R,2S)-2-N-[16'-(1"-pyridinium)-hexadecanoyl]-1-(4'''-phenyl)-1,3-propanediol bromide.
(1R,2R)-2-N-[1'-(1"-pyridinium)-acetylamino]-1-(4'''-phenyl)-1,3-propanediol bromide;
(1R,2R)-2-N-[6'-(1"-pyridinium)-hexanoylamino]-1-(4'''-phenyl)-1,3-propanediol bromide;
(1R,2R)-2-N-[12'-(1"-pyridinium)-dodecanoylamine]-1-(4'''-phenyl)-1,3-propanediol bromide;
(R)-2-N-[16'-(1"-pyridinium)-hexadecanoyl]-3-phenyl-1-propanol bromide; (S)-2-N-[16'-(1"-pyridinium)-tetradecanoyl]-3-phenyl)-1-propanol bromide; (R)-2-N-[16'-(1"-pyridinium)-dodecanoyl]-3-phenyl)-1-propanol bromide; (S)-2-N-[16'-(1"-pyridinium)-hexadecanoyl]-3-phenyl)-1-propanol bromide; (R)-2-N-[16'-(1"-pyridinium)-tetradecanoyl]-3-phenyl)-1-propanol bromide; (S)-2-N-[16'-(1"-pyridinium)-dodecanoyl]-3-phenyl)-1-propanol bromide;
(2S,3R,4E)-2-N-(1'-octylnicotinoyl)-sphingosine bromide (LCL 275);
(2S,3R,4E)-2-N-[3'-(1"-butyl pyridinium)-propanoyl]-sphingosine bromide;
(2S,3S,4E)-2-N-(1'-octylnicotinoyl)-sphingosine bromide;
(2S,3S,4E)-2-N-[3'-(1"-butyl pyridinium)-propanoyl]-sphingosine bromide;
(2S,3R,4E)-2-N-[1'-(1"-pyridinium)-N-ethylformamide]-sphingosine bromide;
(2S,3R,4E)-2-N-[6'-(1"-pyridinium)-N'-hexylformamide]-sphingosine bromide;
(2S,3R,4E)-2-N-[12'-(1"-pyridinium)-N'-dodecylformamide]-sphingosine bromide;
(2S,3R,4E)-2-N-[16'-(1"-pyridinium)-N'-hexadecylformamide]-sphingosine bromide;
(2S,3S,4E)-2-N-[1'-(1"-pyridinium)-N'ethylformamide]-sphingosine bromide;

(2S,3S,4E)-2-N-[6'-(1"-pyridinium)-N'-hexylformamide]-sphingosine bromide;
(2S,3S,4E)-2-N-[12'-(1"-pyridinium)-N'-dodecylformamide]-sphingosine bromide;
(2S,3S,4E)-2-N-[16'-(1"-pyridinium)-N'-hexadecylformamide]-sphingosine bromide;
(2S,3R,4E)-2-N-[1'-(1"-pyridinium)-N'-ethylformamide-imine]-sphingosine bromide;
(2S,3R,4E)-2-N-[6'-(1"-pyridinium)-N'-hexylformamide-imine]-sphingosine bromide;
(2S,3R,4E)-2-N-[12'-(1"-pyridinium)-N'-dodecylformamideimine-sphingosine bromide;
(2S,3R,4E)-2-N-[16'-(1"-pyridinium)-N-hexadecylformamideimine-sphingosine bromide;
(2S,3S,4E)-2-N-[6'-(1"-pyridinium)-N'-hexylformamide-imine]-sphingosine bromide;
(2S,3S,4E)-2-N-[12'-(1"-pyridinium)-N'-dodecylformamideimine-sphingosine bromide;
(2S,3S,4E)-2-N-[16'-(1"-pyridinium)-N-hexadecylformamideimine-sphingosine bromide.
(2S,3R,4E)-2-N-[1'-(1"-pyridinium)-acetyl]-sphingosine bromide;
(2S,3R,4E)-2-N-[6'-(1"-pyridinium)-hexyl]-sphingosine bromide;
(2S,3R,4E)-2-N-[12'-(1"-pyridinium)-dodecyl]-sphingosine bromide;
(2S,3R,4E)-2-N-[16'-(1"-pyridinium)-hexadecyl]-sphingosine bromide;
(2S,3S,4E)-2-N-[1'-(1"-pyridinium)-acetyl]-sphingosine bromide;
(2S,3S,4E)-2-N-[6'-(1"-pyridinium)-hexyl]-sphingosine bromide;
(2S,3S,4E)-2-N-[12'-(1"-pyridinium)-dodecyl]-sphingosine bromide; and
(2S,3S,4E)-2-N-[16'-(1"-pyridinium)-hexadecyl]-sphingosine bromide.

5.3. The Compounds of Formula II

The present invention also encompasses the compounds of formula II wherein:
$R_1$ is -1'-pyridinium or -3'-pyridinium;
$R_2$ is —H or —($C_1$-$C_6$)alkyl;
$R_3$ is —$CH_3$, —$CH_2R_7$, —$COOR_{12}$—, —CHO—, —$CH_2OR_{12}$—, —$CH_2SH$, —$CH_2NH_2$, —$CH_2N_3$, —$CH_2NH(OH)$, —CH=(OH), —CH=N($NH_2$), —$CH_2OCH_3$, —$CH_2F$, —$CH_2Cl$, —$CH_2Br$, —$CH_2OC(O)R_7$, or —$CH_2OP(O)_2OR_4$;
$R_4$ is —H, —$CH_3$, —($CH_2$)$_2$N(($CH_3$)$_3$)—, or -phenyl, optionally substituted with one or more $R_8$;
each $R_5$ is independently —H; —($C_1$-$C_{10}$)alkyl, —($C_2$-$C_{10}$)alkenyl, or —($C_2$-$C_{10}$)alkynyl, each of which is unsubstituted or substituted with one or more $R_9$; -halo; —OH; —$NO_2$; —C(O)OH; —C(O)$NH_2$; —C(O)$NHR_7$; —C(O)—NH—OH—$CH_2R_7$; —$OR_{10}$; —C(O)$R_{10}$; —C(O)$CF_3$; —C(O)$NR_{10}$; —C(OH)$R_{10}$; —OC(O)$R_{10}$; —C(O)$OR_{10}$; or —N($R_{10}$)$_2$;
$R_6$ is —H, —($C_1$-$C_{16}$)alkyl, —($C_2$-$C_{16}$)alkenyl, —($C_2$-$C_{16}$)alkynyl, each of which, other than —H, is unsubstituted or substituted with one or more $R_9$;
$R_7$ is -five-membered monocyclic N-, O- or S-based heterocycle; or a -six-membered monocyclic N-, O- or S-based heterocycle; each of which can be unsubstituted or substituted with one or more $R_9$;
$R_8$ is —($C_1$-$C_6$)alkyl; —C(O)$R_{10}$; -halo, —$NO_2$, —OH; —$NH_2$; —NH($R_{10}$), or —N($R_{10}$)$_2$;
$R_9$ is -halo; —OH; —C(O)($R_{10}$); —$CF_3$; —$NH_2$; —NH($R_{10}$); or —N($R_{10}$)$_2$; or -phenyl, unsubstituted or substituted with one or more —$R_8$;
$R_{10}$ is —($C_1$-$C_6$)alkyl;
$R_{11}$ is H, $R_{12}$, $COR_{12}$;
$R_{12}$ is H, ($C_1$-$C_{20}$)alkyl, —($C_2$-$C_{20}$)alkenyl, glucose or galactose;
a is an integer from 0 to 26;
b is 0 or 1;
c is 0 or 1;
d is 0 or 1;
e is 0 or 1;
f is an integer from 0 to 20;
A is —$CH_2$—, —CH(OH)—, —CH($R_7$)—, —C(O)—, —C(=NOH)—, or —C(=N—$NH_2$)—;
B is —$CH_2CH_2$—, —CH(OH)$CH_2$—, -trans-CH=CH—, —C≡CH—,

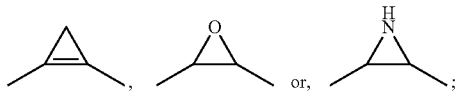

and
X is —C(O)—, —C(S)—, —CH($R_{10}$)—, —C(=NH)—, or —N(H)—;
Y is —N(H)—, —O—, —C(O)—, —CH($R_{10}$)—, —$CH_2$C(O)—, or —$CH_2$CH($R_{10}$)—; and
$M^-$ is a counter anion.

In one embodiment $R_1$ is -1'-pyridinium.
In another embodiment $R_1$ is -3'-pyridinium.
In one embodiment $R_3$ is —$CH_2OH$.
In one embodiment each $R_5$ is independently —H, —($C_1$-$C_{10}$)alkyl, —($C_2$-$C_{10}$)alkenyl, or —($C_2$-$C_{10}$)alkynyl, each of which is unsubstituted or substituted with one or more R6.
In another embodiment each $R_5$ is —H.
In another embodiment, each $R_5$ is independently —H, —($C_1$-$C_{10}$)alkyl, —($C_2$-$C_{10}$)alkenyl, or —($C_2$-$C_{10}$)alkynyl, each of which, other than —H, substituted with one or more $R_6$.
In another embodiment, one of $R_5$ is -2-ethenyl-(4-N,N-dimethlyamino)phenyl.
In another embodiment $R_1$ is -1'-4'-(2-ethenyl-(4-N,N-dimethylamino)phenyl)-pyridinium.
In one embodiment d is 1, and A is —CH(OH)—.
In another embodiment d is 1, A is —(R)—CH(OH)—.
In another embodiment d is 1, A is —(S)—CH(OH)—.
In one embodiment e is 1; and B is —$CH_2CH_2$—, -trans-CH=CH—, or —CH(OH)$CH_2$.
In another embodiment e is 1; and B is —$CH_2CH_2$—.
In another embodiment e is 1; and B is -trans-CH=CH—.
In another embodiment e is 1; and B is —CH(OH)$CH_2$.
In another embodiment e is 1; and B is (R)—CH(OH)$CH_2$.
In another embodiment e is 1; and B is (S)—CH(OH)$CH_2$.
In one embodiment c is 1; and X is —C(O)—, —N(H)—, or —C(=N(H))—.
In another embodiment c is 1; and X is —C(O)—.
In another embodiment c is 1; and X is —N(H)—.
In another embodiment c is 1; and X is —C(=N(H))—
In another embodiment b is 1; and Y is —$CH_2$—, —N(H)—, or a bond.
In one embodiment $R_1$ is -3-pyridinium; and $R_6$ is —H, —($C_1$-$C_{16}$)alkyl, —($C_2$-$C_{16}$)alkenyl, or —($C_2$-$C_{16}$)alkynyl.
In another embodiment $R_1$ is -3-pyridinium; and $R_6$ is —H or —($C_1$-$C_{16}$)alkyl.

In another embodiment $R_1$ is -3-pyridinium; and $R_6$ is —($C_1$-$C_{16}$)alkyl.

In another embodiment f is an integer from 10 to 15.

In another embodiment f is 12 or 13.

In another embodiment a is an integer from 0 to 16.

In another embodiment, $M^-$ is $F^-$, $Cl^-$, $Br^-$, $I^-$, acetate, propanoate, $PO_4^{3-}$, $PO_4H^{2-}$, $PO_4H^{2-}$; or $OH^-$.

In another embodiment, $M^-$ is $Br^-$.

In one embodiment $R_1$ is -1'-pyridinium; $R_3$ is —$CH_2OH$; d is 1; e is 1; A is —CH(OH)—; and B is —$CH_2CH_2$—, -trans-CH=CH—, or —CH(OH)$CH_2$.

In another embodiment $R_1$ is -1'-pyridinium; $R_3$ is —$CH_2OH$; b is 0; c is 1; d is 1; e is 1; A is —CH(OH)—; B is —$CH_2CH_2$—, -trans-CH=CH—, or —CH(OH)$CH_2$; and X is —C(O)—.

In another embodiment $R_1$ is -1'-pyridinium; $R_2$ is —H; $R_3$ is —$CH_2OH$; each $R_5$ is —H; a is 1, 5, 11 or 15; b is 0; c is 1; d is 1; e is 1; f is 13; A is —(R)—CH(OH)—; B is -trans-CH=CH—; X is —C(O)—; and carbon atom 2 of the compound of formula 1 is the (S)-conformer.

In another embodiment $R_1$ is -1'-pyridinium; $R_3$ is —$CH_2OH$; each $R_5$ is —H; a is 1, 5, 11 or 15; b is 0; c is 1; d is 1; e is 1; f is 13; A is —(R)—CH(OH)—; B is -trans-CH=CH—; X is —C(O)—; and carbon atom 2 of the compound of formula 1 is the (R)-conformer.

In another embodiment $R_1$ is -1'-pyridinium; $R_2$ is —H; $R_3$ is —$CH_2OH$; each $R_5$ is —H; a is 1, 5, 11 or 15; b is 0; c is 1; d is 1; e is 1; f is 13; A is —(S)—CH(OH)—; B is -trans-CH=CH—; X is —C(O)—; and carbon atom 2 of the compound of formula 1 is the (S)-conformer.

In another embodiment $R_1$ is -1'-pyridinium; $R_2$ is —H; $R_3$ is —$CH_2OH$; each $R_5$ is —H; a is 1, 5, 11 or 15; b is 0; c is 1; d is 1; e is 1; f is 13; A is —(R)—CH(OH)—; B is -trans-CH=CH—; X is —C(O)—; and carbon atom 2 of the compound of formula 1 is the (R)-conformer.

In one embodiment $R_1$ is -1'-pyridinium; $R_3$ is —$CH_2OH$; each $R_5$ is —H; b is 1; c is 1; d is 1; e is 1; A is —CH(OH)—; B is —$CH_2CH_2$—, -trans-CH=CH—, or —CH(OH)$CH_2$; X is —C(O)—; and Y is —N(H)—.

In another embodiment $R_1$ is -1'-pyridinium; $R_2$ is —H; $R_3$ is —$CH_2OH$; each $R_5$ is —H; a is 3, 9 or 13; b is 1; c is 1; d is 1; e is 1; f is 13; A is —CH(OH)—; B is -trans-CH=CH—; X is —C(O)—; and Y is —N(H)—.

In another embodiment $R_1$ is -1'-pyridinium; $R_2$ is —H; $R_3$ is —$CH_2OH$; each $R_5$ is —H; a is 3, 9 or 13; b is 1; c is 1; d is 1; e is 1; f is 13; A is —(S)—CH(OH)—; B is -trans-CH=CH—; X is —C(O)—; Y is —N(H)—; and carbon atom 2 of the compound of formula 1 is the (S)-conformer.

In another embodiment $R_1$ is -1'-pyridinium; $R_2$ is —H; $R_3$ is —$CH_2OH$; each $R_5$ is —H; a is 3, 9 or 13; b is 1; c is 1; d is 1; e is 1; f is 13; A is —(S)—CH(OH)—; B is -trans-CH=CH—; X is —C(O)—; Y is —N(H)—; and carbon atom 2 of the compound of formula 1 is the (R)-conformer.

In another embodiment $R_1$ is -1'-pyridinium; $R_2$ is —H; $R_3$ is —$CH_2OH$; each $R_5$ is —H; a is 3, 9 or 13; b is 1; c is 1; d is 1; e is 1; f is 13; A is —(R)—CH(OH)—; B is -trans-CH=CH—; X is —C(O)—; Y is —N(H)—; and carbon atom 2 of the compound of formula 1 is the (S)-conformer.

In another embodiment $R_1$ is -1'-pyridinium; $R_2$ is —H; $R_3$ is —$CH_2OH$; each $R_5$ is —H; a is 3, 9 or 13; b is 1; c is 1; d is 1; e is 1; f is 13; A is —(R)—CH(OH)—; B is -trans-CH=CH—; X is —C(O)—; Y is —N(H)—; and carbon atom 2 of the compound of formula 1 is the (R)-conformer.

In one embodiment $R_1$ is -1'-pyridinium; $R_3$ is —$CH_2OH$; b is 0; c is 0; d is 1; e is 1; A is —CH(OH)—; and B is —$CH_2CH_2$—, -trans-CH=CH—, or —CH(OH)$CH_2$.

In another embodiment $R_1$ is -1'-pyridinium; $R_2$ is —H; $R_3$ is —$CH_2OH$; each $R_5$ is —H; a is 5, 11, or 15; b is 0; c is 0; d is 1; e is 1; f is 13; A is —CH(OH)—; and B is -trans-CH=CH—.

In another embodiment $R_1$ is -1'-pyridinium; $R_2$ is —H; $R_3$ is —$CH_2OH$; each $R_5$ is —H; a is 5, 11, or 15; b is 0; c is 0; d is 1; e is 1; f is 13; A is —(R)—CH(OH)—; B is -trans-CH=CH—; and carbon atom 2 of the compound of formula 1 is the (S)-conformer.

Illustrative Compounds of Formula II are Listed Below:

(2S,3R,4E)-2-N-acetyl-18-(1'-pyridinium)-sphingosine bromide;

(2S,3R,4E)-2-N-hexanoyl-18-(1'-pyridinium)-sphingosine bromide;

(2S,3R,4E)-2-N-dodecanoyl-18-(1'-pyridinium)-sphingosine bromide;

(2S,3R,4E)-2-N-hexadecanoyl-18-(1'-pyridinium)-sphingosine bromide;

(2S,3S,4E)-2-N-acetyl-18-(1'-pyridinium)-sphingosine bromide;

(2S,3S,4E)-2-N-hexanoyl-18-(1'-pyridinium)-sphingosine bromide;

(2S,3S,4E)-2-N-dodecanoyl-18-(1'-pyridinium)-sphingosine bromide;

(2S,3S,4E)-2-N-hexadecanoyl-18-(1'-pyridinium)-sphingosine bromide;

(2S,3R,4E)-2-N-(N'-butylformamide)-18-(1'-pyridinium)-sphingosine bromide;

(2S,3R,4E)-2-N-(N'-decylformamide)-18-(1'-pyridinium)-sphingosine bromide;

(2S,3R,4E)-2-N-(N-tetradecylformamide)-18-(1'-pyridinium)-sphingosine bromide;

(2S,3S,4E)-2-N-(N'-butylformamide)-18-(1'-pyridinium)-sphingosine bromide, (2S,3S,4E)-2-N-(N'-decylformamide)-18-(1'-pyridinium)-sphingosine bromide;

(2S,3S,4E)-2-N-(N-tetradecylformamide)-18-(1'-pyridinium)-sphingosine bromide;

(2S,3R,4E)-2-N-acetyl-18-(1'-pyridinium)-sphingosine bromide;

2S,3R,4E)-2-N-hexyl-18-(1'-pyridinium)-sphingosine bromide;

(2S,3R,4E)-2-N-dodecyl-18-(1'-pyridinium)-sphingosine bromide;

(2S,3R,4E)-2-N-hexadecyl-18-(1'-pyridinium)-sphingosine bromide;

(2S,3S,4E)-2-N-acetyl-18-(1'-pyridinium)-sphingosine bromide;

(2S,3S,4E)-2-N-hexyl-18-(1'-pyridinium)-sphingosine bromide;

(2S,3S,4E)-2-N-dodecyl-18-(1'-pyridinium)-sphingosine bromide;

(2S,3S,4E)-2-N-hexadecyl-18-(1'-pyridinium)-sphingosine bromide;

(2S,3R,4E)-18-(1'-pyridinium)-sphingosine bromide;

(2R,3R,4E)-18-(1'-pyridinium)-sphingosine bromide;

(2S,3S,4E)-18-(1'-pyridinium)-sphingosine bromide;

(2R,3S,4E)-18-(1'-pyridinium)-sphingosine bromide; and (2S,3R,4E)-18-(1'-pyridinium)-4,5-dihydrosphingosine bromide.

5.4. Methods for Making the CCPS Analogs

The present invention also provide methods for making CCPS analogs. The compounds of formula I (Compounds of Classes A, B, and D) can be made using conventional organic syntheses and/or by the following illustrative methods depicted in Schemes 1, 2, and 3 below. As depicted, two parallel approaches, based upon the use of known protocols reported previously for the preparation of Cers from sphingoid bases 1a-d obtained in stereocontrolled synthesis from the Garner's aldehydes (see Garner, J. Org. Chem., 53, 4395-4398 (1988); Ninkar, S. Tetrahedron Lett., 29, 3037-3040 (1988); Herold, P. E. J. Org. Chem., 71, 354-362 (1988); Bielawska, A., et al., Methods Enzymol. 311, 518-535 (1999); Usta, J. et al., (2001). Biochemistry 40 (32), 9657-9668) and separately or generated in situ) to provide 2i and 2j in yields of up to about 50%, the yield being hindered due to low reaction rate and complex mixtures formation. Subsequent quaternization of pyridine or its 4-N,N-dimethylaminostyryl derivative (see Cherioux, F. Chem. Mater. 10, 1984-1989 (1998)) with the formed ω-bromo-Cers 2a-l, is then carried out in toluene solution at 75-80° C. to provide the pyridinium bromides LCL-29, 30, 88, 89, 124, 143, 150, 186, 187, 249, 272, 319 and 345, respectively.

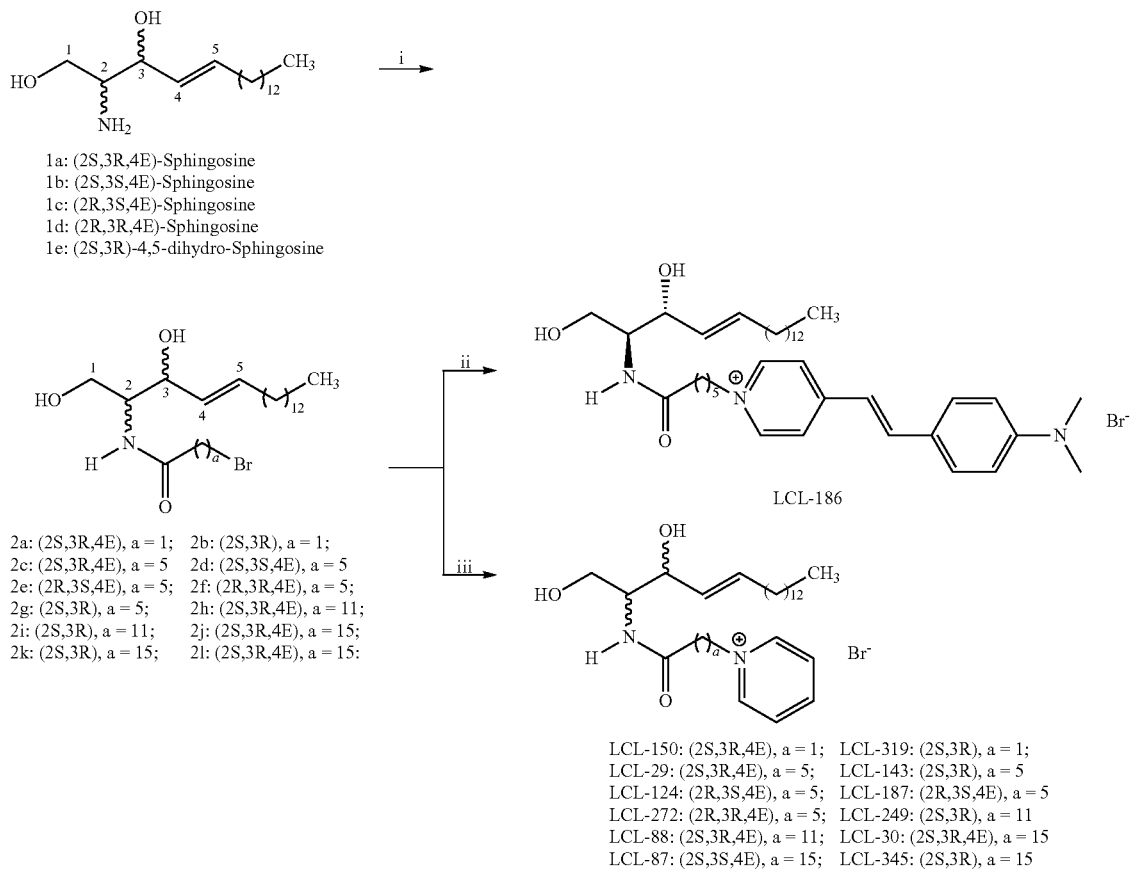

Scheme 1: Synthesis of Class A of CCPS analogs

Reaction conditions: i: Br(CH$_2$)$_a$COX, where a = 1, 5, 11 or 15 and X = Br or Cl; 50% CH$_3$COONa, THF, 25° C.; ii: 4-(N,N-dimethylaminostyryl)-pyridine, toluene, ~75° C., 70 hrs; iii: pyridine, toluene, ~75° C., 4-6 hrs.

pyridinium salts from pyridine derivatives (see Cherioux, F. Chem. Mater. 10, 1984-1989 (1998); Kloc, K; Can. J. Chem., 57, 1506 (1979)).

5.4.1. Methods for Making Compounds of Formula I

CCPS analogs of Class A: CPPS Analogs of Class A can be prepared by N-acylation of 1a-e with varied chain ω-bromo acid chlorides. The reaction is carried out under two-phase based conditions (~50% aqueous sol. of CH$_3$COONa/THF) and preceded very quickly (15-25 min) with complete consumption of sphingoid bases to give ω-bromo-Cers 2a-l in high yields (vide infra). One method for making the long chains ω-bromo-Cers 2i and 2j involves the condensation of 1a with the activated forms of the corresponding C12- or C16-FAs (i.e, NHS-esters, Imd-derivatives, etc., synthesized CCPS analogs of Class D: CCPS analogs of class D can be prepared in a manner similar to that described in Scheme 3 (FIG. 3A) by reacting compounds of formula A for phenylaminoalcohols(2-amino-phenyl-1,3-dihydroxy or 1- or 3-nomohydroxy)

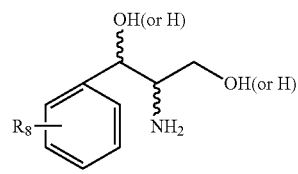

with a compound of formula Br(CH2)aCOX where a=1, 5, 11 or 15; or Br(CH$_2$)$_a$X where a=2, 6, 12 or 16; followed by reaction with pyridine, where X is halogen or p-nitro-phenyl.

CCPS analogs of Class B: In order to prepare CCPS analogs of class B, the pyridine moiety has to be introduced first into the SPL structure following its further quaternization with the selected alkyl halide. Thus, the N-acylation of 1a with 3-pyridinepropionic or nicotinic acid chlorides gave -pyridino-Cers 3 and 4, which were easily N-alkylated in the next step with n-butyl or n-octyl bromides, to give LCL-275 and 277, respectively (Scheme 2). The key intermediates 2a-l, 3 and 4 as well as the final products were easily purified by flash column chromatography or by recrystallization, where appropriate.

Compounds 1a-e can be made by methods described in the Examples section (see Section 6).

In one embodiment, the invention relates to methods for making a compound of formula I comprising:
(a) contacting a compound of formula B:

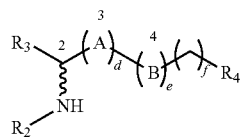

B

Scheme 2: Synthesis of Class B of CCPS analogs

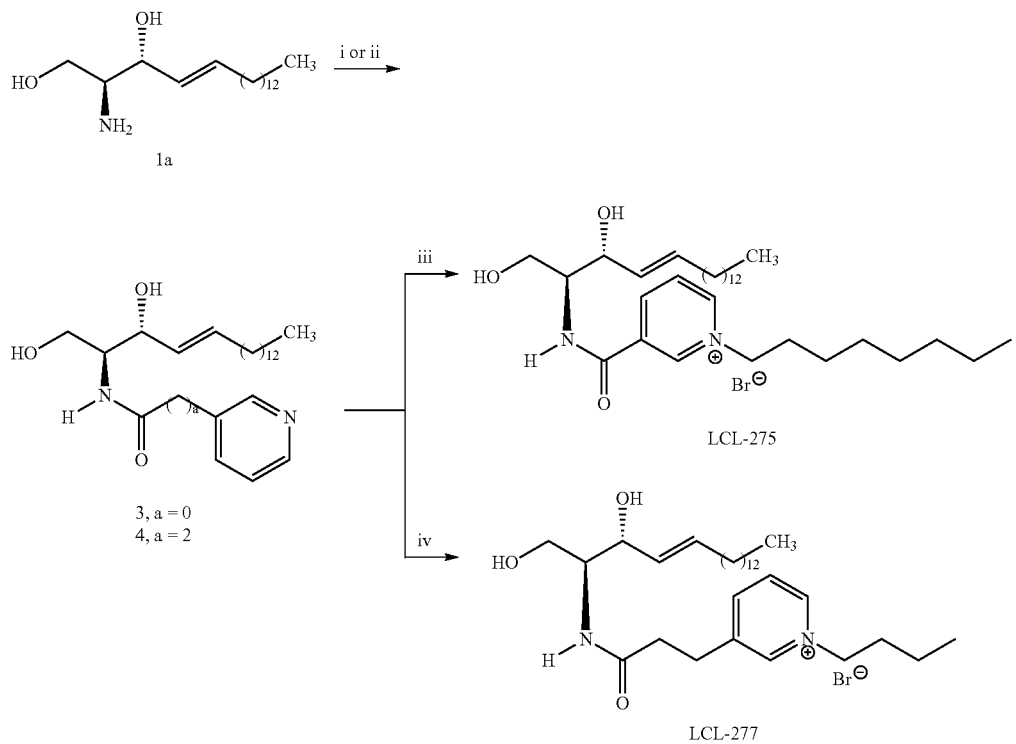

Reaction conditions: i: nicotinoyl acid chloride, 50% CH₃COONa, THF, 25° C.; ii: 3-pyridinepropionic acid chloride, 50% CH₃COONa, THF, 25° C.; iii: n-octyl bromide, toluene, ~75° C., 8 hrs; iv: n-butyl bromide, toluene, ~75° C., 6 h.

The above-described two-step general synthetic approach revealed to be fast and amenable for scaling up to a practical process, which provides the CCPS analogs in good to excellent overall yields (40-85%). Finally, that strategy opens unrestricted access to structurally varied CCPS analogs having modified N-acyl parts as well as based on the complex hybrid SPLs (phospho- and glyco-SPLs).

All synthesized CCPS analogs were fully characterized by spectroscopic methods (mass spectroscopy (MS), nuclear magnetic resonance (NMR) spectroscopy, optical rotation) and elemental analysis. Stability studies of LCL-29, 30, 88 and 150 by MS analysis, performed under aqueous conditions at pH 4.5, 7.5 and 8.5 over the period of 48 hrs find no evidence of their decomposition.

with a compound of formula C

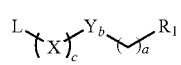

C to form a compound of formula D;

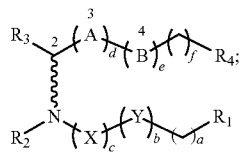

D and (b) contacting the compound of formula D with a compound of formula E;

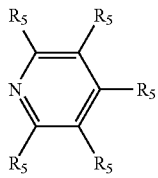

E wherein $R_1$ is 1'-pyridinium;
A, B, $R_2$, $R_3$, $R_4$, $R_5$, $R_6$, $R_7$, $R_8$, $R_9$, $R_{10}$, $R_{11}$, a, b, c, d, e, X, Y and M are as defined above; and
L is a leaving group.

Non-limiting examples of useful leaving group include, —Cl, —Br, —I, —Si(($C_1$-$C_6$)alkyl)$_3$, -tosylate, -trifluoromethanesulfonate, -methanesulfonate, and the like. In one embodiment, L is —Br. In another embodiment, L becomes $M^-$.

In another embodiment, the invention relates to methods for making a compound of formula I comprising:

(a) contacting a compound of formula B:

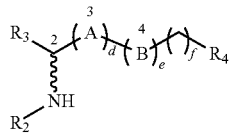

B with a compound of formula F;

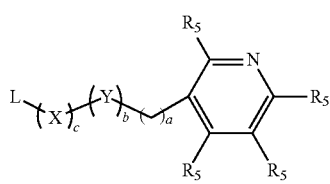

F to form a compound of formula G;

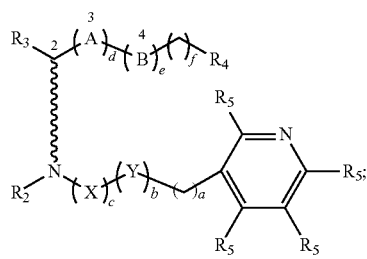

G and (b) contacting the compound of formula G with a compound of formula L-$R_6$;
wherein $R_1$ is 3'-pyridinium; and
A, B, $R_2$, $R_3$, $R_4$, $R_5$, $R_6$, $R_7$, $R_8$, $R_9$, $R_{10}$, $R_{11}$, a, b, c, d, e, f, X, Y, M and L are as defined above.

In one embodiment, L is —Br. In another embodiment, L becomes $M^-$.

5.4.2. Methods for Making Compounds of Formula II

Figure 3B:
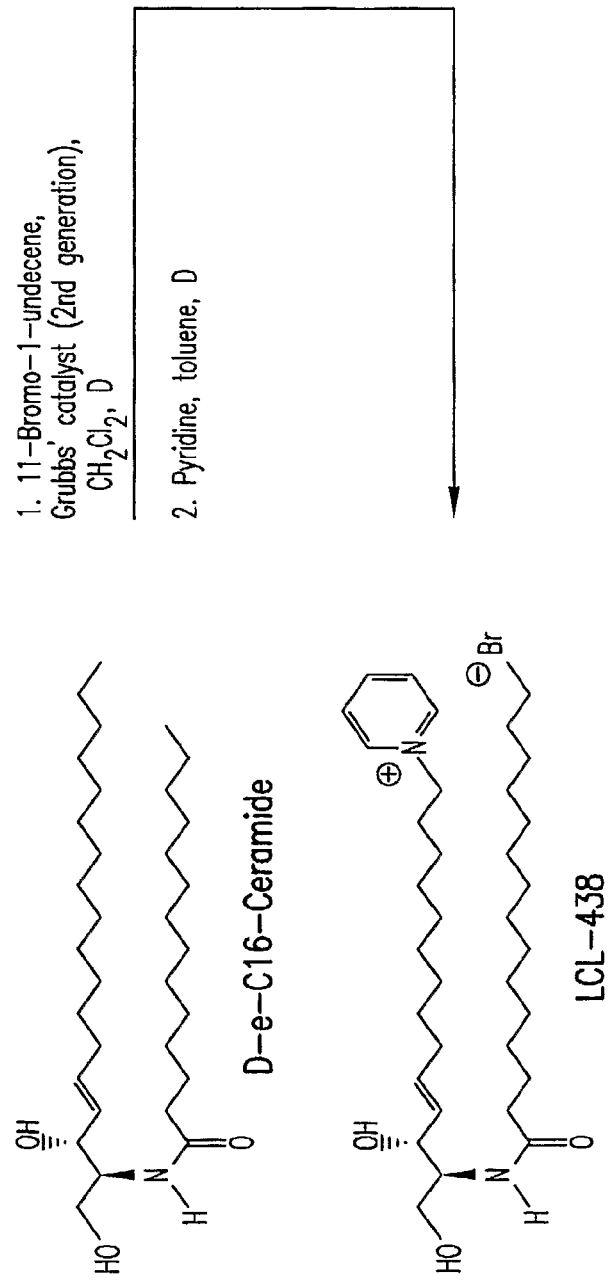
FIG. 3B shows Scheme 4, the synthesis of class C ceramidoids.

CCPS analogs of Class C: CPPS Analogs of Class C of general structure of Formula II (shown in FIG. 1) can be prepared as depicted in Scheme 4 (FIG. 3B). Description of the general synthesis of Class C compounds and exemplary compounds are shown in Section 6, Example 31, infra.

5.5. Therapeutic Uses of the CCPS Analogs

The present invention provides the uses of CCPS analogs of the invention for treatment and/or prophylaxis of various diseases and disorders related to cell proliferation and/or sphingolipid signal transduction in a subject.

Ceramide modulates a number of biochemical and cellular responses to stress, including apoptosis, cell-cycle arrest and cell senescence. (For review, see Hannun et al., 2000, Trends in Cell Biol. 10:73-80; Mathias et al., 1998, Biochem. J. 335:465-480). Several extracellular agents and stress stimuli, such as tumor necrosis factor α, chemotherapeutic agents and heat are known to cause ceramide accumulation. One approach to cause accumulation of ceramide is accomplished by regulating the activities of enzymes such as ceramidase which is involved in the metabolism of ceramide. The changes in the ceramide concentration are sufficient to reproduce many of the biological effects of cytokines and stress inducers that are coupled to ceramide accumulation. The accumulation of ceramides also reproduce many of the features of cell senescence. In many cell types, ceramides cause cell differentiation, both morphologically and through the activation of biochemical programs of cell differentiation. Ceramide also causes apoptosis in most cancer cells which can be accompanied by cell-cycle arrest. Furthermore, there is evidence which suggests that ceramide is closely associated with TNFα-induced apoptosis. Thus, according to the present invention, modulation of the levels of ceramide or sphingosine through the methods of the present invention can bring about treatment and prevention of diseases that are related to stress response and apoptosis. Several exemplary diseases and disorders are disclosed below which may be treated or prevented by the methods of the present invention. The compounds can also be used for management or amelioration of one or more symptoms associated with these diseases.

Without being bound by any theories, the CCPS analogs modulate sphingolipid components and act as a modulator of sphingolipid enzymes that are present in a cell or in organelles of a cell. The CCPS analogs may also act by inhibiting telomerase as it has been shown that inhibition of telomerase by ceramide is mainly linked to rapid degradation of c-Myc via the ubiquitin/proteasome pathway. The CCPS analogs may also act by altering permeability of the inner and/or outer membranes. Regardless of the underlying mechanism(s), in various embodiments, the CCPS analogs can induce cell death in vitro and in vivo.

In one embodiment, the present invention provides a method of increasing the level of ceramide and for changing ceramide composition in a cell comprising contacting the cell with one or more CCPS analogs. In a related embodiment, at least one of the CCPS analog modulates a ceramidase activity in the cell.

In another embodiment, the invention provides a method of inhibiting the formation of sphingosine in a cell comprising contacting the cell with one or more CCPS analogs such that the amount of sphingosine formed as a result of conversion from ceramide is reduced.

In yet another embodiment, the invention provides a method of increasing the intracellular levels of ceramide in an animal comprising administering to the animal one or more CCPS analogs.

In yet another embodiment, the invention provides a method of increasing the intracellular levels of ceramide in an animal comprising administering to the animal an effective amount of one or more CCPS analogs that inhibit the ceramidase activity of a ceramidase protein in the animal's cells.

In yet another embodiment, the invention provides a method of inhibiting the intracellular formation of sphingosine in an animal comprising administering to said animal an effective amount of one or more CCPS analogs. Preferably, at least one of the CCPS analogs inhibit the ceramidase activity of the ceramidase protein in the animal's cells.

In yet another embodiment, the invention provides a method of inhibiting the activity of telomerase, or the activity of proteins that act on the same pathway as telomerase in sustaining cancer cell proliferation. The invention also provides a method of inhibiting cell proliferation, and particularly arresting cancer cell growth at G0/G1.

In yet another embodiment, the invention provides a method of increasing the permeability of mitochondrial inner membrane comprising contacting a cell comprising mitochondria, with a CCPS analog of the invention. Also encompassed are a method for activating an ion transporter in mitochondria which results in an alteration in the permeability of mitochondria membrane; and a method for releasing mitochondrial cytochrome c.

In specific embodiments, one or more different CCPS analogs can be administered to a subject in need of a CCPS analog therapeutically or prophylactically: (1) in diseases or disorders of which treatment involves cell death, such as apoptosis; (2) in diseases or disorders wherein in vitro (or in vivo) assays indicate the utility of ceramide administration; or (3) in diseases or disorders involving an increased (relative to normal or desired) level of ceramidase protein or function, for example, in patients where ceramidase protein is biologically overactive or overexpressed.

The increased level in ceramidase protein or function can be readily detected, e.g., by obtaining a patient tissue sample (e.g., from biopsy tissue) and assaying it in vitro for RNA or protein levels, structure and/or activity of one or more of the expressed ceramidase RNAs or proteins. Many methods standard in the art can be thus employed, including but not limited to ceramidase enzyme assays, immunoassays to detect and/or visualize one or more of different ceramidase proteins (e.g., Western blot, immunoprecipitation followed by sodium dodecyl sulfate polyacrylamide gel electrophoresis, immunocytochemistry, etc.) and/or hybridization assays to detect ceramidase expression by detecting and/or visualizing specific ceramidase mRNA (e.g., Northern assays, dot blots, in situ hybridization, etc.), etc.

According to the invention, disorders involving cell hyperproliferation or dysfunctional sphingolipid signal transduction are treated or prevented by administration of a compound to a subject that inhibits ceramidase function. These diseases and disorders include, but are not limited to, diseases or disorders related to cell proliferation, cell attachment, cell immigration, granulation tissue development, primary and metastatic neoplastic diseases, inflammation, cardiovascular disease, stroke, ischemia or atherosclerosis. Diseases and disorders involving cell overproliferation that can be treated or prevented include but are not limited to cancers, premalignant conditions (e.g., hyperplasia, metaplasia, dysplasia), benign tumors, hyperproliferative disorders, and benign dysproliferative disorders. Cancer is characterized primarily by an increase in the number of abnormal cells derived from a given normal tissue, invasion of adjacent tissues by these abnormal cells, and lymphatic or blood-borne. Malignancies and related disorders that can be treated, prevented, managed, amerliorated, particularly metastatic cancer, by administration of a compound of the invention that inhibits ceramidase function as discussed below (for a review of such disorders, see Fishman et al., 1985, *Medicine,* 2d Ed., J.B. Lippincott Co., Philadelphia):

In another embodiment, disorders in which cell proliferation is deficient or is desired can be treated or prevented by administration of a CCPS analog to a subject that promotes ceramidase function or mimics the result of ceramidase function.

In various embodiments, "treatment" or "treating" refers to an amelioration of disease or disorder, or at least one discernible symptom thereof. "Treatment" or "treating" also refers to an amelioration of at least one measurable physical parameter associated with disease or disorder not necessarily discernible by the subject. "Treatment" or "treating" may also refer to inhibiting the progression of a disease or disorder either physically, e.g., stabilization of a discernible symptom, physiologically, e.g., stabilization of a physical parameter, or both. "Treatment" or "treating" also refers to delaying the onset of a disease or disorder.

In certain embodiments, the methods and compositions of the present invention are useful as a preventative measure against disease or disorder. As used herein, "prevention" or "preventing" refers to a reduction of the risk of acquiring a given disease or disorder.

In certain embodiments, the invention provides methods for treating or preventing diseases or disorders comprising administration of a CCPS analog in combination with other therapeutic modalities.

Cancers and related disorders that can be treated or prevented by methods and compositions of the present invention include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; head and neck cancers; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine,* 2d Ed., J.B. Lippincott Co., Philadelphia and Murphy et al., 1997, *Informed Decisions: The Complete Book of Cancer Diagnosis, Treat-*

*ment, and Recovery*, Viking Penguin, Penguin Books U.S.A., Inc., United States of America).

In preferred embodiments, the methods and compositions of the invention are used for the treatment and/or prevention of breast cancer, colon cancer, and head and neck cancer, are provided below by example rather than by limitation.

The CCPS analogs of the invention that induce cell death are preferred.

The CCPS analogs can also be administered to treat pre-malignant conditions and to prevent progression to a neoplastic or malignant state. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology,* 2d Ed., W.B. Saunders Co., Philadelphia, pp. 68-79.)

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a compound that inhibits ceramidase function. Such characteristics of a transformed phenotype include morphology changes, looser substratum attachment, loss of contact inhibition, loss of anchorage dependence, protease release, increased sugar transport, decreased serum requirement, expression of fetal antigens, etc.

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia) is indicative of the desirability of prophylactic intervention. In other embodiments, a patient which exhibits one or more of the following predisposing factors for malignancy is treated by administration of an effective amount of the CCPS analog of the invention: a chromosomal translocation associated with a malignancy (e.g., the Philadelphia chromosome for chronic myelogenous leukemia, t(14; 18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 197, *Basic Pathology,* 2d Ed., W.B. Saunders Co., Philadelphia, pp. 112-113) etc.)

The invention encompasses methods for treating or preventing a cancer or metastasis in a subject comprising in any order the steps of administering to the subject a CCPS analog. In certain embodiments, the compositions and methods of the invention can be used to prevent, inhibit or reduce the growth or metastasis of cancerous cells. In a specific embodiment, the administration of a CCPS analog inhibits or reduces the growth or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of the administration of said CCPS analog.

The invention encompasses methods of disease treatment or prevention that provide better therapeutic profiles than current single agent therapies or even current combination therapies. Encompassed by the invention are combination therapies that have additive potency or an additive therapeutic effect while reducing or avoiding unwanted or adverse effects. In a specific embodiment, the CCPS analog is administered before the administration of the second therapy modality. In another specific embodiment, the second modality is administered before the administration of the CCPS analog.

Other cancer treatment that may be used in combination of the administration of the CCPS analog of the present invention include the use of one or more molecules, or compounds for the treatment of cancer (L e., cancer therapeutics), which molecules, compounds or treatments include, but are not limited to, chemoagents, immunotherapeutics, cancer vaccines, anti-angiogenic agents, cytokines, hormone therapies, gene therapies, biological therapies, and radiotherapies. While maintaining or enhancing efficacy of treatment, preferably the methods of the present invention increase patient compliance, improve therapy and/or reduce unwanted or adverse effects.

In a specific embodiment, a CCPS analog is administered to a subject receiving a treatment modality for the treatment of cancer wherein the subject may experience unwanted or adverse effects to treatment with the treatment modality alone, e.g., the treatment modality may be toxic or harmful at its effective dose, administered alone. Given the invention, the CCPS analog can improve the therapeutic benefit of the treatment modality such that the dosage or frequency of administration of the treatment modality can be lowered when administered in conjunction with the CCPS analog. In a preferred embodiment, a CCPS analog is administered to allow lower and/or less frequent doses of chemotherapy or radiation therapy. In a specific embodiment, a lower dose or dosing frequency of certain chemotherapeutic agents, such as Doxorubicin, that are toxic to heart tissues can be used in combination with a CCPS analog.

In a specific embodiment, the methods of the invention encompass the administration of one or more angiogenesis inhibitors such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin;

amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; aza osine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+ myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stein cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferably, the therapeutic agent used in combination with CCPS analogs of the invention is one that does not comprise a pyridinium moiety and a sphingosine backbone.

In a specific embodiment, the anti-cancer drug used in combination is an anthracycline compound. In a more specific embodiment, the anti-cancer drug is Doxorubicin. In other embodiments, the anti-cancer drug used in combination with the CCPS analogs of the invention is gemcitabine, methotrexate, daunorubicin, cisplatin, palitaxel, carboplatin, and 5-fluorouracil. In certain embodiments, the anti-cancer drug used in combination with the CCPS analogs of the invention is not an anthracycline compound, or is not Doxorubicin.

In another embodiment, the treatment of the present invention further includes the administration of one or more immunotherapeutic agents, such as antibodies and immunomodulators, which include, but are not limited to, HERCEPTIN®, RITUXAN®, OVAREX™, PANOREX®, BEC2, IMC-C225, VITAXIN™, CAMPATH® I/H, Smart MI95, LYMPHOCIDE™, Smart I D10, and ONCOLYM™, rituximab, gemtuzumab, or trastuzumab.

In another embodiment, the treatment of the present invention further includes administering one or more anti-angiogenic agents, which include, but are not limited to, angiostatin, thalidomide, kringle 5, endostatin, other Serpins, antithrombin, 29 kDa N-terminal and 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51:2077), a 14-amino acid peptide corresponding to a fragment of collagen I (Tolma et al., 1993, J. Cell Biol. 122:497), a 19 amino acid peptide corresponding to a fragment of Thrombospondin I (Tolsma et al., 1993, J. Cell Biol. 122: 497), a 20-amino acid peptide corresponding to a fragment of SPARC (Sage et al., 1995, J. Cell. Biochem. 57:1329-), or any fragments, family members, or derivatives thereof, including pharmaceutically acceptable salts thereof.

In another embodiment, the treatment method further comprise the use of radiation.

In another embodiment, the treatment method further comprises the administration of one or more cytokines, which includes, but is not limited to, lymphokines, tumor necrosis factors, tumor necrosis factor-like cytokines, lymphotoxin-a, lymphotoxin-b, interferon-a, interferon-b, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In yet another embodiment, the treatment method further comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

Other disorders of proliferation that may benefit from the use of CCPS analog include cardiovascular diseases. Vascular interventions, including angioplasty, stenting, atherectomy and grafting for the treatment of cardiovascular diseases are often complicated by undesirable effects. One of the adverse reactions to vascular intervention include endothelial and smooth muscle cell proliferation which can lead to hyperplasia, or more specifically, restenosis, occlusion of blood vessels, reperfusion injury, platelet aggregation, and calcification. In this model, an injurious stimulus induces expression of growth-stimulatory cytokines such as interleukin 1 and tumor necrosis factor. Libby et al., *Cascade Model of Restenosis* 1992, Circulation 86(6): III-47-III52. There is evidence which shows that ceramide inhibit the growth of endothelia and smooth muscle cells of the coronary artery.

Various therapies have been attempted to treat or prevent restenosis. However, there remains a great need for therapies directed to the prevention and treatment of cardiovascular diseases caused by hyperplasia of endothelia and smooth muscle cells. Since it has been shown that ceramide inhibit the growth of endothelia and smooth muscle cells of the coronary artery, it is therefore desirable to raise the level of ceramide for the treatment and prevention of cardiovascular diseases. Recently, Kester et al. show that ceramide used in angioplasty prevents restenosis. Kester et al., 2000, Circ. Res. 87(4):282-8. Alternative, and more effectively, one aspect of the present invention provides treatment and prevention of restenosis by adjusting the level of ceramide through administering one or more CCPS analog.

Accordingly, it is therefore desirable to raise the level of ceramide for the treatment and prevention of cardiovascular diseases. This can be accomplished by adjusting the intracellular level of ceramide by using the compounds and methods of the invention. The outcome of a treatment is to at least produce in a treated subject a healthful benefit, which in the case of cardiovascular diseases, includes but is not limited to a reduced risk of re-clogging of arteries after a vascular intervention procedure, and improved circulation.

In a specific embodiment, the present invention provides a method for preventing, treating, managing or ameliorating an autoimmune or inflammatory disorder or one or more symptoms thereof, said method comprising administering to a subject in need thereof a prophylactically or therapeutically effective amount of CCPS analog and a prophylactically or therapeutically effective amount of one or more immunomodulatory agents.

Interleukin-1 is a major inducer of inflammation and TNF is an important regulator of the reaction. Both cytokines can activate ceramidase, and thus inhibiting the activity of ceramidase can result in an anti-inflammatory effect. This may involve the prevention of the formation of sphingosine and sphingosine phosphate which have pro-inflammatory effects. Also, inhibition of ceramidase may prevent the hyperproliferation of immune cells that are important for inflammation. There is evidence which suggests that an increase in ceramide and a decrease in sphingosine leads to a decrease in sphingosine phosphate. Preliminary data show that in mouse fibroblast cells, L929, TNFα increases the level of ceramide and leads to PGE2 release from these cells. The release of PGE2 is also shown to be inhibited by D-(N-myristolyamino)-1-phenyl-1-propanol), D-MAPP, which is an inhibitor of one of the ceramidase. This observation may be important for inhibiting inflammatory reactions that occur in conditions, such as but not limited to rheumatoid arthritis. Thus, it is possible to treat or prevent inflammation by regulating the level of cellular ceramide using the method of the invention. As discussed above, ceramide level can be increased by administering compounds of the present invention that can inhibit mitochondrial ceramidase.

Examples of autoimmune disorders include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. Some autoimmune disorders are associated with an inflammatory condition. Thus, there is overlap between what is considered an autoimmune disorder and an inflammatory disorder. Therefore, some autoimmune disorders may also be characterized as inflammatory disorders.

The present invention provides methods of preventing, treating, managing or ameliorating an autoimmune or inflammatory disorder or one or more symptoms thereof, said methods comprising administering to a subject in need of a CCPS analog, and one or more immunomodulatory agents. Preferably, the immunomodulatory agents are not administered to a subject with an autoimmune or inflammatory disorder whose mean absolute lymphocyte count is less than 500 cells/mm$^3$, less than 550 cells/mm$^3$, less than 600 cells/mm$^3$, less than 650 cells/mm$^3$, less than 700 cells/mm$^3$, less than 750 cells/mm$^3$, less than 800 cells/mm$^3$, less than 850 cells/mm$^3$ or less than 900 cells/mm$^3$. Thus, in a preferred embodiment, prior to or subsequent to the administration of one or more dosages of one or more immunomodulatory agents to a subject with an autoimmune or inflammatory disorder, the absolute lymphocyte count of said subject is determined by techniques well-known to one of skill in the art, including, e.g., flow cytometry or trypan blue counts.

Examples of immunomodulatory agents include, but are not limited to, methothrexate, leflunomide, cyclophosphamide, cyclosporine A, and macrolide antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators. Examples of T cell receptor modulators include, but are not limited to, anti-T cell receptor antibodies (e.g., anti-CD4 monoclonal antibodies, anti-CD3 monoclonal antibodies, anti-CD8 monoclonal antibodies, anti-CD40 ligand monoclonal antibodies, anti-CD2 monoclonal antibodies) and CTLA4-immunoglobulin. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF), anti-cytokine receptor antibodies (e.g., anti-IL-2 receptor antibodies, anti-IL-4 receptor antibodies, anti-IL-6 receptor antibodies, anti-IL-10 receptor antibodies, and anti-IL-12 receptor antibodies), anti-cytokine antibodies (e.g., anti-IFN receptor antibodies, anti-TNF-α antibodies, anti-IL-1β antibodies, anti-IL-6 antibodies, and anti-IL-12 antibodies).

Anti-inflammatory agents have exhibited success in treatment of inflammatory and autoimmune disorders and are now a common and a standard treatment for such disorders. Any anti-inflammatory agent well-known to one of skill in the art can be used in the compositions and methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

Techniques for the determination of effective doses and administration of such compounds are described in Section 5.5. Any technique which serves to selectively administer chemicals to a cell population of interest can be used, for example, by using a delivery complex. Such a delivery complex can comprise an appropriate chemical and a targeting means. Such targeting means can comprise, for example, sterols, lipids, viruses or target cell specific binding agents.

5.6. Pharmaceutical Preparation and Methods of Administration

The CCPS analogs described herein can be administered to a patient at therapeutically effective doses to treat or prevent diseases and disorder discussed above. A therapeutically effective dose refers to that amount of a compound sufficient to result in a healthful benefit in the treated subject. See, the *Physician's Desk Reference*® (53$^{rd}$ ed., 1999).

The subject to which a compound of the invention is administered is preferably an animal, including but not limited to mammal such as non-primate (e.g., cows, pigs, horses, chickens, cats, dogs, rats, etc.), and a primate (e.g. monkey such as acynomolgous monkey and a human. In a preferred embodiment, the subject is a human. The compound of the invention can be utilized for the prevention of a variety of cancers, e.g., in individuals who are predisposed as a result of familial history or in individuals with an enhanced risk to cancer due to environmental factors, such as smoking, viral infection.

The methods and compositions of the invention may be used in patients who are treatment naive, in patients who have previously received or are currently receiving treatment with other pharmaceutical agents or combinations, including but not limited to anti-cancer agents. Other subjects may include patients that have metastasis or no metastasis.

The methods and compositions of the invention are useful not only in untreated patients but are also useful in the treatment of patients partially or completely un-responsive to other treatments. In various embodiments, the invention provides methods and compositions useful for the treatment of diseases or disorders in patients that have been shown to be or may be refractory or non-responsive to therapies comprising the administration of other agents.

The compound of the invention can also be administered to an animal, preferably a mammal, such as farm animals and pets, to treat, prevent or ameliorate one or more symptoms associated with the disease, disorder, or infection as discussed in Section 5.3.

5.6.1. Effective Dose

Toxicity and therapeutic efficacy of CCPS analogs can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. For example, the dosage can range from 10 nM to 100 µM, and preferably 1 to 10 µM. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Suitable daily doses for the treatment or prevention of a disorder described herein can be readily determined by those skilled in the art. A recommended dose of a compound of the invention is from about 0.1 mg to about 100 mg per day, given as a single once-a-day dose in the morning or as divided doses throughout the day. Preferably, a daily dose is from about 2 mg to about 25 mg per day, more preferably from about 5 mg to about 10 mg per day.

The anti-cancer activity of the therapies used in accordance with the present invention also can be determined by using various experimental animal models of such as cancer animal models such as scid mouse model or nude mice with human tumor grafts known in the art and described in Yamanaka, 2001, Microbiol Immunol 2001; 45(7):507-14.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed. A lower level of proliferation or survival of the contacted cells indicates that the compound is effective to treat the condition in the patient. Alternatively, instead of culturing cells from a patient, the compounds may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

Compounds for use in therapy can be tested in suitable animal model systems prior to testing in humans, including but not limited to in rats, mice, chicken, cows, monkeys, rabbits, etc. The principle animal models for cancer known in the art and widely used include mice: all described in Hann et al., 2001, Curr Opin Cell Biol 2001, 13(6):778-84, which is incorporated herein by reference in its entirety.

Further, any assays known to those skilled in the art can be used to evaluate the prophylactic and/or therapeutic utility of the combinatorial therapies disclosed herein for treatment, prophylaxis, management or amelioration of one or more symptoms associated with the disease, disorder as described in Section 5.5.

Efficacy in treating inflammatory disorders may be demonstrated by detecting the ability of the CCPS analogs of the present invention, or a composition of the invention to reduce or inhibit the inflammation in an animal or to ameliorate or alleviate one or more symptoms associated with an inflammatory disorder. The treatment is considered therapeutic if there is, for example, a reduction is in inflammation or amelioration of one or more symptoms following administration of the CCPS analog, or a composition of the invention.

5.6.2. Formulation and Use

Various methods can be used to administer a CCPS analog of the invention. Methods of introduction include but are not limited to intradermal, intramuscular, intraperitoneal, intravenous, subcutaneous, intranasal, epidural, inhalation, insufflation (either through the mouth or the nose), oral, buccal, or rectal routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, by means of a catheter, by means of a suppository, or by means of an implant, said implant being of a porous, non-porous, or gelatinous material, including membranes, such as sialastic membranes, or fibers.

In another embodiment, the CCPS analog can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the CCPS analog can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)). Other method of delivery of the therapeutics of the present invention may be used for example, as described in U.S. Pat. No. 5,679,350, which is incorporated by reference in its entirety.

The present invention also provides pharmaceutical compositions. Such compositions comprise a therapeutically effective amount of a CCPS analog and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the cationic pyridinium ceramides preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The CCPS analogs of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of CCPS analog of the invention which will be effective in the treatment of a particular disorder or condition will depend on the nature of the disorder or condition, and can be determined by standard clinical techniques. In addition, in vitro assays and animal models may optionally be employed to help identify optimal dosage ranges. The precise dose to be employed in the formulation will also depend on the route of administration, and the seriousness of the disease or disorder, and should be decided according to the judgment of the practitioner and each patient's circumstances.

Suppositories generally contain active ingredient in the range of 0.5% to 10% by weight; oral formulations preferably contain 10% to 95% active ingredient.

The invention also provides a pack or kit for therapeutic use comprising one or more containers filled with one or more of the ingredients of the pharmaceutical compositions of the invention. Optionally associated with such container(s) can be an instruction sheet, and/or a notice in the form prescribed by a governmental agency regulating the manufacture, use or sale of pharmaceuticals or diagnostic products, which notice reflects approval by the agency of manufacture, use or sale for human administration.

Pharmaceutical compositions for use in accordance with the present invention can be formulated in conventional manner using one or more physiologically acceptable carriers or excipients.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

6. EXAMPLES

Synthesis of CCPS Analogs

General: All solvents and general reagents were purchased from Aldrich. Stereoisomers of sphingosine (1a-d) and D-erythro-4,5-dihydro-sphingosine (1e) were prepared from L- or D-serine as described in Garner, P. *J. Org. Chem.*, 53, 4395-4398 (1988); Ninkar, S. *Tetrahedron Lett.*, 29, 3037-3040 (1988); Herold, P. E. *J. Org. Chem.*, 71, 354-362 (1988); Bielawska et al., *Methods Enzymol.* 311, 518-535 (1999); Usta et al., (2001) *Biochemistry* 40 (32), 9657-9668. D-erythro-$C_2$—, $C_6$- and $C_{16}$-ceramides were prepared by acylation of 1a using acetyl, hexanoyl or palmitoyl chlorides. 4-[4'-(N,N-Dimethyl aminostyryl)]-pyridine (3) was prepared according to Cherioux et al., *Chem. Mater.* 10, 1984-1989 (1998). The reactions were monitored by analytical thin layer chromatography (TLC) using aluminium sheets with 0.25 mm silica gel 60-$F_{254}$(Merck), detection by UV (254 nm) and spraying with a solution of PMA and heating at 170° C. Flash chromatography was performed using EM Silica Gel 60 (230-400 mesh) with the indicated eluent system. Melting points were determined in open capillaries on an Electrothermal IA 9200 melting point apparatus and are reported uncorrected. Optical rotation data were acquired using a Jasco P-1010 polarimeter. $^1$H-NMR spectra were recorded using a Bruker AVANCE 500 MHz spectrometer equipped with Oxford Narrow Bore Magnet. Chemical shifts are given in ppm on the delta scale from an internal standard of residual chloroform (7.26 ppm). Mass spectral data were obtained in a positive ion electrospray ionization (ESI) mode on a Finningam LCQ ion trap mass spectrometer. Samples were infused in methanol solution with an ESI voltage of 4.5 kV and capillary temperature of 200° C.

6.1. Example 1

D-erythro-2-N-(2'-Bromoacetyl)-sphingosine (2a). To a well-stirred mixture of D-erythro-sphingosine (1a, 200 mg, 0.67 mmol), 50% aqueous solution of sodium acetate (5 mL) and THF (12 mL) bromoacetyl bromide (98%, 0.180 mL, 2 mmol) was added drop-wise at room temperature. The reaction mixture was stirred for 20 min until a complete conversion of 1a to 2a was achieved (TLC monitoring). After the reaction was completed, the organic phase was separated and the aqueous layer was extracted with ethyl acetate (2×10 mL). The organic phases were combined, dried over anhydrous magnesium sulfate and evaporated under reduced pressure to dryness to give crude product. This material was purified by flash column chromatography (elution with $CHCl_3$-MeOH-conc. $NH_4OH$, 5:1:0.05, v/v/v) following recrystallization from ethyl acetate, to give 204 mg (73%) of pure 2a as white microcrystalline powder, mp 79-81° C.; TLC: $R_f$ ($CHCl_3$-MeOH, 5:1, v/v) $R_f$ 0.52; $[\alpha]^{22}_D$=+6.0° (c=1, $CHCl_3$); $[\alpha]^{22}_{365}$=+17.4° (c=1, $CHCl_3$); $^1$H NMR (500 MHz, $CDCl_3$) δ 7.19 (d, 1H, J=7.8, NH), 5.81 (dtd, 1H, J=15.5, 6.8, 1.1, 5-H), 5.52 (ddt, 1H, J=15.5, 6.8, 1.1, 4-H), 4.35 (t, 1H, J=5.1, 3-H), 4.02 (dd, 1H, J=11.4, 3.4, 1-Ha), 3.9 (d, 2H, J=2.4, $CH_2Br$), 3.88 (m, 1H, 2-H), 3.73 (dd, J=11.4, 3.5, 1-Hb), 2.06 (q, 2H, J=7.1, C(6)$H_2$), 1.36 (m, 2H, C(7)$H_2$), 1.24 (m, 20H, $CH_2$), 0.87 (t, 3H, J=7.1, $CH_3$); ESI-MS ($CH_3OH$, relative intensity, %) m/z 864.8, 862.7 and 860.8 ([2M+Na]$^+$, 50, 100 and 60), 442.1 and 444.1 ([M+Na]$^+$, 4 and 4), 419.7 and 421.7 (MH$^+$, 3 and 3), 402.0 and 404.0 ([MH—$H_2O$]$^+$, 21 and 20), 264.2 (3). Calcd for $C_{20}H_{38}$ $^{79}BrNO_3$ m/z 419.2; Calcd for $C_{20}H_{38}$ $^{81}BrNO_3$ m/z 421.2;

Anal. Calcd. for $C_{20}H_{38}BrNO_3$ (420.40): C, 57.14; H, 9.11; N, 3.33; Br, 19.01. Found: C, 57.24; H, 9.19; N, 3.30; Br, 18.97.

6.2. Example 2

D-erythro-2-N-(2'-Bromoacetyl)-4,5-dihydro-sphingosine (2b). To a well-stirred mixture of D-erythro-4,5-dihydro-sphingosine (1e, 250 mg, 0.83 mmol), 50% aqueous solution of sodium acetate (5 mL) and THF (12 mL) bromoacetyl bromide (98%, 0.223 mL, 2.5 mmol) was added drop-wise at room temperature. The reaction mixture was stirred for 25 min until a complete conversion of 1 e to 2b was achieved (TLC). After the reaction was completed, the organic phase was separated and the aqueous layer was extracted with ethyl acetate (2×10 ml). The combined organic layers were dried over anhydrous magnesium sulfate and evaporated under reduced pressure to dryness to give crude product. The crude Cer was purified by flash column chromatography (elution with $CHCl_3$-MeOH-conc. $NH_4OH$, 5:1:0.05, v/v/v) following recrystallization from n-hexane-acetone (3:1, v/v) to give 230 mg (65%) of pure 2b as white microcrystalline powder, mp 129-131° C.; TLC ($CHCl_3$-MeOH, 5:1, v/v) $R_f$ 0.54; $[\alpha]^{25}_D$=+5.60° (c=1, MeOH); $[\alpha]^{25}_{365}$=+11.20° (c=1, MeOH) $^1H$ NMR (500 MHz, MeOD-$CDCl_3$, 1:10, v/v) δ 3.86 (dd, 1H, J=11.5, 3.7, 1-Ha), 3.70 (m, 1H, 2-H), 3.63 (m, 2H, 3-H and 1-Hb), 3.07 (s, 21-1, $CH_2Br$), 1.45 (m, 4H, C(4)$H_2$ and C(S)$H_2$), 1.18 (m, 24H, $CH_2$), 0.81 (t, 31-1, J=7.1, $CH_3$); ESI-MS ($CH_3OH$, relative intensity, %) m/z 868.7, 866.8 and 864.7 ([2M+Na]$^+$, 45, 100 and 60), 446.3 and 444.5 ([M+Na]$^+$, 8 and 9), 423.7 and 421.9 (MH$^+$, 11 and 13), 406.0 and 404.0 ([MH—$H_2O$]$^+$, 5 and 4). Calcd for $C_{20}H_{40}$ $^{79}BrNO_3$ m/z 421.2; Calcd for $C_{20}H_{40}$ $^{81}BrNO_3$ m/z 423.2;

Anal. Calcd for $C_{20}H_{40}BrNO_3$ (422.4): C, 56.86; H, 9.54; N, 3.32; Br, 18.91. Found: C, 57.04; H, 9.58; N, 3.31; Br, 18.89.

6.3. Example 3

D-erythro-2-N-(6'-Bromohexanoyl)-sphingosine (2c). To a well-stirred mixture of D-erythro-sphingosine (1a, 335 mg, 1.12 mmol), 50% aqueous solution of sodium acetate (10 mL) and THF (24 mL) 6-bromohexanoyl chloride (97%, 0.269 mL, 1.7 mmol) was added drop-wise at room temperature. The reaction mixture was stirred for 20 min until a complete conversion was achieved (TLC). After the reaction was completed, the organic phase was separated and the aqueous layer was extracted with ethyl acetate (2×15 mL). The organic phases were combined, dried over anhydrous magnesium sulfate and evaporated under reduced pressure to dryness to give crude product. This material was purified by flash column chromatography (elution with $CHCl_3$-MeOH-conc. $NH_4OH$, 5:1:0.05, v/v/v) following recrystallization from n-hexane-ethyl acetate (4:1, v/v) to give 446 mg (79%) of pure 2c as white microcrystalline powder, mp 48-50° C.; TLC ($CHCl_3$-MeOH, 5:1, v/v) $R_f$ 0.60; $[\alpha]^{22}_D$=-2.95° (c=1, $CHCl_3$) and -10.3° (c=1, MeOH); $[\alpha]^{22}_{365}$=-16.2° (c=1, $CHCl_3$) and -35.1° (c=1, MeOH); $^1H$ NMR (500 MHz, $CDCl_3$) δ 6.28 (d, 1H, J=7.4, NH), 5.78 (dt, 1H, J=15.4, 6.8, 5-H), 5.52 (dd, 1H, J=15.4, 6.4, 4-H), 4.31 (t, 1H, J=4.8, 3-H), 3.95 (dd, 1H, J=11.3, 3.6, 1-Ha), 3.90 (m, 1H, 2-H), 3.69 (dd, J=11.4, 3.6, 1-Hb), 3.40 (t, 2H, J=6.8, C(6')$H_2Br$), 2.24 (t, 2H, J=7.5, $COCH_2$), 2.04 (q, 2H, J=7.1, C(6)$H_2$), 1.88 (m, 2H, C(5')$H_2$C(6')$H_2Br$), 1.66 (m, 2H, $COCH_2CH_2$), 1.48 (m, 2H, $COCH_2CH_2CH_2$), 1.35 (m, 2H, C(7)$H_2$), 1.25 (m, 20H, $CH_2$), 0.87 (t, 3H, J=7.0, $CH_3$); ESI-MS ($CH_3OH$, relative intensity, %) m/z 976.9, 974.9 and 972.8 ([2M+Na]$^+$, 60, 100 and 85), 477.8 and 475.8 (MH$^+$, 21 and 23), 460.0 and 458.0 ([MH—$H_2O$]$^+$, 14 and 17), 264.2 (3). Calcd for $C_{24}H_{46}$ $^{79}BrNO_3$ m/z 475.3; Calcd for $C_{24}H_{46}$ $^{81}BrNO_3$ m/z 477.3;

Anal. Calcd for $C_{24}H_{46}BrNO_3$ (476.5): C, 60.49; H, 9.73; N, 2.94; Br, 16.77. Found: C, 60.22; H, 9.73; N, 2.96; Br, 16.88.

6.4. Example 4

L-threo-2-N-(6'-Bromohexanoyl)-sphingosine (2d). To a well-stirred mixture of L-threo-sphingosine (1b, 225 mg, 0.75 mmol), 50% aqueous solution of sodium acetate (8 mL) and THF (20 mL) 6-bromohexanoyl chloride (97%, 0.203 mL, 1.33 mmol) was added drop-wise at room temperature. The reaction mixture was stirred for 20 min until a complete conversion was achieved (TLC). After the reaction was completed, the organic phase was separated and the aqueous layer was extracted with ethyl acetate (2×10 mL). The organic phases were combined, dried over anhydrous magnesium sulfate and evaporated under reduced pressure to dryness to give crude product. This material was purified by flash column chromatography (elution with $CHCl_3$-MeOH-conc.$NH_4OH$, 5:1:0.05, v/v/v) following recrystallization from n-hexane-ethyl acetate (8:1, v/v) to give 275 mg (70%) of pure 2d as white microcrystalline powder, mp 71-73° C. (wet at 64° C.); TLC ($CHCl_3$-MeOH, 5:1, v/v) $R_f$ 0.59; $[\alpha]^{22}_D$=-2.30° (c=1, $CHCl_3$) and -19.0° (c=1, MeOH); $[\alpha]^{22}_{365}$=-15.3° (c=1, $CHCl_3$) and -71.0° (c=1, MeOH); $^1H$ NMR (500 MHz, $CDCl_3$) δ 6.10 (d, 1H, J=7.4, NH), 5.73 (dt, 1H, J=15.4, 6.7, 5-H), 5.45 (dd, 1H, J=15.4, 6.5, 4-H), 4.37 (dd, 1H, J=6.1 and 4.5, 3-H), 3.91 (m, 1H, 2-H), 3.80 (m, 2H, 1-Ha and 1-Hb), 3.40 (t, 2H, J=6.8, C(6')$H_2Br$), 2.52 (bs, 2H, OH), 2.23 (t, 2H, J=7.5, $COCH_2$), 2.04 (q, 2H, J 6.9, C(6)$H_2$), 1.87 (m, 2H, C(5')$H_2$C(6')$H_2Br$), 1.67 (m, 2H, $COCH_2CH_2$), 1.48 (m, 2H, CO $CH_2CH_2CH_2$), 1.33 (m, 2H, C(7)$H_2$), 1.24 (m, 20H, $CH_2$), 0.87 (t, 3H, J=7.1, $CH_3$); ESI-MS ($CH_3OH$, relative intensity, %) m/z 977.2, 975.1 and 973.2 ([2M+Na]$^+$, 45, 100 and 71), 477.6 and 475.6 (MH$^+$, 19 and 21), 460.1 and 458.1 ([MH—$H_2O$]$^+$, 16 and 19), 264.2 (4). Calcd for $C_{24}H_{46}$ $^{79}BrNO_3$ m/z 475.3; Calcd for $C_{24}H_{46}$ $^{81}BrNO_3$ m/z 477.3;

Anal. Calcd for $C_{24}H_{46}BrNO_3$ (476.5): C, 60.49; H, 9.73; N, 2.94; Br, 16.77. Found: C, 60.31; H, 9.68; N, 2.91; Br, 17.09.

Anal. Calcd for $C_{29}H_{51}BrN_2O_3 \cdot H_2O$ (573.65): C, 60.72; H, 9.31; N, 4.88; Br, 13.93. Found: C, 60.23; H, 9.03; N, 4.64; Br, 13.63.

6.5. Example 5

D-erythro-2-N-(6'-Bromohexanoyl)-4,5-dihydro-sphingosine (2g). To a well-stirred mixture of D-erythro-4,5-dihydro-sphingosine (1e, 250 mg, 0.83 mmol), 50% aqueous solution of sodium acetate (10 mL) and THF (24 mL) bromohexanoyl chloride (97%, 0.198 mL, 1.25 mmol) was added drop-wise at room temperature. The reaction mixture was stirred for 20 min until a complete conversion was achieved (TLC). After the reaction was completed, the organic phase was separated and the aqueous layer was extracted with ethyl acetate (2×15 mL). The organic phases were combined, dried over anhydrous magnesium sulfate and evaporated under reduced pressure to dryness to give crude product. This material was purified by flash column chromatography (elution with $CHCl_3$-MeOH-conc. $NH_4OH$, 5:1: 0.05, v/v/v) following recrystallization from n-hexane-ethyl acetate (4:1, v/v) to give 274 mg (69%) of pure 2c as white microcrystalline powder, mp 101-103° C., TLC ($CHCl_3$-MeOH, 5:1, v/v) $R_f$ 0.62; $[\alpha]^{22}_D$=+4.08° (c=1, MeOH); $[\alpha]^{25}_{365}$=+5.63° (c=1, MeOH) $^1H$ NMR (500 MHz, MeOD-$CDCl_3$, 1:10, v/v) δ 3.90 (dd, 1H, J=11.4, 3.7, 1-Ha), 3.72 (m, 1H, 2-H), 3.60 (m, 2H, 3-H and 1-Hb), 3.43 (t, 2H, J=6.8, C(6')$H_2Br$), 2.20 (t, 2H, J=7.5, CO $CH_2$), 2.01 (p, 2H, J=7.5, C(5')$H_2$C(6')$H_2Br$), 1.85 (m, 2H, $COCH_2CH_2$), 1.68 (m, 2H, C(4)$H_2$), 1.46 (m, 2H, CO $CH_2CH_2CH_2$), 1.20 (m, 24H, $CH_2$), 0.80 (t, 3H, J=7.1, $CH_3$); ESI-MS ($CH_3OH$, relative intensity, %) m/z 980.8, 978.9 and 976.9 ([2M+Na]$^+$, 55, 100 and 50), 502.1 and 498.1 ([M+Na]$^+$, 12 and 11), 480.1 and 478.1 (MH$^+$, 36 and 43), 462.1 and 460.1 ([MH—$H_2O$]$^+$, 4 and 4). Calcd for $C_{24}H_{48}$ $^{79}BrNO_3$ m/z 477.3; Calcd for $C_{24}H_{48}$ $^{81}BrNO_3$ m/z 479.3;

Anal. Calcd for $C_{24}H_{48}BrNO_3$ (478.5): C, 60.24; H, 10.11; N, 2.93; Br, 16.70. Found: C, 59.93; H, 10.11; N, 2.90; Br, 16.91.

6.6. Example 6

L-erythro-2-N-(6'-Bromohexanoyl)-sphingosine (2e). The title compound was prepared from L-erythro-sphingosine (1c, 200 mg, 0.67 mmol) in the same fashion as compound 2c from 1a. Yield: 227 mg (71%). Analytical sample of 2e was obtained by crystallization from n-hexane-EtOAc (4:1, v/v/; white powder); $[\alpha]^{22}_D$=+2.75° (c=1, CHCl$_3$) and +9.90° (c=1, MeOH); $[\alpha]^{22}_{365}$=+16.8° (c=1, CHC$_{l3}$) and +36.1° (c=1, MeOH). Remaining data identical as reported for 2c.

Anal. Calcd for $C_{24}H_{46}BrNO_3$ (476.5): C, 60.49; H, 9.73; N, 2.94; Br, 16.77. Found: C, 60.10; H, 9.42; N, 2.81; Br, 16.71.

6.7. Example 7

D-threo-2-N-(6'-Bromohexanoyl)-sphingosine (2f). The title compound was prepared from D-threo-sphingosine (1d, 200 mg 0.67 mmol) in the same fashion as compound 2d from 1b. Yield: 205 mg (64%). Analytical sample of 2f was obtained by crystallization from n-hexane-EtOAc (6:1, v/v/; white powder); $[\alpha]^{22}_D$=+2.15° (c=1, CHCl$_3$) and +20.0° (c=1, MeOH); $[\alpha]^{22}_{365}$=+14.2° (c=1, CHCl$_3$) and +75.0° (c=1, MeOH). Remaining data identical as reported for 2d.

Anal. Calcd for $C_{24}H_{46}BrNO_3$ (476.5): C, 60.49; H, 9.73; N, 2.94; Br, 16.77. Found: C, 60.21; H, 9.66; N, 2.82; Br, 16.63.

6.8. Example 8

D-erythro-2-N-(12'-Bromododecanoyl-sphingosine (2h)

(A). Synthesis of 12-bromododecanoyl chloride. 12-Bromododecanoic acid (97%, 288 mg, 1.1 mmol) was dissolved in dry cyclohexane (4 mL) by stirring at 45° C. for 20 min. To this well-stirred and water-cooled mixture a one drop (~0.02 mL) of dry pyridine was added following oxalyl chloride (99%, 0.145 mL, 1.65 mmol) over 1 min. After the addition was completed, the cooling bath was removed and the reaction mixture was heated at 50° C. for 15 min and then left to reach room temperature for an additional 30 min. The reaction mixture was evaporated to dryness by purging dry nitrogen gas into the reaction flask following drying the residue under vacuum (~1 ton) at +4° C. over 30 min. The freshly prepared acid chloride was dissolved in dry THF and taken directly to the next reaction.

(B). Synthesis of •h. To a well-stirred mixture of D-erythro-sphingosine (1a, 200 mg, 0.67 mmol), 50% aqueous solution of sodium acetate (5 ml) and THF (10 mL) a solution of 12-bromododecanoyl chloride (0.326 mg) in dry THF (3.0 mL) was added drop-wise over 1 min. After the addition was completed, the reaction mixture was stirred for an additional 20 min at room temperature. The organic layer was separated and the aqueous phase was extracted with ethyl acetate (3×5 mL). The combined organic extracts were dried (MgSO$_4$), filtered, and evaporated to dryness under reduced pressure to give crude product. This material was purified by flash column chromatography (CHCl$_3$: MeOH: conc. NH$_4$OH, 10:2: 0.5, v/v/v) to give pure 2h (274 mg, 73%) as a white solid. An analytical sample of 2h was obtained by recrystallization from n-hexane-ethyl acetate (5:1, v/v) to give white microcrystalline powder, mp 71-73° C.; TLC R$_f$(CHCl$_3$-MeOH, 5:1, v/v) R$_f$ 0.65; $[\alpha]^{22}_D$=−2.0° (c=1, CHCl$_3$) and −15.6° (c=1, MeOH); $[\alpha]^{22}_{365}$=12.5° (c=1, CHCl$_3$) and −50.1° (c=1, MeOH); $^1$H NMR (500 MHz, CDCl$_3$) δ 6.23 (d, 1H, J=7.4, NH), 5.78 (dt, 1H, J=15.4, 6.6, 5-H), 5.52 (dd, 1H, J=15.4, 6.5, 4-H), 4.31 (t, 1H, J=4.6, 3-H), 3.95 (dd, 1H, J=11.2, 3.7, 1-Ha), 3.90 (m, 1H, 2-H), 3.69 (dd, 1H, J=11.2, 3.7, 1-Hb), 3.39 (t, 2H, J=6.8, C(12')H$_2$Br), 2.22 (t, 2H, J=7.5, COCH$_2$), 2.04 (q, 2H, J=7.1, C(6)H$_2$), 1.84 (m, 2H, C(11') H$_2$C(12')H$_2$Br), 1.63 (m, 2H, COCH$_2$CH2), 1.40 (m, 2H, $\overline{C}$(10')H$_2$C(11')H$_2$C(12')H$_2$Br), 1.35 (m, $\overline{2}$H, C(7)H$_2$), 1.25 (m, 32$\overline{H}$, CH$_2$), 0.87 (t, 3H, J=7.0, CH$_3$); ESI-MS (CH$_3$OH, relative intensity, %) m/z 1145.0, 1142.9 and 1141.9 ([2M+Na], 54, 100, 55), 1122.7, 1120.7 and 1118.4 ([2M+H]$^+$, 30, 96, 34), 584.2 and 582.2 ([M+Na], 10 and 8), 561.9 and 559.9 (MH$^+$, 50 and 58), 543.8 and 541.9 ([MH—H$_2$0]$^+$, 17 and 19). Calcd for $C_{30}H_{58}^{79}BrNO_3$ m/z 559.4; Calcd for $C_{30}H_{58}^{81}BrNO_3$ m/z 561.4;

Anal. Calcd. for $C_{30}H_{58}BrNO_3$ (560.7): C, 64.26; H, 10.43; N, 2.50; Br, 14.25. Found: C, 64.06; H, 10.45; N, 2.51; Br, 14.54.

6.9. Example 10

D-erythro-2-N-(16'-Bromohexadecanoyl)-sphingosine (2j)

(A). Synthesis of 16-bromohexadecanoyl chloride. 16-Bromohexadecanoic acid (97%, 1.9 g, 5.7 mmol) was dissolved in dry cyclohexane (30 mL) by stirring at 45° C. for 30 min. To this well-stirred and water-cooled mixture one drop (~0.02 mL) of dry pyridine was added following oxalyl chloride (99%, 0.75 mL, 8.6 mmol) over 1 min. After the addition was completed, the cooling bath was removed and the reaction mixture was heated at 50° C. for 15 min and then left to reach room temperature for an additional 30 min. The reaction mixture was evaporated to dryness by purging dry nitrogen gas into the reaction flask following drying the residue under vacuum (~1 torr) at +4° C. over 30 min. The freshly prepared acid chloride was dissolved in dry THF and taken directly to the next reaction.

(B). Synthesis of •j. To a well-stirred mixture of D-erythro-sphingosine (1a, 1.11 g, 3.7 mmol), 50% aqueous solution of sodium acetate (18 ml) and THF (32 mL) a solution of 16-bromohexadecanoyl chloride (~2.1 g) in dry THF (8.0 mL) was added dropwise over 1 min. After the addition was completed, the reaction mixture was stirred for an additional 25 min at room temperature. The organic layer was separated and the aqueous phase was extracted with ethyl acetate (2×15 mL). The combined organic extracts were dried (MgSO$_4$), filtered, and evaporated to dryness under reduced pressure to give crude product. This material was purified by flash column chromatography (CHCl$_3$:MeOH: conc. NH$_4$OH, 8:1:0.05, v/v/v) to give pure 2j (2.2 g, 96% yield) as a white powder. An analytical sample of 2j was obtained by recrystallization from n-hexane-ethyl acetate (1:2, v/v) to give a white microcrystalline powder, mp 87-89° C.; TLC R$_f$ (CHCl$_3$-MeOH, 8:1, v/v) R$_f$ 0.65. $[\alpha]^{22}_D$=−3.1° (c=1, CHCl$_3$) and −12.3° (c=1, MeOH); $[\alpha]^{22}_{365}$=−14.2° (c=1, CHCl$_3$) and −46.4° (c=1, MeOH); $^1$H NMR (500 MHz, CDCl$_3$) δ 6.22 (d, 1H, J=7.5, NH), 5.77 (dt, 1H, J=15.4, 6.8, 5-H), 5.52 (dd, 1H, J=15.4, 6.8, 4-H), 4.31 (t, 1H, J=4.7, 3-H), 3.95 (dd, 1H, J=11.2, 3.8, 1-Ha), 3.90 (m, 1H, 2-H), 3.70 (dd, J=11.2, 3.8, 1-Hb), 3.40 (t, 2H, J=6.8, C(16')H$_2$Br), 2.22 (t, 2H, J=7.5, COCH$_2$), 2.04 (q, 2H, J=7.1, C(6)H$_2$), 1.84 (m, 2H, C(15')$\underline{H}_2$C(16')H$_2$Br), 1.63 (m, 2H, COCH$_2$CH$_2$), 1.40 $\overline{\text{(m}}$, 2H, C(14') H$_2$C(15')H$_2$C(16')H$_2$Br), 1.35 (m, 2H, C(7)H$_2$), 1.25 (m, $\overline{40}$H, CH$_2$), 0.87 (t, 3H, J=7.1, CH$_3$); ESI-MS (CH$_3$OH, relative intensity, %) m/z 1235.7, 1233.8, 1232.8 and 1230.7 ([2M+H]$^+$ 38, 86, 100 and 65), 618.0 and 616.0 (MH$^+$, 76 and 78), 600.2 and 598.2 ([MH—H$_2$O]$^+$, 17 and 19). Calcd for $C_{34}H_{66}^{79}BrNO_3$ m/z 615.4; Calcd for $C_{34}H_{66}^{81}BrNO_3$ m/z 617.4;

Anal. Calcd. for $C_{34}H_{66}BrNO_3$ (616.8): C, 66.21; H, 10.79; N, 2.27; Br, 12.95. Found: C, 66.09; H, 10.78; N, 2.32; Br, 12.74.

6.10. Example 10

D-erythro-2-N-[12'-Bromododecanoyl]-4,5-dihydrosphingosine (2i)

To a well-stirred mixture of D-erythro-4,5-dihydrosphingosine (ie, 200 mg, 0.66 mmol), 50% aqueous solution of sodium acetate (5 ml) and THF (10 mL) a solution of 12-bromododecanoyl chloride (~0.326 mg) in dry THF (3.0 mL) was added drop-wise over 1 min. After the addition was completed, the reaction mixture was stirred for an additional 20 min at room temperature. The organic layer was separated and the aqueous phase was extracted with ethyl acetate (3×5 mL). The combined organic extracts were dried ($MgSO_4$), filtered, and evaporated to dryness under reduced pressure to give crude product. This material was purified by flash column chromatography ($CHCl_3$:MeOH: conc. $NH_4OH$, 10:2: 0.05, v/v/v) to give pure 2i (265 mg, 71%) s a white solid. An analytical sample of 2i was obtained by recrystallization from n-hexane-ethyl acetate (5:1, v/v) to give white microcrystalline powder, mp 97-98° C.; TLC $R_f$ ($CHCl_3$-MeOH, 5:1, v/v) $R_f$ 0.67; $[\alpha]^{21}_D$=+5.9° (c=1, $CHCl_3$) and +3.1° (c=1, MeOH); $[\alpha]^{21}_{365}$=+14.5° (c=1, $CHCl_3$) and +5.5° (c=1, MeOH); $^1H$ NMR (500 MHz, $CDCl_3$) δ 6.35 (d, 1H, J=7.7, NH), 4.01 (dd, 1H, J=11.3, 3.5, 1-Ha), 3.83 (m, 1H, 2-H), 3.78 (m, 1H, 3-H), 3.75 (dd, 1H, J=11.3, 3.5, 1-Hb), 3.41 (t, 2H, J=6.9, C(12')$H_2Br$), 2.65 (bs, 2H, OH) 2.23 (t, 2H, J=7.5, $COCH_2$), 1.85 (p, 2H, J=7.7, C(11')$H_2$C(12')$H_2Br$), 1.65 (m, 2H, $COCH_2CH_2$), 1.54 (m, 2H, $\overline{C}(4)H_2$), 1.42 (m, 2H, C(10')H2C($\overline{11}'$)$H_2$C(12')$H_2Br$), 1.25 (m, 36H, $CH_2$), 0.88 (t, 3H, J=7.1, $\overline{C}H_3$); ESI-MS ($CH_3OH$, relative intensity, %) m/z 1149.9, 1147.8, 1146.8 and 1144.8 ([2M+Na], 25, 65, 100 and 50), 1126.7, 1125.7 and 1123.7 ([2M+H]$^+$, 22, 20 and 4). Calcd for $C_{30}H_{60}{}^{79}BrNO_3$ m/z 561.4; Calcd for $C_3OH60 {}^{81}BrNO_3$ m/z 563.4;

Anal. Calcd. for $C_{30}H_{60}BrNO_3$ (562.7): C, 64.03; H, 10.75; N, 2.49; Br, 14.20. Found: C, 63.79; H, 10.92; N, 2.54; Br, 14.44.

6.11. Example 12

D-erythro-2-N-[16'-Bromododecanoyl]-4,5-dihydrosphingosine (2k)

To a well-stirred mixture of D-erythro-4,5-dihydrosphingosine (1e, 200 mg, 0.66 mmol), 50% aqueous solution of sodium acetate (5 ml) and THF (10 mL) a solution of 16-bromohexadecanoyl chloride (~0.380 mg) in dry THF (4 mL) was added dropwise over 1 min. After the addition was completed, the reaction mixture was stirred for an additional 20 min at room temperature. The organic layer was separated and the aqueous phase was extracted with ethyl acetate (2×5 mL). The combined organic extracts were dried ($MgSO_4$), filtered, and evaporated to dryness under reduced pressure to give crude product. This material was purified by flash column chromatography ($CHCl_3$:MeOH: conc. $NH_4OH$, 8:1: 0.05, v/v/v) to give pure 2k (320 mg, 78% yield) as a white powder. An analytical sample of 2k was obtained by recrystallization from n-hexane-ethyl acetate (1:3, v/v) to give a white microcrystalline powder, mp 93-95° C.; TLC $R_f$ ($CHCl_3$-MeOH, 8:1, v/v) $R_f$ 0.67. $[\alpha]^{22}_D$=+4.94° (c=1, $CHCl_3$); $[\alpha]^{22}_{365}$=+12.6° (c=1, $CHCl_3$); 1H NMR (500 MHz, $CDCl_3$) δ 6.25 (d, 1H, J=7.6, NH), 3.95 (dd, 1H, J=11.3, 3.4, 1-Ha), 3.77 (m, 1H, 2-H), 3.72 (m, 1H, 3-H), 3.69 (dd, 1H, J=11.3, 3.4, 1-Hb), 3.34 (t, 2H, J=6.9, C(16')$H_2Br$), 2.16 (t, 2H, J=7.5, $COCH_2$), 1.77 (p, 2H, J=7.0, C(15')$\underline{H}_2$C(16')$H_2Br$), 1.59 (m, 2H, $COCH_2CH_2$), 1.45 (m, 2H, $\overline{C}(4)H_2$), $\overline{1.35}$ (m, 2H, C(14')$H_2$C(15')$H_2$C(16')$H_2Br$), 1.19 (m, $\overline{36}H$, $CH_2$), 0.81 (t, 3H, $J=\overline{7.0}$, $\overline{CH_3}$); ESI-MS ($CH_3OH$, relative intensity, %) m/z 1240.2, 1238.3, 1237.3 and 1235.3 ([2M+H]$^+$, 30, 62, 97 and 40), 621.5.0 and 618.4 (MH$^+$, 28 and 100), 602.5 and 600.5 ([MH—H20]$^+$, 7 and 8). Calcd for $C_{34}H_{68}{}^{79}BrNO_3$ m/z 617.4; Calcd for $C_{34}H_{68}{}^{81}BrNO_3$ m/z 619.4;

Anal. Calcd. for $C_3{}_4H_{68}BrNO_3$ (618.8): C, 65.99; H, 11.08; N, 2.26; Br, 12.91. Found: C, 65.63; H, 10.88; N, 2.19; Br, 12.86.

6.12. Example 13

L-threo-2-N-[16'-Bromohexadecanoyl-sphingosine (2l)

To a well-stirred mixture of L-threo-sphingosine (1b, 200 mg, 0.67 mmol), 50% aqueous solution of sodium acetate (5 ml) and THF (10 mL) a solution of 16-bromohexadecanoyl chloride (~0.380 mg) in dry THF (4 mL) was added dropwise over 1 min. After the addition was completed, the reaction mixture was stirred for an additional 20 min at room temperature. The organic layer was separated and the aqueous phase was extracted with ethyl acetate (2×5 mL). The combined organic extracts were dried ($MgSO_4$), filtered, and evaporated to dryness under reduced pressure to give crude product. This material was purified by flash column chromatography ($CHCl_3$:MeOH: conc. $NH_4OH$, 8:1:0.05, v/v/v) to give pure 21 (mg, 82% yield) as a white powder. An analytical sample of 2l was obtained by recrystallization from n-hexane-ethyl acetate (1:2, v/v) to give a white microcrystalline powder, mp 98-100° C.; TLC $R_f$ ($CHCl_3$-MeOH, 8:1, v/v) $R_f$ 0.66. $[\alpha]^{22}_D$=2.70° (c=1, $CHCl_3$); $[\alpha]^{22}_{365}$=−16.0° (c=1, $CHCl_3$); $^1H$ NMR (500 MHz, $CDCl_3$) δ 6.09 (d, 1H, J=7.7, NH), 5.73 (dtd, 1H, J=15.4, 6.7, 1.0, 5-H), 5.45 (ddt, 1H, J=15.4, 6.7, 1.0, 4-H), 4.38 (dd, 1H, J=6.3 and 3.5, 3-H), 3.90 (m, 1H, 2-H), 3.80 (m, 2H, 1-Ha and 1-Hb), 3.39 (t, 2H, J=6.8, C(16')$H_2Br$), 2.21 (t, 2H, J=7.3, $COCH_2$), 2.02 (q, 2H, J=7.0, C(6)$H_2$), 1.85 (m, 2H, C(15')$H_2$C(16')$H_2Br$), 1.61 (m, 2H, $COCH_2CH_2$), 1.42 (m, 2H, C(14')$H_2$C(15')$H_2$C(16')$H_2Br$), 1.24 (m, $\overline{20}H$, $CH_2$), 0.87 (t, $3\overline{H, J}$=7.1, $CH_3$); ESI-MS ($CH_3OH$, relative intensity, %) m/z 1235.3, 1233.3, 1232.5 and 1230.5 ([2M+H]$^+$67, 100, 61 and 18), 618.4 and 616.4 (MH$^+$, 54 and 56), 600.5 and 598.5 ([MH—$H_2O$]$^+$, 35 and 33). Calcd for $C_{34}H_{66}{}^{79}BrNO_3$ m/z 615.4; Calcd for $C_{34}H_{66}{}^{81}BrNO_3$ m/z 617.4;

Anal. Calcd. for $C_{34}H_{66}BrNO_3$ (616.8): C, 66.21; H, 10.79; N, 2.27; Br, 12.95. Found: C, 66.13; H, 10.83; N, 2.32; Br, 12.81.

6.13. Example 13

D-erythro-2-N-Nicotinoyl-sphingosine (3). To a well-stirred mixture of D-erythro-sphingosine (1a, 200 mg, 0.67 mmol), 50% aqueous solution of sodium acetate (5 mL) and THF (12 mL) nicotinoyl chloride hydrochloride (97%, 245 mg, 1.34 mmol) was added portion-wise at room temperature. The reaction mixture was stirred for 40 min until a complete conversion was achieved (TLC). After the reaction was completed, the organic phase was separated and the aqueous layer was extracted with ethyl acetate (3×10 mL). The organic phases were combined, dried over anhydrous magnesium sulfate and evaporated under reduced pressure to dryness to give crude product. This material was purified by flash column chromatography (elution with CHCl$_3$-MeOH-conc. NH$_4$OH, 5:1:0.05, v/v/v) following recrystallization from n-hexane-ethyl acetate (2:1) to give 195 mg (72%) of pure 3 as white microcrystalline powder, mp 104-106° C.; TLC R$_f$ (CHCl$_3$-MeOH, 8:1, v/v) R$_f$ 0.17; $^1$H NMR (500 MHz, CDCl$_3$) δ: 9.01 (d, 1H, J=2.0, 2-H$_{Py}$), 8.70 (dd, 1H, J=1.6 and 4.8, 6-H$_{Py}$), 8.11 (dt, 1H, J=2.0 and 7.9, 4-H$_{Py}$), 7.37 (dd, 1H, J=4.8 and 7.9, 5-H$_{Py}$), 7.12 (d, 1H, J=7.2, NH), 5.84 (dtd, 1H, J=15.4, 6.7, 1.1, 5-H), 5.60 (ddt, 1H, J=15.4, 6.7, 1.1, 4-H), 4.48 (t, 1H, J=4.8, 3-H), 4.12 (m, 2H, 1-Ha and 2-H), 3.83 (dd, J=4.0 and 12.1, 1-Hb), 2.05 (q, 2H, J=7.1, C(6)H$_2$), 1.36 (m, 2H, C(7)H$_2$), 1.24 (m, 20H, CH$_2$), 0.87 (t, 3H, J=7.1, CH$_3$); ESI-MS (CH$_3$OH, relative intensity, %) m/z 830.9 ([2M+Na]$^+$, 100), 405.2 (MH$^+$, 3 and 3). Calcd. for C$_{24}$H$_{40}$N$_2$O$_3$ m/z 404.3.

Anal. Calcd. for C$_{24}$H$_{40}$N$_2$O$_3$ (404.6): C, 71.25; H, 9.97; N, 6.92. Found: C, 68.90; H, 9.85; N, 6.71.

6.14. Example 14

D-erythro-2-N-Nicotinoyl-sphingosine (3). To a well-stirred mixture of D-erythro-sphingosine (1a, 200 mg, 0.67 mmol), 50% aqueous solution of sodium acetate (5 mL) and THF (12 mL) nicotinoyl chloride hydrochloride (97%, 245 mg, 1.34 mmol) was added portion-wise at room temperature. The reaction mixture was stirred for 40 min until a complete conversion was achieved (TLC). After the reaction was completed, the organic phase was separated and the aqueous layer was extracted with ethyl acetate (3×10 mL). The organic phases were combined, dried over anhydrous magnesium sulfate and evaporated under reduced pressure to dryness to give crude product. This material was purified by flash column chromatography (elution with CHCl$_3$-MeOH-conc. NH$_4$OH, 5:1:0.05, v/v/v) following recrystallization from n-hexane-ethyl acetate (2:1) to give 195 mg (72%) of pure 3 as white microcrystalline powder, mp 104-106° C.; TLC R$_f$ (CHCl$_3$-MeOH, 8:1, v/v) R$_f$ 0.17; $^1$H NMR (500 MHz, CDCl$_3$) δ: 9.01 (d, 1H, J=2.0, 2-H$_{Py}$), 8.70 (dd, 1H, J=1.6 and 4.8, 6-H$_{Py}$), 8.11 (dt, 1H, J=2.0 and 7.9, 4-H$_{Py}$), 7.37 (dd, 1H, J=4.8 and 7.9, 5-H$_{Py}$), 7.12 (d, 1H, J=7.2, NH), 5.84 (dtd, 1H, J=15.4, 6.7, 1.1, 5-H), 5.60 (ddt, 1H, J=15.4, 6.7, 1.1, 4-H), 4.48 (t, 1H, J=4.8, 3-H), 4.12 (m, 2H, 1-Ha and 2-H), 3.83 (dd, J=4.0 and 12.1, 1-Hb), 2.05 (q, 2H, J=7.1, C(6)H$_2$), 1.36 (m, 2H, C(7)H$_2$), 1.24 (m, 20H, CH$_2$), 0.87 (t, 3H, J=7.1, CH$_3$); ESI-MS (CH$_3$OH, relative intensity, %) m/z 830.9 ([2M+Na]$^+$, 100), 405.2 (MH$^+$, 3 and 3). Calcd. for C$_{24}$H$_{40}$N$_2$O$_3$ m/z 404.3.

Anal. Calcd. for C$_{24}$H$_{40}$N$_2$O$_3$ (404.6): C, 71.25; H, 9.97; N, 6.92. Found: C, 68.90; H, 9.85; N, 6.71.

6.15. Example 15

D-erythro-2-N-[3'-(3"-Pyridyl)-propionoyl]-sphingosine (4)

(A). Synthesis of 3-pyridinopropionyl chloride hydrochloride. 3-Pyridinopropionic acid (97%, 288 mg, 1.1 mmol) was dissolved in anhydrous ethylene glycol dimethyl ether (8 mL) by stirring at 45° C. for 30 min. To this well-stirred and water-cooled mixture one drop (~0.02 mL) of dry pyridine was added following oxalyl chloride (99%, 0.145 mL, 1.65 mmol) over 1 min. After the addition was completed, the cooling bath was removed and the reaction mixture was heated at 50° C. for 15 min and then left to reach room temperature for an additional 30 min. The reaction mixture was evaporated to dryness by purging dry nitrogen gas into the reaction flask following drying the residue under vacuum (~1 torr) at +4° C. over 30 min. The freshly prepared acid chloride was dissolved in dry THF and taken directly to the next reaction.

To a well-stirred mixture of D-erythro-sphingosine (1a, 200 mg, 0.67 mmol), 50% aqueous solution of sodium acetate (5 ml) and THF (5 mL) a solution of 3-pyridinopropionyl chloride hydrochloride (0.380 mg) in dry THF (10 mL) was added drop-wise over 1 min. After the addition was completed, the reaction mixture was stirred for an additional 20 min at room temperature. The organic layer was separated and the aqueous phase was extracted with ethyl acetate (2×10 mL). The combined organic extracts were dried (MgSO$_4$), filtered, and evaporated to dryness under reduced pressure to give crude product. This material was purified by flash column chromatography (CHCl$_3$:MeOH: conc. NH$_4$OH, 65:10:1, v/v/v) to give pure 4 (240 mg, 64%) as a white solid. An analytical sample of 4 was obtained by recrystallization from n-hexane-ethyl acetate (5:1, v/v) to give white microcrystalline powder, mp 83-84.5° C.; TLC R$_f$ (CHCl$_3$-MeOH, 8:1, v/v) R$_f$ 0.18; $^1$H NMR (500 MHz, CDCl$_3$) δ 8.44 (d, 1H, J=1.5, 2-H$_{Py}$), 8.40 (dd, 1H, J=1.5 and 4.2, 6-H$_{Py}$), 7.45 (d, 1H, J=7.7, 4-H$_{Py}$), 7.37 (dd, 1H, J=10.3 and 15.1, 5-H$_{Py}$), 6.36 (d, 1H, J=7.8, NH), 5.76 (dtd, 1H, J=15.4, 6.7, 1.1, 5-H), 5.48 (ddt, 1H, J=15.4, 6.2, 1.1, 4-H), 4.24 (t, 1H, J=4.5, 3-H), 3.91 (dd, 1H, J=3.5 and 11.4, 1-Ha), 3.85 (m, 1H, 2-H), 3.63 (dd, 1H, J=3.4 and 11.1, 1-Hb), 2.97 (t, 2H, J=7.4, C(O)C H$_2$CH$_2$), 2.52 (t, 2H, J=7.4, C(O)CH$_2$CH$_2$), 2.02 (q, 2H, J=7.1, C(6)H$_2$), 1.34 (m, 2H, C(7)H$_2$), 1.24 (m, 20H, CH$_2$), 0.87 (t, 3H, J=7.1, CH$_3$); ESI-MS (CH$_3$OH, relative intensity, %) m/z 887.0 ([2M+Na]$^+$, 100), 864.8 ([2M+H]$^+$, 35), 433.0 (MH$^+$, 4). Calcd. for C$_{26}$H$_{44}$N$_2$O$_3$ m/z 432.3.

Anal. Calcd. for C$_{26}$H$_{44}$N$_2$O$_3$ (432.64): C, 72.18; H, 10.25; N, 6.48. Found: C, 71.44; H, 10.29; N, 6.45.

6.16 Example 16

D-erythro-2-N-[16'-(1"-Pyridinium)-hexadecanoyl]-sphingosine Bromide (LCL30)

A mixture of D-erythro-2-N-(16'-bromohexadecanoyl)-sphingosine 2j (2.15 g, 3.48 mmol), anhydrous pyridine (10 mL) and anhydrous toluene (8 mL) was heated in a closed glass test-tube in an oil bath at 75-85° C. over 6 hrs. After completion, the reaction mixture was cooled to room temperature and diluted with ethyl acetate (20 ml) and left in the refrigerator (+4° C.) for 6 hrs. The formed precipitate was separate by filtration, washed with ethyl acetate-acetone (10 ml, 1:1, v/v/) and dried to give crude product (2.31 g). This material was recrystallized from acetone-ethanol (5:1, v/v) to give LCL30 (2.16 g, 89%) as a white microcrystalline powder, mp 116-118° C.; TLC (CHCl$_3$—(CH$_3$)$_2$CO-MeOH—CH$_3$COOH—H$_2$O, 20:8:4:2:1, v/v/v) R$_f$ 0.33; RP TLC (C18 Silica, CH$_3$CN-MeOH-1M NH$_4$Cl (aq), 4:1:1.5 V/V) R$_f$ 0.22; $[\alpha]^{22}_D$=-1.20° (c=1, CHCl$_3$) and -8.86° (c=1, MeOH); $[\alpha]^{22}_{365}$=-11.8° (c=1, CHCl$_3$) and -35.4° (c=1, MeOH); $^1$H NMR (500 MHz, CDCl$_3$) δ 9.37 (d, 2H, J=6.0, 2.6-H$_{Py}$) 8.47 (t, 1H, J=7.8, 4-H$_{Py}$), 8.11 (t, 2H, J=7.1, 3,5-H$_{Py}$), 6.80 (d, 1H, J=6.7, NH), 5.73 (dtd, 1H, J=15.2, 6.6, 0.6, 5-H), 5.52 (ddt, 1H, J=15.2, 6.5, 1.2, 4-H), 4.96 (t, 2H, J=7.5, C(16) H$_2$-pyridinium ring), 4.30 (m, 1H, 3-H), 3.93 (dd, 2H, J=11.1, 4,5,1-Ha), 3.91 (m, 2H, 2-H), 3.69 (dd, 1H, J=11.1, 2.7, 1-Hb), 2.29 (t, 2H, J=7.4, COCH$_2$), 2.06 (m, 4H, C(15) H$_2$C(16)H$_2$-pyridinium ring and C(6)H$_2$), 1.65 (m, 2H, COCH$_2$CH$_2$), 1.26 (m, 44H, CH$_2$), 0.88 (t, 3H, J=7.1, CH$_3$); (MeOD) 9.00 (dd, 2H, J=5.5, 1.2, 2.5-H$_{Py}$) 8.59 (tt, 1H, J=7.8, 1.2 4-H$_{Py}$), 8.11 (t, 2H, J=7.0, 3,5-H$_{Py}$), 5.68 (dtd, 1H, J=15.3, 6.7, 0.8, 5-H), 5.44 (ddt, 1H, J=15.3, 7.5, 1.3, 4-H), 4.63 (t, 2H, J=7.5, C(16)H$_2$-pyridinium ring), 4.04 (t, 1H, J=7.4, 3-H), 3.84 (dt, 1H, J=7.5, 5.0, 2-H), 3. (d, 2H, J=5.1, 1-Ha,b), 2.18 (t, 2H, J=7.5, COCH$_2$), 2.03 (m, 4H, C(15)H$_2$C(16)H$_2$-pyridinium ring and C(6)H$_2$), 1.57 (m, 2H, COCH$_2$CH$_2$), 1.38 (m, 4H, C(14)H$_2$C(15)H$_2$C(16)H$_2$-pyridinium ring and C(7)H$_2$), 1.27 (m, 40H, CH$_2$), 0.88 (t, 3H, J=7.0, CH$_3$); ESI-MS (CH$_3$OH, relative intensity, %) m/z 615.6 (M$^+$, 100). Calcd. for [C$_{39}$H$_{71}$N$_2$O$_3$]$^+$ m/z 615.5.

Anal. Calcd. for C$_{39}$H$_{71}$BrN$_2$O$_3$ (695.9): C, 67.3; H, 10.28; N, 4.03; Br, 11.48. Found: C, 67.03; H, 10.34; N, 4.06; Br, 11.26.

6.17. Example 17

D-erythro-2-N-[6'-(1"-Pyridinium)-hexanoyl]-sphingosine Bromide (LCL29)

A mixture of D-erythro-2-N-(6'-bromohexanoyl)-sphingosine (2c, 240 mg, 0.50 mmol), anhydrous pyridine (2 mL) and anhydrous toluene (2 mL) was heated in a closed glass test-tube in an oil bath at 75-85° C. over 4.5 hrs. After completion, the reaction mixture was cooled and the mixture was evaporated to dryness. The afforded residue was dried under high vacuum (~1 torr at rt over 6 hr) and recrystallized from anhydrous ethyl acetate-acetone (1:1, v/v) to give LCL29 (230 mg, 82%) as a white slightly hygroscopic microcrystalline powder. TLC (CHCl$_3$—(CH$_3$)$_2$CO-MeOH—CH$_3$COOH—H$_2$O, 20:8:6:2:1, v/v) R$_f$ 0.19; RP TLC (C18 Silica, CH$_3$CN-MeOH-1M NH$_4$Cl (aq), 4:1:1.5 v/v) R$_f$ 0.39; [α]$^{22}_D$=−3.20° (c=1, CHCl$_3$) and −14.0° (c=1, MeOH); [α]$^{22}_{365}$=−15.0° (c=1, CHCl$_3$) and −50.0° (c=1, MeOH); $^1$H NMR (500 MHz, CDCl$_3$) δ 9.40 (d, 2H, J=5.8, 2,6-H$_{Py}$) 8.46 (t, 1H, J=7.6 4-H$_{Py}$), 8.08 (t, 2H, J=7.1, 3,5-H$_{Py}$), 7.72 (d, 1H, J=7.0, NH), 5.72 (dtd, 1H, J=15.4, 6.7, 0.6, 5-H), 5.49 (ddt, 1H, J=15.4, 6.7, 1.1, 4-H), 4.8 (m, 2H, C(6)H$_2$-pyridinium ring), 4.30 (m, 1H, 3-H), 3.85 (m, 2H, 2-H and 1-Ha), 3.69 (d, 1H, J=11.3, 1-Hb), 2.34 (m, 2H, COCH$_2$), 2.15 (m, 2H, C(5)H$_2$C(6)H$_2$-pyridinium ring), 2.0 (q, 2H, J=7.2, C(6)H$_2$), 1.77 (m, 2H, COCH$_2$CH$_2$), 1.49 (m, 2H, C(4)H$_2$C(5)H$_2$C(6)H$_2$-pyridinium ring), 1.33 (m, 2H, C(7)H$_2$), 1.27 (m, 20H, CH$_2$), 0.87 (t, 3H, J=6.9, CH$_3$); (MeOD) 9.01 (d, 2H, J=6.4, 2,5-H$_{Py}$) 8.59 (t, 1H, J=7.7, 4-H$_{Py}$), 8.11 (t, 2H, J=6.8, 3,5-H$_{Py}$), 7.71 (d, 1H, J=8.8, NH), 5.68 (dtd, 1H, J=15.4, 6.8, 0.7, 5-H), 5.45 (ddt, 1H, J=15.4, 7.3, 1.2, 4-H), 4.63 (t, 2H, J=7.6, C(6)H$_2$-pyridinium ring), 4.06 (t, 1H, J=6.9, 3-H), 3.88 (m, 1H, 2-H), 3.67 (dd, 1H, J=11.4, 4.2, 1-Ha), 3.64 (dd, 1H, J=11.4, 6.5, 1-Hb), 2.24 (m, 2H, COCH$_2$), 2.02 (m, 4H, C(5)(H$_2$)C(6)H$_2$-pyridinium ring and C(6)H$_2$), 1.67 (m, 2H, COCH$_2$CH$_2$)), 1.40 (m, 4H, C(4)(H$_2$)C(5)(H$_2$)C(6)H$_2$-pyridinium ring and C(7)H$_2$), 1.27 (m, 20H, CH$_2$), 0.89 (t, 3H, J=7.0, CH$_3$); (D$_2$O) 8.96 (d, 2H, J=6.4, 2,6-H$_{Py}$), 8.60 (dt, 1H, J=7.8, 1.1, 4-H$_{Py}$), 8.14 (t, 2H, J=6.8, 3,5-H$_{Py}$), 5.65 (dtd, 1H, J=15.1, 6.8, 0.8, 5-H), 5.45 (ddt, 1H, J=15.1, 6.8, 1.3, 4-H), 4.69 (t, 2H, J=7.4, C(6)H$_2$-pyridinium ring), 4.21 (t, 1H, J=6.1, 3-H), 3.95 (m, 1H, 2-H), 3.74 (dd, 1H, J=11.5, 2.1, 1-Ha), 3.71 (dd, 1H, J=11.5, 3.8, 1-Hb), 2.30 (m, 2H, COCH$_2$), 2.07 (m, 4H, C(5)H$_2$C(6)H$_2$-pyridinium ring and C(6)H$_2$), 1.68 (m, C(7)H$_2$), 1.44 (m, 4H, C(4)H$_2$C(5)H$_2$C(6)H$_2$-pyridinium ring and COCH$_2$CH$_2$), 1.29 (m, 20H, CH$_2$), 0.89 (t, 3H, J=7.1, CH$_3$); $^{13}$C-NMR (500 MHz, MeOD) δ 75.8 (C=O), 147.0 (C4$_{Py}$), 146.1 (C2,6$_{Py}$), 134.8 (C4=C5), 131.2 (C4=C5), 129.6 (C3,5$_{Py}$), 73.9 (C3), 62.9 (C6-pyridinium-ring), 62.2 (C1), 57.0 (C2), 36.6 (C=OC2), 33.5 (C5C6-pyridinium ring), 33.2 (C9 or C10), 32.1 (C6), 30.95, 30.92, 30.83, 30.63, 30.56 and 30.47 (C7-C16), 26.7 (C4C5C6-pyridinium ring), 26.1 (C=OC2C3), 23.8 (C17), 14.5 (CH$_3$); ESI-MS (CH$_3$OH, relative intensity, %) m/z 475.4 (M$^+$, 100). Calcd. for [C$_{29}$H$_{51}$N$_2$O$_3$]$^+$ m/z 475.4.

Anal. Calcd. for C$_{29}$H$_{51}$BrN$_2$O$_3$. H$_2$O (573.65): C, 60.72; H, 9.31; N, 4.88; Br, 13.93. Found: C, 60.19; H, 9.22; N, 4.78; Br, 14.21.

6.18. Example 18

D-erythro-2-(1'-Octylnicotinoyl)-sphingosine Bromide (LCL275)

A mixture of D-erythro-2-N-nicotinoyl-sphingosine (3, 202 mg, 0.5 mmol), anhydrous toluene (2 mL) and octyl bromide (2 mL) was heated in a closed glass test-tube in an oil bath at 75-85° C. over 8 hrs. After completion, the reaction mixture was evaporated to dryness under reduced pressure and the afforded residue was dried in a high vacuum (1 ton, 6 h at r.t.). The resulting crude product was washed with a warm n-hexane and recrystallized twice from ethyl acetate to give pure LCL275 (174 mg, 58%) as a pale yellow powder, mp 117-118° C.; TLC (CHCl$_3$—(CH$_3$)$_2$CO-MeOH—CH$_3$COOH—H$_2$O, 20:8:6:2:1, v/v) R$_f$ 0.45; RP TLC (C18 Silica, CH$_3$CN-MeOH-1M NH$_4$Cl (aq), 4:1:1.5 v/v) R$_f$ 0.47; [α]$^{20}_D$=+4.60° (c=1, MeOH); [α]$^{20}_{365}$=+20.1° (c=1, MeOH); $^1$H NMR (500 MHz, CDCl$_3$) δ 10.53 (s, 1H, 2-H$_{Py}$), 9.11 (d, 1H, J=8.1, 4-H$_{Py}$), 9.07 (d, 1H, J=7.4, NH), 8.73 (d, 1H, J=6.0, 6-H$_{Py}$) 8.08 (dd, 1H, J=8.1 and 6.1, 5-H$_{Py}$), 5.85 (dtd, 1H, J=15.4, 6.6, 1.2, 5-H), 5.45 (ddt, 1H, J=15.4, 7.1, 1.2, 4-H), 4.81 (t, 2H, J=7.6, CH$_2$-pyridinium ring), 4.56 (m, 1H, 3-H), 4.38 (bs, 1H, 3-OH), 4.2 (bs, 1H, 1-OH), 4.07 (dd, 1H, J=12.1, 5.7, 1-Ha), 4.00 (m, 1H, 2-H), 3.90 (dd, 1H, J=12.1, 2.3, 1-Hb), 2.10 (m, 2H, CH$_2$ CH$_2$-pyridinium ring), 2.03 (q, 2H, J=7.2, C(6)H$_2$), 1.35 (m, 6H, C(7)H$_2$, CH$_2$ H$_2$ CH$_2$-pyridinium ring and CH$_2$CH$_2$H$_2$CH$_2$-pyridinium ring), 1.24 (m, 26H, CH$_2$), 0.87 (t, 3H, J=6.9, CH$_3$), 0.86 (t, 3H, J=7.1, CH$_3$), ESI-MS (CH$_3$OH, relative intensity, %) m/z 1515.3 ([2M+Br]$^+$, 65), 517.5 (M$^+$, 100). Calcd. for [C$_{32}$H$_{57}$N$_2$O$_3$]$^+$ m/z 517.4.

Anal. Calcd. for C$_{32}$H$_{57}$BrN$_2$O$_3$ (597.7): C, 64.30; H, 9.61; N, 4.69; Br, 13.37. Found: C, 64.05; H, 9.57; N, 4.71; Br, 13.24.

6.19. Example 19

D-erythro-2-N-[6'-[1"-[4'"-[(4""-N,N-Dimethylamino)styryl]-pyridinium]-hexanoyl]]-sphingosine Bromide (LCL186). A mixture of D-erythro-N-(6-bromohexanoyl)-sphingosine (2c, 167 mg, 0.35 mmol), 4-[4'-(N,N-dimethylamino)-styryl]-pyridine (314 mg, 1.4 mmol) in anhydrous toluene (15 mL) was heated in a closed glass test-tube in an oil bath at 75-85° C. over 70 hrs. The mixture was concentrated to the half and left in the refrigerator overnight. The red precipitate that separated out was filtered off, washed twice by ethyl acetate and dried in vacuo. This material was treated with warm (~45° C.) mixture of ethanol-chloroform (10 mL, 2:3, v/v), sonicated for 10 min, and filtered off to separate the excess of 4-[4'-(N,N-dimethylamino)styryl]-pyridine. The collected filtrate was concentrated to a volume of 3 mL and the afforded mixture was subjected to a two-step flash column chromatography. Elution with the mixture of CHCl$_3$-EtOH (3:2, v/v) delivered first the less polar side by products and the starting materials. Changing the eluent system to CHCl$_3$-

MeOH (3:2, v/v) gave pure LCL186 (131 mg, 53% yield) as a red solid. An analytical sample of LCL186 was obtained by recrystallization from acetone to give a deep orange microcrystalline powder, mp>105° C. (decomp.); TLC (CHCl$_3$—(CH$_3$)$_2$CO-EtOH—CH$_3$COOH—H$_2$O, 20:8:6:2:1, v/v) R$_f$ 0.40; RP TLC (C18 Silica, CH$_3$CN-MeOH-1M NH$_4$Cl (aq), 4:1:1.5 v/v) R$_f$ 0.40; UV-VIS (50% EtOH) λ$_{max}$(log ε)=481.5 nm(4.72); Fluorescence (em., 50% EtOH) λ$_{max}$(rel.int.)=525 nm(2.0); $^1$H NMR (500 MHz, CDCl$_3$) δ 8.84 (d, 2H, J=7.7, 2-H$_{Py}$), 7.98 (d, 1H, J=4.7, NH), 7.77 (d, 2H, J=7.7, 3-H$_{Py}$), 7.60 (d, 1H, J=15.9, Ar—CH=CH-pyridinium ring), 7.50 (d, 2H, J=9.0, 2-H—Ar), 6.83 (d, 1H, J=15.9, Ar—CH=CH-pyridinium ring), 6.68 (d, 2H, J=9.0, 3-Ar), 5.73 (dt, 1H, J=15.4, 6.8, 5-H), 5.45 (dd, 1H, J=15.4, 6.8, 4-H), 4.75 (bs, 1H, 3-OH), 4.54 (m, 3H, 3-OH and C(6)H$_2$-pyridinium ring), 4.35 (m, 1H, 3-H), 3.90 (m, 2H, 1-Ha and 2-H), 3.67 (d, 2H, J=7.7, 1-Hb), 3.06 (s, 6H, N(CH$_3$)$_2$), 2.43 (m, 2H, COCH$_2$), 2.1 (m, 2H, C(5)H$_2$C(6)H$_2$-pyridinium ring), 1.90 (q, 2H, J=7.2, C(6)H$_2$), 1.78 (m, 2H, COCH$_2$CH$_2$), 1.48 (m, 2H, COCH$_2$CH$_2$CH$_2$), 1.23 (m, 22H, CH$_2$), 0.86 (t, 3H, J=7.1, CH$_3$); ESI-MS (CH$_3$OH, relative intensity, %) m/z 620.4 (M$^+$, 100). Calcd. for [C$_{39}$H$_{62}$N$_3$O$_3$]$^+$ m/z 620.5

Anal. Calcd. for C$_{39}$H$_{62}$BrN$_3$O$_3$ (700.8): C, 66.84; H, 8.92; N, 6.00; Br, 11.40. Found: C, 63.56; H, 8.75; N, 5.64; Br, 11.30.

6.20. Example 20

D-erythro-2-N-[2'-(1''-Pyridinium)-acetyl]-sphingosine Bromide (LCL150)

A mixture of D-erythro-2-N-(2'-bromoacetyl)-sphingosine (2a, 210 mg, 0.50 mmol), anhydrous pyridine (2 mL) and anhydrous toluene (2 mL) was heated in a closed glass test-tube in an oil bath at 75-85° C. over 4.5 hrs. After completion, the reaction mixture was cooled and the mixture was evaporated to dryness. The afforded residue was dried under high vacuum (~1 torr at rt over 6 hr) and recrystallized from anhydrous ethanol-acetone (1:5, v/v) to give LCL150 (180 mg, 72%) as a white microcrystalline powder, mp>104 (decomp.)° C.; LC (CHCl$_3$—(CH$_3$)$_2$CO-MeOH—CH$_3$COOH—H$_2$O, 20:8:6:2:1, v/v) R$_f$ 0.17; RP TLC (C18 Silica, CH$_3$CN-MeOH-1M NH$_4$Cl (aq), 4:1:1.5 v/v) R$_f$ 0.44; [α]$^{22}_D$=−7.8° (c=1, CHCl$_3$) and −15.7° (c=1, MeOH); [α]$^{22}_{365}$=−30.0° (c=1, CHCl$_3$) and −61.3° (c=1, MeOH); $^1$H NMR (500 MHz, CDCl$_3$) (MeOD) δ 8.89 (dd, 2H, J=6.8, 1.3, 2,6-H$_{Py}$) 8.66 (dt, 1H, J=7.8, 1.3, 4-H$_{Py}$), 8.14 (t, 2H, J=6.8, 3,5-H$_{Py}$), 5.73 (dtd, 1H, J=15.3, 6.7, 0.9, 5-H), 5.45 (dd, 1H, J=15.3, 6.5, 1.0, 4-H), 5.43 (d, 2H, J=6.9, CH$_2$-pyridinium ring), 4.16 (t, 1H, J=6.7, 3-H), 3.98 (m, 1H, 2-H), 3.73 (dd, 1H, J=11.3, 4.3, 1-Ha), 3.63 (dd, 1H, J=11.3, 7.3, 1Hb), 2.05 (q, 2H, J=6.9, C(6)H$_2$), 1.39 (m, 2H, C(7)H$_2$), 1.28 (m, 20H, CH$_2$), 0.89 (t, 3H, J=7.1, CH$_3$); (D$_2$O) 8.92 (d, 2H, J=6.0, 2,6-H$_{Py}$), 8.72 (t, 1H, J=7.8, 4-H$_{Py}$), 8.20 (t, 2H, J=6.7, 3,5-H$_{Py}$), 5.86 (m, 1H, 5-H), 5.60 (m, 1H, 4-H), 4.67 (m, 2H, CH$_2$-pyridinium ring), 4.35 (m, 1H, 3-H), 4.12 (m, 1H, 2-H), 3.82 (dd, 1H, J=8.5, 2.3, 1-Ha), 3.63 (dd, 1H, J=8.5, 5.1, 1Hb), 2.11 (q, 2H, J=7.0, C(6)H$_2$), 1.43 (m, 2H, C(7)H$_2$), 1.34 (m, 20H, CH$_2$), 0.93 (t, 3H, J=7.0, CH$_3$); ESI-MS (CH$_3$OH, relative intensity, %) m/z 419.4 (M$^+$, 100). Calcd. for [C$_{25}$H$_{43}$N$_2$O$_3$]$^+$ m/z 419.3.

Anal. Calcd. for C$_{25}$H$_{43}$BrN$_2$O$_3$ (499.5): C, 60.11; H, 8.68; N, 5.61; Br, 16.0. Found: C, 59.52; H, 8.77; N, 5.49; Br, 15.61.

6.21. Example 21

D-erythro-2-N-[2'-(1''-Pyridinium)-acetyl]-4,5-dihydrosphingosine Bromide (LCL319)

A mixture of D-erythro-2-N-(2'-bromoacetyl)-4,5-dihydrosphingosine (2b, 100 mg, 0.24 mmol), anhydrous pyridine (1 mL) and anhydrous toluene (1 mL) was heated in a closed glass test-tube in an oil bath at 75-85° C. over 4.5 hrs. After completion, the reaction mixture was cooled and the mixture was evaporated to dryness. The afforded residue was dried under high vacuum (~1 torr at rt over 6 hr) and recrystallized from anhydrous ethanol-acetone (1:5, v/v) to give LCL319 (95 mg, 80%) as a white microcrystaline powder, mp 119-121° C.; TLC (CHCl$_3$—(CH$_3$)$_2$CO-MeOH—CH$_3$COOH—H$_2$O, 20:8:6:2:1, v/v) R$_f$ 0.21; RP TLC (C18 Silica, CH$_3$CN-MeOH-1M NH$_4$Cl (aq), 4:1:1.5 v/v) R$_f$ 0.34; [α]$^{22}_D$=−6.0° (c=0.5, MeOH); [α]$^{22}_{365}$=−28.0° (c=0.5, MeOH); $^1$H NMR (500 MHz, CDCl$_3$) δ 9.32 (d, 2H, J=5.6, 2,6-H$_{Py}$), 8.70 (bs, 1H, NH), 8.44 (t, 1H, J=6.0, 4-H$_{Py}$), 8.02 (t, 2H, J=6.8, 3,5-H$_{Py}$), 6.02 (m, 2H, CH$_2$-pyridinium ring), 4.00 (dd, 1H, J=11.1, 3.5, 1-Ha), 3.85 (m, 1H, 2-H), 3.80 (m, 2H, 3-H and 1-Hb), 1.59 (m, 2H, C(4)H$_2$), 1.49 (m, 2H, C(5)H$_2$), 1.25 (m, 24H, CH$_2$), 0.88 (t, 3H, J=7.0, CH$_3$); (D$_2$O) 8.75 (d, 2H, J=6.0, 2,6-H$_{Py}$) 8.52 (t, 1H, J=7.8, 4-H$_{Py}$), 8.00 (t, 2H, J=7.1, 3,5-H$_{Py}$), 5.48 (bs, 2H, CH$_2$-pyridinium ring), 3.93 (m, 1H, 3-H), 3.65 (m, 3H, 1Hab and 2-H), 1.40 (m, 2H, C(4)H$_2$), 1.34 (m, 26H, CH$_2$), 0.74 (t, 3H, J=7.0, CH$_3$); ESI-MS (CH$_3$OH, relative intensity, %) m/z 421.4 (m$^+$, 100). Calcd. for [C$_{25}$H$_{45}$N$_2$O$_3$]$^+$ m/z 421.3.

Anal. Calcd. for C$_{25}$H$_{43}$BrN$_2$O$_3$ (501.5): C, 59.87; H, 9.04; N, 5.59; Br, 15.93. Found: C, 59.71; H, 9.09; N, 5.55; Br, 15.93.

6.22. Example 22

L-threo-2-N-[6'-(1''-Pyridinium)-hexanoyl]-sphingosine Bromide (LCL124)

A mixture of L-threo-2-N-(6'-bromohexanoyl)-sphingosine (2d, 240 mg, 0.50 mmol), anhydrous pyridine (2 mL) and anhydrous toluene (2 mL) was heated in a closed glass test-tube in an oil bath at 75-85° C. over 4.5 hrs. After completion, the reaction mixture was cooled and the mixture was evaporated to dryness. The afforded residue was dried under high vacuum (~1 torr at rt over 6 hr) and recrystallized from anhydrous ethyl acetate-acetone (1:1, v/v) to give LCL124 (205 mg, 73%) as a white hygroscopic microcrystalline powder. TLC (CHCl$_3$—(CH$_3$)$_2$CO-MeOH—CH$_3$COOH—H$_2$O, 20:8:6:2:1, v/v) R$_f$ 0.17; RP TLC (C18 Silica, CH$_3$CN-MeOH-1M NH$_4$Cl (aq), 4:1:1.5 v/v) R$_f$ 0.38 [α]$^{21}_D$=−6.40° (c=1, CHCl$_3$); [α]$^{21}_{365}$=−25.1° (c=1, CHCl$_3$); $^1$H NMR (500 MHz, CDCl$_3$) δ 9.39 (d, 2H, J=5.6, 2,6-H$_{Py}$) 8.47 (t, 1H, J=7.8, 4-H$_{Py}$), 8.09 (t, 2H, J=7.5, 3,5-H$_{Py}$), 7.53 (d, 1H, J=7.9, NH), 5.72 (dtd, 1H, J=15.4, 6.7, 0.5, 5-H), 5.49 (ddt, 1H, J=15.4, 6.7, 1.1, 4-H), 4.88 (t, 2H, J=7.6, C(6)H$_2$-pyridinium ring), 4.25 (t, 1H, J=5.8, 3-H), 3.83 (m, 1H, 2-H), 3.72 (dd, 1H, J=11.5, 4.0, 1-Ha), 3.67 (dd, 1H, J=11.5, 5.5, 1-Hb), 2.36 (t, 2H, J=7.1, COCH$_2$), 2.14 (m, 2H, C(5)H$_2$C(6)H$_2$-pyridinium ring), 1.98 (q, 2H, J=7.0, C(6)H$_2$), 1.74 (m, 2H, COCH$_2$CH$_2$), 1.47 (m, 2H, C(4)H$_2$C(5)H$_2$C(6)H$_2$-pyridinium ring), 1.32 (m, 2H, C(7)H$_2$), 1.23 (m, 20H, CH$_2$), 0.86 (t, 3H, J=6.9, CH$_3$); (MeOD; $^{13}$C-NMR (CDCl$_3$) δ 174.9 (C=O), 145.5 (C4$_{Py}$), 145.3 (C2,6$_{Py}$), 133.6 (C4=C5), 139.6 (C4=C5), 128.8 (C3,5$_{Py}$), 72.8 (C3), 62.9 (C1), 62.0 (C6-pyridinium-ring), 56.5 (C2), 35.8 (C=O C2), 32.66 (C$_6$), 32.16 (C9 or C10), 31.13 (C5C6-pyridinium ring), 29.96, 29.92, 29.90, 29.81, 29.62, 29.60 and 29.55 (C8-C17), 25.11 (C4C5C6-pyridinium ring), 24.76 (C=OC2C3), 22.92 (C7), 14.35 (CH$_3$); ESI-MS (CH$_3$OH, relative intensity, %) m/z 475.4 (M$^+$, 100). Calcd. for [C$_{39}$H$_{51}$N$_2$O$_3$]$^+$ m/z 475.4.

Anal. Calcd. for C$_{29}$H$_{51}$BrN$_2$O$_3$·H$_2$O (573.65): C, 60.72; H, 9.31; N, 4.88; Br, 13.93. Found: C, 60.45; H, 9.09; N, 4.68; Br, 14.01.

6.23. Example 23

L-erythro-2-N-[6'-(1"-Pyridinium)-hexanoyl]-sphingosine Bromide (LCL-187)

The title compound was prepared from L-erythro-2-N-(6'-Bromohexanoyl)-sphingosine (2e, 200 mg 0.67 mmol) in the same fashion as compound LCL-29 from 2a. Yield: 167 mg (71%). Analytical sample of 2e was obtained by crystallization from n-hexane-EtOAc (4:1, v/v; white hygroscopic powder); [α]$^{22}_D$=+3.10° (c=1, CHCl$_3$) and +14.5° (c=1, MeOH); [α]$^{22}_{365}$=+14.2° (c=1, CHCl$_3$) and +51.2° (c=1, MeOH). Remaining data identical as reported for LCL-29.

Anal. Calcd for C$_{29}$H$_{51}$BrN$_2$O$_3$·H$_2$O (573.65): C, 60.72; H, 9.31; N, 4.88; Br, 13.93. Found: C, 60.11; H, 9.12; N, 4.98; Br, 13.71.

6.24. Example 24

D-threo-2-N-[6'-(1"-Pyridinium)-hexanoyl]-sphingosine Bromide (LCL272)

The title compound was prepared from D-threo-2-N-(6'-bromohexanoyl)-sphingosine (2f, 200 mg 0.67 mmol) in the same fashion as compound LCL-124 from 2d. Yield: 161 mg (68%). Analytical sample of 2f was obtained by crystallization from n-hexane-EtOAc (6:1, v/v; white hygroscopic powder); [α]$^{22}_D$=6.2° (c=1, CHCl$_3$); [α]$^{22}_{365}$=+26.0° (c=1, CHCl$_3$). Remaining data identical as reported for LCL-124.

Anal. Calcd for C$_{29}$H$_{51}$BrN$_2$O$_3$·H$_2$O (573.65): C, 60.72; H, 9.31; N, 4.88; Br, 13.93. Found: C, 60.23; H, 9.03; N, 4.64; Br, 13.63.

6.25. Example 25

D-erythro-2-N-[6'-(1"-Pyridinium)-hexanoyl]-4,5-dihydrosphingosine Bromide (LCL143)

A mixture of D-erythro-2-N-(6'-bromohexanoyl)-4,5-dihydrosphingosine (2 g, 220 mg, 0.46 mmol), anhydrous pyridine (2 mL) and anhydrous toluene (2 mL) was heated in a closed glass test-tube in an oil bath at 75-85° C. over 4.5 hrs. After completion, the reaction mixture was cooled and the mixture was evaporated to dryness. The afforded residue was dried under high vacuum (~1 torr at rt over 6 hr) and recrystallized from anhydrous ethyl acetate-acetone (1:1, v/v) to give LCL-143 (183 mg, 71%) as a white microcrystalline powder. mp: wet at 95 and melts with decomposition above 155° C.; TLC (CHCl$_3$—(CH$_3$)$_2$CO-MeOH—CH$_3$COOH—H$_2$O, 20:8:6:2:1, v/v) R$_f$ 0.20; RP TLC (C18 Silica, CH$_3$CN-MeOH-1M NH$_4$Cl (aq), 4:1:1.5 v/v) R$_f$ 0.30; [α]$^{22}_D$=−0.55° (c=0.5, MeOH); [α]$^2_{365}$=−3.5° (c=0.5, MeOH); $^1$H NMR (500 MHz, MeOD) δ 9.01 (d, 2H, J=6.7, 2,5-H$_{Py}$), 8.59 (t, 1H, J=7.8, 4-H$_{Py}$), 8.12 (t, 2H, J=6.8, 3,5-H$_{Py}$), 4.63 (t, 2H, J=7.5, C(6)H2-pyridinium ring), 3.83 (m, 1H, 3-H), 3.70 (dd, 1H, J=11.2, 4.1, 1-Ha), 3.65 (dd, 1H, J=11.4, 6.4, 1-Hb), 3.58 (m, 1H, 2-H), 2.26 (m, 2H, COCH$_2$), 2.04 (m, 2H, C(5) H$_2$C(6)H$_2$-pyridinium ring), 1.69 (m, 2H, COCH$_2$CH$_2$), 1.51 (m, 2H, C(4)H$_2$), 1.40 (m, 2H, C(4) H$_2$C(5)H$_2$C(6)H$_2$-pyridinium ring), 1.27 (m, 26H, CH$_2$), 0.89 (t, 3H, J=7.1, CH$_3$); ESI-MS (CH$_3$OH, relative intensity, %) m/z 477.3 (M$^+$, 100). Calcd. for [C$_{29}$H$_{53}$N$_2$O$_3$]$^+$ m/z 477.4.

Anal. Calcd. for C$_{29}$H$_{53}$BrN$_2$O$_3$ (557.65): C, 62.46; H, 9.58; N, 5.02; Br, 14.33. Found: C, 59.98; H, 9.60; N, 4.80; Br, 14.19.

6.26. Example 26

D-erythro-2-N-[3'-[3"-(1"-Butyl)-pyridinium]-propionoyl]-sphingosine Bromide (LCL277)

A mixture of D-erythro-2-N-[3'-(3"-pyridyl)-propionoyl]-sphingosine 4 (216 mg, 0.5 mmol), anhydrous toluene (2 mL) and butyl bromide (2 mL) was heated in a closed glass test-tube in an oil bath at 75-85° C. over 8 hrs. After completion, the reaction mixture was evaporated to dryness under reduced pressure and the afforded residue was dried in a high vacuum (1 ton, 6 h at r.t.). The resulting crude product was washed with a warm n-hexane and recrystallized twice from ethyl acetate to give pure LCL277 (194 mg, 68%) as a pale yellow powder, mp•134-135° C.; TLC (CHCl$_3$—(CH$_3$)$_2$CO-MeOH—CH$_3$COOH—H$_2$O, 20:8:6:2:1, v/v) R$_f$ 0.21; RP TLC (C18 Silica, CH$_3$CN-MeOH-1M NH$_4$Cl (aq), 4:1:1.5 v/v) R$_f$ 0.43; [α]$^{22}_D$=−10.0° (c=1, MeOH); [α]$^{22}_{365}$=−37.1° (c=1, MeOH); $^1$H NMR (500 MHz, CDCl$_3$) δ 9.39 (s, 1H, 2-H$_{Py}$), 8.45 (d, 1H, J=6.1, 6-H$_{Py}$), 8.32 (d, 1H, J=7.8, 4-H$_{Py}$), 8.17 (d, 1H, J=6.9, NH), 7.85 (dd, 1H, J=7.8 and 6.1, 5-H$_{Py}$), 5.85 (dtd, 1H, J=15.2, 6.7, 1.1, 5-H), 5.45 (ddt, 1H, J=15.2, 7.1, 1.1, 4-H), 4.81 (m, 2H, CH$_2$-pyridinium ring), 4.12 (m, 1H, 3-H), 3.76 (dd, 1H, J=12.1, 5.8, 1-Ha), 3.63 (m, 1H, 2-H), 3.52 (dd, 1H, J=12.1, 2.4, 1-Hb), 3.27 (m, 2H, COCH$_2$), 3.05 (m, 1H, COCH$_2$CHa), 2.95 (m, 1H, COCH$_2$CHb), 2.0 (m, 4H, CH$_2$ CH$_2$-pyridinium ring and C(6)H$_2$), 1.43 (m, 2H, C H$_2$)CH$_2$CH$_2$-pyridinium ring), 1.31 (m, 2H, C(7)H$_2$), 1.24 (m, 20H, CH$_2$), 0.98 (t, 3H, J=7.3, CH$_3$), 0.86 (t, 3H, J=7.2, CH$_3$); (MeOD) δ 8.89 (s, 1H, 2-H$_{Py}$), 8.87 (d, 1H, J=6.1, 6-H$_{Py}$), 8.46 (d, 1H, J=7.9, 4-H$_{Py}$), 7.99 (dd, 1H, J=7.9, 6.1, 5-H$_{Py}$), 5.68 (dtd, 1H, J=15.2, 6.8, 1.1, 5-H), 5.43 (ddt, 1H, J=15.2, 7.0, 1.1, 4-H), 4.58 (t, 2H, J=7.6, CH$_2$-pyridinium ring), 4.03 (t, 1H, J=7.0, 3-H), 3.86 (m, 1H, 2-H), 3.63 (dd, 1H, J=11.2, 4.2, 1-Ha), 3.56 (dd, 1H, J=11.2, 6.9, 1-Hb), 3.14 (m, 2H, COCH$_2$), 2.66 (m, 2H, COCH$_2$CH$_2$), 2.0 (m, 4H, C H$_2$CH2-pyridinium ring, C(6)H$_2$), 1.40 (m, 4H, C(7)H$_2$, C H$_2$CH$_2$CH$_2$-pyridinium ring), 1.27 (m, 20H, CH$_2$), 1.0 (t, 3H, J=7.4, CH$_3$), 0.89 (t, 3H, J=6.9, CH$_3$);

ESI-MS (CH$_3$OH, relative intensity, %) m/z 489.5 (M$^+$, 100). Calcd. for [C$_{30}$H$_{53}$N$_2$O$_3$]$^+$ m/z 489.4.

Anal. Calcd. for C$_{30}$H$_{53}$BrN$_2$O$_3$ (569.7): C, 63.25; H, 9.38; N, 4.92; Br, 14.03. Found: C, 63.03; H, 9.47; N, 4.86; Br, 14.28.

6.27. Example 27

D-erythro-2-N-[12'-(1"-Pyridinium)-dodecanoyl]-sphingosine Bromide (LCL88)

A mixture of D-erythro-2-N-(12'-bromohexadecanoyl)-sphingosine 2h (281 mg, 0.5 mmol), anhydrous pyridine (2 mL) and anhydrous toluene (2 mL) was heated in a closed glass test-tube in an oil bath at 75-85° C. over 4.5 hrs. After completion, the reaction mixture was cooled and the mixture was evaporated to dryness. The afforded residue was dried under high vacuum (~1 torr at rt over 6 hr) and recrystallized from anhydrous ethyl acetate-acetone(2:1, v/v) to give LCL88 (237 mg, 74%) as a white microcrystalline powder., mp 79-80° C.; TLC (CHCl$_3$—(CH$_3$)$_2$CO-MeOH—CH$_3$COOH—H$_2$O, 20:8:4:2:1, v/v) R$_f$ 0.28; RP TLC (C18 Silica, CH$_3$CN-MeOH-1M NH$_4$Cl (aq), 4:1:1.5 v/v) R$_f$ 0.38; $[\alpha]^{20}_D$=−0.51° (c=1, CHCl$_3$) and −12.9° (c=1, MeOH); $[\alpha]^{20}_{365}$=−8.50° (c=1, CHCl$_3$) and −48.5° (c=1, MeOH); $^1$H NMR (500 MHz, CDCl$_3$) δ 9.40 (d, 2H, J=6.0, 2,6-H$_{Py}$) 8.48 (t, 1H, J=7.4, 4-H$_{Py}$), 8.12 (t, 2H, J=6.9, 3,5-H$_{Py}$), 7.14 (d, 1H, J=7.0, NH), 5.74 (dtd, 1H, J=15.3, 6.7, 0.6, 5-H), 5.52 (ddt, 1H, J=15.3, 6.7, 1.1, 4-H), 4.94 (t, 2H, J=7.5, C(12)H$_2$-pyridinium ring), 4.29 (m, 1H, 3-H), 3.89 (m, 2H, 2-H and 1-Ha), 3.68 (dd, 1H, J=13.0, 4.5, 1-Hb), 2.28 (t, 2H, J=7.4, COCH$_2$), 2.05 (m, 4H, C(11)H$_2$C(12)H$_2$-pyridinium ring and C(6)H$_2$), 1.63 (m, 2H, COCH$_2$CH$_2$), 1.24 (m, 36H, CH$_2$), 0.86 (t, 3H, J=7.3, CH$_3$); (MeOD) 9.01 (dd, 2H, J=6.7, 1.3, 2,5-H$_{Py}$) 8.61 (tt, 1H, J=7.8, 1.3 4-H$_{Py}$), 8.11 (t, 2H, J=7.8, 3,5-H$_{Py}$), 7.60 (d, ~0.2H, J=8.2, NH), 5.68 (dtd, 1H, J=15.2, 6.6, 0.7, 5-H), 5.45 (ddt, 1H, J=15.2, 7.4, 1.2, 4-H), 4.62 (t, 2H, J=7.6, C(12)H$_2$-pyridinium ring), 4.04 (t, 1H, J=7.3, 3-H), 3.85 (m, 1H, 2-H), 3.67 (d, 2H, J=5.1, 1-Ha,b), 2.18 (t, 2H, J=7.1, COCH$_2$), 2.01 (m, 4H, C(11)H$_2$C(12)H$_2$-pyridinium ring and C(6)H$_2$), 1.57 (m, 2H, COCH$_2$CH$_2$), 1.38 (m, 4H, C(10)H$_2$C(11)H$_2$C(12)H$_2$-pyridinium ring and C(7)H$_2$), 1.27 (m, 32H, CH$_2$), 0.88 (t, 3H, J=7.1, CH$_3$); ESI-MS (CH$_3$OH, relative intensity, %) m/z 559.4 (M$^+$, 100). Calcd. for $[C_{35}H_{63}N_2O_3]^+$ m/z 559.5.

Anal. Calcd. for C$_{35}$H$_{63}$BrN$_2$O$_3$ (639.8): C, 65.71; H, 9.93; N, 4.38; Br, 12.49. Found: C, 65.32; H, 9.94; N, 4.30; Br, 12.10.

6.28. Example 28

D-erythro-2-N-[12'-(1"-Pyridinium)-dodecanoyl]-4,5-dihydrosphingosine Bromide (LCL249). A mixture of D-erythro-2-N-(12'-bromohexadecanoyl)-4,5-dihydrosphingosine 2i (192 mg, 0.34 mmol), anhydrous pyridine (2 mL) and anhydrous toluene (2 mL) was heated in a closed glass test-tube in an oil bath at 75-85° C. over 4.5 hrs. After completion, the reaction mixture was cooled and the mixture was evaporated to dryness. The afforded residue was dried under high vacuum (~1 torr at rt over 6 hr) and recrystallized from anhydrous ethyl acetate-acetone (2:1, v/v) to give LCL249 (158 mg, 72%) as a white microcrystalline powder., mp 69-71° C.; TLC (CHCl$_3$—(CH$_3$)$_2$CO-MeOH—CH$_3$COOH—H$_2$O, 20:8:4:2:1, v/v) R$_f$ 0.29; RP TLC (C18 Silica, CH$_3$CN-MeOH-1M NH$_4$Cl (aq), 4:1:1.5 v/v) R$_f$ 0.26; $[\alpha]^{21}_D$=+7.0° (c=1, CHCl$_3$); $[\alpha]^{22}_{365}$=+17.4° (c=1, CHCl$_3$); $^1$H NMR (500 MHz, CDCl$_3$) δ 9.41 (d, 2H, J=5.6, 2,6-H$_{Py}$), 8.49 (t, 1H, J=7.7, 4-H$_{Py}$), 8.13 (t, 2H, J=7.5, 3,5-H$_{Py}$), 7.31 (d, 1H, J=7.8, NH), 4.93 (t, 2H, J=7.5, C(12)H$_2$-pyridinium ring), 3.93 (dd, 1H, J=11.5, 4.5, 1-Ha), 3.82 (m, 1H, 2-H), 3.74 (m, 1H, 3-H), 3.70 (dd, 1H, J=11.5, 3.0, 1-Hb), 2.28 (t, 2H, J=7.5, COCH$_2$), 2.05 (m, 2H, C(11)H$_2$C(12)H$_2$-pyridinium ring), 1.63 (m, 2H, COCH$_2$CH$_2$), 1.49 (m, 2H, C(4)H$_2$), 1.23 (m, 40H, CH$_2$), 0.86 (t, 3H, J=7.1, CH$_3$); (MeOD) 9.01 (dd, 2H, J=6.6, 1.2, 2,6-H$_{Py}$), 8.59 (dt, 1H, J=6.8, 1.2, 4-H$_{Py}$), 8.11 (t, 2H, J=6.9, 3,5-H$_{Py}$), 4.62 (t, 2H, J=7.6, C(12)H$_2$-pyridinium ring), 3.81 (m, 1H, 2-H), 3.70 (dd, 1H, J=11.2, 4.3, 1-Ha), 3.70 (dd, 1H, J=11.4, 3.0, 1-Hb) 3.68 (dd, 1H, J=11.4, 6.0, 1-Hb), 3.58 (m, 1H, 3-H), 2.21 (t, 2H, J=7.5, COCH$_2$), 2.01 (m, 2H, C(11)H$_2$C(12)H$_2$-pyridinium ring), 1.60 (m, 2H, COCH$_2$CH$_2$), 1.52 (m, 2H, COCH$_2$CH$_2$CH$_2$), 1.38 (m, 4H, C(10)H$_2$C(11)H$_2$C(12)H$_2$-pyridinium ring C(4)H$_2$), 1.27 (m, 36H, CH$_2$), 0.89 (t, 3H, J=7.1, CH$_3$); ESI-MS (CH$_3$OH, relative intensity, %) m/z 561.4 (M$^+$, 100). Calcd. for $[C_{35}H_{65}N_2O_3]^+$ m/z 561.5.

Anal. Calcd. for C$_{35}$H$_{63}$BrN$_2$O$_3$ (639.8): C, 65.50; H, 10.21; N, 4.36; Br, 12.45. Found: C, 65.19; H, 10.14; N, 4.32; Br, 12.35.

6.29. Example 29

L-threo-2-N-[16'-(1"-Pyridinium)-hexadecanoyl]-sphingosine Bromide (LCL87)

A mixture of L-threo-2-N-(16'-bromohexadecanoyl)-sphingosine 2l (115 mg, 0.18 mmol), anhydrous pyridine (2 mL) and anhydrous toluene (2 mL) was heated in a closed glass test-tube in an oil bath at 75-85° C. over 6 hrs. After completion, the reaction mixture was cooled to room temperature and diluted with ethyl acetate (4 ml) and left in the refrigerator (+4° C.) for 6 hrs. The formed precipitate was separate by filtration, washed with ethyl acetate-acetone (2 ml, 1:1, v/v/) and dried to give crude product (100 mg). This material was recrystallized from acetone-ethanol (50:1, v/v) to give LCL87 (87 mg, 67%) as a white microcrystalline powder, mp 113-115° C.; TLC(CHCl$_3$—(CH$_3$)$_2$CO-MeOH—CH$_3$COOH—H$_2$O, 20:8:4:2:1, v/v) R$_f$ 0.32; RP TLC (C18 Silica, CH$_3$CN-MeOH -1M NH$_4$Cl (aq), 4:1:1.5 v/v) R$_f$ 0.23 $[\alpha]^{22}_D$=−12.1° (c=1, MeOH); $[\alpha]^{22}_{365}$=46.8° (c=1, MeOH); $^1$H NMR (500 MHz, CDCl$_3$) δ 9.33 (d, 2H, J=6.0, 2,6-H$_{Py}$) 8.44 (t, 1H, J=7.8, 4-H$_{Py}$), 8.08 (t, 2H, J=7.0, 3,5-H$_{Py}$), 6.51 (d, 1H, J=7.8, NH), 5.69 (dtd, 1H, J=15.2, 6.6, 0.6, 5-H), 5.42 (ddt, 1H, J=15.2, 6.5, 1.2, 4-H), 4.92 (t, 2H, J=7.5, C(16)H$_2$-pyridinium ring), 4.35 (t, 1H, J=4.5, 3-H), 3.84 (m, 1H, 2-H), 3.70 (m, 2H, 1-Ha,b), 2.21 (t, 2H, J=7.4, COCH$_2$), 2.01 (m, 4H, C(15)H$_2$C(16)H$_2$-pyridinium ring and C(6)H$_2$), 1.58 (m, 2H, COCH$_2$CH$_2$), 1.22 (m, 44H, CH$_2$), 0.84 (t, 3H, J=7.0, CH$_3$); (MeOD) 9.00 (dd, 2H, J=6.5, 1.2, 2,5-H$_{Py}$) 8.59 (tt, 1H, J=7.8, 1.2 4-H$_{Py}$), 8.11 (t, 2H, J=7.1, 3,5-H$_{Py}$), 5.67 (dtd, 1H, J=15.3, 6.7, 0.8, 5-H), 5.46 (ddt, 1H, J=15.3, 7.5, 1.3, 4-H), 4.62 (t, 2H, J=7.6, C(16)H$_2$-pyridinium ring), 4.04 (t, 1H, J=7.2, 3-H), 3.85 (dt, 1H, J=7.4, 5.0, 2-H), 3.67 (d, 2H, J=5.1, 1-Ha,b), 2.18 (t, 2H, J=7.7, COCH$_2$), 2.02 (m, 4H, C(15)H$_2$C(16)H$_2$-pyridinium ring and C(6)H$_2$), 1.57 (m, 2H, COCH$_2$CH$_2$), 1.38 (m, 4H, C(14)H$_2$C(15)H$_2$C(16)H$_2$-pyridinium ring and C(7)H$_2$), 1.28 (m, 40H, CH$_2$), 0.89 (t, 3H, J=7.0, CH$_3$); ESI-MS (CH$_3$OH, relative intensity, %) m/z 615.6 (M$^+$, 100). Calcd. for $[C_{39}H_{77}N_2O_3]^+$ m/z 615.5.

Anal. Calcd. for C$_{39}$H$_{71}$BrN$_2$O$_3$ (695.9): C, 67.3; H, 10.28; N, 4.03; Br, 11.48. Found: C, 67.03; H, 10.21; N, 4.00; Br, 11.44.

6.30. Example 30

D-erythro-2-N-[16'-(1"-Pyridinium)-hexadecanoyl]-4,5-dihydrosphingosine Bromide (LCL345). A mixture of D-erythro-2-N-(16'-bromohexadecanoyl)-4,5-dihydrosphingosine (2k, 125 mg, 0.2 mmol), anhydrous pyridine (2 mL) and anhydrous toluene (2 mL) was heated in a closed glass test-tube in an oil bath at 75-85° C. over 6 hrs. After completion, the reaction mixture was cooled to room temperature and diluted with ethyl acetate (4 ml) and left in the refrigerator (+4° C.) for 6 hrs. The formed precipitate was separate by filtration, washed with ethyl acetate-acetone (2 ml, 1:1, v/v/) and dried to give crude product (135 mg). This material was recrystallized from acetone-ethanol (5:1, v/v) to give LCL345 (107 mg, 76%) as a white microcrystalline powder, mp 100-101° C.; TLC ($CHCl_3$—$(CH_3)_2CO$-MeOH—$CH_3COOH$—$H_2O$, 20:8:4:2:1, v/v) $R_f$ 0.36; RP TLC (C18 Silica, $CH_3CN$-MeOH-1M $NH_4Cl$ (aq), 4:1:1.5 v/v) $R_f$ 0.15; $[\alpha]^{22}_D$=+3.4° (c=0.5, MeOH); $[\alpha]^{22}_{365}$=+3.3° (c=0.5, MeOH); $^1H$ NMR (500 MHz, $CDCl_3$) δ 9.27 (d, 2H, J=5.8 2,6-$H_{Py}$), 8.41 (t, 1H, J=7.7, 4-$H_{Py}$), 8.05 (t, 2H, J=7.0, 3,5-$H_{Py}$), 7.18 (m, 1H, NH), 4.88 (t, 2H, J=7.6, C(16)$H_2$-pyridinium ring), 3.91 (dd, 1H, J=11.6, 5.2, 1-Ha), 3.78 (m, 1H, 2-H), 3.71 (m, 1H, 3-H), 3.65 (dd, 1H, J=11.6, 2.8, 1-Hb), 2.26 (t, 2H, J=7.7, $COCH_2$), 2.0 (m, 2H, C(15)$H_2C$(16)$H_2$-pyridinium ring), 1.60 (m, 2H, $COCH_2CH_2$), 1.44 (m, 2H, C(4)$H_2$), 1.21 (m, 44H, $CH_2$), 0.80 (t, 3H, J=7.0, $CH_3$); (MeOD) to be chack with new spectrum 9.01 (dd, 2H, J=6.6, 1.2, 2,6-$H_{Py}$), 8.59 (dt, 1H, J=6.8, 1,2, 4-$H_{Py}$), 8.11 (t, 2H, J=6.9, 3,5-$H_{Py}$), 4.62 (t, 2H, J=7.6, C(12)$H_2$-pyridinium ring), 3.81 (m, 1H, 2-H), 3.70 (dd, 1H, J=11.2, 4.3, 1-Ha), 3.70 (dd, 1H, J=11.4, 3.0, 1-Hb) 3.68 (dd, 1H, J=11.4, 6.0, 1-Hb), 3.58 (m, 1H, 3-H), 2.21 (t, 2H, J=7.5, $COCH_2$), 2.01 (m, 2H, C(11)$H_2C$(12)$H_2$-pyridinium ring), 1.60 (m, 2H, $COCH_2CH_2$), 1.52 (m, 2H, $COCH_2CH_2CH_2$), 1.38 (m, 4H, C(10)$H_2C$(11)$H_2C$(12)$H_2$-pyridinium ring C(4)$H_2$), 1.27 (m, 36H, $CH_2$), 0.89 (t, 3H, J=7.1, $CH_3$); ESI-MS ($CH_3OH$, relative intensity, %) m/z 617.7 ($M^+$, 100). Calcd. for $[C_{39}H_{73}N_2O_3]^+$ m/z 617.6.

Anal. Calcd. for $C_{39}H_{73}BrN_2O_3$ (697.9): C, 67.12; H, 10.54; N, 4.01; Br, 11.45. Found: C, 66.93; H, 10.45; N, 3.91; Br, 11.19.

6.31. Example 31

General method for the preparation of class C of CCPS analogs.

General directions: CCPS analogs class C can be synthesized from ceramides or their congeners and ω-bromo-1-alkenes via the olefin cross-metathesis reaction following cationization of the formed ω-bromo-ceramides with pyridine as shown in Scheme 4 (Trnka, T. M.; Grubbs R. H. *Acc. Chem. Res.* 2001, 34, 18-29; Nussbaumer, P.; Ettmayer, P.; Carsten, P.; Rosenbeiger, D; Högenauer, K. *Chem. Commun.*, 2005, (40), 5086-5087).

Synthesis of LCL438 is shown as an example. In the first synthetic step, alkyl chain of the sphingosine backbone of D-erythro-C16-ceramide was exchanged with 11-bromo-1-undecene under the standard cross-metathesis conditions using the Grubbs' $2^{nd}$ generation catalyst. In the second step, the formed intermediate, D-erythro-2-N-hexadecanoyl-14-bromo-sphingosine, was condensed with pyridine in a similar fashion as described for the preparation of the class A and B of CCPS analogs.

(2S,3R,4E) D-eaythro-2-N-Hexadecanoyl-14-(1'-pyridinium)-sphingosine bromide (LCL438) (A), Cross-metathesis of ceramide with ω-bromo-1-alkene. To a well-stirred mixture of D-erythro-C16-Ceramide (400 mg, 0.74 mmol) and the Grubbs' catalyst ($2^{nd}$ generation: benzylidene [1,3-bis-(2,4,6-trimethylphenyl)-2-imidazolidinylidiene]dichloro (tricyclohexylphosphine)ruthenium, 95 mg, 15% mol; Aldrich #569747) in anhydrous dichloromethane (20 mL) 11-bromo-1-undecene (1.7 mL, 7.4 mmol, 95%) was added drop-wise at room temperature with the exclusion of moisture. After the addition was completed, the reaction mixture was stirred and heated under reflux for 1.5 h. The reaction mixture was evaporated under reduced pressure to dryness and the obtained residue was washed with n-hexane (2×5 mL). The obtained crude product was purified by silica gel flash column chromatography using $CHCl_3$-methanol (1:1, v/v). Fractions within the $R_f$ values of 0.48-0.51 ($CHCl_3$-MeOH, 8:1, v/v/) were collected and evaporated to dryness to give the intermediate product: D-erythro-2-N-hexadecanoyl-14-bromo-sphingosine (217 mg, 50% yield; pale brown microcrystalline solid after recrystallization from acetone-ethyl acetate, 1:1, v/v; TLC (silica gel, EtOAc-EtOH—$CH_3CN$, 20:1:1, v/v) $R_f$ 0.38). This material was used directly to the next step for cationization with pyridine.

(B). Cationization of D-eryhtro-14-bromo-C16-Ceramide. A mixture of D-erythro-2-N-hexadecanoyl-14-bromo-sphingosine (150 mg, 0.27 mmol), anhydrous pyridine (2 mL) and anhydrous toluene (3 mL) were heated in sealed glass test-tube in the oil bath at 85-95° C. over 7 hrs. The reaction mixture was cooled down to room temperature and evaporated under a reduced pressure to dryness following drying of the residue in a high vacuum for 2 hrs. The obtained residue was washed with n-hexane (2×3 mL) and ethyl-acetate-n-hexane (5×2 mL, 4:1, v/v). Crude product was recrystallized from anhydrous acetone to give pure LCL438 (112 mg, 65% yield) as a grey microcrystaline powder. Analytical sample of LCL438 was obtained by recrystallization from anhydrous acetone-ethanol (15:1, v/v) as a pale grey microcrystalline solid, mp 101-102.5° C.; TLC ($CHCl_3$—$(CH_3)_2CO$-MeOH—$CH_3COOH$—$H_2O$, 20:8:8:2:1, v/v) $R_f$ 0.39; $[\alpha]^{20}_D$=−6.3° (c=1, MeOH); $[\alpha]^{20}_{365}$=−28.0° (c=1, MeOH); $^1H$ NMR (500 MHz, MeOD) δ 9.00 (d, 2H, J=5.5, 2,5-$H_{Py}$) 8.59 (tt, 1H, J=7.8, 1.3, 4-$H_{Py}$), 8.11 (t, 2H, J=7.0, 3,5-$H_{Py}$), 5.66 (dtd, 1H, J=15.3, 6.7, 0.8, 5-H), 5.45 (ddt, 1H, J=15.3, 7.3, 1.3, 4-H), 4.63 (t, 2H, J=7.5, C(14)$H_2$-pyridinium ring), 4.04 (t, 1H, J=7.1, 3-H), 3.84 (dt, 1H, J=7.1, 5.1, 2-H), 3.67 (d, 2H, J=5.1, 1-Ha,b), 2.18 (t, 2H, J=7.5, $COCH_2$), 2.01 (m, 4H, C(13)$H_2C$(14)$H_2$-pyridinium ring and C(6)$H_2$), 1.57 (m, 2H, $COCH_2CH_2$), 1.38 (m, 4H, C(12)$H_2C$(13)$H_2C$(14)$H_2$-pyridinium ring and C(7)$H_2$), 1.27 (m, 32H, $CH_2$), 0.89 (t, 3H, J=7.1, $CH_3$); ESI-MS ($CH_3OH$, relative intensity, %) m/z 559.5 ($M^+$, 100) Calcd. for $[C_{35}H_{63}N_2O_3]^+$ m/z 559.48. ESI-MS/MS ($CH_3OH$, daughter ions generated from the parent ion of 559.4 m/z at 45 eV, relative intensity,%) m/z 559.4 ($M^+$, 30), 224 ($[M-H_2O—C_5H_5N$—$COC_{15}H_{31}]^+$, 30), 206 ($[M-C_5H_5N$—$COC_{15}H_{31}$-$2H_2O]^+$, 100), 80 ($[C_5H_5NH]^+$, 60).

7. EXAMPLES

Effects on MCF7 Cancer Cells

Cell Culture: MCF7 cells (breast adenocarcinoma, pleural effusion) were purchased from American type Culture Collection (ATCC) (Rockville, Md., USA) and grown in RPMI 1640 media (Life Technologies, Inc) supplemented with 10% fetal calf serum (FCS) (Summit Biotechnology, CO) and maintained under standard incubator conditions (humidified atmosphere 95% air, 5% $CO_2$ 37° C.). A parallel set of cells was used to determine cell proliferation and to prepare lipid extracts for MS analysis.

Cell Proliferation: Cells were seeded into plates at a density of approx. 50% corresponding to $1\times10^6$ cells, in 10 ml of 10% FCS and after an over night incubation the cells were treated with LCL compounds at concentration 0-20 μM in ethanol (ethanol level was kept below 0.1%) and the changes in cell numbers after 48 h were determined and expressed as a percentage of the untreated controls.

Briefly, media was removed, cells were washed twice with PBS, detached using 1% Trypsin and centrifuged at 800 rpm. Cell pellets were resuspended in PBS and Trypan blue (Sigma Chemicals, St. Louis, Mo., USA) was added (1:1 dilution). Under light microscope, the percentage of unstained and stained cells was assessed.

Endogenous ceramide: ESI/MS/MS analysis of endogenous sphingoid bases, sphingoid base 1-phosphates and ceramide species was performed on a Thermo Finnigan TSQ 7000 triple quadrupole mass spectrometer, operating in a Multiple Reaction Monitoring (MRM) positive ionization mode using modified version (Bielawski, J. et al., SERMACS 2003, poster #68) of the protocol previously published (Sullard, M. C., Merrill, A. H., Sciences stke 2001/67/p 11).

Briefly, for the indicated points, media was removed, cells were washed twice with PBS, scraped into cold PBS (2×1.0 ml), transferred to glass vials and centrifuged for 5 min at 800 rpm. Cell pellets corresponding to ~1×10$^6$ cells, were fortified with the internal standards IS ($C_{17}$ base D-erythro-sphingosine: 17Sph, $C_{17}$ sphingosine-1-phosphate: 17Sph-1P, N-palmitoyl-D-erythro-$C_{13}$ sphingosine: 13CC16-Cer and N-heptadecanoyl-D-erythro-$C_{17}$shingosine: 17CC17-Cer) and extracted (2×2 ml) into a one-phase solvent system with ethyl acetate/iso-propanol/water (60/30/10 v/v). One ml of this extract was used for Pi determination after lipid re-extraction by the Bligh and Dyer method. Remaining lipid extract was evaporated, reconstituted in 100 µl of methanol, and samples were injected on the Surveyor/TSQ 7000 LC/MS system and gradient eluted from the BDS Hypersil C8, 150× 3.2 mm, 3 µm particle size column, with 1.0 mM methanolic ammonium formate/2 mM aqueous ammonium formate mobile phase system. Peaks corresponding to the target analytes and IS were collected and processed using the Xcalibur software system.

Quantitative analysis was based on the calibration curves generated by spiking an artificial matrix with the known amounts of the target analyte synthetic standards and an equal amount of the internal standards (IS). The target analyte peak area ratios from the samples were similarly normalized to their respective IS and compared to the calibration curves using a linear regression model.

Final data were adjusted and results were expressed as level of particular sphingolipids/Pi (pmol/nmol).

7.1. Cellular Level of CCPS Analogs

Cellular level of CCPS analogs was established by MS methodology. Experimental data from cell treatment with 5 µM concentration of CCPS analogs over the time, showed a very fast cellular uptake for CCPSs and dhCCPSs. Intracellular level of these analogs after 15 min of treatment was established as 2-3% concentration applied (~500-750 pmols) with a progressive increase of 7.5-12% for 1 h treatment (FIGS. 4a and 4b). At this time, the level of pyr dh $C_6$-ceramide (LCL143) went up to 15% and was twice higher than for pyr $C_6$-ceramide (LCL29). The cellular level of CCPS analogs was increasing up to 5 h reaching ~17% for $C_2$, $C_6$ and $C_{16}$ homologs (LC129, 30 and 150) and 23% for C12 ceramide (LCL88). When treatment time was extended to 24 h, differences in cellular level of the short chain and long chain homologs were noticed. Levels of LCL150 and LCL29 were continuously increased up to 24 h reaching 50% and 32% for $C_2$ and $C_6$ homologs respectively, whereas the levels of $C_{12}$ and $C_{16}$-homolgs at 24 h were similar to that for 5 h treatment.

Cellular levels of dihydro analogs were also time- and chain length-dependent. The cellular level of short chain homologs was permanently increased reaching 13% and 27% at 5 h and 35% and 52% at 24 h for $C_6$ and $C_2$ homologs respectively (LCL143 and LCL319), whereas cellular levels of long chain dihydro homologs did not change with the time showing comparable levels for 5 and 24 h treatments.

Comparison of the cellular levels of the parallel pairs of CCPS and dhCCPS showed that the short chain analogs are on a similar level, whereas the long chain CCPSs are present at a higher level than their dihydro-partners: 17% versus 4% and 23% versus 7% for 5 h treatment (LCL345/LCL30 and LCL148/LCL88, respectively). Further investigation showed that dihydro CCPS analogs were metabolized to the corresponding CCPS analogs.

7.2. Inhibitory Effect of CCPS Analogs of Class A on MCF7 Cell Growth

To examine the anticancer activity of CCPS analogs of the invention, their inhibitory effect on MCF7 breast carcinoma cells were analyzed and compared to the activity of D-e-$C_6$-ceramide, which is commonly used as a model of action for ceramides. Cell proliferation and cell viability were determined by Trypan blue exclusion assay. Dose and time-dependent effects on cell growth induced by incubation with CCPS analogs are shown in FIG. 5.

As shown in FIG. 5a, all tested ω-D-erythro-Cn-pyridinium ceramide bromides ($C_2$-$C_{16}$) showed an inhibitory effect on cell growth as established for 48 h treatment with the following IC$_{50}$ values [µM]: 8.0/C2-cer, 1.0/C6-cer, 0.6/C12-cer and 1.6/$C_{16}$-cer. Regular D-e-$C_6$-ceramide was the least potent compound (only ~35% inhibition for 10 µM treatment). At 1.0 µM concentration the most effective was pyridinium C12-homolog (LCL88) and the least potent was C2-homolog (LCL150). Some inhibitory effect (20-30%) was already observed for 0.2 µM C12-, $C_6$- and $C_{16}$-homologs. We have noticed remarkable differences in the activity profile between $C_6$- and $C_{16}$-homologs. Pyridinium $C_{16}$-ceramide bromide (LCL-30) showed a systematic, dose-dependent inhibitory effect on cell growth from 0.2-10.0 µM being at concentration of 5 µM more potent than $C_6$-homolog LCL-29. LCL29 was very potent at concentration 0.1-1.0 µM. When concentration was increased up to 10 µM we did not find any further drastic changes. This observation may suggest a different mechanism of action for the short and the long chain ceramides.

Effect of D-erythro-dihydroCCPS analogs on cell growth was also investigated (FIG. 5b). D-erythro-dihydroceramides are known as biologically inactive compounds as was shown for $C_2$- and $C_6$-analogs (ref). $C_{16}$-, $C_{12}$- and $C_6$-dhCCPS homologs (LCL345, 249, 143) showed a concentration dependent inhibitory effect on cell growth, but with a lower potency as compared to their 4-5 unsaturated counterparts (LCL-30, 88, 29). IC50 values [µM] for 48 h treatment were as follow: 2.5/LCL345, 2.5/LCL249 and 5.0/LCL143. C2-homolog LCL319 had low activity, only 15% inhibitory effect was observed for 10 µM treatment.

Stereospecific effect of $C_6$-CCPS analogs is shown in FIG. 5c. All tested stereoisomers (LCL-29, 124,187 and 272) caused inhibitory effect on MCF7 cell growth with the (2S) isomers (LCL-29, 124) being more potent than their (2R) enantiomers (LCL-187, 272). A similar stereo-profile was observed for the parent $C_6$-ceramides in HL-60 cell.

(2S) diastereoisomers of C16-CCPS (D-erythro: LCL-30 and L-threo-: LCL-87), had a similar, concentration dependent (1.0-10.0 µM) inhibitory effect on cell growth at 48 h and a time dependent antiproliferative effect for 2 µM or 1.5 µM treatment over a 0-72 h time period.

The inhibitory effect on cell growth of LCL-275 and 277 (CCPS analogs representing class B) is shown in FIG. 5f. Considering the length of their N-acyl-part, LCL-275 and LCL-277 are C12 and C10 homologs and can be treated as close analogs of LCL-88. Considering a placement of pyridinium ring into the α or γ position to the carbonyl group, these analogs can be treated as analogs of LCL-150 (where pyridinium ring is at the β-position to the carbonyl group.) Neither LCL275 nor LCL277 followed the activity pattern of LCL88, rather their activity can be compared to the effect of LCL150. The inhibitory effect was observed at higher concentration (IC50 values are 8.5 µM/LCL277 and ~20 µM/LCL275).

In summary, location of the pyridine disc ring close to the polar part of ceramide structure caused these analogs to be less potent with LCL275 being the least potent compound from the CCPS family.

Fluorescent analog LCL186 also showed inhibitory effect on MCF7 cells growth (IC50/~4 µM for 48 h treatment).

The inhibitory effect of these newly synthesized CCPS analogs was compared to the activity of D-erythro-C2-ceramide and D-erythro-$C_6$-ceramide. These two synthetic ceramides are commonly used in cell experiments as cell permeable homologs of naturally occurring long chain ceramides, which are not able to enter the cells. Study with those short chain ceramides at concentration 1.0-20.0 µM showed that C2-ceramide was inactive and $C_6$-ceramide had only low antiproliferative effect with $IC_{50}$ value corresponding to 15.0 µM at 48 h (FIG. 5a).

The antiproliferative effect of the CCPS analogs was examined in MCF7 breast cancer cell line and compared to the activity of D-e-$C_6$-ceramide (IC50/48 h: 15 µM). The markedly highest effect was found for ω-CCPS Compounds (IC50 value/LCL#: 8.0 µM/LCl150, 1.0 µM/LCL29, 0.6 mM/LCL88 and 1.8 µM/LCL30). Analogs from class B were less potent (IC50: 13 µM/LCL-277 and 15 µM/LCL-275). No remarkable differences for activity of $C_6$-stereoisomers were found, however 2S diastereoisomers were more potent as compared to the 2R counterparts. Interestingly, pyridinium dihydro-ceramides (dhCCPS) were also active, but with a lower potency as compared to their unsaturated analogs (IC50/LCL#: 12.5 µM/LCL319, 5.02 µM/LCL143, 2.8 µM/LCL249 and 2.5 µM/LCL345). As established by LC-MS analysis, dhCCPSs were metabolized to the corresponding CCPSs. (FIG. % B)

Regulatory Effect of CCPS Analogs on EndCer in MCF7 Cells.

The effects of CCPS analogs on EndCer is shown in FIG. 6a-6c. Treatment with 5 µM of LCL29, 30 and 88 caused generation of an "early Cer" and had an early regulatory effect on Cer composition (FIG. 6c). The CCPS Compounds caused a very early (15 min) down regulatory effect on the level of endogenous ceramide (ECer) and sphingosine (ESph) and a up regulatory effect on sphingosine-1-phosphate (Sph-1P) (FIG. 7a.) Following the time course, Sph-1P was decreased below the control level and the total Cers level was increased. Increase in ECer and changes in its composition were observed starting from 0.5 h (up regulation of C16, C14 and C18 Cers and extended down regulation of C24:0 and C24:1 Cers). Apoptotic effect of CCPS analogs can be correlated with the induction of endogenous "early C14, C18 and C16 Cers". It is also possible that an apoptotic signal was started by an earlier appearance of S1P. (FIG. 7A, FIG. 7B). The regulator effect of LCL85 and LCL120 on endogenous ceramide at 24 hours is shown in FIG. 10. Regulatory effect of LCL85 on endogenous $C_n$-Ceramide compositions at 24 hours is shown in FIG. 11.

8. EXAMPLES

Inhibition of Cancer Cell Growth and Telomerase

Head and neck squamous cell carcinoma (HNSCC) is notoriously resistant to chemotherapy. The sphingolipid ceramide and its analogs have been demonstrated to exert antitumor activity in many cell types; however, the effectiveness of these analogs has been limited by potency and solubility. Telomerase, an RNA-dependent DNA polymerase which elongates telomeres at the end of chromosomes, is active in about 80-90% of the tumor tissues of the HNSCCs, whereas it is not active in normal head and neck tissues. Since abnormal activation of telomerase in tumors appears to be required for their immortality, telomerase is a significant therapeutic target for the development of cancer-specific novel treatment strategies of HNSCCs. In this example, the roles of water-soluble $C_6$-Pyr-Cer in the inhibition of cell cycle and telomerase activity as compared to the conventional ceramides and/or chemotherapeutic agents, alone or in combination, in various HNSCC cell lines, were examined. The in vivo anticancer properties of these compounds were tested in a SCID mouse model.

8.1. Materials and Methods

Ceramides and chemotherapeutic agents. Short chain ceramide analogs (D-erythro and L-threo-ceramides with $C_2$-$C_{16}$ fatty acid chain lengths) were synthsized as described above. Cetylpyridinium bromide (CPB) monohydrate was purchased from Aldrich.

Cell lines and culture conditions. Human head and neck cancer cell lines UM-SCC-1 (retromolar trigone/floor of the mouth), UM-SCC-12 (primary tumor of larynx), and UM-SCC-22A cells were obtained from clinical samples. Cells were grown in DMEM containing 10% FCS and 1% penicillin/streptomycin at 37° C. in 5% $CO_2$. The Wi-38 human lung fibroblasts were obtained from American Type Culture Collection, and were grown in DMEM as described above. Adult human epidermal keratinocytes were purchased from Cascade Biologics, and were maintained in EpiLife medium with growth supplements as described by the manufacturer.

MTT cell survival assay and isobologram studies. The concentrations of agents that inhibited cell growth by 50% ($IC_{50}$) were determined from cell survival plots obtained by MTT. Triplicate wells were used for each treatment. The final concentration of DMSO (a solvent for conventional ceramides, GMZ and DOX) in the growth medium was less than 0.1% (v/v) which has no effect on cell growth and survival. Pyridinium ceramides were dissolved in sterile water or growth medium. In short, after cells (5-10×10³/well) were seeded in 96-well-plates for 24 hr, they were treated with increasing concentrations of ceramide analogs for an additional 48 or 96 hr. For combination treatments, ceramides and chemotherapeutic agents (gemcitabine (GMZ) or doxorubicin (DOX)) were added to the growth medium simultaneously during treatment. Isobologram plots were then constructed using $IC_{50}$ values of the two agents alone or in combination obtained from MTT assays. A straight line joining points on x- and y-axes represent the $IC_{50}$ concentrations of two agents, and the points representing the $IC_{50}$ concentrations of the combination of the two agents are represented as scatter plots on the same graphs. In general, the points that fall within the left of the straight line indicate synergism. The experiments were performed as triplicates in at least 3 independent experiments.

Analysis of cell cycle profiles. The effects of pyridinium ceramides on the cell cycle profiles of A549 cells at 24 hr were analyzed in the presence of DNase-free RNase and propidium iodine (PI) by flow cytometry as described in Ogretmen et al., *J. Biol. Chem.* 2001; 276: 24901-24910, which is incorporated herein by reference in its entirety. Untreated cells were used as controls.

Determination of telomerase activity. Telomerase activity in cell extracts was measured by the PCR-based telomere repeat amplification protocol (TRAP) using TRAPeze kit (Intergen, Gaithersburg, Md.) which includes a 36-bp internal control to allow quantification of activity. In short, the intensity of telomere-specific DNA bands, measured using Quantity One (BioRad) software, were normalized to the intensity of internal control bands for each sample on polyacrylamide gels for quantification.

8.2. Results

Exogenous ceramides have been shown to mediate antiproliferative responses such as cell cycle arrest, apoptosis or senescence in various cancer cells. However, since the solubility and bio-availability of these exogenous ceramides are known to be limited, the water soluble CCPS analogs were developed.

First, to examine the effects of pyridinium ceramides containing different fatty acid chain length in cell growth, the cells were treated with $C_6$-, $C_{12}$- and $C_{16}$-D-e- and L-th-pyr-cer for 48 hr (FIG. 12A and 12B, respectively). The $IC_{50}$ concentrations of $C_6$-, $C_{12}$- and $C_{16}$-D-e- and L-th-Pyr-Cer were comparable in UM-SCC-22A cells at 48 hr of treatment (FIGS. 12A and 12B), and these values (about 1 μM) were higher than those obtained after 96 hr treatment (about 300 nM). These results also demonstrate that the longer fatty acid chains in these pyridinium conjugated ceramide analogues did not appear to play a major role in their growth suppressing effects in these cells. Since the $IC_{50}$ concentrations of D-e- and L-th-$C_6$-Pyr-Cer were almost identical (at both 48 and 96 hr), they have been used interchangeably throughout this study. The effects of $C_6$-Pyr-Cer on the inhibition of cell survival were also examined in other HNSCC cell lines (UM-SCC-1 and UM-SCC12), and similar results with $IC_{50}$ values between 250-300 nM at 96 hr were obtained.

Next, the growth inhibitory effects of conventional exogenous ceramides, D-erythro (D-e-)-$C_6$-ceramide and L-threo (L-th)-$C_6$-ceramide, and their newly developed highly water soluble cationic analogues, D-e-$C_6$-Pyr-Cer and L-th-$C_6$-Pyr-Cer in the UM-SCC-22A cells were determined using MTT assays after 96 hr treatment. As seen in FIG. 12C, D-e-$C_6$-Pyr-Cer and L-th-$C_6$-Pyr-Cer showed $IC_{50}$ values ranging from 250-300 nM, whereas conventional $C_6$-ceramides failed to achieve an $IC_{50}$ at concentrations up to 1300 nM, showing that the newly developed $C_6$-Pyr-Cer is >4-fold more effective in inhibiting cell growth. Interestingly, it seems that $C_6$-Pyr-Cer contains the optimum chain length for growth inhibition, as the $C_2$-Pyr-Cer did not exert a significant effect on cell growth (FIG. 12C). Thus, to date, these novel $C_6$-Pyr-ceramides represent the most potent analogs of ceramide in exerting growth suppressing activity.

To evaluate the effects of the Lt-$C_6$-Pyr-Cer in non-cancerous cells, the inhibition of cell growth in non-cancerous Wi-38 human lung fibroblasts and adult human epidermal keratinocytes (HEK) in response to increasing concentrations of $C_6$-pyridinium ceramide was assessed. Since the contents of growth media to maintain HEK and UM-SCC-22A cells in culture are largely different than each other, the effects of $C_6$-Pyr-Cer on the growth of HEK and UM-SCC-22A cells were examined in two independent experiments by growing both of these cell lines either in the DMEM containing 10% FBS, or in EpiLife medium, with growth supplements in which HEK cells are normally maintained. Interestingly, $C_6$-Pyr-Cer was not active in EpiLife medium, $IC_{50}$ concentrations were >2 μM at 96 hr for both of the cell lines. However, when these cell lines were grown in DMEM, the $IC_{50}$ value of $C_6$-Pyr-Cer was greater than 1000 nM (FIG. 12D) for keratinocytes, whereas its $IC_{50}$ concentration in UM-SCC-22A cells was about 300 nM. Similar results were also obtained using Wi-38 fibroblasts (grown in DMEM), in which $IC_{50}$ concentration of $C_6$-Pyr-Cer was >1000 nM (FIG. 12D). These results, therefore, suggest that $C_6$-Pyr-Cer is >4-fold more effective in inhibiting cell growth in squamous cell carcinoma cells than non-cancerous fibroblasts or keratinocytes in vitro, indicating a lower potential for general toxicity. This was further confirmed in vivo, in which the maximum tolerated dose (MTD) of $C_6$-Pyr-Cer with no detectable toxicity in SCID mice was found to be around 80-100 mg/kg, which is comparable to the MTD of GMZ (80 mg/kg) whereas the MTD of DOX was between 1-2 mg/kg in mice.

The effects of pyridinium-ceramides on cell cycle profiles and telomerase activity in UM-SCC-22A cells were examined using flow cytometry and TRAP assays as described in Materials and Methods. The results showed that treatment of UM-SCC-22A cells with D-e-$C_6$-, $C_{12}$- and $C_{16}$-Pyr-Cer at 1 μM for 48 hr resulted in a significant increase in the population of cells in G0/G1 when compared to untreated controls (FIG. 13A). Thus, these analogs caused an arrest in cycle progression.

Importantly, examination of apoptotic cell death using annexin V staining in response to $C_6$-Pyr-Cer did not show any detectable signal, and no sub G0/G1 apoptotic peaks in flow cytometry analysis were observed in the presence or absence of $C_6$-Pyr-Cer in these cells (FIG. 13A). Thus, these ceramide analogs appear to exert minimal apoptotic activity on their own, with selective cell cycle arrest in these cells.

The selective effects on cell cycle raised the possibility that these compounds may regulate telomerase function. Indeed, treatment of cells with 100, 250 and 500 nM $C_6$-Pyr-Cer for 96 hr causes about 30, 50 and 75% inhibition of telomerase activity, respectively, when compared to that of untreated controls (FIG. 13B, lanes 2-4 versus 1). Additional results also showed that $C_6$-Pyr-Cer had no significant effect on telomerase activity when applied directly to the extracts in vitro even at 10, 20 and 100 μM (FIG. 13B, lanes 7-9), demonstrating that the inhibition of telomerase by $C_6$-Pyr-Cer is not due to a direct inhibition of the enzyme, but involves transcriptional and/or post-transcriptional regulation of telomerase. Thus, these data demonstrate that these ceramide analogs cause a significant inhibition of telomerase, which correlates with cell cycle arrest at G0/G1 in UM-SCC-22A cells.

Figures 14A, 14B:
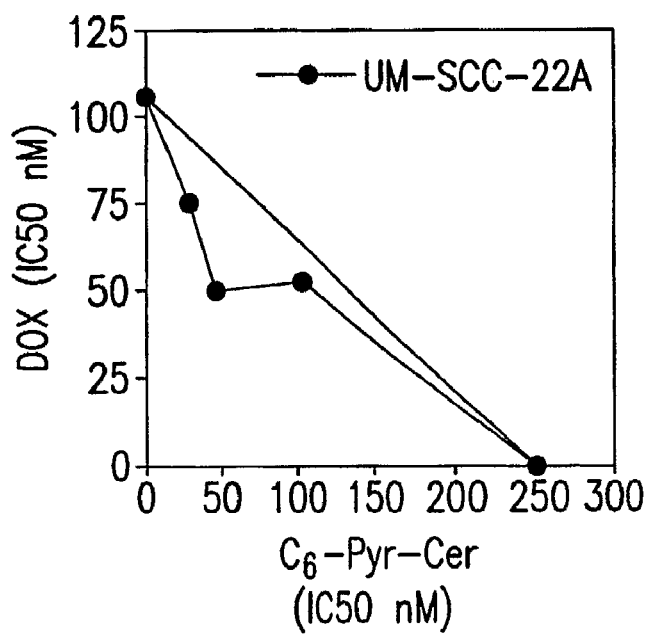

The conventional chemotherapy for head and neck cancers is the combination of cisplatinum with 5-FU, or taxol. Experiments were conducted to determine whether the combination of $C_6$-Pyr-Cer would be synergistic in inhibiting growth when combined with anti-cancer drugs. First, the $IC_{50}$ values of various chemotherapeutic agents were determined in UM-SCC-22A cells using MTT assays. As shown in FIG. 14A, doxorubicin (DOX), daunorubicin (DNR), methotrexate (MTX) and gemcitabine (GMZ) exhibited the lowest $IC_{50}$ values between 100-250 nM, whereas cisplatinum (CSP), paclitaxel (PAX), carboplatinum (CRBP) and 5-fluorouracil (5-FU) showed $IC_{50}$ values between >1-100 μM in these cells.

Next, experiments were performed to determine whether $C_6$-Pyr-Cer inhibited cell growth synergistically in combination with DOX in UM-SCC-22A cells, the most potent inhibitor of cell survival in these cells. Quantitative isobologram studies were performed as described in Materials and Methods. The results demonstrated that the combination of $C_6$-Pyr-Cer at 25, 50 and 100 nM with DOX for 96 hr decreased growth synergistically, detected as shift of the $IC_{50}$ values of DOX in the isobologram (FIG. 14B) to the left of the line plot joining the x and y-axes that represent the $IC_{50}$ of $C_6$-Pyr-Cer and DOX alone, respectively. Interestingly, the optimum concentration of $C_6$-Pyr-Cer was 50 nM for its synergistic interaction with DOX, and using 100 nM $C_6$-Pyr-Cer did not enhance synergy with DOX in these cells (FIG. 14B).

Figure 14C:
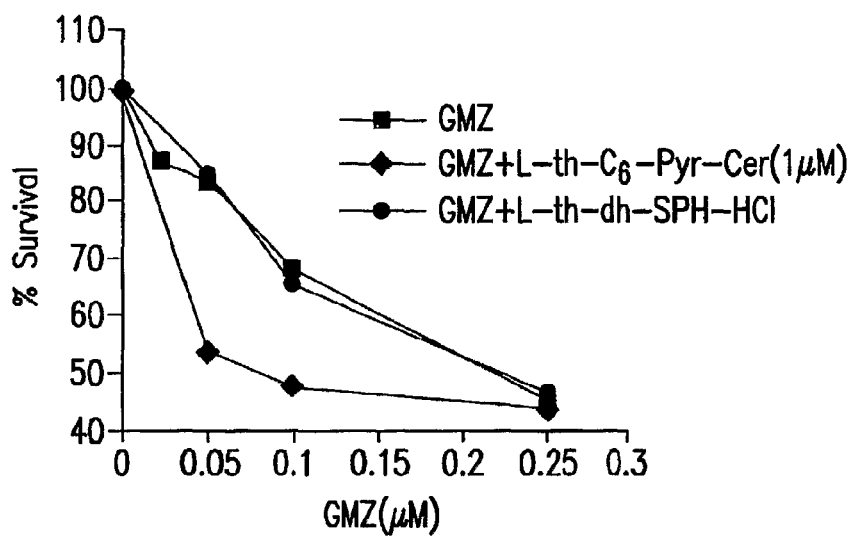
Figure 14D:
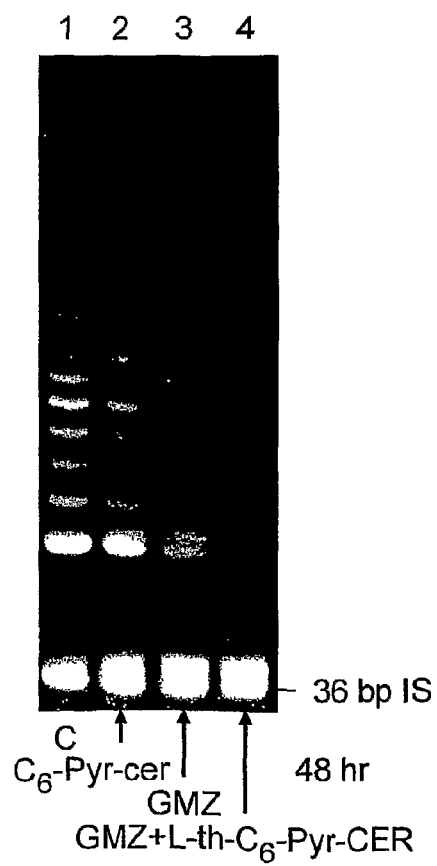

Since GMZ has been reported to delay tumor development in a xenograft model of human squamous cell carcinoma-contaminated surgical wounds, and also it was found to be one of the more potent inhibitors of cell growth in UM-SCC-22A cells in the present study, the effects of treatment of cells with the combination of $C_6$-Pyr-Cer on cell survival and telomerase activity were assessed. As seen in FIG. 14C, combining 1 μM $C_6$-Pyr-Cer with various concentrations of GMZ for 48 hr treatment enhanced the anti-proliferative effects of GMZ when compared to treatments with GMZ alone. The combination of cetyl-pyridinium itself without conjugation to ceramide (used as a non-specific control) with GMZ did not have any role on the efficacy of GMZ in these cells (FIG. 14C), demonstrating a specific role for ceramide in the synergistic growth inhibition response to GMZ in these cells. To determine whether $C_6$-Pyr-Cer and GMZ also synergistically inhibited telomerase activity, UM-SCC-22A cells were treated with $C_6$-Pyr-Cer (1 μM), GMZ (100 nM) or the combination of $C_6$-Pyr-Cer and GMZ for 48 hr. Then, telomerase activity was measured using TRAP assay as described in Materials and Methods. As seen in FIG. 14D, treatment of UM-SCC-22A cells with $C_6$-Pyr-Cer (lane 2) or GMZ (lane 3) resulted in the 30-50% inhibition of telomerase activity, respectively, whereas treatment of cells with the combination of $C_6$-Pyr-Cer and GMZ (lane 4) caused a significant additional inhibition of telomerase activity (about 90%) in these cells, as compared to untreated controls (lane 1).

The compound was further tested in an animal model of SCID mouse and UM-SCC-22A xenografts (hypopharynx). Xenograft development and treatment was carried out by standard methods. Once the xenograft achieved a standard volume, the animals were randomized to receive no treatment (control), LCL-194 alone (40 mg/kg), LCL-124 alone (40 mg/kg), LCL-124 (40 mg/kg) plus GMZ (80 mg/kg), GMZ (80 mg/kg)+DOX (2 mg/kg), or 5FU plus cisplatin (25 mg/kg each). Tumors were measured every 4 days. See FIG. 21 for a comparison of tumor sizes after 24 days of treatment. The data clearly indicate that the CCPS analog of the invention (LCL-124) can act alone or in combination with GMZ to suppress growth of chemotherapy-resistant classes of tumors.

Taken together, these results suggest that these newly developed cationic pyridinium ceramides can synergistically inhibit cell survival when combined with chemotherapeutic drugs for the treatment of HNSCC.

8.3. Discussion

The results presented here show that the newly developed novel water-soluble CCPS analogs (pyridinium-ceramides) can inhibit cell growth of HNSCCs with about 250-300 nM $IC_{50}$ concentrations in vitro. The data demonstrate that the action of $C_6$-Pyr-Cer mechanistically involves the inhibition of telomerase, which correlates with growth arrest at G0/G1 in these cells. In addition, the treatment of non-cancerous Wi-38 or adult HEK cells, which do not express detectable telomerase activity, with $C_6$-Pyr-Cer did not cause a significant inhibition of cell survival, indicating a lower potential for overall toxicity. More importantly, it has been also demonstrated in this study that pyridinium-ceramides can potentiate the anti-proliferative effects of known chemotherapeutic drugs such as GMZ and DOX in UM-SCC-22A cells.

The standard of treatment for advanced squamous cell carcinomas of the head and neck (HNSCC) is continuing to evolve with increased emphasis on the use of organ sparing chemoradiotherapy regimens. While survival data are comparable for early stage T1-2 oral cavity tumors with either radiation therapy or surgery, most oral cavity cancers are treated surgically. Post-operative radiation therapy may be beneficial for Stage III and IV oral cancer although chemotherapy has not been proven as a curative option for oral cancer at this time. Surgical resection requires complete tumor removal and frozen section margin analysis remains the standard of care. Novel molecular diagnostic techniques are currently being studied as markers for residual, persistent and recurrent disease. Recent studies have shown that telomerase is activated in about 90% of the HNSCC tumors, while it is not active in the majority of normal H&N tissue, indicating that the inhibition of telomerase might provide cancer-specific therapeutic strategies for the treatment of HNSCC. The results here show that one of the mechanisms involved in the inhibition of cell survival by pyridinium-ceramides is the inhibition of telomerase.

The conventional chemotherapy of the HNSCCs in the clinic involves mainly the combination of CSP with 5-FU or PAX. However, these compounds had no significant effects on cell growth when applied either alone or in combination in UM-SCC-22A cells. Interestingly, GMZ and DOX seem to be very effective in inhibiting the growth of these cells in vitro, with very low $IC_{50}$ concentrations. Recent studies have evaluated the combination of GMZ with the antineoplastic vinka alkaloid vinorelbine in HNSCCs which showed no reported pharmacokinetic or synergistic interaction. Combination therapy involving anthracyclines has been analyzed recently, advocating the dosage limitations of these cardiotoxic compounds in HNSCCs. However, since the results with GMZ in combination with pyridinium ceramides appear to be particularly promising, their synergistic roles in the inhibition of cell growth in HNSCC and development as therapeutic agents are very promising.

9. EXAMPLE

Mitochondrial Permeabilization

The following example demonstrates that the positively charged or cationic pyridinium ceramide analogs readily accumulate in isolated and in situ mitochondria. Accumulated, positively charged ceramides increased inner membrane permeability and triggered release of mitochondrial cytochrome C. Furthermore, positively charged ceramide-induced permeability increase was suppressed by cyclosporin A (60% "CSA")) and 1,3-dicyclohexylcarbodiimide (90% "DCCD"). The results suggest that the inner membrane permeability increase is due to activation of specific ion transporters, not the generalized loss of lipid bilayer barrier functions. The difference in sensitivity of ceramide-induced ion fluxes to the inhibitors of mitochondrial transporters suggests activation of at least two transport systems, the permeability transition pore and the electrogenic H+ channel.

9.1. Materials and Methods

Materials. RPMI 1640, DMEM and Fetal bovine serum were from Invitrogen. TMRM was from Molecular Probes. $C_6$-NBD-ceramide was from Matreya. Ceramides and their derivatives were from Lipidomics Core of the Medical University of South Carolina. All other reagents were from Sigma.

Preparation of mitochondria from rat liver. Mitochondria were prepared from livers of male Sprague-Dawley rats (220-250 g) fasted overnight. Livers from two rats were homogenized in 100 ml of isolation medium containing 230 mM mannitol, 70 mM sucrose, 2 mM EDTA and 10 mM HEPES (pH 7.4 adjusted by KOH). Homogenate was centrifuged at 579×g max for 10 mM to pellet the nucleus and unbroken cells. Supernatant from previous step was centrifuged at 8000×gmax for 10 min to pellet mitochondria. The mitochondrial pellet was washed in 25 ml and then in 12.5 ml of isolation medium without EDTA. The final mitochondrial pellet was resuspended in the above medium to provide a protein concentration of 60 mg/ml. Mitochondrial protein concentration was determined by the Bicinchoninic acid assay using BSA as standard.

Mitochondrial incubation medium. Unless otherwise specified, incubations of isolated mitochondria were conducted at 25° C., with 1 mg/ml of protein in a medium containing 250 mM sucrose; 10 mM HEPES (pH 7.4 adjusted by KOH); 10 mM succinate; 5 mM $KH_2PO_4$; and rotenone (2 µM). Deviations from this medium and other reagents employed are described in Section 4.

Mitochondrial respiration. Oxygen consumption by mitochondria was measured in a chamber equipped with a Clark type oxygen electrode (Instech laboratories) at the conditions described in Mitochondrial incubation medium.

Synthesis of mitochondrially targeted ceramide molecules.

The mitochondrially targeted compounds consisted of the lipophilic cation pyridinium covalently linked to ceramide. These pyridinium-ceramides were prepared by N-acylation of D-e-sphingosine with co-bromo acid chlorides following following quaternization of pyridine with the formed ω-bromoceramides.

Measurement of mitochondrial permeabilization. Inner membrane permeabilization was assayed by measurements of $\Delta\Psi$, mitochondrial swelling, and by changes in mitochondrial ultrastructure. $\Delta\Psi$ was estimated from the accumulation of TPP+ in mitochondrial matrix as described by Kamo et al. (1979) Journal Membrane Biology 49, 105-121. TPP+ at 2 µM was added to the incubation medium as indicated in the legends to figures. Mitochondrial swelling was measured by changes in absorbance at 520 nm using Brinkmann PC 900 probe colorimeter and fiberoptic probe. Changes in mitochondrial ultrastructure were examined by electron microscopy. Mitochondria were fixed with 3% glutaraldehyde for 15 mM, followed by sedimentation and additional fixation overnight. The fixed mitochondria were washed three times with 0.1 M sodium cacodylate, pH 7.4, treated with 2% osmium tetroxide for 1 h, dehydrated through a graded ethanol series, and embedded in Embed 812 resin. Thin sections (70 nm) were stained with uranyl acetate and lead citrate and subsequently examined using JEOL/JEMI 1010 electron microscope.

Cytochrome C release from mitochondria. Aliquots of mitochondrial suspension were taken as indicated in figure legends and centrifuged at 15,000 g for 3 min. The supernatant and mitochondrial pellet were frozen and stored at −200C. Cytochrome C in supernatants and pellets was quantified using the Quantikine cytochrome C ELISA kit (R&D Systems, Minniapolis, Minn.).

Cell culture. Hep G2 cells (obtained from ATCC) were cultured in Minimum essential medium (Eagle) supplemented with 10% fetal bovine serum, 2 mM L-glutamine, non-essential amino acids, 1 mM sodium pyruvate, and 1.5 g/L sodium bicarbonate in humidified air (5% $CO_2$) at 37° C. For confocal microscopy, cells were plated onto poly-D-lysine-treated 35-mm glass bottom microwell dishes at a density of 20,000-25,000/$cm^2$ and were grown for 2 days. MCF7 cells (obtained from ATCC) were cultured in RPMI 1640 Medium supplemented with 10% fetal bovine serum and 2 mM glutamine in humidified air (5% $CO_2$) at 37° C. All media were supplemented with 100 U/ml penicillin and 100 µg/ml streptomycin.

Isolation of mitochondria from Hep G2 cells. For studies with mitochondria isolated from Hep G2 cells, cells were cultured in the medium described under Cell culture for 3 days in 75 cm2 flasks (70% confluent). Cells were detached by treatment with 3 ml Tripsin (0.05%)-EDTA (0.53 mM), diluted to 13 ml with incubation medium and sedimented at 900×g for 10 min. The pellet was washed with 1 ml of ice-cold PBS, cells were resuspended in 3000 of isolation medium containing 230 mM mannitol, 70 mM sucrose, 2 mM EDTA and 10 mM HEPES (pH 7.4 adjusted by KOH), and then the cells were disrupted by 20 passages through 28G½ needle. Homogenate was centrifuged at 900×g for 10 min to pellet the nucleus and unbroken cells. The supernatant from previous step was centrifuged at 10000×g for 10 min to pellet mitochondria which were then resuspended in the incubation medium to provide a protein concentration of about 10 mg/ml.

Measurement of cell viability. Hep G2 or MCF7 cells were plated at a density of $10^4$ cells/well in 96-well plates in the medium described under Cell culture. After 24 hours of incubation, the cells were treated with ceramides for 46 hours in 2% fetal bovine serum medium. Cell viability was determined by MTT (3-[4,5-dimethylthiazol-2-yl]-2,5-diphenyl tetrasodium bromide) based assay according manufacture recommendation (Sigma, St. Louis, Mo.).

Confocal microscopy. For experiments, plated cells were washed once with serum-free medium and treated with 2 ml of 10 nM TMRM, 2 µM $C_6$ pyridinium-DMAS-ceramide, or 2 µM $C_6$-NBD-ceramide dissolved in the culture medium supplemented with 2% fetal bovine serum. After 30 min, unbound dyes were washed out and images were collected using a Zeiss LSM 510 META system equipped with krypton/Argon laser and a 63× oil objective (NA 1.4). In parallel experiments, after initial loading of cells with TMRM or with ceramides, cells were treated with uncoupling cocktail (10 µM FCCP, 5 µg/ml antimycin A and 10 µg/ml oligomycin A) for an additional 30 min to discharge mitochondrial inner membrane potential. The TMRM images were taken by excitation at 543 nm and emission at 560 nm long-path emission filter. $C_6$ pyridinium-DMAS-ceramide and $C_6$-NBD-ceramide images were collected by excitation at 488 nm and emission at 505 nm with a long-path emission filter.

Analysis of ceramides by mass spectroscopy (MS). Accumulated ceramides in mitochondria were analyzed by MS using normal-phase, high-performance liquid chromatography (HPLC) coupled to atmospheric pressure chemical ionization. Separations were performed using a ThermoFinnigan (Foster City, Calif.) LCQ ion trap mass spectrometer.

Statistical analysis. Standard curve and the data for cytochrome C release were computed by generation of a four-parameters logistic curve-fit. The values for ceramide accumulation and cytochrome C release were expressed as the mean+standard error of the mean. Difference between data were analyzed for significance by performing a Student's t-test. The results were considered significant at $p<0.05$.

9.2. Results $C_6$ pyridinium ceramide accumulates in intact cell mitochondria in an energy dependent manner.

To determine whether whole cells will accumulate exogenous pyridiniunceramides in the mitochondrial matrix, we used a fluorescent analog of $C_6$ pyridiniun ceramide, $C_6$ pyridinium-DMAS-ceramide. Both $C_6$ pyridinium-DMAS-ceramide- and TMRM treated cells demonstrated a similar punctate pattern of staining, characteristic of mitochondria. Thus, $C_6$ pyridinium-DMAS-ceramide accumulates selectively in mitochondria in living cells. Subsequent addition of uncoupler FCCP in combination with inhibitors of the respiratory chain and ATPase (antimycin A and oligomycin, respectively) resulted in diffuse staining of the cytoplasm for both fluorophores, indicating that mitochondrial accumulation of $C_6$ pyridinium-DMAS-ceramide in intact cells is indeed energy dependent. In the presence of uncouplers, the diffuse staining of $C_6$ pyridinium-DMAS-ceramide probably reflects equilibration of this molecule in cell membranes without specific concentration in any one compartment.

In contrast to $C_6$ pyridinium-DMAS-ceramide, cells treated with a fluorescent analog of neutral $C_6$ ceramide, namely $C_6$-NBD-ceramide, developed prominent fluorescence in a perinuclear region whereas mitochondrial staining was minimal. These results are consistent with several previous studies that have identified this compartment as the Golgi apparatus, and indeed $C_6$-NBD-ceramide has been forwarded as a specific marker of this compartment. Also, in agreement with previous observations that accumulation of $C_6$-NBD-ceramide in the Golgi apparatus is energy independent demonstrates that uncouplers of oxidative phosphorylation do not affect staining of the perinuclear compartment by C-6-NBD-ceramide. Taken together, these experiments provide evidence that the exogenously added pyridinium ceramide localizes preferentially to mitochondria, and its mitochondrial accumulation in situ is energy dependent.

To demonstrate definitively that $C_6$ pyridinium ceramide preferentially accumulates in mitochondria, Hep G2 cells were treated with equal concentrations of $C_6$ ceramide and $C_6$ pyridinium ceramide (3 µM) for 30 min, mitochondria were then isolated, and ceramide values were determined by MS. The amount of $C_6$ pyridinium ceramide in mitochondria was approximately 7-fold higher compared to the amount of $C_6$ ceramide (985 and 142 pmol/mg protein, respectively). $C_6$ pyridinium ceramide is a potent effector of cell viability. Next C6 pyridinium ceramide was tested to see it is a more potent cell killing agent compared to its uncharged analog. Indeed, $C_6$ pyridinium ceramide readily induced killing of hepatocarcinoma Hep G2 cells (IC50 of about 8 µM) (FIG. 15A, trace 2), while electroneutral $C_6$ ceramide was much less effective in the same range of concentrations (IC50 of about 31 µM; FIG. 15A, trace 1). The effect of $C_6$ pyridinium ceramide is not unique for Hep G2 cells. MCF7 breast cancer cells also respond to this compound (FIG. 15B). MCF7 cells appear to be more sensitive to $C_6$-ceramide than Hep G2 cells (IC50 of about 16 µM), and demonstrate considerable increase in sensitivity to $C_6$ pyridinium ceramide (IC50 of about 2 µM).

Accumulation of $C_6$ pyridinium ceramide in isolated rat liver mitochondria isenergy dependent. Next it was determined if the accumulation of $C_6$ pyridinium ceramide by isolated mitochondria was energy dependent. Addition of $C_6$ pyridinium ceramide (10 µM) to mitochondria resulted in 95% association with mitochondria (FIG. 16). Dissipation of mitochondrial $\Delta\Psi$ by simultaneous addition of the complex III inhibitor antimycin and the protonophore FCCP suppressed accumulation of $C_6$ pyridinium ceramide by 66.8% (FIG. 16). The difference in the amount of ceramide bound in the absence and in the presence of uncouplers of oxidative phosphorylation provides the amount of ceramide accumulated by mitochondria in an energy dependent manner whereas the component resistant to uncouplers indicates the ceramide that maybe partitioned into the lipid phase of mitochondrial membranes or associated with non specific binding sites. Calculating the approximate mitochondrial matrix volume as 1.6 µl/mg protein and $\Delta\Psi$-dependent uptake of pyridinium ceramide as 6.28 nmol/mg protein, the concentration of pyridinium ceramide in the matrix space can reach 3.9 mM. On the other hand addition of uncharged $C_6$ ceramide (10 µM) also resulted in its considerable (79.3%) association with mitochondria. The striking difference between association of positively charged $C_6$ pyridinium and electroneutral $C_6$ ceramides is that association of the latter is insensitive to dissipation of $\Delta\Psi$. Thus, association of $C_6$ ceramide with mitochondria is exclusively related to its partitioning into the lipid phase of mitochondria and/or its association with nonspecific mitochondrial binding sites. Therefore, $C_6$ ceramide is evenly redistributed between the lipid phase of the inner and outer membranes with equal concentration of free ceramide in the intermembrane space and the matrix. In contrast, $C_6$ pyridinium ceramide is highly enriched in the inner membrane of energized mitochondria and its free concentration in the matrix space is considerably elevated compared to that of the intermembrane space.

$C_6$ pyridinium ceramide is a potent and specific inducer of the inner mitochondrial membrane permeabilization. The results shown above suggest that $C_6$ pyridinium ceramide, because of its greater accumulation in the mitochondrial matrix, should affect mitochondrial function more potently than neutral ceramides. To this end, we compared the effects of $C_6$ pyridinium ceramide and its neutral derivative on permeability of the inner mitochondrial membrane for low molecular weight solutes. Respiring liver mitochondria which contain about 10-15 nmol of endogenous Ca2+/mg protein maintained accumulated TPP+, an index of $\Delta\Psi$, for more then 30 min. (FIG. 17A, trace 1). Only slight decreases in the absorbance of the mitochondrial suspension, indicative of swelling, was observed under these conditions (FIG. 17B, trace 1), consistent with previous results on isolated mitochondria. The addition of 40 µM $C_6$ pyridinium ceramide induced a biphasic release of accumulated TPP+ (FIG. 17A, trace 2). The initial partial release of TPP+ was accomplished within 4 min and was followed by a slower phase of total TPP+ release that reflects complete dissipation of $\Delta\Psi$. This later phase was accompanied by rapid decrease in absorbance which indicates stimulation of large-amplitude swelling caused by increased permeability of the inner membrane to the components of the incubation medium (FIG. 17B, trace 2). Indeed, the effects of $C_6$ pyridinium ceramide are very similar to those of the pore-forming peptide alamethicin (ALA) whose addition to the mitochondrial suspension produced essentially the same light-scattering response as $C_6$ pyridinium ceramide (FIG. 17B, trace 3), suggesting that this ceramide enhances pore formation.

Importantly, examination of mitochondrial ultrastructure by electron microscopy before and 30 min after the addition of $C_6$ pyridinium ceramide revealed a typical picture of large-amplitude mitochondrial swelling whereas in the absence of $C_6$ pyridinium ceramide mitochondria remained in the aggregated configuration characterized by a shrunken matrix space and large intracristal space. Incubation of mitochondria with $C_6$ pyridinium ceramide resulted in an extensive increase of matrix volume and unfolded cristae, characteristic of colloido-osmotic swelling. The inner membrane remained apparently intact, whereas the outer membrane was mostly ruptured and detached from the inner membrane. Thus, the above results show that $C_6$ pyridinium ceramide exerts significant effects on isolated mitochondria which is characterized by a relatively specific increase in permeability of the inner membrane. In contrast to $C_6$ pyridinium ceramide, which induced dissipation of $\Delta\Psi$ (FIG. 17A, trace 2) as well as mitochondrial swelling with an IC50 of about 27.5 μM (FIG. 17C, trace 1), neutral C6 ceramide failed to induce dissipation of $\Delta\Psi$ (FIG. 17A, trace 3) or mitochondrial permeabilization at concentrations up to 60 μM (FIG. 17, traces B3 and $C_2$).

To determine the effect of the pyridinium moiety on mitochondrial permeabilization, we evaluated the effect of a short chain $C_2$ pyridinium ceramide. FIG. 16 shows that employed at the same concentration as $C_6$ pyridinium ceramide (40 μM), $C_2$ pyridinium ceramide caused only minor changes in the magnitude of mitochondrial swelling and the value of $\Delta\Psi$ compared to control (traces A4 and B4). Even employed at 60 μM (FIG. 23A, trace 2; binding 29.8±nmol/mg protein at 4 min), $C_2$ pyridinium ceramide failed to induce the same degree of swelling that was observed with 30 μM of $C_6$ ceramide (FIGS. 24A & B, trace 2 binding 5±0.8 nmol/mg protein at 4 min). These results indicate that the potency of ceramide to induce mitochondrial permeabilization increases with the introduction of a positive charge into the molecule and with the elongation of the alkyl moiety.

Figure 23B:
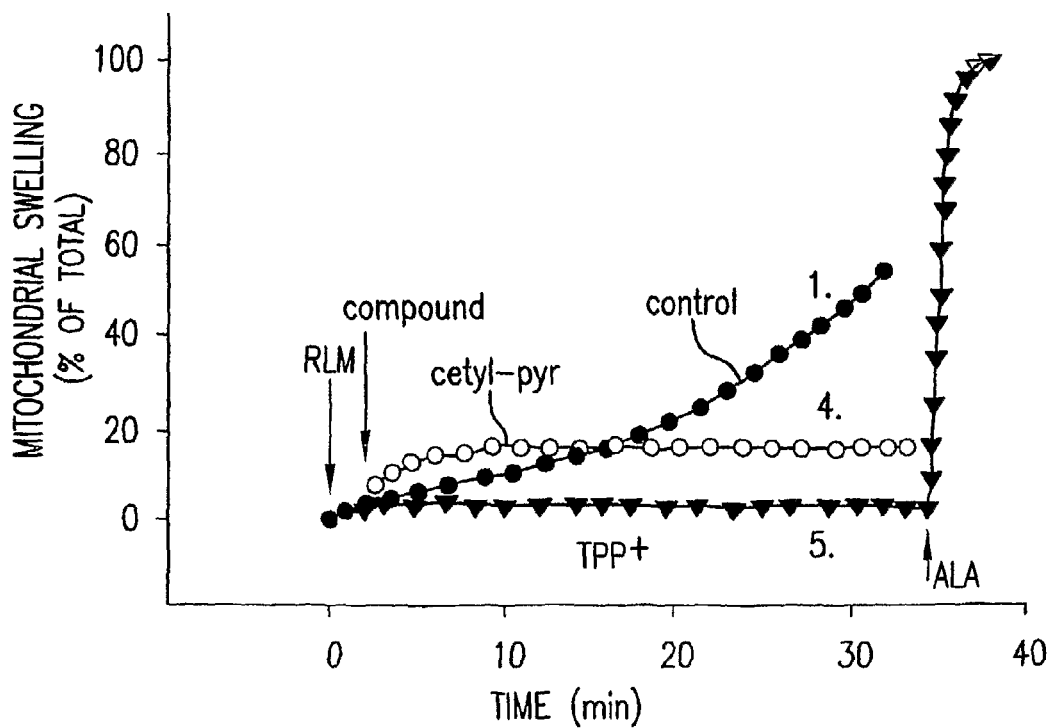

As for cetyl pyridinium, when used at 60 μM, provides only moderate mitochondrial swelling (FIG. 23B, trace 4). In line with this notion, two other hydrophobic cations, namely TPP+ and TMRM, that readily accumulate in mitochondrial matrix driven by $\Delta\psi$ (negative inside), fail to induce large-amplitude swelling even at concentrations twice as much as $C_6$ pyridinium ceramide (TPP+, TMRM-FIGS. 23A & B, traces 3 and 5, concentration 60 μM, binding 50±2.6 nmol/mg protein at 4 min; $C_6$ pyridinium ceramide—FIG. 24A, trace 2, concentration 30 μM, binding 5±0.8 nmol/mg protein at 4 min). To the contrary, inhibition of the basal swelling rate is observed.

Figure 24A:
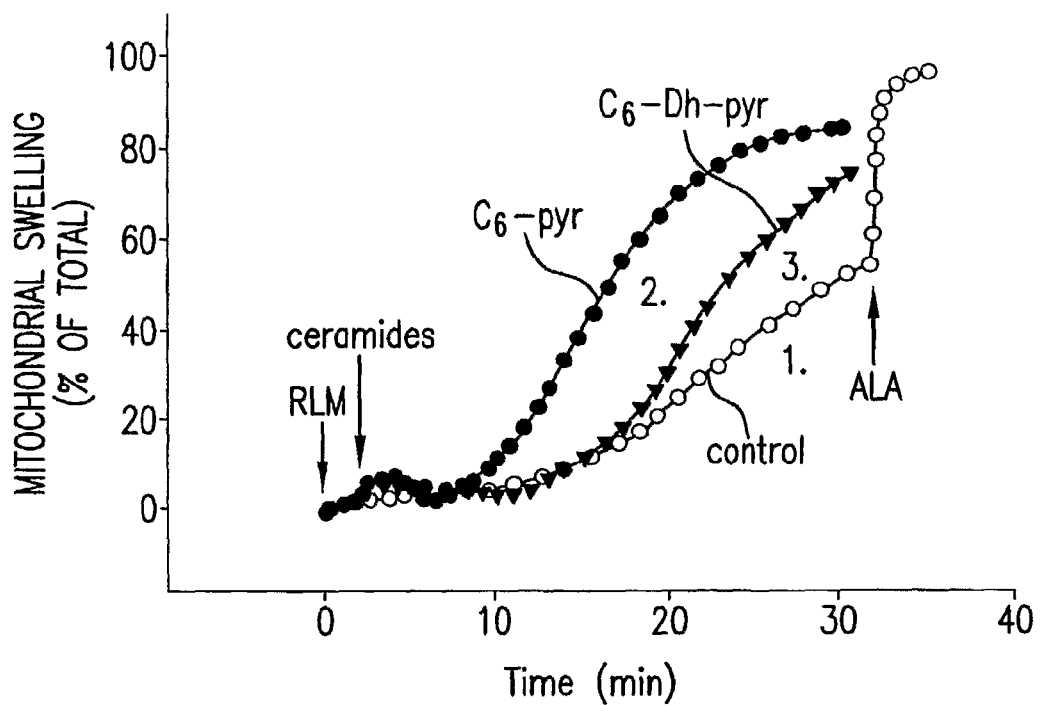
Figure 24B:
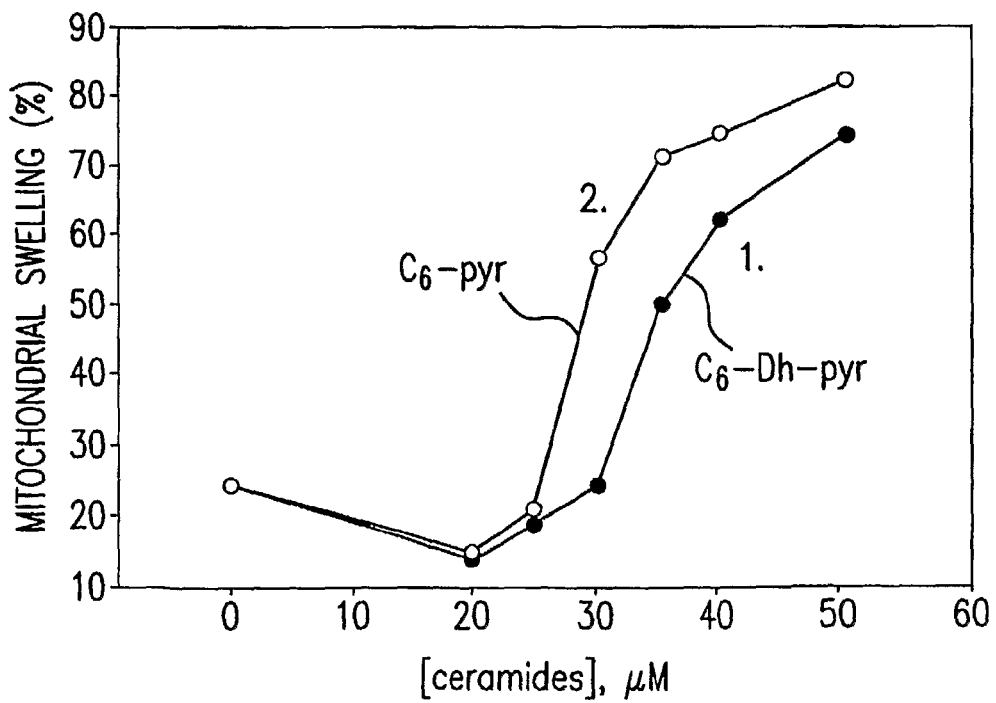

To further confirm that the effect of $C_6$-pyridinium ceramide is specific with respect to the structure of this molecule we investigated the permeabilizing properties of its structural analog, viz. $C_6$-pyridinium dihydroceramide, which differs only by the lack of a 4,5-trans double bond in the sphingoid backbone. FIG. 24A shows a three fold increase in the lag period of the induction of mitochondrial swelling in the presence of $C_6$-pyridinium dihydroceramide (trace 3; concentration of 30 μM, binding of 9.8±0.7 nmol/mg of protein at 4 min) compared with $C_6$-pyridinium-ceramide (trace 2; concentration of 30 μM, binding of 5±0.8 nmol/mg of protein at 4 min). Moreover, the dose-response curves (FIG. 24B) demonstrate that increases in the different ceramide concentrations shortens the lag periods of $C_6$-pyridinium- and $C_6$-pyridinium dihydroceramide-induced swelling. These data indicate that the unsaturated pyridinium ceramide analogue is somewhat more effective than the pyridinium dihydroceramide analogue.

Overall, these results indicate that $C_6$ pyridinium ceramide can be considered as an analog of the uncharged ceramide and its action does not reflect non-specific mitochondrial perturbation that could be expected with any cationic hydrophobic compound.

Inhibitors of mitochondrial ion transporters CSA and DCCD suppress $C_6$ pyridinium ceramide-induced mitochondrial permeability increase. The permeability increase observed in the presence $C_6$ pyridinium ceramide could arise from the formation of lipid channels as a result of perturbation of the hydrophobic portion of the inner membrane, or alternatively, $C_6$ pyridinium ceramide could regulate specific transport pathways resulting in equilibration of small molecules and ions across the inner membrane, large-amplitude swelling, and dissipation of $\Delta\Psi$. To discriminate between these two possibilities and address the mechanism by which $C_6$ pyridinium ceramide induces mitochondrial permeability, we investigated the effects of the potent PTP inhibitor CSA and the non-selective inhibitor of mitochondrial ion porters DCCD on $C_6$ pyridinium ceramide-induced permeabilization of the inner membrane.

As shown in FIG. 18, CSA substantially (60%) suppressed and delayed the pyridinium ceramide-induced decreases in $\Delta\Psi$ and large-amplitude swelling (traces A3 and B3, respectively). Chelation of Ca2+, the PTP activator, by EDTA, as well as, the use of another PTP inhibitor, bongkrekic acid, resulted in a similar degree of suppression of ceramide-induced mitochondrial alterations. The carboxylic group modifier dicyclohexilcarbodiimide (DCCD) although not as specific as CSA, is also known as an inhibitor of PTP opening. DCCD also suppressed the permeability increase induced by $C_6$ pyridinium ceramide by 90% (FIG. 24, trace A2). This inhibition reached a maximum at a DCCD concentration of about 40 nmol/mg protein. In contrast to the slow phase of $\Delta\Psi$ discharge, the initial fast phase was insensitive to CSA (FIG. 18; traces A1, A3) and was accompanied by the shrinkage of mitochondria rather than by large-amplitude swelling (FIG. 18; traces B1, B3). This rapid discharge in $\Delta\Psi$ could be explained by ceramide-induced suppression of respiratory chain activity that could occur directly as described in, or indirectly as a result of cytochrome C release from the intermembrane space. However, addition of 10 μM cytochrome C (an amount exceeding that for maximum activation of respiratory chain activity) to the incubation medium did not modify the mitochondrial response to $C_6$ pyridinium ceramide. Moreover, measurement of oxygen consumption of the mitochondrial suspension showed nearly maximum acceleration of respiration within the first minutes after $C_6$ pyridinium ceramide addition (FIG. 19, panel B). These data strongly suggest activation of an electrogenic H+ leak across the inner membrane as a cause of decreased $\Delta\Psi$. Similar to PTP opening described above, electrogenic ion fluxes arising in the first minutes after $C_6$ pyridinium ceramide addition are sensitive to DCCD as can be seen from suppression of acceleration of oxygen consumption (FIG. 19 trace A2, panel B). Therefore, electrogenic H+ flux activated by ceramide is mediated by some specific porter, not by disturbance of the lipid phase of the inner membrane.

The possible mitochondrial sites of ceramide action was investigated. The results shown earlier indicate that uncoupling of mitochondria correlates with the loss of $C_6$ pyridinium ceramide from the mitochondrial matrix. Under these same conditions, addition of FCCP suppressed the swelling phase of the mitochondrial response to ceramide (FIG. 18B, trace 4). These observations, therefore, indicate that the sites of action of $C_6$ pyridinium ceramide to activate PTP is localized in the inner membrane or matrix space of the mitochondria. $C_6$ pyridinium ceramide induces cytochrome C release in an energy dependent manner. Studies aimed at elucidating the mechanisms of ceramide-induced cell death showed that ceramide acts at least in part by inducing the release of cytochrome C from mitochondria. Formation by ceramides of specific pores for cytochrome C and molecules of up to 60 kDa in the outer mitochondrial membrane was suggested as a preferential mechanism for cytochrome C release. Yet, induction by ceramides of the classical permeability transition of mitochondria which is accompanied by the their osmotic swelling, rupture of the outer membrane, and, as a result, by release of cytochrome C from the intermembrane space was proposed as an alternative model. To determine whether $C_6$ pyridinium ceramide is able to release cytochrome C from mitochondria and to address the mechanism by which this occurs, experiments were conducted to evaluate its effect on cytochrome C release at conditions that result in mitochondrial swelling vs conditions when $C_6$ pyridinium ceramide large-amplitude swelling was suppressed by FCCP (FIG. 18B, trace 4).

As shown in FIG. 20B, incubation of mitochondria with $C_6$ pyridinium ceramide results in progressive large amplitude swelling. After 20 minutes of incubation with $C_6$ pyridinium ceramide, about 40% of cytochrome C is released from mitochondria (FIG. 20A). When $C_6$ pyridinium ceramide-induced mitochondrial swelling was suppressed by the addition of FCCP plus antimycin A (FIG. 20B), approximately a 3-fold decrease in cytochrome C release was observed (FIG. 20A), which was comparable to the control value. $C_6$ ceramide exerted no effect on cytochrome C release both in the absence and in the presence of uncouplers of oxidative phosphorylation as compared to the control (FIG. 20A). Under the same conditions $C_6$ ceramide failed to increase large amplitude swelling (FIG. 20B). Addition of pore forming peptide alamethicin provided 100% response in the parameters of interest that can be observed under conditions employed. These results indicate that the preferential mechanism of cytochrome C release by $C_6$ pyridinium ceramide is permeabilization of the inner membrane as an initial step, with subsequent swelling and rupture of the outer membrane.

9.3. Discussion

In this example, the data show that positively charged $C_6$ pyridinium ceramide readily permeates the lipid bilayer and specifically targets the inner mitochondrial membrane and matrix space. Because of the large mitochondrial inner membrane potential (negative inside), these molecules accumulate inside isolated mitochondria and within mitochondria in cultured cells. Moreover, accumulation of these molecules is reversible and can be prevented by discharge of $\Delta\Psi$. In addition the accumulation of these ceramides in the mitochondrial matrix space increases permeability of mitochondrial membranes by activating putative ion porters of the inner mitochondrial membrane-permeability transistion pore "PTP", and the electrogenic H+ channel.

The conclusion is supported by a number of observations. First, $C_6$ pyridinium ceramide induced a light-scattering response (indicative of change in mitochondrial ultrastructure) that was similar in magnitude to that observed under conventional Ca2+ treatment, or in the presence of the pore forming peptide alamethicin (FIG. 17B, trace 3). This suggests that the light-scattering response observed in the presence of $C_6$ pyridinium ceramide reflects mitochondrial large-amplitude swelling which is colloido-osmotic in nature as opposed to non specific amphiphilic compound-mediated solubilization of mitochondrial membranes. Additional support for the relative specificity of the permeability defect created by $C_6$ pyridinium ceramide in the inner membrane comes from examination of mitochondrial ultrastructure by electron microscopy. Comparison of mitochondrial ultrastructure before and after ceramide treatment revealed all the features of classical permeability transition: increased mitochondrial volume, unfolded cristae, ruptured outer membranes, and apparent intactness of the inner membrane. A second observation in support of PTP opening came from the use of the PTP inhibitors (CSA and DCCD). Both these inhibitors suppressed or delayed mitochondrial large-amplitude swelling and discharge of $\Delta\Psi$ by 60% and 90%, respectively. This indicates that the permeability transition observed in the presence of $C_6$ pyridinium ceramide is likely attributed to the activation of protein porters of the inner mitochondrial membrane, rather than the formation of lipid channels created by segregation of ceramides in a special domain as was proposed earlier for the outer membrane.

The data provided herein also indicate that $C_6$ pyridinium ceramide activates additional ion transport pathways distinct from PTP. Indeed, the shrinkage phase observed during the first minutes after ceramide addition and accompanying discharge of $\Delta\Psi$ indicates selective loss of cations from the mitochondrial matrix and an activation of electrogenic ion fluxes, without a simultaneous increase in permeability to sucrose, which is usually observed in classical models of permeability transition. These relatively specific cation fluxes reflect operation of PTP in a low conductance (impermeable to sucrose) state.

The best explanation for the initial mitochondrial response to ceramide treatment is the simultaneous activation of selective electrogenic K+ and H+ fluxes. K+ is known to be the most abundant ion in the mitochondrial matrix, playing a major role in regulation of mitochondrial volume. In this model, increased H+ permeability across the inner membrane dissipates $\Delta\Psi$, which allows K+ to be lost from the matrix according to its electrochemical potential, that, in turn, results in mitochondrial shrinkage. The observation disclosed herein that suppression of $C_6$ pyridinium ceramide-induced mitochondrial swelling by FCCP also resulted in suppression of cytochrome C release indicates that mitochondrial swelling is a prerequisite for the outer membrane permeability alterations. As for neutral $C_6$ ceramide, even at 40 nmol/mg of protein, a concentration twice that used by Siskind et al., (2002) *J Biol Chem* 277, 26796-26803, this ceramide failed to induce considerable cytochrome C release as compared to the control. It has been reported that the loss by mitochondria of cytochrome C under the effect of C2 ceramide is highly dependent on the redox state of this protein, with the oxidized state favoring the release. However there is no substantial release (as compared to the control) of cytochrome C by $C_6$ and $C_6$ pyridinium ceramides under conditions in which the respiratory chain downstream of complex III is completely oxidized by the presence of oxidative phosphorylation uncouplers. On the contrary, suppression of cytochrome C release was observed. This provides evidence that, in these examples, the limiting step in cytochrome C release is not a redox state value, but the formation of a permeability pathway for cytochrome C across the outer membrane.

Notably, previous studies suggested that either Ca2+ in the range of 100-150 µM or Bax were required in addition to ceramide to cause permeability change in the outer and inner membranes. In contrast, in our experiments, $C_6$ pyridinium ceramide by itself induced permeabilization of the mitochondria or the requirement for Ca2+ was extremely low (estimated endogenous Ca2+ is about 10 nmol/mg protein). This effectiveness of $C_6$ pyridinium ceramide is explained by its greater accumulation in the mitochondrial matrix. In addition the low potency of $C_2$ pyridinium compared to $C_6$ pyridinium ceramide likely excludes the possibility of a nonspecific effect of the pyridinium group on mitochondrial membranes and underscores the importance of the length of N-fatty acyl-sphingosine moiety in mitochondrial permeabilization. The results obtained by in vitro experiments indicate that mitochondria are the primary targets for $C_6$ pyridinium ceramide in cell death, and that the mechanism of cell death involves disruption of mitochondrial function. Indeed, with confocal microscopy, it was observed that preferential accumulation of $C_6$ pyridinium ceramide in the mitochondrial compartment, and the relative potency of $C_6$ pyridinium ceramide to induce permeabilization of isolated mitochondria corresponds well with its ability to kill cells. One of the factors that should be kept in mind, while considering the effect of ceramide treatment on cell viability is the concentration of ceramide in the vicinity of its target. Electroneutral ceramides redistribute preferentially in the Golgi apparatus, which decreases their effective concentration in mitochondria. In contrast, positively charged ceramides are specifically concentrated within their immediate target—the inner mitochondrial membrane, whereas redistribution to other compartments is relatively small. This specific redistribution of positively charged ceramide correlates well with its higher potency in cell killing compared to its neutral counterpart. In such a way, the data support the utility of the invention which is based on a mechanism by which ceramides induce cell killing, i.e., permeabilization of the inner mitochondrial membrane with subsequent release of cytochrome C. With respect to the mechanism of pyridinium ceramide induced cell death it should be noticed that permeability alterations of the inner membrane and subsequent release of cytochrome C observed in isolated mitochondria under effect of pyridinium ceramide are compatible with both apoptotic and necrotic pathways. Also, MTT assay of cell viability based on measurement of mitochondrial dehydrogenase activities reflects both necrotic or late apoptotic cell death.

Irrespective of the mechanism of cell death, the data suggest that positively charged ceramides could be effective for selective killing of cancer cells. The basis for this selectivity is a substantial difference in $\Delta\Psi$ between normal and tumor cells. The difference in $\Delta\Psi$ between carcinoma and control epithelial cells can be greater than 60 mV higher in carcinoma cells, a difference that may allow for 10 times greater accumulation of positively charged ceramides in tumor mitochondria. Thus, future studies are aimed at better understanding the nature of molecular targets for ceramide in mitochondria and on optimization of the molecular structure of positively charged ceramides to increase their accumulation in the mitochondrial matrix. Overall, the results indicate the presence of specific ceramide targets in the mitochondrial matrix, occupation of which alters permeability of the inner and outer membranes; these findings confirm the therapeutic utility of positively charged CCPS analogs of the invention.

10. EXAMPLE

Xenograft Model of Human Head ND Neck Squamous Cell Carcinoma

The following example demonstrates the therapeutic roles of a novel cationic ceramide analogue L-threo-$C_6$-Pyridinium-Ceramide-bromide (L-t-$C_6$-Pyr-Cer), alone or in combination with gemcitabine (GMZ) in the inhibition of growth and/or progression of human head and neck squamous cell carcinomas (HNSCCs) in vitro and in vivo. L-t-$C_6$-Pyr-Cer, which exhibits high solubility and bio-availability, inhibited the growth of various HNSCC cell lines. In addition to its growth inhibitory function as a single agent, the synergistic interaction of L-t-$C_6$-Pyr-Cer with GMZ, a chemotherapeutic agent used in HNSCC, was determined using quantitative isobologram studies. Then, the in vivo therapeutic efficacy of this ceramide, alone or in combination with GMZ, for the treatment of mice harboring UM-SCC-22A xenografts was assessed. Importantly, the results demonstrate that treatment with L-t-$C_6$-Pyr-Cer in combination with GMZ significantly diminished the growth of HNSCC tumors in vivo. The combination of L-t-$C_6$-Pyr-Cer and GMZ resulted in a significant inhibition of telomerase activity, and decrease in telomeric length in vivo.

10.1. Materials and Methods

Ceramides and chemotherapeutic agents. The novel water soluble cationic L-t-$C_6$-Pyr-Cer was synthesized by the Synthetic Lipidomics Core at the Department of Biochemistry and Molecular Biology, Medical University of South Carolina (MUSC). Cetyl-pyridinium bromide (CPB) monohydrate was purchased from Aldrich. Gemcitabine, 5-FU, cis-platinum, and doxorubicin were obtained from the pharmacy at the Hollings Cancer Center, MUSC.

Cell lines and culture conditions. Human head and neck cancer cell lines UM-SCC-1 (retromolar trigone/floor of the mouth), UM-SCC-14A (SCC of anterior floor of the mouth), and UM-SCC-22A (SCC of hypopharynx) cells were obtained. Cells were grown in DMEM containing 10% FCS and 1% penicillin/streptomycin at 37° C. in 5% $CO_2$. Possible mycoplasma contaminations were monitored regularly by MycoAlert mycoplasma detection kit (Cambrex, Me.), and treated with Plasmocin (InvivoGen; San Diego, Calif.).

Subcellular fractionation, and the analysis of ceramide subspecies by mass spectroscopy (MS). The sub-cellular accumulation of L-t-$C_6$-Pyr-Cer was analyzed by utilizing normal phase high performance liquid chromatography and mass spectroscopy (LC/MS). The subcellular fractionations were done using differential centrifugation as described previously (Novgorodov, et al. *J Biol Chem* 2005; 280:16096-16105). In short, cells were incubated in a buffer containing 300 mM sucrose, 10 mM Hepes (pH 7.4), 1 mM EDTA and 0.5 mM PMSF for 30 minutes on ice. The cells were then passed through 25-gauge needle for 5 strokes, and centrifuged at 1,000×g for 10 mM, 10,000×g for 10 min, and 100,000×g for 60 min at 4° C., for collection of the nuclei-, mitochondria-enriched fractions, and microsomes, respectively. Each fraction was subjected to Western blotting with voltage-dependent anion channel (porin 31HL) and lamin B antibodies to confirm the purity of mitochondrial and nuclear fractions.

MTT cell survival assay and isobologram studies. The concentrations of agents that inhibited cell growth by 50% ($IC_{50}$) were determined from cell survival plots obtained by MTT assays. To determine the synergistic interaction between L-t-$C_6$-Pyr-Cer and GMZ, isobologram plots Id. were constructed using $IC_{50}$ values of the two agents alone or in combination obtained from MTT assays. A straight line joining points on x- and y-axes represent the $IC_{50}$ concentrations of GMZ and L-t-$C_6$-Pyr-Cer alone, and the points representing the $IC_{50}$ concentrations of the combination of the two agents are represented as scatter plots on the same graphs. In general, the points that fall within the left of the straight line indicate synergism. The experiments were performed as triplicates in at least 3 independent experiments. Error bars represent standard deviations.

Analysis of cell cycle profiles. The effects of L-t-$C_6$-Pyr-Cer, alone or in combination with GMZ, on the cell cycle profiles of UM-SCC-22A cells at various time points were analyzed in the presence of DNase-free RNase and propidium iodine (PI) by flow cytometry. Untreated cells were used as controls.

Animal studies. The use of animals for determining the maximum tolerated dose (MTD), pharmacokinetics, and therapeutic efficacy of L-t-$C_6$-Pyr-Cer, alone or in combination with GMZ, were performed according to protocols which were reviewed and approved by the Institutional Animal Care and Use Committee at the Medical University of South Carolina. The maximum tolerated dose (MTD) of L-t-$C_6$-Pyr-Cer was determined by dose escalation studies. In short, 7-week-old BALB/c mice were treated with increasing concentrations of the compound for various time intervals. Possible toxicity of the compound to the vital organs of the animals was analyzed by both gross examination, and histopathology. The accumulation of the compound in vital organs and in the serum was also determined by LC/MS as described previously Koybasi S et al. J Biol Chem 2004; 279:44311-44319). The blood counts, and enzyme assays in the serum of the animals were performed by Anilytics, Inc. (Gaithersburg, Md.).

The role of L-t-$C_6$-Pyr-Cer, alone or in combination, in the inhibition of tumor growth in vivo was examined as follows: UM-SCC-22A cell xenografts were obtained by subcutaneous injection of $4 \times 10^6$ cells in the posterior flank of the female SCID mice. After tumors were grown to about 200-400 mm³ (about two weeks after implantation), the mice were treated without or with chemotherapeutic agents with intraperitoneal (IP) injection (alone or in combination) at half of their maximum tolerated doses (MTD) every 4 days for 20 days. Tumor volumes and the weights of the animals were measured before each treatment, and tumor sizes were measured at the end of the study. The endpoint was tumor rate of growth and/or tumor volume, which was calculated using the formula: length×width²×0.52. Each experiment included at least 6 mice (which harbored two SCC tumors in flanks) per each treatment, and experiments were done at least in two independent trials. The concentrations of the drugs used in this study are as follows: L-t-$C_6$-Pyr-Cer (40 mg/kg), GMZ (40 mg/kg), DOX (1 mg/kg), 5-FU (25 mg/kg), and CP (9 mg/kg). The known MTDs of these compounds are 80, 120, 2, 25, and 9 mg/kg for L-t-$C_6$-Pyr-Cer, GMZ, DOX, 5-FU and CP, respectively (Veerman, et al. Cancer Chemother Pharmacol 1996; 38:335-342; Inaba. Cancer 1989; 64:1577-1582; Makino, et al. Cancer Chemther Pharmacol 2001; 48:370-374; van Moorsel et al., Eur J Cancer 1999; 35:808-814).

Determination of telomerase activity, hTERT mRNA and protein levels in tumor tissues. Telomerase activity in tissues was measured by the PCR-based telomere repeat amplification protocol (TRAP) using TRAPeze kit (Invitrogen) which includes a 36-bp internal control to allow quantification of activity. The intensity of telomere-specific DNA bands, measured using Quantity One (BioRad) software, were normalized to the intensity of internal control bands for each sample on polyacrylamide gels for quantification. The mRNA levels of the catalytic subunit of telomerase, hTERT (human telomerase reverse transcriptase) was measured after extraction of total RNA from tumor tissues extracted from the control or treated animals, and normalized to mRNA levels of beta-actin by Applied Biosystems 7300 real-time quantitative PCR (Q-PCR) system using TaqMan primer and probe sets for hTERT and beta-actin (Applied Biosystems). The protein levels of hTERT in these tumor tissue extracts (in CHAPS buffer) were determined by Western blot analysis using anti-hTERT rabbit polyclonal antibody (CalBiochem) at 1:1000 dilution. The specificity of the antibody was confirmed using extracts from telomerase positive and negative extracts in Western blots.

Analysis of telomere length in tumor tissues. The measurement of telomere length was performed in total genomic DNA samples isolated from tumor tissues of the SCID mice using Telomere Restriction Fragment (TRF) Length measurement kit (Roche) by Southern blotting as described in Sundararaj, et al. J Biol Chem 2004; 279:6152-6162.

Statistical analysis. The statistical analysis of studies to determine the efficacy of L-t-$C_6$-Pyr-Cer in combination with GMZ in the inhibition of the growth of HNSCC tumors in vivo was performed using Tukey's Student Range Test and SAS-MIXED procedures. Tukey's Student Range Test controls the over-all Type-I error rate, probability of detecting difference in at least one pair of means below a pre-specified level (5%) for all (multiple) pair-wise comparisons between treatment groups.

In SAS, the MIXED procedure for mixed-model approach is the flagship procedure for fitting linear models with fixed effects (effects of observed explanatory variables to mean response) as well as random-effects (unobservable effects due to random unobservable factors and unobservable within subject effects). SAS-MIXED fits a variety of such models to data and enables to use these fitted models to make statistical inferences about the data. The default fitting method maximizes the restricted likelihood of the data under the assumption that the data are normally distributed, and any missing data are missing at random. This general framework accommodates many common correlated-data methods, including repeated measures analyses.

10.2. Results

The Sub-Cellular Localization of L-t-$C_6$-Pyr-Cer in UM-SCC-22A Cells

Figure 25A:
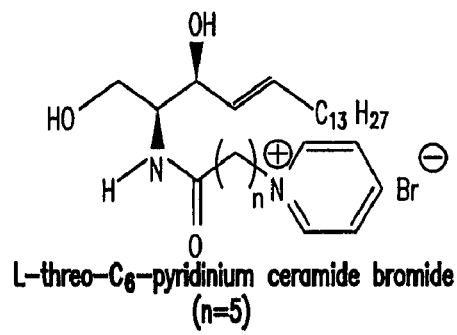
Figure 25B:
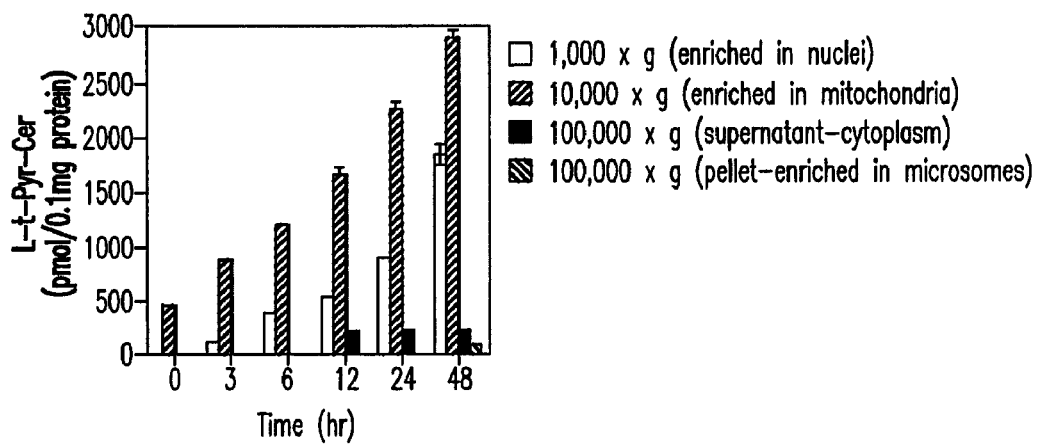

Exogenous short chain ceramides are known to mediate cell cycle arrest, apoptosis or senescence in various cancer cells. However, because of their limited solubility and bioavailability, the water soluble pyridinium-conjugated analogues of ceramides were developed. The chemical structure of the novel cationic ceramide L-t-$C_6$-Pyr-Cer is shown in FIG. 25A. Pyridinium ceramide (Pyr-Cer) analogues were designed to preferentially localize into negatively charged intracellular compartments, especially mitochondria and nucleus. Therefore, the sub-cellular accumulation of L-t-$C_6$-Pyr-Cer in UM-SCC-22A cells was examined using LC/MS after treatment of cells with 1 µM L-t-$C_6$-Pyr-Cer for various time points (1, 3, 6, 12, 24 and 48 hr). The results showed that the compound mainly accumulated in the 10,000×g fraction, which is enriched mainly in mitochondria, as early as 1 hr after treatment, and then it continued to increase to higher levels (1,000-3,000 pmol/0.1 mg protein) in this fraction between 3-48 hr treatment (FIG. 25B). Similarly, L-t-$C_6$-Pyr-Cer was detectable in the 1,000×g fraction, which is enriched in nuclei, within 3 hr, and reached to 250-2,500 pmol/0.1 mg protein levels in this fraction between 6-48 hr (FIG. 25B). The amounts of the compound in the supernatant or the pellet of 100,000×g fractions were either not detectable (at 1-6 hr), or minimal (at 12-48 hr) in these cells (FIG. 25B). The enrichment of mitochondria and nucleus in 10,000×g and 1,000×g fractions, respectively, were confirmed by Western blotting with antibodies that detect the mitochondrial protein porin 31HL, and nuclear lamin B in these fractions. The absence of GAPDH in 10,000×g mitochondria enriched fractions also showed the lack of cytoplasmic contamination. Taken together, these data demonstrate that L-t-$C_6$-Pyr-Cer mainly accumulates in the mitochondria and, to a lesser extent, in the nucleus, within a short-time after exposure, as expected by its chemical composition and design, in UM-SCC-22A cells.

Figure 25C:
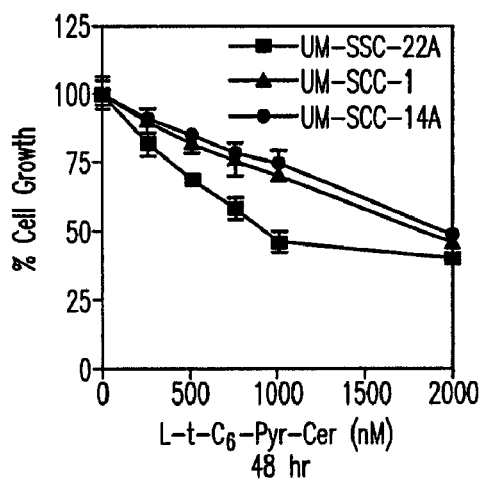

The effects of L-t-$C_6$-Pyr-Cer, alone or in combination with GMZ on the growth of HNSCC cells in vitro. To determine the effects of L-t-$C_6$-Pyr-Cer on growth, various HNSCC cell lines which represent various forms of HNSCC were treated with increasing concentrations of L-t-$C_6$-Pyr-Cer for 48 hr, and its inhibitory concentration 50 (IC50), a concentration that inhibits the growth by 50%, was determined by MTT assays, L-t-$C_6$-Pyr-Cer inhibited the growth of human HNSCC cell lines UM-SCC-22A, UM-SCC-1, and UM-SCC14A cells with similar IC50 concentrations of about 1-2 µM at 48 hr (FIG. 25C). Since UM-SCC-1 cells express wild type p53, whereas UM-SCC-14A cells express mutated p53, their similar IC50 values for L-t-$C_6$-Pyr-Cer show that it regulates cell growth independent of p53 status.

Figure 26A:
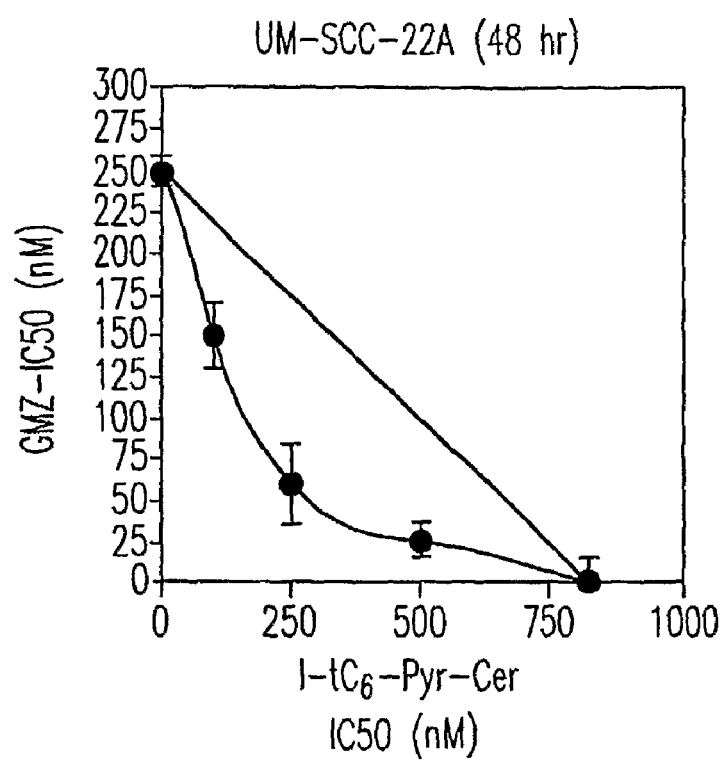
Figure 26B:
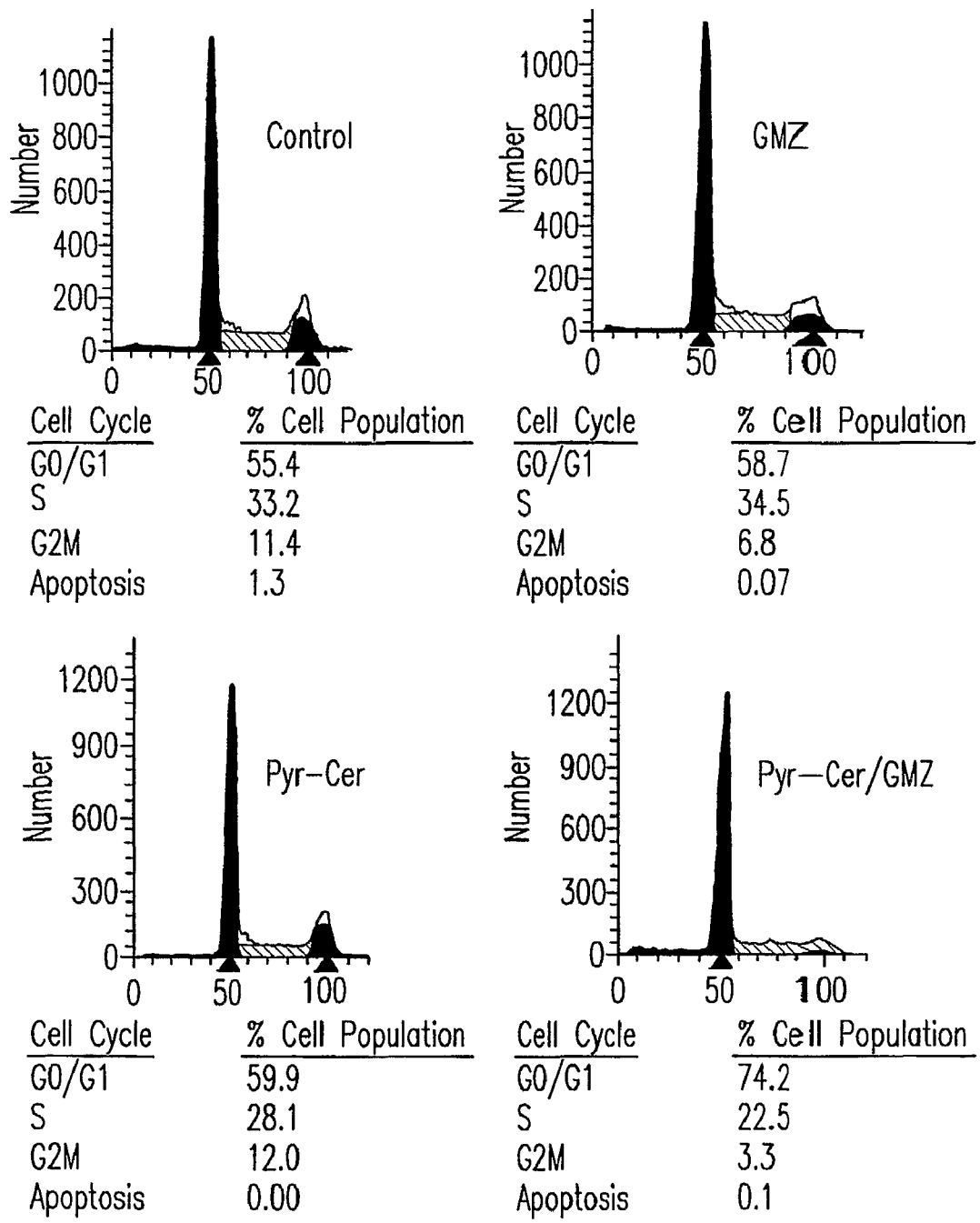

Growth inhibitory effects of L-t-$C_6$-Pyr-Cer in combination with various conventional chemotherapeutic agents were tested. The synergistic interaction between L-t-$C_6$-Pyr-Cer and GMZ in the inhibition of growth of UM-SCC-22A cells was evaluated using quantitative isobologram studies. The data showed that the combination of L-t-$C_6$-Pyr-Cer at its sub-IC50 values (100, 250 and 500 nM) with increasing concentrations of GMZ for 48 hr decreased growth synergistically, as detected by the shift of the $IC_{50}$ values of GMZ in the isobologram to the left of the line plot joining the x and y-axes that represent the $IC_{50}$ of L-t-$C_6$-Pyr-Cer and GMZ, respectively (FIG. 26A). In addition, analysis of cell cycle profiles showed that treatment with L-t-$C_6$-Pyr-Cer in combination with GMZ (at 500 and 50 nM, respectively, for 48 hr) resulted in a cell cycle arrest at G0/G1, and decreased S-phase and G2/M cell population as compared to controls (FIG. 26B). Interestingly, there was no apparent apoptosis in response to this combination treatment in these cells (FIG. 26B).

The inhibition of HNSCC tumor growth by L-t-$C_6$-Pyr-Cer, alone or in combination with GMZ, in vivo. First, in order to evaluate the effects of L-t-$C_6$-Pyr-Cer in the inhibition of growth in vivo, its maximum tolerated dose (MTD) was determined by treatment of BALB/c mice with increasing concentrations of L-t-$C_6$-Pyr-Cer at 10-150 mg/kg for various time points. The data demonstrated that treatment of mice with a single dose of L-t-$C_6$-Pyr-Cer at 120-150 mg/ml resulted in toxicity with extreme abdominal bloating and intestinal malfunction in some animals after about 6 hr of IP injection (FIG. 27A), whereas treatment of animals with 10-80 mg/kg of the compound for 1-4 days did not have any detectable toxicity to the animals (FIG. 27A) as determined by both gross examination of the animals, and histo-pathological examination of the tissue sections of brain, heart, lungs, liver, kidney, intestines, and bone marrow. Thus, the MTD of L-t-$C_6$-Pyr-Cer was determined as 80 mg/kg in mice, which did not cause any detectable toxicity in these animals after either single (FIG. 27A), or multiple cycles (every 4 days for 20 days) of treatment.

Figure 27B:
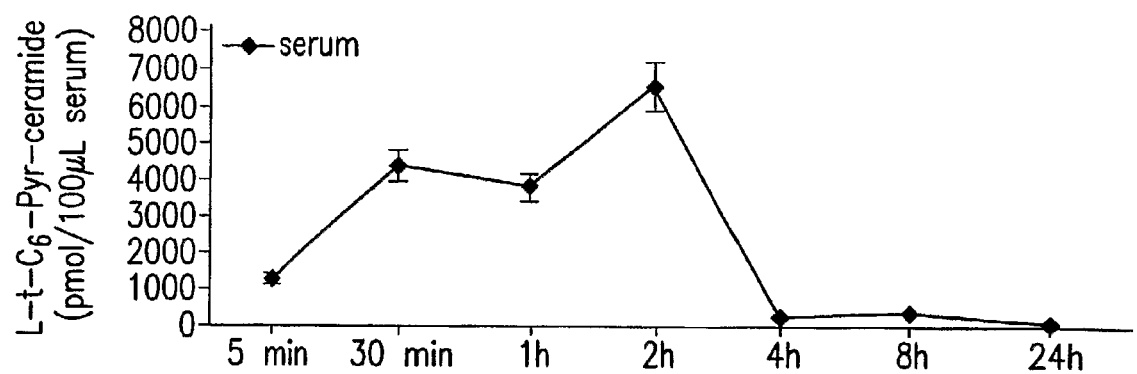

Next, the pharmacokinetic parameters of L-t-$C_6$-Pyr-Cer, such as clearance from the blood, and bioaccumulation in various organs, were examined by LC/MS after IP injections of the compound at 40 mg/ml (half of the MTD that would be used for the in vivo therapeutic studies) for various time points. As shown in FIG. 27B, the serum levels of the compound reached 4,500 to 6,500 pmol/0.1 ml serum between 0.5-2 hr of injection, respectively, and cleared from the serum within 4 hr. The levels of the compound increased slightly first in the intestines after 5 min, and in the liver after 2 hr at about 600 and 500 pmol/mg protein, respectively (FIG. 27C).

Figure 27C:
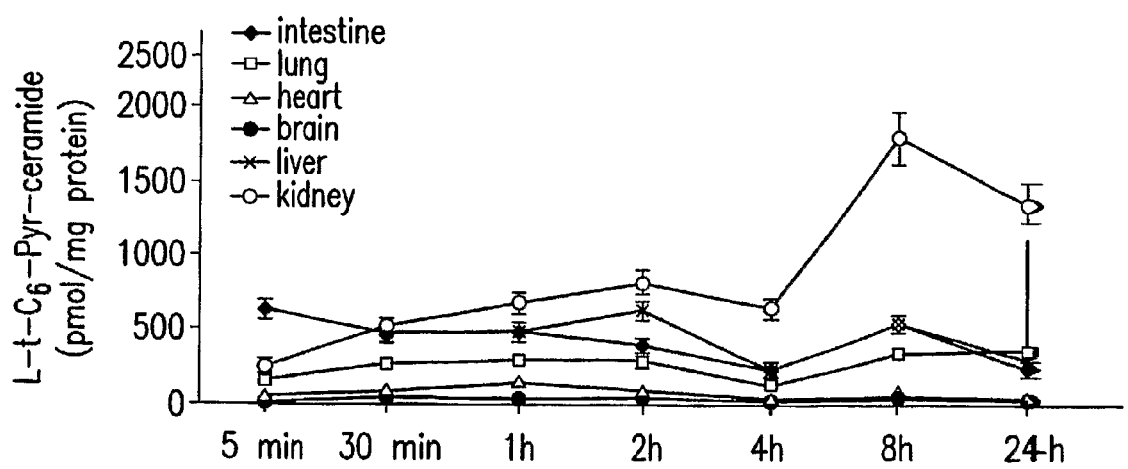

The compound started to accumulate mainly in the kidney between 4-8 hr (FIG. 27C). There was some accumulation in the lungs after 24 hr, and no significant accumulation in the brain or heart (FIG. 27C). These data suggest that L-t-$C_6$-Pyr-Cer goes through systemic delivery within 2-4 hr, and accumulates in the intestines, liver and lungs at moderate levels, and at high levels in the kidneys within 8-24 hr, possibly for excretion. These data showed the main accumulation of other lipophilic pyridinium cations in the kidneys, and excretion in the urine.

To determine the therapeutic efficacy of L-t-$C_6$-Pyr-Cer, alone or in combination with GMZ, HNSCC xenografts in SCID mice were developed by subcutaneous injection of UM-SCC-22A cells to the both sides of the flank. After the tumors were established, the animals were treated with L-t-$C_6$-Pyr-Cer or GMZ, alone or in combination at 40 mg/kg/each (at or below their half of MTDs), every 4 days for 20 days. As FIG. 22A shows, treatment with L-t-$C_6$-Pyr-Cer or GMZ as single agent caused some inhibition of HNSCC tumor growth in vivo as compared to untreated controls, which were not statistically significant (p values were 0.67 and 0.17, respectively). However, the combination of L-t-$C_6$-Pyr-Cer with GMZ almost completely inhibited the tumor growth in a statistically significant manner (p<0.01), and the efficacy of this combination was about 2-fold better than that of 5-FU/CP combination (p<0.05) (FIG. 22A), which is used as a conventional therapy for the treatment of HNSCC in clinic. Importantly, treatment of animals with L-t-$C_6$-Pyr-Cer alone or in combination with GMZ did not cause any significant changes (not more than 5%) in the total body weight of the animals. Interestingly, treatment of SCID mice bearing UM-SCC-22A xenografts with 40 mg/kg cetylpyridinium bromide (without ceramide conjugate) for 4 days was lethal to all animals tested (n=6). Also, combination of L-t-$C_6$-Pyr-Cer (40 mg/kg) with doxorubicin (1 mg/kg) was toxic to the animals (n=6), killing all the animals at day 2-3 of treatment.

To confirm the lack of toxicity in response to L-t-$C_6$-Pyr-Cer/GMZ treatment, tumors and the vital organs were surgically removed after the completion of the study, and H&E staining of the tissue sections was performed. The histopathologic analysis of the tumors confirmed that they were SCC (FIG. 22A, bottom panel), and further analysis of the vital organs of the animals treated with L-t-$C_6$-Pyr-Cer alone or in combination with GMZ showed no detectable toxicity. The blood counts, the levels of enzyme activities, and electrolytes in the serum of the animals after these treatments (about 20 parameters including red blood cell and hemoglobin, blood urea nitrogen, creatinine, Na, Mg, alanine amino transferase and amylase) were also analyzed (FIG. 22C). There were no detectable abnormalities in these levels in response to L-t-$C_6$-Pyr-Cer alone or in combination with GMZ, confirming the lack of overall toxicity.

More importantly, analysis of the levels of L-t-$C_6$-Pyr-Cer in HNSCC tumors removed after the completion of the study by LC/MS, showed that its accumulation in the tumor site was about 2,200 pmol/mg when used as a single agent, whereas its levels in the tumors increased about 40% (up to 3,100 pmol/mg) when combined with GMZ (FIG. 22B). The levels of the compound in the intestines and the liver in the absence of GMZ were about 120 and 100 pmol/mg protein, which increased to 1,000 and 300 pmol/mg protein in the presence of GMZ. Thus, these data demonstrate that the levels of the compound in tumors were about 3-6-fold higher than its levels in intestines or liver of the animals, in the absence or presence of GMZ (FIG. 22B). Interestingly, analysis of the effects of L-t-$C_6$-Pyr-Cer, alone or in combination of GMZ, on the endogenous levels of ceramide in tumor site (FIGS.

Figure 28A:
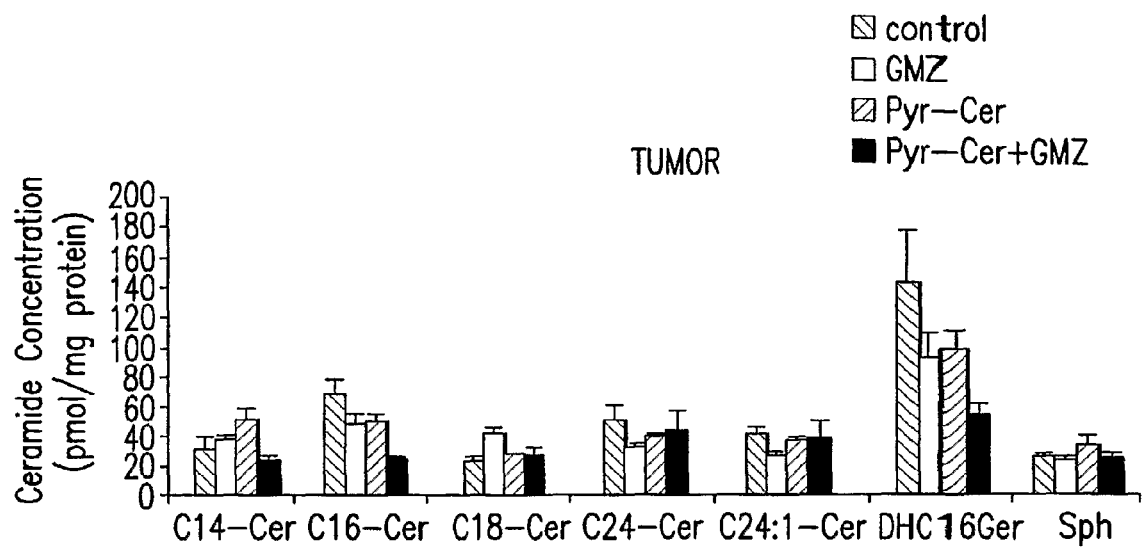
Figure 28B:
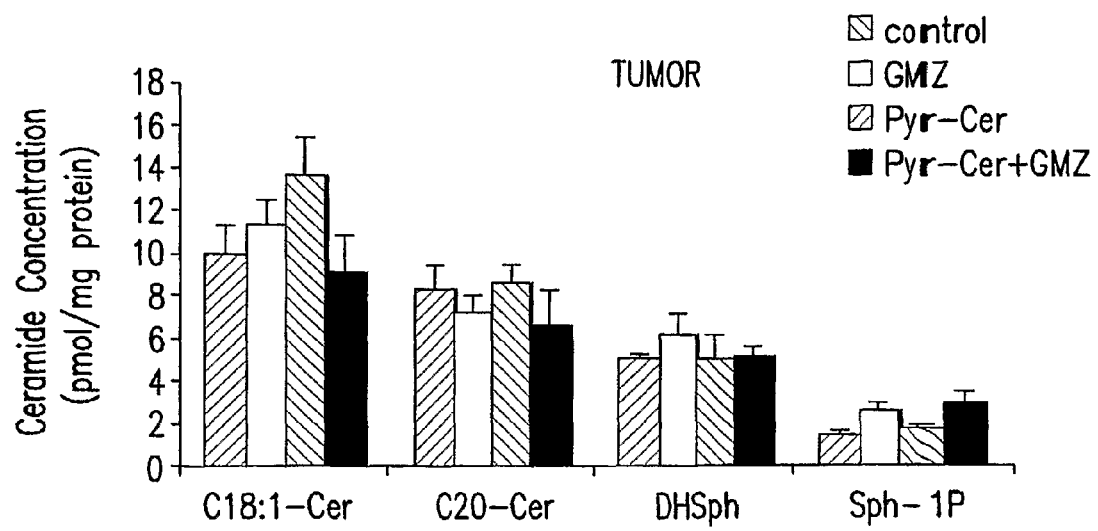
Figure 28C:
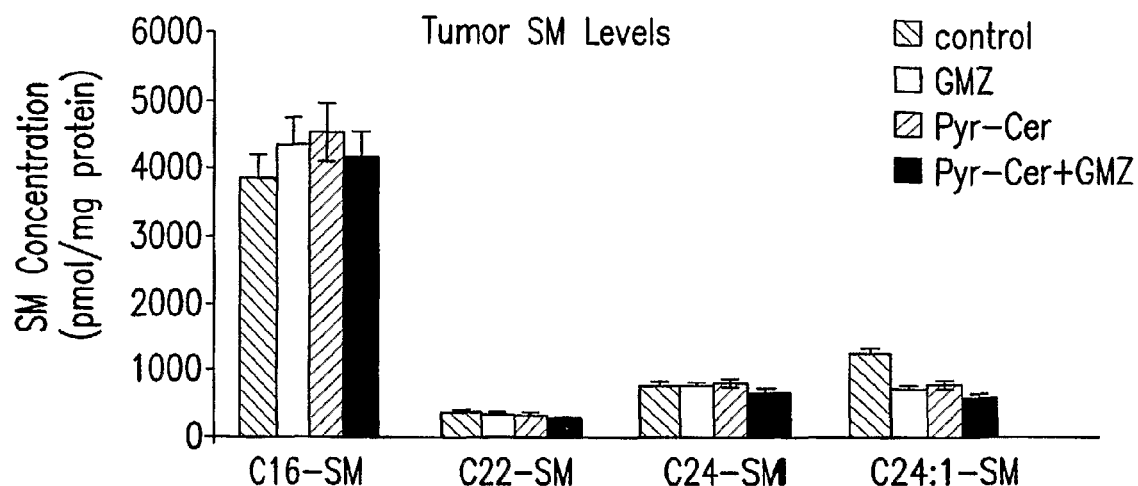
Figure 28D:
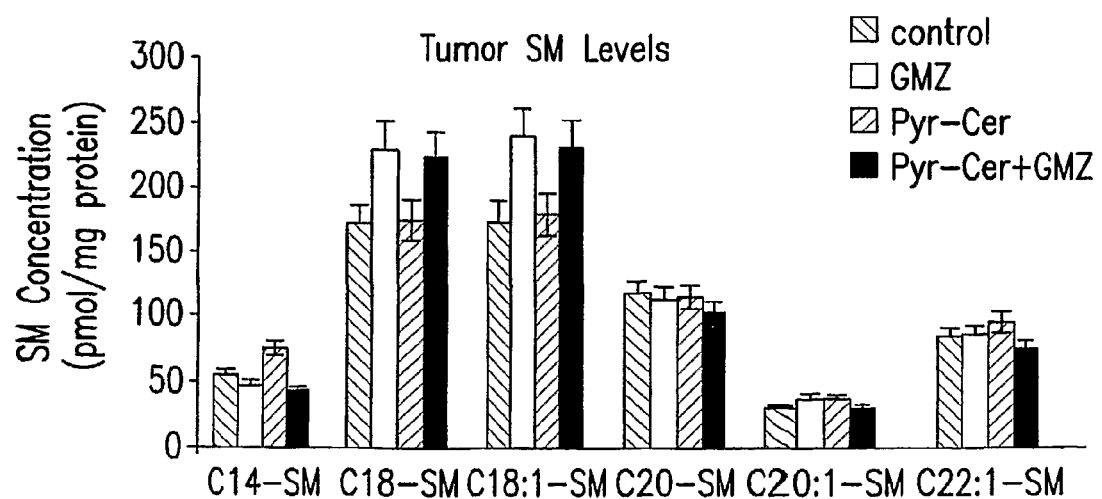

28A and B), or in the vital organs of the animals showed that treatments with L-t-$C_6$-Pyr-Cer, alone or in combination with GMZ, did not cause any sustained elevation of endogenous ceramides when compared to untreated controls (FIGS. 28A and B), suggesting that it does not affect the long-term metabolism of endogenous ceramide directly or indirectly. Similar data were also observed for the endogenous SM levels, in which no significant changes were observed in response to these treatments when compared to untreated controls (FIGS. 28C and D).

Figure 29A:
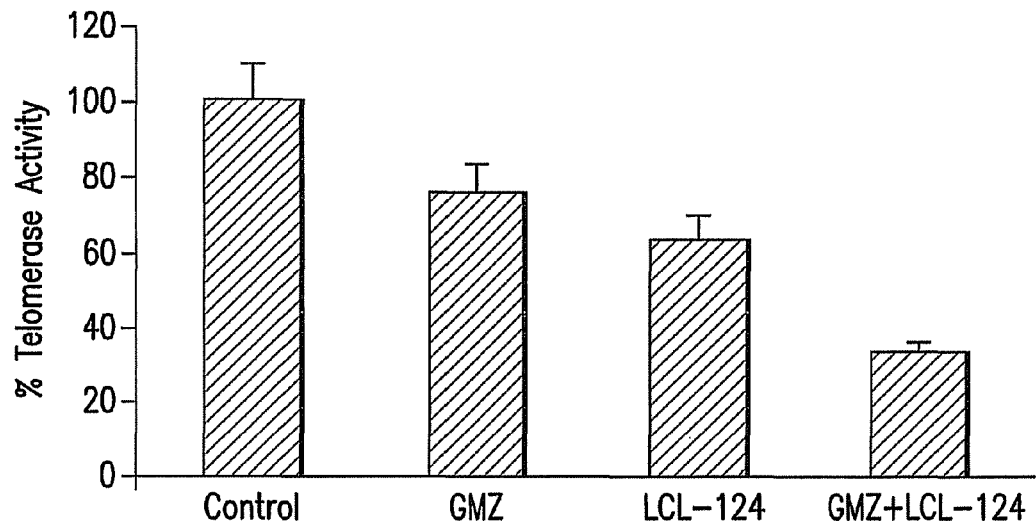
Figure 29B:
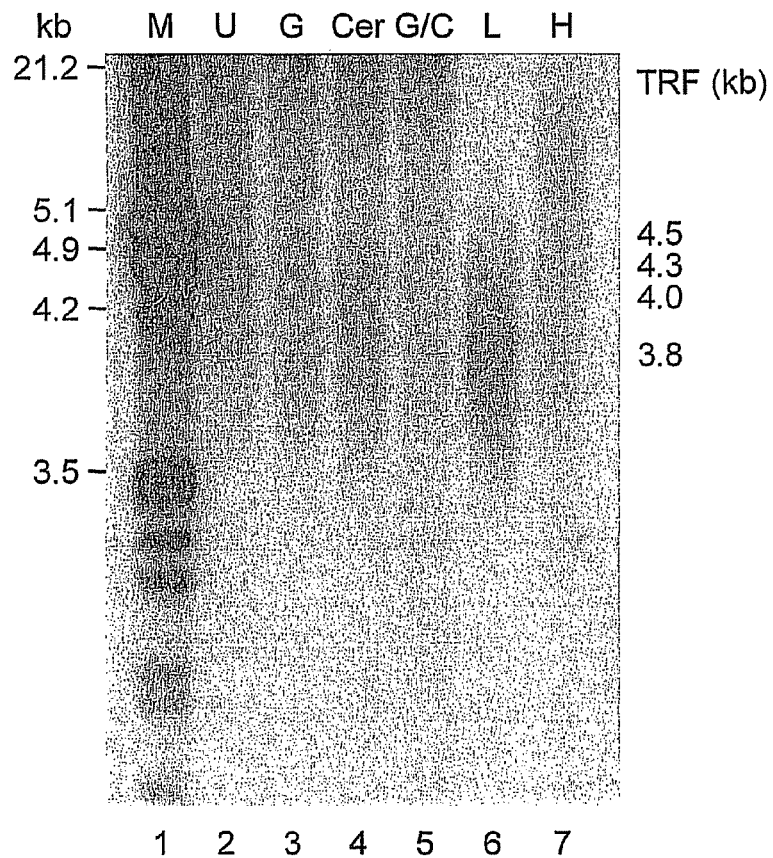

Role of L-t-$C_6$-Pyr-Cer in combination with GMZ in the regulation of telomerase in vivo. To examine whether the inhibition of HNSCC tumor growth in response to L-t-$C_6$-Pyr-Cer, alone or in combination with GMZ, mechanistically involves the inhibition of telomerase in vivo, the levels of enzyme activity, hTERT mRNA and protein levels were measured in tumor extracts by TRAP, Q-PCR and Western blotting, respectively. As FIG. 29A shows, telomerase activity was inhibited significantly in HNSCC tumors of the animals treated with the combination of L-t-$C_6$-Pyr-Cer and GMZ by about 60%, which was concomitant with a significant reduction of TRF length (about 700 bp) in these tumors as compared to untreated controls (FIG. 29B, lanes 4 and 1, respectively). Treatment with L-t-$C_6$-Pyr-Cer and GMZ as single agents also caused attrition in telomere length, about 500 and 200 bp, respectively, as compared to controls (FIG. 29B, lanes 3, 2 and 1, respectively).

Figure 29C:
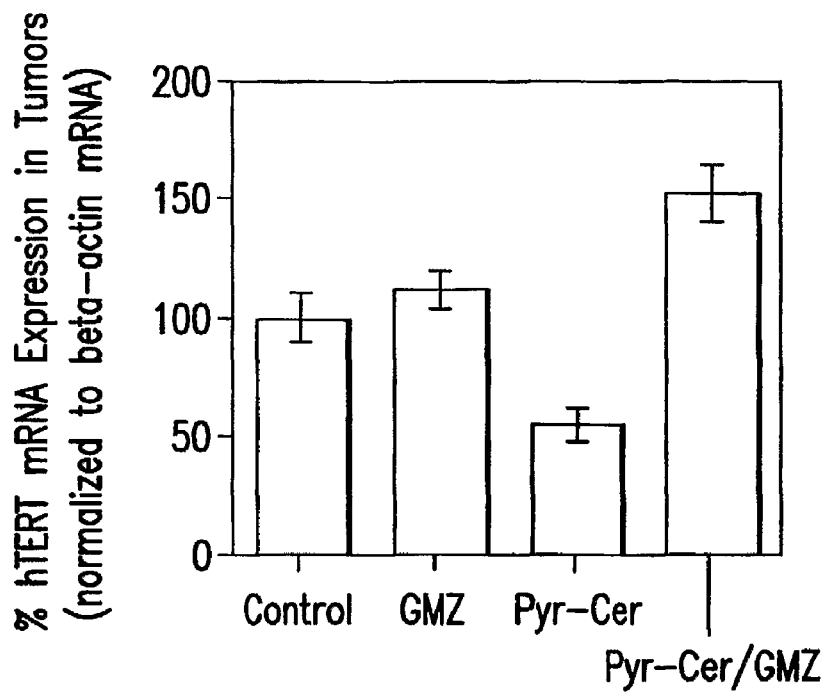
Figure 29D:
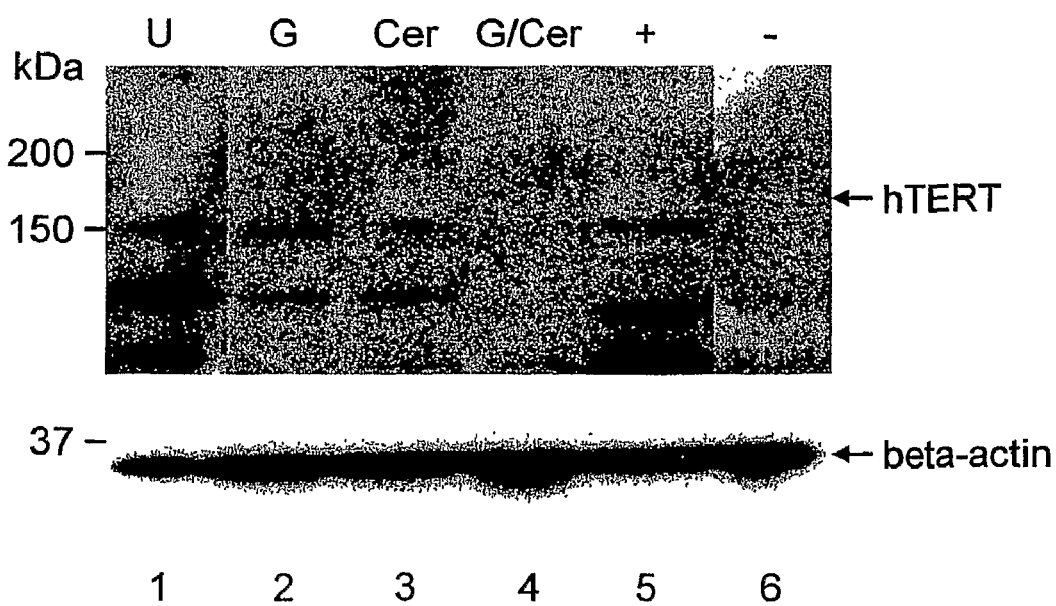

Consistent with the mechanisms of action of ceramide in the regulation of telomerase activity at the mRNA levels of hTERT in various human cancer cell lines in vitro, the inhibition of telomerase by L-t-$C_6$-Pyr-Cer (FIG. 29A) correlated with the decreased levels of hTERT mRNA and protein expression when compared to controls in vivo (FIGS. 29C, and 29D, lanes 3 and 1, respectively). However, although treatment with the combination of L-t-$C_6$-Pyr-Cer and GMZ did not cause any detectable changes in the mRNA levels of hTERT (FIG. 29C), the protein levels of hTERT were significantly inhibited (FIG. 29D, lane 4) in response to this combination, indicating a post-transcriptional regulation, which is distinct from the effects of L-t-$C_6$-Pyr-Cer alone. The protein levels of beta-actin in these samples were used as loading controls (FIG. 29D, lower panel).

Taken together, these data demonstrate, for the first time, that treatment with the combination of L-t-$C_6$-Pyr-Cer with GMZ results in a significant inhibition of telomerase activity, and decreased telomere length in HNSCC tumors in vivo. In vivo modulation of telomerase activity by this combination at the post-transcriptional level results in a significant decrease on the levels of hTERT protein.

10.3. Discussion

In the present invention, the growth inhibitory roles of the cationic ceramide, L-t-$C_6$-Pyr-Cer, alone or in combination with GMZ, against HNSCC cells both in vitro and in vivo were examined. It was demonstrated that L-t-$C_6$-Pyr-Cer accumulates mainly in the mitochondria- and, to a lesser extend, in the nuclei-enriched sub-cellular fractions, which is consistent with its design and targeting. The data also showed that L-t-$C_6$-Pyr-Cer significantly inhibits the growth of various HNSCC cell lines with similar 1050 concentrations, independent of their p53 status. The synergistic effects of L-t-$C_6$-Pyr-Cer in combination with GMZ were also determined by quantitative isobologram studies, in vitro. More importantly, after preclinical parameters were determined, the data revealed, for the first time, that treatment with L-t-$C_6$-Pyr-Cer/GMZ almost completely inhibited tumor growth in the xenograft models of HNSCC in SCID mice, which was much more effective than the effects of 5-FU/CP combination. The LC/MS analysis showed that the levels of L-t-$C_6$-Pyr-Cer in the tumor site are significantly higher than its levels in the liver and intestines, and interestingly, the combination with GMZ increased the sustained accumulation of this ceramide by about 40%. Mechanistically, the inhibition of HNSCC tumor growth and/or progression by L-t-$C_6$-Pyr-Cer/GMZ was linked to the inhibition of telomerase, and decrease in telomere length. The modulation of telomerase appeared to be regulated at the post-transcriptional level of hTERT protein, leading to a significant decrease in the levels of hTERT in response to this combination, in vivo.

Because of inherent limitations in their solubility and bioavailability of conventional exogenous ceramides, novel Pyr-Cers with greater water solubility, cell-membrane permeability and cellular uptake have been designed and synthesized as described in the present invention. The presence of the positive charge by the pyridinium ring in their structures was designed to target and accumulate these ceramide analogues into negatively charged intracellular compartments, especially mitochondria and nucleus. These properties of Pyr-Cer is important for targeting these molecules preferentially into tumor sites. The accumulation of L-t-$C_6$-Pyr-Cer preferentially in mitochondria-, and to a lesser extend, in nuclei-enriched fractions was established in UM-SCC-22A cells in vitro, and this was also consistent with the higher accumulation of the compound in the tumor site than in the liver and intestines in vivo. Novgorodov et al., 2005, J. Biol. Chem. 280(16):16096-16105.

The lack of overall toxicity in animals in response to the combination of L-t-$C_6$-Pyr-Cer and GMZ is significant indicating that this combination provides alternative approaches for the treatment of HNSCC with limited toxicity.

Importantly, the results presented here also indicated, for the first time, that one of the mechanisms by which L-t-$C_6$-Pyr-Cer/GMZ combination inhibits the growth and/or progression of HNSCC tumors is via the modulation of telomerase activity, and decreased telomere length in vivo.

In summary, the results presented here indicate that treatment with CCPS analogs, such as water soluble L-t-$C_6$-Pyr-Cer in combination with nucleoside analogs, such as GMZ inhibits HNSCC tumor growth and/or progression via a mechanism which involves the inhibition of telomerase, and decrease in telomere length with no detectable overall toxicity in vivo. Thus, combination of L-t-$C_6$-Pyr-Cer and GMZ, and combinations of other CCPS analogs with chemotherapeutic agents can provide alternative strategies for the improved management/control of HNSCC in vivo.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A compound of formula:

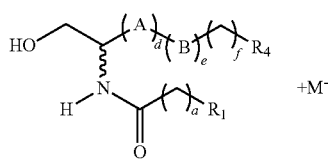

wherein:
$R_1$ is

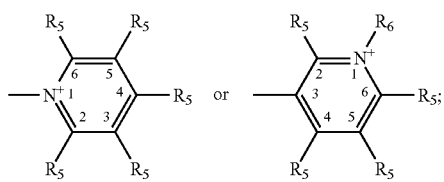

A is —$CH_2$— or —CH(OH)—;
B is —$CH_2CH_2$—, —CH(OH)$CH_2$—, or -trans-CH=CH—;
$R_4$ is —H, —$CH_3$, or -phenyl, optionally substituted with one or more $R_8$;
each $R_5$ is independently —H or —($C_1$-$C_{10}$)alkyl;
$R_6$ is —($C_1$-$C_{16}$)alkyl;
$R_8$ is —($C_1$-$C_6$)alkyl;
a is an integer from 0 to 26;
d is 1;
e is 1;
f is an integer from 0 to 20; and
$M^-$ is a counter anion.

2. The compound of claim 1, wherein $R_1$ is

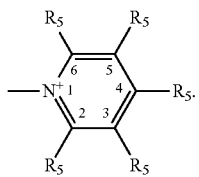

3. The compound of claim 2, wherein A is —CH(OH)—.

4. The compound of claim 3, wherein B is -trans-CH=CH—, and each $R_5$ is —H.

5. The compound of claim 4, wherein A is —(R)—CH(OH)—.

6. The compound of claim 5, wherein said compound is (2S,3R,4E)-2-N-[1-(1"-pyridinium)-acetyl]-sphingosine bromide; (2S,3R,4E)-2-N-[6'-(1"-pyridinium)-hexanoyl]-sphingosine bromide; or (2S,3R,4E)-2-N-[12'-(1"-pyridinium)-dodecanoyl]-sphingosine bromide; or (2S,3R,4E)-2-N-[16'-(1"-pyridinium)-hexadecanoyl]-sphingosine bromide.

7. The compound of claim 5, wherein said compound is (2R,3R,4E)-2-N-[1-(1"-pyridinium)-acetyl]-sphingosine bromide; (2R,3R,4E)-2-N-[16'-(1"-pyridinium)-hexanoyl]-sphingosine bromide; (2R,3R,4E)-2-N-[12'-(1"-pyridinium)-dodecanoyl]-sphingosine bromide; or (2R,3R,4E)-2-N-[16'-(1"-pyridinium)-hexadecanoyl]-sphingosine bromide.

8. The compound of claim 4, wherein A is —(S)—CH(OH)—.

9. The compound of claim 8, wherein said compound is (2S,3S,4E)-2-N-[1'-(6"-pyridinium)-acetyl]-sphingosine bromide; (2S,3S,4E)-2-N-[6'-(1"-pyridinium)-hexanoyl]-sphingosine bromide; (2S,3S,4E)-2-N-[12'-(1"-pyridinium)-dodecanoyl]-sphingosine bromide; or (2S,3S,4E)-2-N-[16'-(1"-pyridinium)-hexadecanoyl]-sphingosine bromide.

10. The compound of claim 8, wherein said compound is (2R,3S,4E)-2-N-[1'-(6"-pyridinium)-acetyl]-sphingosine bromide; (2R,3S,4E)-2-N-[6'-(1"-pyridinium)-hexanoyl]-sphingosine bromide; (2R,3S,4E)-2-N-[12'-(1"-pyridinium)-dodecanoyl]-sphingosine bromide; or (2R,3S,4E)-2-N-[16'-(1"-pyridinium)-hexadecanoyl]-sphingosine bromide.

11. The compound of claim 3, wherein B is —$CH_2CH_2$—.

12. The compound of claim 11, wherein A is —(R)—CH(OH)—.

13. The compound of claim 12, wherein said compound is (2S,3R)-2-N-(1'-[1"-pyridinium)-acetyl]-4,5-dihydrosphingosine bromide; (2S,3R)-2-N-[6'-(1"-pyridinium)-hexanoyl]-4,5-dihydrosphingosine bromide; (2S,3R)-2-N-[12'-(1"-pyridinium)-dodecanoyl]-4,5-dihydrosphingosine bromide; or (2S,3R)-2-N-[16'-(1"-pyridinium)-hexadecanoyl]-4,5-dihydrosphingosine bromide.

14. The compound of claim 11, wherein A is —(S)—CH(OH)—.

15. The compound of claim 14, wherein said compound is (2S,3S)-2-N-[1'-(1"-pyridinium)-acetyl]-4,5-dihydrosphingosine bromide; (2S,3S)-2-N-[6'-(1"-pyridinium)-hexanoyl]-4,5-dihydrosphingosine bromide; (2S,3S)-2-N-[12'-(1"-pyridinium)-dodecanoyl]-4,5-dihydrosphingosine bromide; or (2S,3S)-2-N-[16'-(1"-pyridinium)-hexadecanoyl]-4,5-dihydrosphingosine bromide.

16. The compound of claim 3, wherein B is —CH(OH)$CH_2$—.

17. The compound of claim 16, wherein B is —(R)—CH(OH)$CH_2$—.

18. The compound of claim 17, wherein A is —(S)—CH(OH)—.

19. The compound of claim 18, wherein said compound is (2S,3S,4R)-2-N-[1'-(1"-pyridinium)-acetyl]-4-hydroxy-4,5-dihydrosphingosine bromide; (2S,3S,4R)-2-N-[6'-(1"-pyridinium)-hexanoyl]-4-hydroxy-4,5-dihydrosphingosine bromide; (2S,3S,4R)-2-N-[12'-(1"-pyridinium)-dodecanoyl]-4-hydroxy-4,5-dihydrosphingosine bromide; or (2S,3S,4R)-2-N-[16'-(1"-pyridinium)-hexadecanoyl]-4-hydroxy-4,5-dihydrosphingosine bromide.

20. The compound of claim 17, wherein A is —(R)—CH(OH)—.

21. The compound of claim 20 wherein said compound is (2S,3R,4R)-2-N-[1'-(1"-pyridinium)-acetyl]-4-hydroxy-4,5-dihydrosphingosine bromide; (2S,3R,4R)-2-N-[6'-(1"-pyridinium)-hexanoyl]-4-hydroxy-4,5-dihydrosphingosine bromide; (2S,3R,4R)-2-N-[12'-(1"-pyridinium)-dodecanoyl]-4-hydroxy-4,5-dihydrosphingosine bromide; or (2S,3R,4R)-2-N-[16'-(1"-pyridinium)-hexadecanoyl]-4-hydroxy-4,5-dihydrosphingosine bromide.

22. The compound of claim 1, wherein $R_1$ is

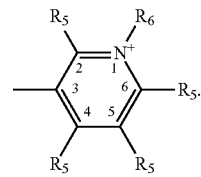

23. The compound of claim 22, wherein A is —CH(OH)—.

24. The compound of claim 23, wherein B is -trans-CH=CH—; and each $R_5$ is —H.

25. The compound of claim 24, wherein A is —(R)—CH(OH)—.

26. The compound of claim 25, wherein said compound is (2S,3R,4E)-2-N-(1'-octylnicotinoyl)-sphingosine bromide or (2S,3R,4E)-2-N-[3'-(1''-butyl pyridinium)-propanoyl]-sphingosine bromide.

27. The compound of claim 24, wherein A is —(S)—CH(OH)—.

28. The compound of claim 27, wherein said compound is (2S,3S,4E)-2-N-(1'-octylnicotinoyl)-sphingosine bromide or (2S,3S,4E)-2-N-[3'-(1''-butyl pyridinium)-propanoyl]-sphingosine bromide.

29. A compound of formula:

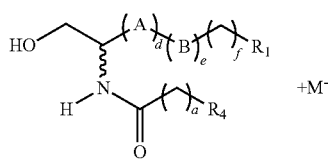

wherein:
$R_1$ is

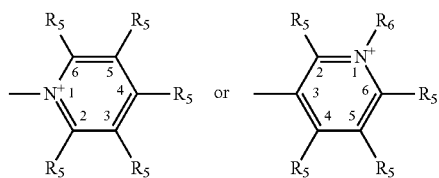

A is —$CH_2$— or —CH(OH)—;
B is —$CH_2CH_2$—, —CH(OH)$CH_2$—, or -trans-CH=CH—;
$R_4$ is —H, —$CH_3$, or phenyl optionally substituted with one or more $R_8$;
each $R_5$ is independently —H or —($C_1$-$C_{10}$)alkyl;
$R_6$ is —($C_1$-$C_{16}$)alkyl;
$R_8$ is —($C_1$-$C_6$)alkyl;
a is an integer from 0 to 26;
d is 1;
e is 1;
f is an integer from 0 to 20; and
$M^-$ is a counter anion.

30. The compound of claim 29, wherein $R_1$ is

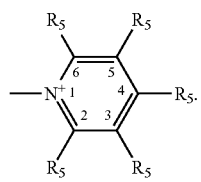

31. The compound of claim 30, wherein B is -trans-CH=CH—, each $R_5$ is —H, and f is 13.

32. The compound of claim 31, wherein A is —(R)—CH(OH)—.

33. The compound of claim 32, wherein said compound is (2S,3R,4E)-2-N-acetyl-18-(1'-pyridinium)-sphingosine bromide; (2S,3R,4E)-2-N-hexanoyl-18-(1'-pyridinium)-sphingosine bromide, (2S,3R,4E)-2-N-dodecanoyl-18-(1-pyridinium)-sphingosine bromide, or (2S,3R,4E)-2-N-hexadecanoyl-18-(1'-pyridinium)-sphingosine bromide.

34. The compound of claim 31, wherein A is —(S)—CH(OH)—.

35. The compound of claim 34, wherein said compound is (2S,3S,4E)-2-N-acetyl-18-(1'-pyridinium)-sphingosine bromide; (2S,3S,4E)-2-N-hexanoyl-18-(1'-pyridinium)-sphingosine bromide, (2S,3S,4E)-2-N-dodecanoyl-18-(1'-pyridinium)-sphingosine bromide, or (2S,3S,4E)-2-N-hexadecanoyl-18-(1'-pyridinium)-sphingosine bromide.

36. A method for treating a disorder involving cell hyperproliferation or dysfunctional sphingolipid signal transduction in a subject, said method comprising administering at least one compound of claim 1 to said subject.

37. A method for treating a disorder involving cell hyperproliferation or dysfunctional sphingolipid signal transduction in a subject, said method comprising administering at least one compound of claim 1 in combination with a therapeutic agent not comprising a pyridinium moiety and a sphingosine backbone to said subject.

38. The method of claim 36 or 37, wherein said disorder is cancer, autoimmune disease, or inflammation.

39. The method of 37, wherein the disorder is cancer and said therapeutic agent is Gemcitabine or Doxorubicin.

40. A method for treating a disorder involving cell hyperproliferation or dysfunctional sphingolipid signal transduction in a subject, said method comprising administering at least one compound of claim 29 to said subject.

41. A method for treating a disorder involving cell hyperproliferation or dysfunctional sphingolipid signal transduction in a subject, said method comprising administering at least one compound of claim 29 in combination with a therapeutic agent not comprising a pyridinium moiety and a sphingosine backbone to said subject.

42. The method of claim 40 or 41, wherein said disorder is cancer, autoimmune disease, or inflammation.

43. The method of claim 41, wherein the disorder is cancer and said therapeutic agent is Gemcitabine or Doxorubicin.

44. A method for treating a cancer in a subject in need thereof, said method comprising administering at least one compound of claim 1 or claim 29 to said subject, wherein said cancer is breast cancer, colon cancer, or head and neck cancer.

45. The method of claim 44, comprising administering the at least one compound in combination with a therapeutic agent not comprising a pyridinium moiety and a sphingosine backbone.

46. The method of claim 45, wherein the therapeutic agent is Gemcitabine or Doxorubicin.

47. A method of targeting mitochondria, the method comprising administering a composition containing a compound of claim 1 to a subject or a sample containing mitochondria.

48. A method of targeting mitochondria, the method comprising administering a composition containing a compound of claim 29 to a subject or a sample containing mitochondria.

* * * * *